US008614245B2

(12) United States Patent
Gruss et al.

(10) Patent No.: US 8,614,245 B2
(45) Date of Patent: *Dec. 24, 2013

(54) CRYSTALLINE (1R,4R)-6'-FLUORO-N,N-DIMETHYL-4-PHENYL-4',9'-DIHYDRO-3'H-SPIRO[CYCLOHEXANE-1,1'-PYRANO[3,4,B]INDOL]-4-AMINE

(71) Applicant: Gruenenthal GmbH, Aachen (DE)

(72) Inventors: Michael Gruss, Aachen (DE); Stefan Kluge, Riehen (CH); Stefan Pruehs, Neuss (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,565

(22) Filed: Jan. 8, 2013

(65) Prior Publication Data

US 2013/0123324 A1    May 16, 2013

Related U.S. Application Data

(63) Continuation-in-part of application No. 13/542,809, filed on Jul. 6, 2012.

(60) Provisional application No. 61/505,735, filed on Jul. 8, 2011.

(30) Foreign Application Priority Data

Jul. 8, 2011   (EP) .................... 11005587

(51) Int. Cl.
C07D 491/052   (2006.01)
A61K 31/407    (2006.01)

(52) U.S. Cl.
USPC ............... 514/409; 514/411; 548/430

(58) Field of Classification Search
None
See application file for complete search history.

(56) References Cited

U.S. PATENT DOCUMENTS

| | | | |
|---|---|---|---|
| 7,547,707 B2 * | 6/2009 | Hinze et al. ............ | 514/278 |
| 2010/0009986 A1 | 1/2010 | Zemolka et al. | |
| 2011/0015220 A1 | 1/2011 | Linz et al. | |
| 2011/0053970 A1 | 3/2011 | Friderichs et al. | |
| 2011/0319440 A1 | 12/2011 | Hinze et al. | |
| 2012/0034297 A1 | 2/2012 | Gruening et al. | |

FOREIGN PATENT DOCUMENTS

| | | | |
|---|---|---|---|
| WO | WO 2004/043967 A1 | 5/2004 | |
| WO | WO 2006/108565 A1 | 10/2006 | |
| WO | WO 2008/009415 A2 | 1/2008 | |
| WO | WO 2008/040481 A1 | 4/2008 | |

OTHER PUBLICATIONS

Ravin, L. PhD., "Preformulation", Remington Chapter 76, pp. 1409-1423, 1985 (fifteen (15) sheets).
Disanto, A., "Bioavailability and Bioequivalency Testing", Remington Chapter 77, pp. 1424-1431, 1985 (eight (8) sheets).
Knevel, A. PhD., "Separation", Remington Chapter 78, pp. 1432-1442, 1985 (eleven (11) sheets).
Phillips, G Briggs, PhD., "Sterilization", Remington Chapter 79, pp. 1443-1454, 1985 (twelve (12) sheets).
Siegel, F. PhD., "Tonicity, Osmoticity, Osmolality and Osmolarity", Remington Chapter 80, pp. 1455-1472, 1985 (eighteen (18) sheets).
Giles et al., "Plastic Packaging Materials", Remington Chapter 81, pp. 1473-1477, 1985 (five (5) sheets).
Lintner, C. PhD., "Stability of Pharmaceutical Products", Remington Chapter 82, pp. 1478-1486, 1985 (nine (9) sheets).
Erskine, C., Jr., "Quality Assurance and Control" Remington Chapter 83, pp. 1487-1491, 1985 (five (5) sheets).
Nairn, J.G. PhD., "Solutions, Emulsions, Suspensions and Extractives", Remington Chapter 84, pp. 1492-1517, 1985 (twenty-six (26) sheets).
Avis, K. DSc., "Parenteral Preparations", Remington Chapter 85, pp. 1518-1541, 1985 (twenty-four (24) sheets).
Turco et al., "Intravenous Admixtures", Remington Chapter 86, pp. 1542-1552, 1985 (eleven (11) sheets).
Mullins, J. PhD., "Ophthalmic Preparations", Remington Chapter 87, pp. 1553-1566, 1985 (fourteen (14) sheets).
Block, L. PhD., "Medicated Applications", Remington Chapter 88, pp. 1567-1584, 1985 (eighteen (18) sheets).
Rippie, E. PhD., "Powders", Remington Chapter 89, pp. 1585-1602 (eighteen, 1985 (18) sheets).
King et al., "Oral Solid Dosage Forms", Remington Chapter 90, pp. 1603-1632, 1985 (thirty (30) sheets).
Porter, S. PhD., "Coating of Pharmaceutical Dosage Forms", Remington Chapter 91, pp. 1633-1643, 1985 (eleven (11) sheets).
Longer et al., "Sustained-Release Drug Delivery Systems", Remington Chapter 92, pp. 1644-1661, 1985 (eighteen (18) sheets).
Sclarra et al., "Aerosols", Remington Chapter 93, 1985, pp. 1662-1677, 1985 (sixteen (16) sheets).
Reply in U.S. Appl. No. 13/542,809, filed Aug. 16, 2013, and Declaration of Dr. Michael Gruss, dated Aug. 13, 2013.
European Search Report dated Sep. 26, 2011 (Six (6) pages).
cf. R. Hilfiker, "Polymorphism in the Pharmaceutical Industry", 2006 Wiley VCH, pp. 235-242 (Ten (10) pages).
International Search Report dated Oct. 22, 2012 with Written Opinion (Eleven (11) pages).
Co-Pending U.S. Appl. No. 13/835,298, filed Mar. 13, 2013.
Co-Pending U.S. Appl. No. 13/711,455, filed Dec. 11, 2012.

* cited by examiner

*Primary Examiner* — Michael Barker
(74) *Attorney, Agent, or Firm* — Crowell & Moring LLP

(57) ABSTRACT

Crystalline forms of (1r,4r)-6'-fluoro-N,N-dimethyl-4-phenyl-4',9'-dihydro-3'H-spiro[cyclohexane-1,1'-pyrano[3,4,b]indol]-4-amine, pharmaceutical compositions and medicaments comprising these crystalline modifications, the use of these modifications as well as a process for the enrichment of such crystalline modifications.

41 Claims, 20 Drawing Sheets

CRYSTALLINE (1R,4R)-6'-FLUORO-N,N-DIMETHYL-4-PHENYL-4',9'-DIHYDRO-3'H-SPIRO[CYCLOHEXANE-1,1'-PYRANO[3,4,B]INDOL]-4-AMINE

CROSS REFERENCE TO RELATED APPLICATIONS

This application claims priority from U.S. provisional patent application No. 61/505,735, filed Jul. 8, 2011, the entire disclosure of which is incorporated herein by reference. Priority is also claimed based on European patent application no. EP 11 005 587.8, filed Jul. 8, 2011, the entire disclosure of which is likewise incorporated herein by reference.

FIELD OF THE INVENTION

The present invention relates to crystalline forms of (1r,4r)-6'-fluoro-N,N-dimethyl-4-phenyl-4',9'-dihydro-3'H-spiro[cyclohexane-1,1'-pyrano[3,4, b]indol]-4-amine, pharmaceutical compositions and medicaments comprising these modifications, the use of these modifications as well as to a process for the enrichment of them.

BACKGROUND OF THE INVENTION

Pharmaceutically active drugs can exist in different solid forms. For example, a drug may exist in different crystalline forms which have different physical and chemical properties.

Different physical properties can cause different crystalline forms of the same drug to have largely different processing and storage performance. Such physical properties include, for example, thermodynamic stability, crystal morphology [form, shape, structure, particle size, particle size distribution, degree of crystallinity, color], ripple behavior, flowability, density, bulk density, powder density, apparent density, vibrated density, depletability, emptyability, hardness, deformability, grindability, compressability, compactability, brittleness, elasticity, caloric properties [particularly melting point], solubility [particularly equilibrium solubility, pH dependence of solubility], dissolution [particularly dissolution rate, intrinsic dissolution rate], reconstitutability, hygroscopicity, tackiness, adhesiveness, tendency to electrostatic charging, and the like.

In addition, different chemical properties can cause different crystalline forms of the same drug to have largely different performance properties. For example, a crystalline form having a low hygroscopicity (relative to other crystalline forms) can have superior chemical stability and longer shelf-life stability (cf. R. Hilfiker, Polymorphism, 2006 Wiley VCH, pp 235-242).

One particular drug that is of great interest for use in treating cancer pain (and other acute, visceral, neuropathic and chronic pain pain disorders) is (1r,4r)-6'-fluoro-N,N-dimethyl-4-phenyl-4',9'-dihydro-3'H-spiro[cyclohexane-1,1'-pyrano[3,4b]indol]-4-amine. This drug is depicted below as the compound of formula (I).

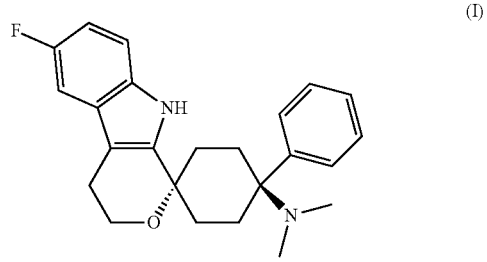 [SMILES: CN(C)[C@]1(c2ccccc2)CC[C@]2(CC1)OCCc1c3cc(F)ccc3[nH]c12]

(I)

(1r,4r)-6'-fluoro-N,N-dimethyl-4-phenyl-4',9'-dihydro-3'H-spiro[cyclohexane-1,1'-pyrano[3,4-b]indol]-4-amine The solid forms of (1r,4r)-6'-fluoro-N,N-dimethyl-4-phenyl-4',9'-dihydro-3'H-spiro[cyclo-hexane-1,1'-pyrano[3,4b]indol]-4-amine that are known so far are not satisfactory in every respect and there is a demand for advantageous solid forms.

In particular, there is a demand for solid forms of (1r,4r)-6'-fluoro-N,N-dimethyl-4-phenyl-4',9'-dihydro-3'H-spiro[cyclohexane-1,1'-pyrano[3,4b]indol]-4-amine that have properties differing from corresponding solid forms or other solid forms of the diastereomer, i.e. of (1s,4s)-6'-fluoro-N,N-dimethyl-4-phenyl-4',9'-dihydro-3'H-spiro[cyclohexane-1,1'-pyrano[3,4b]indol]-4-amine. Every property of one of the two diastereomers that differs from the corresponding property of the other of the two diastereomers may be useful for separating both diastereomers from one another. Isolation of pure solid forms of (1r,4r)-6'-fluoro-N,N-dimethyl-4-phenyl-4',9'-dihydro-3'H-spiro[cyclohexane-1,1'-pyrano[3,4b]indol]-4-amine is very desirable from a pharmaceutical point of view.

SUMMARY OF THE INVENTION

It is an object of the invention to provide forms or modifications of (1r,4r)-6'-fluoro-N,N-dimethyl-4-phenyl-4',9'-dihydro-3'H-spiro[cyclohexane-1,1'-pyrano[3,4, b]indol]-4-amine that have advantages compared to the forms or modifications of the prior art.

This object has been achieved by the present invention. It has surprisingly been found that different crystalline forms of (1r,4r)-6'-fluoro-N,N-dimethyl-4-phenyl-4',9'-dihydro-3'H-spiro[cyclohexane-1,1'-pyrano[3,4b]indol]-4-amine can be prepared which have fundamentally different properties. These inventive crystalline forms are described herein.

BRIEF DESCRIPTION OF THE DRAWINGS

FIGS. 1a, 1b, 1c, 1d, 1e, 1f, 1g, 1h, 1i and 1l show the PXRD patterns of crystalline forms A, B, C, D, E, F, G, H, I and L.

FIGS. 2a, 2b, 2c, 2d, 2e, 2f, 2g, 2h, 2i and 2l show the Raman spectra of crystalline forms A, B, C, D, E, F, G, H, I and L.

DETAILED DESCRIPTION

Figure 1A:
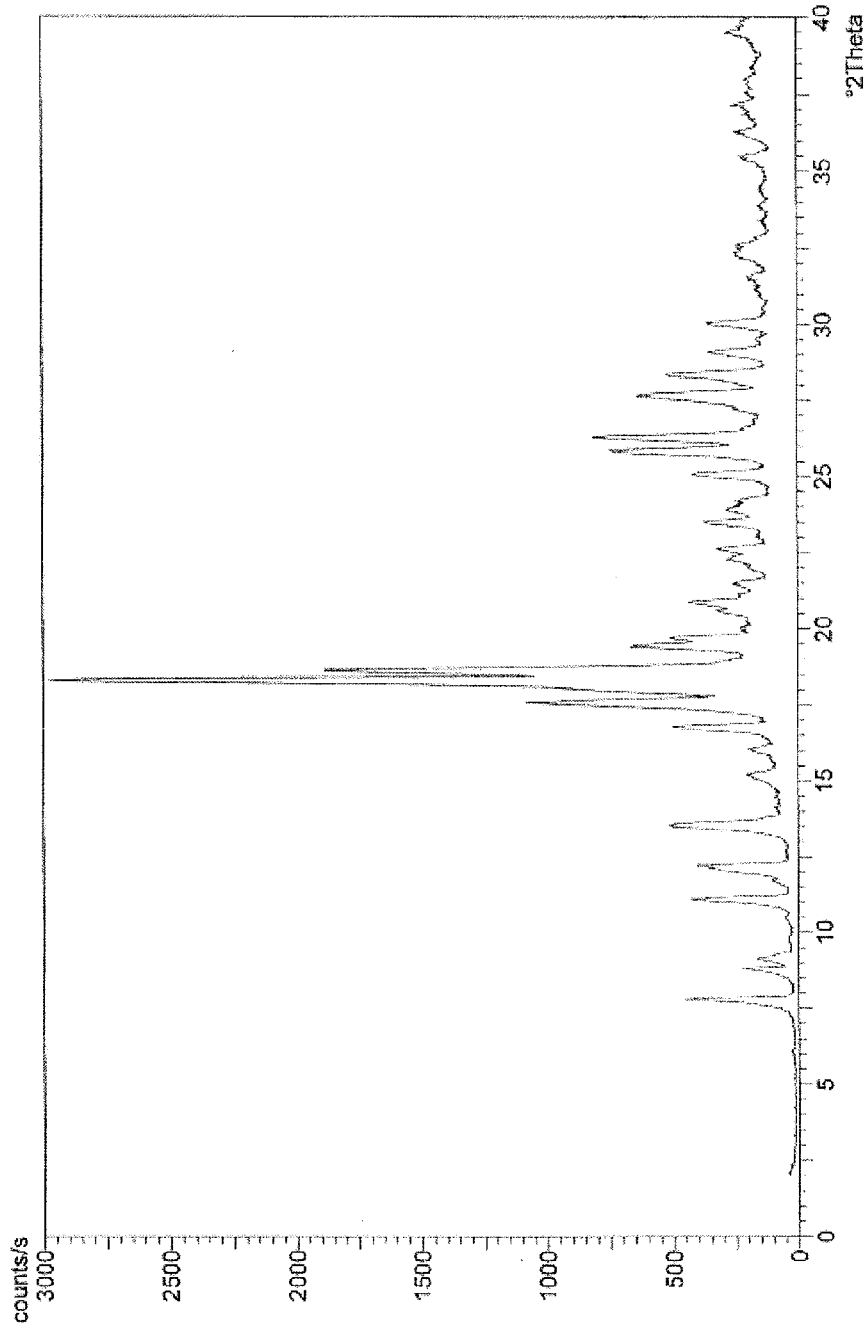

The compound according to general formula (I) can systematically be referred to as "1,1-(3-dimethylamino-3-phenylpentamethylene)-6-fluoro-1,3,4,9-tetrahydropyrano[3,4-b]indole (trans)" or as "(1r,4r)-6'-fluoro-N,N-dimethyl-4-phenyl-4',9'-dihydro-3'H-spiro[cyclohexane-1,1'-pyrano[3, 4, b]indol]-4-amine", respectively.

The compound according to general formula (I) may be present as the free base. The definition of the free base of the compound according to general formula (I) as used herein includes solvates, co-crystals and crystalline forms. For the purpose of the specification, "free base" preferably means that the compound according to general formula (I) is not present in form of a salt, particularly not in form of an acid-addition salt. The most basic functional group of the compound according to general formula (I) is its N,N-dimethylamino moiety, which thus according to the invention is preferably neither protonated nor quaternized. In other words, the free electron pair of the nitrogen atom of the N,N-dimethylamino moiety is present as a Lewis base. Methods to determine whether a chemical substance is present as the free base or as a salt are known to the skilled artisan such as $^{14}N$ or $^{15}N$ solid state NMR, x-ray diffraction, IR, Raman, XPS. $^1$H-NMR recorded in solution may also be used to consider the presence of protonation.

Unless explicitly stated otherwise, all 2Θ values refer to a X-ray diffractogram measured using CuKα radiation having a wavelength of 1.54060 Å. The terms 2Θ values and degrees 2Θ are used synonymously. Unless explicitly stated otherwise, all values in ppm refer to ppm by weight, i.e. ppmw.

One preferred aspect of the present invention relates to a crystalline form of (1r,4r)-6'-fluoro-N,N-dimethyl-4-phenyl-4',9'-dihydro-3'H-spiro[cyclohexane-1,1'-pyrano[3,4b]indol]-4-amine.

In some preferred embodiments, the crystalline form according to the invention comprises an X-ray diffraction peak at about 18.9±0.5 (2Θ). In some preferred embodiments, the crystalline form according to the invention comprises an X-ray diffraction peak at about 18.9±0.4 (2Θ). In some preferred embodiments, the crystalline form according to the invention comprises an X-ray diffraction peak at about 18.9±0.3 (2Θ). All 2Θ values refer to a X-ray diffractogram measured using CuKα radiation having a wavelength of 1.54060 Å.

Preferably, said X-ray diffraction peak exhibits a relative intensity of at least 30%, more preferably of at least 35%, still more preferably of at least 40%, yet more preferably of at least 45%, most preferably of at least 50% and in particular, of at least 55%.

Preferably, the crystalline form according to the invention has a Raman peak at about 921±5 cm$^{-1}$, at about 1002±5 cm$^{-1}$ and at about 1572±5 cm$^{-1}$.

The crystalline form according to the invention may be an ansolvate or a solvate. In a preferred embodiment, the crystalline form is an ansolvate.

In another preferred embodiment, the crystalline form is a solvate. Preferably, the solvate is selected from hydrates, solvates of lower alcohols such as methanol, ethanol, n-propanol, and iso-propanol, and solvates of dimethyl sulfoxide (DMSO), or a solvate of solvent mixtures. Preferably, the solvate is selected from the group consisting of monosolvate, hemi-solvate, disolvate, trisolvate, and mixtures thereof.

In a preferred embodiment, the crystalline form is a hydrate, preferably selected from the group consisting of monohydrate, hemi-hydrate, dihydrate, trihydrate, and mixtures thereof. In some preferred embodiments, the crystalline form is a dihydrate.

In another preferred embodiment, the crystalline form is an alcoholate, preferably selected from the group consisting of methanolate, ethanolate, propanolate (1-propanolate or 2-propanolate), and the mixtures thereof, the 2-propanolate solvate being particularly preferred.

It has been surprisingly found that some crystalline forms of (1r,4r)-6'-fluoro-N,N-dimethyl-4-phenyl-4',9'-dihydro-3'H-spiro[cyclohexane-1,1'-pyrano[3,4b]indol]-4-amine disclosed herein have surprisingly higher stability than other forms, as is demonstrated in the examples. For instance, crystalline form A achieves significantly and surprisingly higher stability than other forms.

In addition, it has been surprisingly found that in some solvents the solubility of alcoholates of (1r,4r)-6'-fluoro-N,N-dimethyl-4-phenyl-4',9'-dihydro-3'H-spiro[cyclohexane-1,1-pyrano[3,4b]indol]-4-amine may substantially differ from the solubility of the diastereomer and its solvates, respectively, namely (1s,4s)-6'-fluoro-N,N-dimethyl-4-phenyl-4',9'-dihydro-3'H-spiro[cyclohexane-1,1'-pyrano[3,4b] indol]-4-amine. Thus, the different solubilities may be used to separate both diastereomers from one another. For example, when the (1r,4r)-diastereomer forms a alcoholate with a comparatively low solubility and the (1s,4s)-diastereomer forms no alcoholate at all or an alcoholate with a substantially higher solubility, the (1r,4r)-diastereomer can be diastereoselectively precipitated and filtered out, thereby allowing for easy large-scale purification of the (1r,4r)-diastereomer.

Another aspect of the present invention relates to a process for the production of the crystalline form according to the invention.

In a preferred embodiment, the process comprises the step of (a-1) suspending (1r,4r)-6'-fluoro-N,N-dimethyl-4-phenyl-4',9'-dihydro-3'H-spiro[cyclo-hexane-1,1'-pyrano[3,4,b]indol]-4-amine in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof. In one preferred embodiment, the solvent comprises water. In another preferred embodiment, the solvent comprises at least one organic solvent selected from the group consisting of methanol, ethanol, n-propanol, iso-propanol, dimethyl formamide and dimethyl sulfoxide. In still another preferred embodiment, the solvent comprises at least one organic solvent selected from the group consisting of the C4 to C6 alcohols such as n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one, ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and mixtures thereof. In a preferred embodiment, the solvent does neither contain water nor any solvent selected from the group consisting of methanol, ethanol, n-propanol, iso-propanol, dimethyl formamide and dimethyl sulfoxide.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, in the process according to the invention, the suspension obtained in step (a-1) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-1) separating, preferably filtering off the solid obtained in step (a-1).

Preferably, the process according to the invention further comprises the step
(c-1) drying of the solid obtained in step (b-1).

Preferably, in the process according to the invention, step (c-1) takes place under air. However, drying under vacuum, more preferably at a vacuum of 0 to 900 mbar, even more preferably at a vacuum of 1 to 500 mbar, and in particular at a vacuum of 10 to 200 mbar is also possible.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4', 9'-dihydro-3'H-spiro[cyclohexane-1,1'-pyrano[3,4, b]indol]-4-amine in a solvent.

Conventional solvents known to persons skilled in the art may be used as solvents in a suspension of this type, in particular organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and also N-methyl-2-pyrrolidone, dimethyl formamide and dimethyl sulfoxide; and mixtures thereof.

Saturated hydrocarbons, such as n-pentane, n-hexane and n-heptane, and water are less suitable, the compound (1r,4r)-6'-fluoro-N,N-dimethyl-4-phenyl-4',9'-dihydro-3'H-spiro-[cyclohexane-1,1'-pyrano[3,4, b]indol]-4-amine being only poorly soluble in these substances. However, mixtures of these substances with at least one of the solvents listed above, such as mixtures containing a saturated hydrocarbon and further at least one solvent selected from the group consisting of ketones, ethers and chlorinated hydrocarbons, may also be used. For example, n-heptane/butanone, n-heptane/dichloromethane, n-heptane/acetone, n-heptane/tetrahydrofuran, n-hexane/butanone, n-hexane/dichloromethane, n-hexane/acetone and n-hexane/tetrahydrofuran mixtures are also preferred.

Preferably, in the process according to the invention, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In a preferred embodiment, the process according to the invention further comprises the step
(b-2) evaporating off the solvent of the solution obtained in step (a-2).

Suitable methods for evaporating the solvent are known to a person skilled in the art. Preferably, in the process according to the invention, the solvent is evaporated in air, air flow, or inert gas flow, in particular argon or nitrogen flow. However, depending on the crystalline form to be obtained evaporating off the solvent under vacuum, for example by means of a rotary evaporator, is also possible.

Preferably, in the process according to the invention, the solvent is evaporated at room temperature. However, depending on the crystalline form to be obtained evaporating off the solvent at an elevated temperature, e.g. within the range of 20° C. to 60° C., is also possible.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4, b]indol]-4-amine from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In one preferred embodiment, step (b-2') is carried out by the addition of a medium in which (1r,4r)-6'-fluoro-N,N-dimethyl-4-phenyl-4',9'-dihydro-3'H-spiro[cyclohexane-1, 1'-pyrano[3,4, b]indol]-4-amine is only poorly soluble ("anti-solvent") to the solution obtained in step (a-2). Said medium is preferably selected from the group consisting of saturated hydrocarbons, such as n-pentane, n-hexane and n-heptane; ethers such as tert-butyl methyl ether and diisopropyl ether; ethanol and water.

The amount of the media in which (1r,4r)-6'-fluoro-N,N-dimethyl-4-phenyl-4',9'-dihydro-3'H-spiro[cyclohexane-1, 1'-pyrano[3,4, b]indol]-4-amine is only poorly soluble, the precipitant or anti-solvent, is preferably selected in such a manner that upon its addition precipitation of the dissolved component begins. The precipitation of the dissolved component preferably begins either immediately upon the addition of the precipitant or alternatively with a delay of 2 seconds to 120 minutes. Preferably, the precipitation of the dissolved component begins within a time period of at most 60 minutes, more preferably at most 30 minutes, still more preferably at most 10 minutes, yet more preferably at most 5 minutes, most preferably at most 2 minutes, and in particular at most 30 seconds. In an especially preferred embodiment, the precipitation of the dissolved component begins immediately upon the addition of the precipitant.

Furthermore, the amount of the media in which (1r,4r)-6'-fluoro-N,N-dimethyl-4-phenyl-4',9'-dihydro-3'H-spiro[cyclohexane-1,1'-pyrano[3,4, b]indol]-4-amine is only poorly soluble, the precipitant or anti-solvent, is preferably selected in such a manner that the dissolved component is completely or at least up to 90% of the initial amount precipitated within a time period of at most 90 minutes, more preferably at most 80 minutes, still more preferably at most 70 minutes, and most preferably at most 60 minutes after the anti-solvent has been completely added.

Preferably, in the process according to the invention, after step (b-2) or respectively (b-2'), all other steps are carried out at a temperature between 40 and 0° C., preferably between 35 and 5° C., more preferably between 25 and 15° C.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow. However, depending on the crystalline form to be obtained evaporating off the solvent at an elevated temperature, e.g. within the range of 20° C. to 60° C., is also possible.

In the following, any reference to a "crystalline form" refers to a crystalline form of (1r,4r)-6'-fluoro-N,N-dimethyl-4-phenyl-4',9'-dihydro-3'H-spiro[cyclohexane-1,1'-pyrano-[3,4, b]indol]-4-amine.

A further aspect of the present invention relates to a crystalline form A. Preferably, the crystalline form A according to the invention has one or more X-ray diffraction peaks selected from the group consisting of about 17.6±0.2 (2Θ), about 18.3±0.2 (2Θ), about 18.6±0.2 (2Θ), about 25.8±0.2 (2Θ) and about 26.3±0.2 (2Θ). In some preferred embodiments, the crystalline form comprises an X-ray diffraction peak at about 18.3±0.2 (2Θ). In some preferred embodiments, the crystalline form comprises X-ray diffraction peaks at about 18.3±0.2 (2Θ) and about 18.6±0.2 (2Θ).

In some preferred embodiments, crystalline form A is characterized by an X-ray powder diffraction pattern comprising characteristic peaks at about 18.3±0.2 degrees 2θ, about 18.6±0.2 degrees 2θ and about 26.3±0.2 degrees 2θ. In some embodiments, the X-ray powder diffraction pattern further comprises characteristic peaks at about 11.7±0.2 degrees 2θ and about 31.6±0.2 degrees 2θ. In some preferred embodiments, crystalline form A is characterized by an X-ray powder diffraction pattern comprising characteristic peaks at about 18.3±0.2 degrees 2θ, about 18.6±0.2 degrees 2θ, about 26.3±0.2 degrees 2θ and optionally at about 17.6±0.2 degrees 2θ and/or about 19.4±0.2 degrees 2θ.

In some preferred embodiments, crystalline form A comprises X-ray diffraction peaks at about 17.6±0.2 (2Θ), about 18.3±0.2 (2Θ), about 18.6±0.2 (2Θ), about 26.3±0.2 (2Θ) and optionally about 25.8±0.2 (2Θ).

The crystalline form A according to the invention may additionally have at least one X-ray diffraction peak selected from the group consisting of about 7.8±0.2 (2Θ), about 13.5±0.2 (2Θ), about 16.8±0.2 (2Θ), about 19.4±0.2 (2Θ), about 19.7±0.2 (2Θ), about 27.6±0.2 (2Θ) and about 28.3±0.2 (2Θ).

Further, the crystalline form A according to the invention may be characterized in that as well as one or more X-ray diffraction peaks selected from the group consisting of about 17.6±0.2 (2Θ), about 18.3±0.2 (2Θ), about 18.6±0.2 (2Θ), about 25.8±0.2 (2Θ) and about 26.3±0.2 (2Θ) and optionally one or more X-ray diffraction peaks selected from the group consisting of about 7.8±0.2 (2Θ), about 13.5±0.2 (2Θ), about 16.8±0.2 (2Θ), about 19.4±0.2 (2Θ), about 19.7±0.2 (2Θ), about 27.6±0.2 (2Θ) and about 28.3±0.2 (2Θ), it additionally has at least one X-ray diffraction peak selected from the group consisting of about 12.2±0.2 (2Θ), about 20.6±0.2 (2Θ), about 22.3±0.2 (2Θ), about 22.6±0.2 (2Θ), about 23.5±0.2 (2Θ), about 23.9±0.2 (2Θ), about 25.0±0.2 (2Θ), about 29.1±0.2 (2Θ) and about 30.0±0.2 (2Θ).

The crystalline form A according to the invention may further be characterized in that as well as one or more X-ray diffraction peaks selected from the group consisting of about 17.6±0.2 (2Θ), about 18.3±0.2 (2Θ), about 18.6±0.2 (2Θ), about 25.8±0.2 (2Θ) and about 26.3±0.2 (2Θ) and optionally one or more X-ray diffraction peaks selected from the group consisting of about 7.8±0.2 (2Θ), about 13.5±0.2 (2Θ), about 16.8±0.2 (2Θ), about 19.4±0.2 (2Θ), about 19.7±0.2 (2Θ), about 27.6±0.2 (2Θ) and about 28.3±0.2 (2Θ), and optionally one or more X-ray diffraction peaks selected from the group consisting of about 12.2±0.2 (2Θ), about 20.6±0.2 (2Θ), about 22.3±0.2 (2Θ), about 22.6±0.2 (2Θ), about 23.5±0.2 (2Θ), about 23.9±0.2 (2Θ), about 25.0±0.2 (2Θ), about 29.1±0.2 (2Θ) and about 30.0±0.2 (2Θ), it additionally has at least one X-ray diffraction peak selected from the group consisting of about 8.8±0.2 (2Θ), about 9.1±0.2 (2Θ), about 10.5±0.2 (2Θ), about 11.7±0.2 (2Θ), about 15.2±0.2 (2Θ), about 16.0±0.2 (2Θ), about 21.5±0.2 (2Θ), about 22.0±0.2 (2Θ), about 24.2±0.2 (2Θ), about 27.2±0.2 (2Θ), about 29.5±0.2 (2Θ), about 31.6±0.2 (2Θ), about 32.3±0.2 (2Θ), about 32.6±0.2 (2Θ), and about 33.8±0.2 (2Θ).

All 2Θ values indicated above refer to a X-ray diffractogram measured using CuKα radiation having a wavelength of 1.54060 Å.

In DSC analyses, the crystalline form A according to the present invention preferably exhibits an endothermal event with a peak temperature above 295° C., or above 296° C., or above 297° C., or above 298° C., or above 299° C. or above 300° C.; preferably at about 295-310° C. (i.e., the crystalline form has a melting endotherm at about 295-310° C.) or at about 300-310° C., such as for example at about 298-308° C., or at about 300-306° C., or at about 301-307° C., or at about 302-308° C., or at about 303-309° C., or at about 302-305° C. In some preferred embodiments, the crystalline form exhibits an endothermal event with a peak temperature at about 303-304° C., or at about 304-305° C., or at about 305-306° C.

The crystalline form A according to the present invention may further be characterized in that it has at least a Raman peak at about 1569±2 cm$^{-1}$ and/or at least a Raman peak at about 1002±2 cm$^{-1}$. In this regard, it should be understood that all Raman peaks recited herein should be understood to additionally include values that are approximate (or about) of the recited value. For example, when it is disclosed herein that the crystalline form has a Raman peak at 1569±2 cm$^{-1}$, it should be understood that the crystalline forms has a Raman peak at about 1569±2 cm$^{-1}$.

The crystalline form A according to the present invention may further be characterized in that it has a Raman peak at about 1569±2 cm$^{-1}$ and/or a Raman peak at about 1002±2 cm$^{-1}$; and/or one or more Raman peaks selected from the group consisting of about 921±2 cm$^{-1}$, about 1308±2 cm$^{-1}$, about 1583±2 cm$^{-1}$, and about 3057±2 cm$^{-1}$; and/or one or more Raman peaks selected from the group consisting of about 152±2 cm$^{-1}$, about 170±2 cm$^{-1}$, about 184±2 cm$^{-1}$, about 202±2 cm$^{-1}$, about 254±2 cm$^{-1}$, about 488±2 cm$^{-1}$, about 679±2 cm$^{-1}$, about 828±2 cm$^{-1}$, about 911±2 cm$^{-1}$, about 981±2 cm$^{-1}$, about 1031±2 cm$^{-1}$, about 1289±2 cm$^{-1}$, about 1453±2 cm$^{-1}$, about 1475±2 cm$^{-1}$, about 2921±2 cm$^{-1}$, about 2947±2 cm$^{-1}$, about 2960±2 cm$^{-1}$, and about 3066±2 cm$^{-1}$.

The crystalline form A according to the present invention may further be characterized in that it has one or more Raman peaks selected from the group consisting of about 365±2 cm$^{-1}$, about 420±2 cm$^{-1}$, about 519±2 cm$^{-1}$, about 544±2 cm$^{-1}$, about 609±2 cm$^{-1}$, about 620±2 cm$^{-1}$, about 636±2 cm$^{-1}$, about 694±2 cm$^{-1}$, about 714±2 cm$^{-1}$, about 785±2 cm$^{-1}$, about 8, about 872±2 cm$^{-1}$, about 943±2 cm$^{-1}$, about 1049±2 cm$^{-1}$, about 1067±2 cm$^{-1}$, about 1111±2 cm$^{-1}$, about 1128±2 cm$^{-1}$, about 1156±2 cm$^{-1}$, about 1188±2 cm$^{-1}$, about 1200±2 cm$^{-1}$, about 1235±2 cm$^{-1}$, about 1265±2 cm$^{-1}$, about 1337±2 cm$^{-1}$, about 1370±2 cm$^{-1}$, about 1405±2 cm$^{-1}$, about 1420±2 cm$^{-1}$, about 1628±2 cm$^{-1}$, about 2793±2 cm$^{-1}$, about 2851±2 cm$^{-1}$, and about 2871±2 cm$^{-1}$.

Another aspect of the present invention relates to a process for the production of the crystalline form A described above.

In one preferred embodiment, the process comprises the step of (a-1) suspending (1r,4r)-6'-fluoro-N,N-dimethyl-4-phenyl-4',9'-dihydro-3'H-spiro[cyclo-hexane-1,1'-pyrano[3,4, b]indol]-4-amine in a solvent.

Preferably, the solvent is selected from the group consisting of the C4 to C6 alcohols such as n-butanol; esters such as ethyl acetate, n-propyl acetate, iso-propyl acetate, n-butyl acetate, and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and mixtures thereof.

Preferably, the solvent does neither contain water nor any solvent selected from the group consisting of methanol, ethanol, n-propanol, iso-propanol, dimethyl formamide and dimethyl sulfoxide.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-1) separating, preferably filtering off the solid obtained in step (a-1).

Preferably, the process according to the invention further comprises the step
(c-1) drying of the solid obtained in step (b-1).

Preferably, in the process according to the invention, step (c-1) takes place under air. However, drying under vacuum, more preferably at a vacuum of 0 to 900 mbar, even more preferably at a vacuum of 1 to 500 mbar, and in particular at a vacuum of 10 to 200 mbar is also possible.

Preferably, in the process according to the invention, step (c-1) takes place in a temperature range from 0 to 60° C., preferably from 10° C. to 50° C. more preferably from 20 to 40° C.

Another aspect of the present invention relates to a process for the production of the crystalline form A described above comprising the step of
(a-2) dissolving (1r,4r)-6'-fluoro-N,N-dimethyl-4-phenyl-4', 9'-dihydro-3'H-spiro[cyclohexane-1,1'-pyrano[3,4, b]indol]-4-amine in a solvent.

Preferably, the solvent is selected from the group consisting of the C4 to C6 alcohols such as n-butanol; esters such as ethyl acetate, n-propyl acetate, iso-propyl acetate, n-butyl acetate, and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and mixtures thereof.

Mixtures of saturated hydrocarbons, such as n-pentane, n-hexane and n-heptane, further containing at least one solvent selected from the group consisting of ketones, ethers and chlorinated hydrocarbons may also be used. For instance, n-heptane/butanone, n-heptane/dichloromethane, n-heptane/acetone, n-heptane/tetrahydrofuran, n-hexane/butanone, n-hexane/dichloromethane n-hexane/acetone and n-hexane/tetrahydro-furan mixtures are also preferred.

Preferably, the solvent does neither contain water nor any solvent selected from the group consisting of methanol, ethanol, n-propanol, iso-propanol, dimethyl formamide and dimethyl sulfoxide.

Preferably, in the process according to the invention, step (a-2) is carried out at a temperature not higher than 80° C., more preferably not higher than 60° C., even more preferably not higher than 40° C., and in particular in a temperature range of 20-40° C.

In a preferred embodiment, the process according to the invention further comprises the step
(b-2) evaporating off the solvent of the solution obtained in step (a-2).

Suitable methods for evaporating the solvent are known to a person skilled in the art. Preferably, in the process according to the invention, the solvent is evaporated in air, air flow, or inert gas flow, in particular argon or nitrogen flow. However, evaporating off the solvent under vacuum, for example by means of a rotary evaporator, is also possible.

Preferably, in the process according to the invention, the solvent is evaporated at room temperature. However, evaporating off the solvent at an elevated temperature, e.g. within the range of 20° C. to 60° C., is also possible.

In another preferred embodiment, the process according to the invention further comprises the step
(b-2') precipitating (1r,4r)-6'-fluoro-N,N-dimethyl-4-phenyl-4',9'-dihydro-3'H-spiro[cyclo-hexane-1,1'-pyrano[3,4, b]indol]-4-amine from the solution obtained in step (a-2).

Suitable methods of precipitation are known to a person skilled in the art. Preferably, in the process according to the invention, step (b-2') may be carried out by reducing the volume of the solution obtained according to step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

Preferably, in the process according to the invention, after the precipitation in step (b-2'), all other steps are carried out at a temperature between 40 and 0° C., preferably between 35 and 5° C., more preferably between 25 and 15° C.

By means of the aforementioned processes any form of (1r,4r)-6'-fluoro-N,N-dimethyl-4-phenyl-4',9'-dihydro-3'H-spiro[cyclohexane-1,1'-pyrano[3,4, b]indol]-4-amine, including the crystalline forms B, C, D, E, F, G, H, I and L according to the invention, may be converted into the crystalline form A according to the invention.

A further aspect of the present invention relates to a crystalline form A that is obtainable by the process as described above.

Crystal crystalline form A is thermodynamically stable up to 60% relative humidity at room temperature. It can be obtained by suspending any other form of (1r,4r)-6'-fluoro-N,N-dimethyl-4-phenyl-4',9'-dihydro-3'H-spiro[cyclohexane-1,1'-pyrano[3,4, b]indol]-4-amine at room temperature in many organic solvents, e.g. ethers such as tert-butyl methyl ether, ketones such as acetone, esters such as ethyl acetate, 1 BuOH or toluene.

The thermodynamic stability is important. By using the most stable modification in a medicament it may specifically be ensured that, during storage, no crystalline conversion or polymorphic conversion of the active ingredient in the pharmaceutical formulation takes place. This is advantageous, because otherwise the properties of the medicament could change as a consequence of a conversion of a less stable modification into a more stable modification. In relation to the pharmacological properties of an administration form, this could lead for example to the solubility of the active ingredient changing, accompanied by a change in the release characteristics and thus also a change in the bioavailability. Lastly, this could result in inadequate storage stability of the medicament.

A further aspect of the present invention relates to a crystalline form B. Preferably, the crystalline form B according to the invention has one or more X-ray diffraction peaks selected from the group consisting of about 8.9±0.2 (2Θ), about 9.8±0.2 (2Θ), about 15.7±0.2 (2Θ), about 16.7±0.2 (2Θ), about 17.8±0.2 (2Θ), about 18.4±0.2 (2Θ), about 19.2±0.2 (2Θ), about 19.7±0.2 (2Θ), about 20.4±0.2 (2Θ), about 21.8±0.2 (2Θ), about 24.1±0.2 (2Θ), about 25.1±0.2 (2Θ), about 26.0±0.2 (2Θ) and about 31.1±0.2 (2Θ). In some preferred embodiments, the crystalline form comprises an X-ray diffraction peak at about 17.8±0.2 (2Θ). In some preferred embodiments, the crystalline form comprises X-ray diffraction peaks at about 9.8±0.2 (2Θ) and about 17.8±0.2 (2Θ).

In some preferred embodiments, crystalline form B comprises X-ray diffraction peaks at about 9.8±0.2 (2Θ), about 16.7±0.2 (2Θ), about 17.8±0.2 (2Θ), about 24.1±0.2 (2Θ) and optionally 19.2±0.2 (2Θ).

The crystalline form B according to the invention may additionally have at least one X-ray diffraction peak selected from the group consisting of about 20.0±0.2 (2Θ), about 25.4±0.2 (2Θ), about 27.1±0.2 (2Θ), about 28.1±0.2 (2Θ) and about 29.2±0.2 (2Θ).

Further, the crystalline form B according to the invention may be characterized in that as well as one or more X-ray diffraction peaks selected from the group consisting of about 8.9±0.2 (2Θ), about 9.8±0.2 (2Θ), about 15.7±0.2 (2Θ), about 16.7±0.2 (2Θ), about 17.8±0.2 (2Θ), about 18.4±0.2 (2Θ), about 19.2±0.2 (2Θ), about 19.7±0.2 (2Θ), about 20.4±0.2 (2Θ), about 21.8±0.2 (2Θ), about 24.1±0.2 (2Θ), about 25.1±0.2 (2Θ), about 26.0±0.2 (2Θ) and about 31.1±0.2 (2Θ), and optionally one or more X-ray diffraction peaks selected from the group consisting of about 20.0±0.2 (2Θ), about 25.4±0.2 (2Θ), about 27.1±0.2 (2Θ), about 28.1±0.2 (2Θ) and about 29.2±0.2 (2Θ), it additionally has at least one X-ray diffraction peak selected from the group consisting of about 12.0±0.2 (2Θ), about 16.2±0.2 (2Θ), about 21.4±0.2 (2Θ), about 22.6±0.2 (2Θ), about 26.7±0.2 (2Θ), about 27.9±0.2 (2Θ), about 29.7±0.2 (2Θ), about 30.3±0.2 (2Θ), about 32.7±0.2 (2Θ), about 32.9±0.2 (2Θ), about 33.5±0.2 (2Θ) and about 34.9±0.2 (2Θ).

The crystalline form B according to the invention may further be characterized in that as well as one or more X-ray diffraction peaks selected from the group consisting of about 8.9±0.2 (2Θ), about 9.8±0.2 (2Θ), about 15.7±0.2 (2Θ), about 16.7±0.2 (2Θ), about 17.8±0.2 (2Θ), about 18.4±0.2 (2Θ), about 19.2±0.2 (2Θ), about 19.7±0.2 (2Θ), about 20.4±0.2 (2Θ), about 21.8±0.2 (2Θ), about 24.1±0.2 (2Θ), about 25.1±0.2 (2Θ), about 26.0±0.2 (2Θ) and about 31.1±0.2 (2Θ), and optionally one or more X-ray diffraction peaks selected from the group consisting of about 20.0±0.2 (2Θ), about 25.4±0.2 (2Θ), about 27.1±0.2 (2Θ), about 28.1±0.2 (2Θ) and about 29.2±0.2 (2Θ), and optionally one or more X-ray diffraction peaks selected from the group consisting of about 12.0±0.2 (2Θ), about 21.4±0.2 (2Θ), about 22.6±0.2 (2Θ), about 26.7±0.2 (2Θ), about 29.7±0.2 (2Θ), about 30.3±0.2 (2Θ), about 32.7±0.2 (2Θ), about 32.9±0.2 (2Θ), about 33.5±0.2 (2Θ) and about 34.9±0.2 (2Θ), it additionally has at least one X-ray diffraction peak selected from the group consisting of about 10.5±0.2 (2Θ), about 14.2±0.2 (2Θ), about 14.6±0.2 (2Θ), about 16.2±0.2 (2Θ), about 23.5±0.2 (2Θ), about 27.9±0.2 (2Θ), about 31.8±0.2 (2Θ), and about 33.9±0.2 (2Θ).

All 2Θ values indicated above refer to a X-ray diffractogram measured using CuKα radiation having a wavelength of 1.54060 Å.

In DSC analyses, the crystalline form B according to the present invention preferably exhibits an endothermal event with a peak temperature at about 108-118° C., more preferably at about 109-117° C., still more preferably at about 110-116° C., yet more preferably at about 111-115° C. and in particular at about 111-114° C.

In DSC analyses, the crystalline form B according to the present invention preferably exhibits an endothermal event with a peak temperature at about 184-194° C., more preferably at about 185-193° C., still more preferably at about 186-192° C., yet more preferably at about 187-191° C. and in particular at about 187-190° C.

In DSC analyses, the crystalline form B according to the present invention may further exhibit an exothermal event with a peak temperature at about 202-204° C., more preferably at about 203-213° C., still more preferably at about 204-212° C., yet more preferably at about 205-211° C. and in particular at about 206-210° C.

The crystalline form B according to the present invention may further exhibit an endothermal event with a peak temperature at about 290-300° C., more preferably at about 291-299° C., still more preferably at about 292-298° C., yet more preferably at about 293-297° C., and in particular at about 294-297° C.

The crystalline form B according to the present invention may further be characterized in that it has at least a Raman peak at about 1003±2 $cm^{-1}$ and/or at least a Raman peak at about 1571±2 $cm^{-1}$ and/or at least a Raman peak at about 1581±2 $cm^{-1}$.

The crystalline form B according to the present invention may further be characterized in that it has a Raman peak at about 1003±2 $cm^{-1}$ and/or at least a Raman peak at about 1571±2 $cm^{-1}$ and/or at least a Raman peak at about 1581±2 $cm^{-1}$; and/or one or more Raman peaks selected from the group consisting of about 154±2 $cm^{-1}$, about 173±2 $cm^{-1}$, about 923±2 $cm^{-1}$, about 1299±2 $cm^{-1}$, about 1476±2 $cm^{-1}$, about 3064±2 $cm^{-1}$ and about 3072±2 $cm^{-1}$; and/or one or more Raman peaks selected from the group consisting of about 217±2 $cm^{-1}$, about 259±2 $cm^{-1}$, about 370±2 $cm^{-1}$, about 492±2 $cm^{-1}$, about 683±2 $cm^{-1}$, about 825±2 $cm^{-1}$, about 1028±2 $cm^{-1}$, about 1204±2 $cm^{-1}$, about 1268±2 $cm^{-1}$, about 1374±2 $cm^{-1}$, about 1433±2 $cm^{-1}$, about 1460±2 $cm^{-1}$, about 2911±2 $cm^{-1}$, about 2950±2 $cm^{-1}$, about 2965±2 $cm^{-1}$ and about 2984±2 $cm^{-1}$.

The crystalline form B according to the present invention may further be characterized in that it has one or more Raman peaks selected from the group consisting of about 301±2 $cm^{-1}$, about 318±2 $cm^{-1}$, about 395±2 $cm^{-1}$, about 437±2 $cm^{-1}$, about 518±2 $cm^{-1}$, about 545±2 $cm^{-1}$, about 560±2 $cm^{-1}$, about 607±2 $cm^{-1}$, about 621±2 $cm^{-1}$, about 633±2 $cm^{-1}$, about 716±2 $cm^{-1}$, about 764±2 $cm^{-1}$, about 785±2 $cm^{-1}$, about 865±2 $cm^{-1}$, about 947±2 $cm^{-1}$, about 983±2 $cm^{-1}$, about 1039±2 $cm^{-1}$, about 1053±2 $cm^{-1}$, about 1074±2 $cm^{-1}$, about 1110±2 $cm^{-1}$, about 1119±2 $cm^{-1}$, about 1141±2 $cm^{-1}$, about 1163±2 $cm^{-1}$, about 1174±2 $cm^{-1}$, about 1191±2 $cm^{-1}$, about 1233±2 $cm^{-1}$, about 1341±2 $cm^{-1}$, about 1356±2 $cm^{-1}$, about 1630±2 $cm^{-1}$, about 2794±2 $cm^{-1}$, about 2846±2 $cm^{-1}$ and about 2879±2 $cm^{-1}$.

Another aspect of the present invention relates to a process for the production of the crystalline form B described above comprising the step of
(a-1) suspending (1r,4r)-6'-fluoro-N,N-dimethyl-4-phenyl-4',9'-dihydro-3'H-spiro[cyclo-hexane-1,1'-pyrano[3,4,b]indol]-4-amine in a solvent.

In the process for the production of the crystalline form B according to the invention, the solvent preferably comprises water.

In one preferred embodiment, the solvent is water. In another preferred embodiment, the solvent comprises water and further at least one organic solvent, preferably selected from the group consisting of the C4 to C6 alcohols such as n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; THF/water mixtures are particularly preferred.

Preferably, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-1) separating, preferably filtering off the solid obtained in step (a-1).

Preferably, the process according to the invention further comprises the step
(c-1) drying of the solid obtained in step (b-1).

Preferably, in the process according to the invention, step (c-1) takes place under air or inert gas flow, such as argon or nitrogen flow. Preferably, step (c-1) is performed at ambient temperature.

Another aspect of the present invention relates to a process for the production of the crystalline form B described above comprising the step of
(a-2) dissolving (1r,4r)-6'-fluoro-N,N-dimethyl-4-phenyl-4',9'-dihydro-3'H-spiro[cyclohexane-1,1'-pyrano[3,4, b]indol]-4-amine in an organic solvent.

In some preferred embodiments, the organic solvent is selected from the group consisting of tetrahydrofuran, 1,4-dioxane and dimethyl sulfoxide.

Preferably, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, the process according to the invention further comprises the step
(b-2') precipitating (1r,4r)-6'-fluoro-N,N-dimethyl-4-phenyl-4',9'-dihydro-3'H-spiro[cyclo-hexane-1,1'-pyrano[3,4, b]indol]-4-amine from the solution obtained in step (a-2) by the addition of water.

The amount of the water can preferably be selected in such a manner that upon its addition precipitation of the dissolved component begins. Preferably, the precipitation begins at most 5 minutes after the water has been added, in particular immediately upon the addition of water.

Preferably, in the process according to the invention, after precipitation step (b-2') all other steps are carried out at a temperature between 40 and 0° C., preferably between 35 and 5° C., more preferably between 25 and 15° C.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow.

A further aspect of the present invention relates to a crystalline form B that is obtainable by the process as described above.

Crystal crystalline form B is thermodynamically stable at ≥40% relative humidity at room temperature. It may be obtained by suspending other forms of (1r,4r)-6'-fluoro-N,N-dimethyl-4-phenyl-4',9'-dihydro-3'H-spiro[cyclohexane-1,1'-pyrano[3,4, b]indol]-4-amine in water.

A further aspect of the present invention relates to a crystalline form C. Preferably, the crystalline form C according to the invention has one or more X-ray diffraction peaks selected from the group consisting of about 9.1±0.2 (2Θ), about 9.5±0.2 (2Θ), about 16.8±0.2 (2Θ), about 18.2±0.2 (2Θ), about 18.6±0.2 (2Θ), about 19.0±0.2 (2Θ), about 19.3±0.2 (2Θ), about 19.5±0.2 (2Θ), about 22.2±0.2 (2Θ), about 25.4±0.2 (2Θ), and about 27.5±0.2 (2Θ). In some preferred embodiments, the crystalline form comprises an X-ray diffraction peak at about 18.2±0.2 (2Θ).

In some preferred embodiments, crystalline form C comprises X-ray diffraction peaks at about 9.1±0.2 (2Θ), about 9.5±0.2 (2Θ), about 16.8±0.2 (2Θ), about 18.2±0.2 (2Θ) and optionally 19.3±0.2 (2Θ).

The crystalline form C according to the invention may additionally have at least one X-ray diffraction peak selected from the group consisting of about 14.3±0.2 (2Θ), about 17.5±0.2 (2Θ), about 20.7±0.2 (2Θ), about 21.7±0.2 (2Θ), about 23.6±0.2 (2Θ), about 24.2±0.2 (2Θ), about 24.9±0.2 (2Θ), about 25.8±0.2 (2Θ) and about 30.3±0.2 (2Θ).

Furthermore, the crystalline form C according to the invention may be characterized in that as well as one or more X-ray diffraction peaks selected from the group consisting of about 9.1±0.2 (2Θ), about 9.5±0.2 (2Θ), about 16.8±0.2 (2Θ), about 18.2±0.2 (2Θ), about 18.6±0.2 (2Θ), about 19.0±0.2 (2Θ), about 19.3±0.2 (2Θ), about 19.5±0.2 (2Θ), about 22.2±0.2 (2Θ), about 25.4±0.2 (2Θ), and about 27.5±0.2 (2Θ), and optionally one or more X-ray diffraction peaks selected from the group consisting of about 14.3±0.2 (2Θ), about 17.5±0.2 (2Θ), about 20.7±0.2 (2Θ), about 21.7±0.2 (2Θ), about 23.6±0.2 (2Θ), about 24.2±0.2 (2Θ), about 24.9±0.2 (2Θ), about 25.8±0.2 (2Θ) and about 30.3±0.2 (2Θ), it additionally has at least one X-ray diffraction peak selected from the group consisting of about 14.8±0.2 (2Θ), about 22.5±0.2 (2Θ), about 26.2±0.2 (2Θ), about 26.5±0.2 (2Θ), about 28.1±0.2 (2Θ), about 28.7±0.2 (2Θ), about 29.4±0.2 (2Θ), about 32.3±0.2 (2Θ) and about 33.6±0.2 (2Θ).

The crystalline form C according to the invention may further be characterized in that as well as one or more X-ray diffraction peaks selected from the group consisting of about 9.1±0.2 (2Θ), about 9.5±0.2 (2Θ), about 16.8±0.2 (2Θ), about 18.2±0.2 (2Θ), about 18.6±0.2 (2Θ), about 19.0±0.2 (2Θ), about 19.3±0.2 (2Θ), about 19.5±0.2 (2Θ), about 22.2±0.2 (2Θ), about 25.4±0.2 (2Θ), and about 27.5±0.2 (2Θ), and optionally one or more X-ray diffraction peaks selected from the group consisting of about 14.3±0.2 (2Θ), about 17.5±0.2 (2Θ), about 20.7±0.2 (2Θ), about 21.7±0.2 (2Θ), about 23.6±0.2 (2Θ), about 24.2±0.2 (2Θ), about 24.9±0.2 (2Θ), about 25.8±0.2 (2Θ) and about 30.3±0.2 (2Θ), and optionally one or more X-ray diffraction peaks selected from the group consisting of about 14.8±0.2 (2Θ), about 22.5±0.2 (2Θ), about 26.2±0.2 (2Θ), about 26.5±0.2 (2Θ), about 28.1±0.2 (2Θ), about 28.7±0.2 (2Θ), about 29.4±0.2 (2Θ), about 32.3±0.2 (2Θ) and about 33.6±0.2 (2Θ), it additionally has at least one X-ray diffraction peak selected from the group consisting of about 7.8±0.2 (2Θ), about 10.4±0.2 (2Θ), about 11.1±0.2 (2Θ), about 12.2±0.2 (2Θ), about 13.5±0.2 (2Θ), about 15.3±0.2 (2Θ), about 16.1±0.2 (2Θ) and about 34.5±0.2 (2Θ).

All 2Θ values indicated above refer to a X-ray diffractogram measured using CuKα radiation having a wavelength of 1.54060 Å.

In DSC analyses, the crystalline form C according to the present invention preferably exhibits an endothermal event with a peak temperature at about 130-140° C., more preferably at about 131-139° C., still more preferably at about 132-138° C., yet more preferably at about 133-137° C. and in particular at about 133-136° C.

In DSC analyses, the crystalline form C according to the present invention may further exhibit an endothermal event with a peak temperature at about 110-120° C., more preferably at about 111-119° C., still more preferably at about 112-118° C., yet more preferably at about 113-117° C. and in particular at about 113-116° C.

The crystalline form C according to the present invention may further exhibit an endothermal event with a peak temperature at about 243-253° C., more preferably at about 244-252° C., still more preferably at about 245-251° C., yet more preferably at about 246-250° C. and in particular at about 246-249° C.

The crystalline form C according to the present invention may further exhibit an endothermal event with a peak temperature at about 292-302° C., more preferably at about 293-301° C., still more preferably at about 294-300° C., and in particular at about 295-299° C.

The crystalline form C according to the present invention may further be characterized in that it has at least a Raman peak at about 1003±2 cm$^{-1}$ and/or at least a Raman peak at about 1570±2 cm$^{-1}$ and/or at least a Raman peak at about 1587±2 cm$^{-1}$.

The crystalline form C according to the present invention may further be characterized in that it has a Raman peak at about 1003±2 cm$^{-1}$ and/or at least a Raman peak at about 1570±2 cm$^{-1}$ and/or at least a Raman peak at about 1587±2 cm$^{-1}$; and/or one or more Raman peaks selected from the group consisting of about 156±2 cm$^{-1}$, about 171±2 cm$^{-1}$, about 183±2 cm$^{-1}$, about 922±2 cm$^{-1}$, about 1299±2 cm$^{-1}$, about 1478±2 cm$^{-1}$, about 2932±2 cm$^{-1}$, about 2951±2 cm$^{-1}$ and about 3070±2 cm$^{-1}$; and/or one or more Raman peaks selected from the group consisting of about 210±2 cm$^{-1}$, about 253±2 cm$^{-1}$, about 491±2 cm$^{-1}$, about 682±2 cm$^{-1}$, about 829±2 cm$^{-1}$, about 913±2 cm$^{-1}$, about 1028±2 cm$^{-1}$, about 1203±2 cm$^{-1}$, about 1373±2 cm$^{-1}$, about 1435±2 cm$^{-1}$, about 1462±2 cm$^{-1}$, about 2845±2 cm$^{-1}$, about 2856±2 cm$^{-1}$, about 2890±2 cm$^{-1}$, about 2977±2 cm$^{-1}$ and about 2990±2 cm$^{-1}$.

The crystalline form C according to the present invention may further be characterized in that it has one or more Raman peaks selected from the group consisting of about 371±2 cm$^{-1}$, about 394±2 cm$^{-1}$, about 432±2 cm$^{-1}$, about 520±2 cm$^{-1}$, about 542±2 cm$^{-1}$, about 560±2 cm$^{-1}$, about 608±2 cm$^{-1}$, about 621±2 cm$^{-1}$, about 633±2 cm$^{-1}$, about 712±2 cm$^{-1}$, about 786±2 cm$^{-1}$, about 885±2 cm$^{-1}$, about 948±2 cm$^{-1}$, about 983±2 cm$^{-1}$, about 1051±2 cm$^{-1}$, about 1077±2 cm$^{-1}$, about 1111±2 cm$^{-1}$, about 1119±2 cm$^{-1}$, about 1157±2 cm$^{-1}$, about 1189±2 cm$^{-1}$, 1231±2 cm$^{-1}$, about 1265±2 cm$^{-1}$, about 1339±2 cm$^{-1}$, about 1630±2 cm$^{-1}$ and about 2794±2 cm$^{-1}$.

Another aspect of the present invention relates to a process for the production of the crystalline form C described above comprising the step of (a-1) suspending (1r,4r)-6'-fluoro-N,N-dimethyl-4-phenyl-4',9'-dihydro-3'H-spiro[cyclo-hexane-1,1'-pyrano[3,4,b]indol]-4-amine in a solvent comprising ethanol.

Preferably, the solvent is ethanol.

Preferably, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-1) separating, preferably filtering out, the solid obtained in step (a-1).

Preferably, the process according to the invention further comprises the step (c-1) drying of the solid obtained in step (b-1).

Preferably, in the process according to the invention, step (c-1) takes place under air or inert gas flow, such as argon or nitrogen flow. Preferably, step (c-1) is performed at ambient temperature.

Another aspect of the present invention relates to a process for the production of the crystalline form C described above comprising the step of (a-2) dissolving (1r,4r)-6'-fluoro-N,N-dimethyl-4-phenyl-4',9'-dihydro-3'H-spiro[cyclohexane-1,1'-pyrano[3,4, b]indol]-4-amine in an organic solvent.

In some preferred embodiments, the organic solvent is selected from the group consisting of acetone, 2-butanone, dichloromethane, tetrahydrofuran, 1,4-dioxane and dimethyl sulfoxide.

Preferably, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably the process according to the invention further comprises the step (b-2') precipitating (1r,4r)-6'-fluoro-N,N-dimethyl-4-phenyl-4',9'-dihydro-3'H-spiro[cyclo-hexane-1,1'-pyrano[3,4, b]indol]-4-amine from the solution obtained in step (a-2) by the addition of ethanol.

The amount of the ethanol can preferably be selected in such a manner that upon its addition precipitation of the dissolved component begins. Preferably, the precipitation starts at most 90 minutes, more preferably at most 75 minutes, most preferably at most 60 minutes, after the ethanol has been added.

Preferably, in the process according to the invention, after step (b-2'), all other steps are carried out at a temperature between 40 and 0° C., preferably between 35 and 5° C., more preferably between 25 and 15° C.

Preferably, the process further comprises the step (c-2') separating, preferably filtering off the precipitate obtained in step (b-2').

Preferably, the process according to the invention further comprises the step (d-2') drying of the solid obtained in step (c-2'). Preferably, in the process according to the invention, step (d-2') takes place under air or inert gas flow, such as argon or nitrogen flow.

A further aspect of the present invention relates to a crystalline form C that is obtainable by the process as described above.

A further aspect of the present invention relates to a crystalline form D. Preferably, the crystalline form D according to the invention has one or more X-ray diffraction peaks selected from the group consisting of about 8.4±0.2 (2Θ), about 8.8±0.2 (2Θ), about 15.0±0.2 (2Θ), about 15.2±0.2 (2Θ), about 17.0±0.2 (2Θ), about 17.6±0.2 (2Θ), about 18.9±0.2 (2Θ), about 21.2±0.2 (2Θ), about 22.4±0.2 (2Θ), about 23.2±0.2 (2Θ), about 26.0±0.2 (2Θ), about 29.5±0.2 (2Θ), and about 30.7±0.2 (2Θ). In some preferred embodiments, the crystalline form comprises an X-ray diffraction peak at about 17.6±0.2 (2Θ).

In some preferred embodiments, crystalline form D comprises X-ray diffraction peaks at about 8.4±0.2 (2Θ), about 8.8±0.2 (2Θ), about 17.6±0.2 (2Θ), about 22.5±0.2 (2Θ) and optionally 15.0±0.2 (2Θ) and/or 15.2±0.2 (2Θ).

The crystalline form D according to the invention may additionally have at least one X-ray diffraction peak selected from the group consisting of about 18.1±0.2 (2Θ), about 20.9±0.2 (2Θ), about 21.6±0.2 (2Θ), about 22.8±0.2 (2Θ), about 24.9±0.2 (2Θ), about 25.7±0.2 (2Θ) and about 30.3±0.2 (2Θ).

Furthermore, the crystalline form D according to the invention may be characterized in that as well as one or more X-ray diffraction peaks selected from the group consisting of about 8.4±0.2 (2Θ), about 8.8±0.2 (2Θ), about 15.0±0.2 (2Θ), about 15.2±0.2 (2Θ), about 17.0±0.2 (2Θ), about 17.6±0.2 (2Θ), about 18.9±0.2 (2Θ), about 21.2±0.2 (2Θ), about 22.4±0.2 (2Θ), about 23.2±0.2 (2Θ), about 26.0±0.2 (2Θ), about 29.5±0.2 (2Θ) and about 30.7±0.2 (2Θ), and optionally one or more X-ray diffraction peaks selected from the group consisting of about 18.1±0.2 (2Θ), about 20.9±0.2 (2Θ), about 21.6±0.2 (2Θ), about 22.8±0.2 (2Θ), about 24.9±0.2 (2Θ), about 25.7±0.2 (2Θ) and about 30.3±0.2 (2Θ), it additionally has at least one X-ray diffraction peak selected from the group consisting of about 19.4±0.2 (2Θ), about 19.8±0.2 (2Θ), about 25.2±0.2 (2Θ), about 26.6±0.2 (2Θ), about 27.5±0.2 (2Θ), about 28.0±0.2 (2Θ), about 28.5±0.2 (2Θ), about 31.3±0.2 (2Θ), about 31.9±0.2 (2Θ), about 32.2±0.2 (2Θ), about 32.8±0.2 (2Θ), about 34.0±0.2 (2Θ) and about 34.9±0.2 (2Θ).

The crystalline form D according to the invention may further be characterized in that as well as one or more X-ray diffraction peaks selected from the group consisting of about 8.43±0.2 (2Θ), about 8.77±0.2 (2Θ), about 15.0±0.2 (2Θ), about 15.2±0.2 (2Θ), about 17.0±0.2 (2Θ), about 17.6±0.2 (2Θ), about 18.9±0.2 (2Θ), about 21.2±0.2 (2Θ), about 22.4±0.2 (2Θ), about 23.2±0.2 (2Θ), about 26.0±0.2 (2Θ), about 29.5±0.2 (2Θ) and about 30.7±0.2 (2Θ), and optionally one or more X-ray diffraction peaks selected from the group consisting of about 18.1±0.2 (2Θ), about 20.9±0.2 (2Θ), about 21.6±0.2 (2Θ), about 22.8±0.2 (2Θ), about 24.9±0.2 (2Θ), about 25.7±0.2 (2Θ) and about 30.3±0.2 (2Θ), and optionally one or more X-ray diffraction peaks selected from the group consisting of about 19.4±0.2 (2Θ), about 19.8±0.2 (2Θ), about 25.2±0.2 (2Θ), about 26.6±0.2 (2Θ), about 27.5±0.2 (2Θ), about 28.0±0.2 (2Θ), about 28.5±0.2 (2Θ), about 31.3±0.2 (2Θ), about 31.9±0.2 (2Θ), about 32.2±0.2 (2Θ), about 32.8±0.2 (2Θ), about 34.0±0.2 (2Θ) and about 34.9±0.2 (2Θ), it additionally has at least one X-ray diffraction peak selected from the group consisting of about 11.19±0.2 (2Θ), about 12.05±0.2 (2Θ), about 13.65±0.2 (2Θ), about 16.13±0.2 (2Θ) and about 33.55±0.2 (2Θ).

All 2Θ values indicated above refer to a X-ray diffractogram measured using CuKα radiation having a wavelength of 1.54060 Å.

In DSC analyses, the crystalline form D according to the present invention preferably exhibits an endothermal event with a peak temperature at about 107-117° C., more preferably at about 108-116° C., still more preferably at about 109-115° C., yet more preferably at about 110-114° C. and in particular at about 110-113° C.

Preferably, in DSC analyses, the crystalline form D according to the present invention further exhibits an endothermal event with a peak temperature at about 118-128° C., more preferably at about 119-127° C., still more preferably at about 120-126° C., yet more preferably at about 121-125° C. and in particular at about 122-125° C.

The crystalline form D according to the present invention may further be characterized in that it has one or more Raman peaks selected from the group consisting of about 169±2 $cm^{-1}$, about 922 $cm^{-1}$, about 1002±2 $cm^{-1}$, about 1570±2 $cm^{-1}$, about 2957±2 $cm^{-1}$ and about 3067±2 $cm^{-1}$.

The crystalline form D according to the present invention may further be characterized in that it has one or more Raman peaks selected from the group consisting of about 169±2 $cm^{-1}$, about 922 $cm^{-1}$, about 1002±2 $cm^{-1}$, about 1570±2 $cm^{-1}$ and about 2957±2 $cm^{-1}$ and about 3067±2 $cm^{-1}$; and/or one or more Raman peaks selected from the group consisting of about 254±2 $cm^{-1}$, about 367±2 $cm^{-1}$, about 491±2 $cm^{-1}$, about 683±2 $cm^{-1}$, about 1302±2 $cm^{-1}$, about 1437±2 $cm^{-1}$, about 1479±2 $cm^{-1}$ and about 2935±2 $cm^{-1}$; and/or one or more Raman peaks selected from the group consisting of about 633±2 $cm^{-1}$, about 786±2 $cm^{-1}$, about 821±2 $cm^{-1}$, about 1028±2 $cm^{-1}$, about 1117±2 $cm^{-1}$, about 1158±2 $cm^{-1}$, about 1202±2 $cm^{-1}$, about 1264±2 $cm^{-1}$, and about 1377±2 $cm^{-1}$.

Another aspect of the present invention relates to a process for the production of the crystalline form D described above comprising the step of (a-1) suspending (1r,4r)-6'-fluoro-N,N-dimethyl-4-phenyl-4',9'-dihydro-3'H-spiro[cyclo-hexane-1,1'-pyrano[3,4,b]indol]-4-amine in a solvent comprising isopropanol.

Preferably, the solvent is isopropanol.

Preferably, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 4 h, more preferably at least 8 h, still more preferably at least 12 h, yet more preferably at least 16 h, most preferably at least 24 h, and in particular at least 2 days.

Preferably, the process according to the invention further comprises the step (b-1) separating, preferably filtering off the solid obtained in step (a-1).

Preferably, the process according to the invention further comprises the step (c-1) drying of the solid obtained in step (b-1).

Preferably, in the process according to the invention, step (c-1) takes place under air or inert gas flow, such as argon or nitrogen flow. Preferably, step (c-1) is performed at ambient temperature.

A further aspect of the present invention relates to a crystalline form D that is obtainable by the process as described above.

A further aspect of the present invention relates to a crystalline form E. Preferably, the crystalline form E according to the invention has one or more X-ray diffraction peaks selected from the group consisting of about 8.8±0.2 (2Θ), about 11.9±0.2 (2Θ), about 17.0±0.2 (2Θ), about 17.7±0.2 (2Θ) and about 18.7±0.2 (2Θ). In some preferred embodiments, the crystalline form comprises an X-ray diffraction peak at about 18.7±0.2 (2Θ).

In some preferred embodiments, crystalline form E comprises X-ray diffraction peaks at about 8.8±0.2 (2Θ), about 17.0±0.2 (2Θ), about 17.7±0.2 (2Θ), about 18.7±0.2 (2Θ) and optionally 11.9±0.2 (2Θ).

The crystalline form E according to the invention may additionally have at least one X-ray diffraction peak selected from the group consisting of about 22.6±0.2 (2Θ), about 23.3±0.2 (2Θ), about 25.7±0.2 (2Θ), about 26.1±0.2 (2Θ), about 26.9±0.2 (2Θ), about 27.6±0.2 (2Θ) and about 30.3±0.2 (2Θ).

Furthermore, the crystalline form E according to the invention may be characterized in that as well as one or more X-ray diffraction peaks selected from the group consisting of about 8.8±0.2 (2Θ), about 11.9±0.2 (2Θ), about 17.0±0.2 (2Θ), about 17.7±0.2 (2Θ) and about 18.7±0.2 (2Θ), and optionally one or more X-ray diffraction peaks selected from the group consisting of about 22.6±0.2 (2Θ), about 23.3±0.2 (2Θ), about 25.7±0.2 (2Θ), about 26.1±0.2 (2Θ), about 26.9±0.2 (2Θ), about 27.6±0.2 (2Θ) and about 30.3±0.2 (2Θ), it additionally has at least one X-ray diffraction peak selected from the group consisting of about 16.3±0.2 (2Θ), about 18.2±0.2 (2Θ), about 20.4±0.2 (2Θ), about 23.9±0.2 (2Θ), about 24.1±0.2 (2Θ), about 26.6±0.2 (2Θ), about 27.8±0.2 (2Θ), about 28.2±0.2 (2Θ), about 29.4±0.2 (2Θ), about 30.8±0.2 (2Θ), about 31.2±0.2 (2Θ) and about 33.0±0.2 (2Θ).

The crystalline form E according to the invention may further be characterized in that as well as one or more X-ray diffraction peaks selected from the group consisting of about 8.8±0.2 (2Θ), about 11.9±0.2 (2Θ), about 17.0±0.2 (2Θ), about 17.7±0.2 (2Θ), and about 18.7±0.2 (2Θ), and optionally one or more X-ray diffraction peaks selected from the group consisting of about 22.6±0.2 (2Θ), about 23.3±0.2 (2Θ), about 25.7±0.2 (2Θ), about 26.1±0.2 (2Θ), about 26.9±0.2 (2Θ), about 27.6±0.2 (2Θ) and about 30.3±0.2 (2Θ), and optionally one or more X-ray diffraction peaks selected from the group consisting of about 16.3±0.2 (2Θ), about 18.2±0.2 (2Θ), about 20.4±0.2 (2Θ), about 23.9±0.2 (2Θ), about 24.1±0.2 (2Θ), about 26.6±0.2 (2Θ), about 27.8±0.2 (2Θ), about 28.2±0.2 (2Θ), about 29.4±0.2 (2Θ), about 30.8±0.2 (2Θ), about 31.2±0.2 (2Θ) and about 33.0±0.2 (2Θ), it additionally has at least one X-ray diffraction peak selected from the group consisting of about 10.7±0.2 (2Θ), about 11.3±0.2 (2Θ), about 12.2±0.2 (2Θ), about 13.8±0.2 (2Θ), about 15.2±0.2 (2Θ), about 15.8±0.2 (2Θ), about 19.4±0.2 (2Θ), about 19.7±0.2 (2Θ), about 21.1±0.2 (2Θ), about 21.9±0.2 (2Θ), about 24.7±0.2 (2Θ), about 25.0±0.2 (2Θ), about 28.7±0.2 (2Θ), about 31.5±0.2 (2Θ) and about 34.4±0.2 (2Θ).

All 2Θ values indicated above refer to a X-ray diffractogram measured using CuKα radiation having a wavelength of 1.54060 Å.

The crystalline form E according to the present invention may further be characterized in that it has one or more Raman peaks selected from the group consisting of about 1003±2 cm$^{-1}$, about 1297±2 cm$^{-1}$, about 1570±2 cm$^{-1}$ and about 1585±2 cm$^{-1}$.

The crystalline form E according to the present invention may further be characterized in that it has one or more Raman peaks selected from the group consisting of about 1003±2 cm$^{-1}$, about 1297±2 cm$^{-1}$, about 1570±2 cm$^{-1}$ and about 1585±2 cm$^{-1}$; and/or one or more Raman peaks selected from the group consisting of about 159±2 cm$^{-1}$, about 188±2 cm$^{-1}$, about 680±2 cm$^{-1}$, about 923±2 cm$^{-1}$, about 1434±2 cm$^{-1}$, about 1461±2 cm$^{-1}$, about 2943±2 cm$^{-1}$, about 2961±2 cm$^{-1}$, about 3070±2 cm$^{-1}$; and/or one or more Raman peaks selected from the group consisting of about 174±2 cm$^{-1}$, about 257±2 cm$^{-1}$, about 370±2 cm$^{-1}$, about 489±2 cm$^{-1}$, about 632±2 cm$^{-1}$, about 823±2 cm$^{-1}$, about 913±2 cm$^{-1}$, about 982±2 cm$^{-1}$, about 1027±2 cm$^{-1}$, about 1037±2 cm$^{-1}$, about 1169±2 cm$^{-1}$, about 1192±2 cm$^{-1}$, about 1202±2 cm$^{-1}$, about 1262±2 cm$^{-1}$, about 1476±2 cm$^{-1}$, about 2836±2 cm$^{-1}$, about 2860±2 cm$^{-1}$, about 2894±2 cm$^{-1}$, about 2994±2 cm$^{-1}$ and about 3057±2 cm$^{-1}$.

The crystalline form E according to the present invention may further be characterized in that it has one or more Raman peaks selected from the group consisting of about 271±2 cm$^{-1}$, about 315±2 cm$^{-1}$, about 394±2 cm$^{-1}$, about 423±2 cm$^{-1}$, about 434±2 cm$^{-1}$, about 518±2 cm$^{-1}$, about 541±2 cm$^{-1}$, about 557±2 cm$^{-1}$, about 604±2 cm$^{-1}$, about 621±2 cm$^{-1}$, about 710±2 cm$^{-1}$, about 760±2 cm$^{-1}$, about 784±2 cm$^{-1}$, about 870±2 cm$^{-1}$, about 945±2 cm$^{-1}$, about 1049±2 cm$^{-1}$, about 1075±2 cm$^{-1}$, about 1117±2 cm$^{-1}$, about 1135±2 cm$^{-1}$, about 1230±2 cm$^{-1}$, about 1337±2 cm$^{-1}$, about 1354±2 cm$^{-1}$, about 1376±2 cm$^{-1}$, about 1629±2 cm$^{-1}$ and about 2791±2 cm$^{-1}$.

Another aspect of the present invention relates to a process for the production of the crystalline form E described above comprising the step of (a-1) suspending (1r,4r)-6'-fluoro-N,N-dimethyl-4-phenyl-4',9'-dihydro-3'H-spiro[cyclo-hexane-1,1'-pyrano[3,4,b]indol]-4-amine in a solvent comprising methanol.

Preferably, the solvent is methanol.

Preferably, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 5 minutes, preferably at least 10 minutes, more preferably at least 15 minutes, still more preferably at least 30 minutes, yet more preferably at least 1 h, and most preferably at least 2 h.

Preferably, the process according to the invention further comprises the step (b-1) separating, preferably filtering out the solid obtained in step (a-1).

Preferably, the process according to the invention further comprises the step (c-1) drying of the solid obtained in step (b-1).

Preferably, in the process according to the invention, step (c-1) takes place under air or inert gas flow, such as argon or nitrogen flow. Preferably, step (c-1) is performed at ambient temperature.

Another aspect of the present invention relates to a process for the production of the crystalline form E described above comprising the step of (a-3) washing (1r,4r)-6'-fluoro-N,N-dimethyl-4-phenyl-4',9'-dihydro-3'H-spiro[cyclohexane-1,1'-pyrano[3,4, b]indol]-4-amine with methanol.

For the purpose of the specification, "washing (1r,4r)-6'-fluoro-N,N-dimethyl-4-phenyl-4',9'-dihydro-3'H-spiro[cyclohexane-1,1'-pyrano[3,4, b]indol]-4-amine with methanol" is to be regarded as being synonymous with "bringing (1r,4r)-6'-fluoro-N,N-dimethyl-4-phenyl-4',9'-dihydro-3'H-spiro [cyclohexane-1,1'-pyrano[3,4, b]indol]-4-amine into contact with an excess of methanol".

Preferably, the (1r,4r)-6'-fluoro-N,N-dimethyl-4-phenyl-4',9'-dihydro-3'H-spiro[cyclohexane-1,1'-pyrano[3,4, b]indol]-4-amine is washed (brought into contact) with at least 0.5 µL, more preferably 1.0 µL, still more preferably at least 2 µL, yet more preferably at least 3 µL, most preferably at least 4 µL, and in particular at least 5 µL of methanol per mg of (1r,4r)-6'-fluoro-N,N-dimethyl-4-phenyl-4',9'-dihydro-3'H-spiro[cyclohexane-1,1'-pyrano-[3,4, b]indol]-4-amine.

Preferably, the (1r,4r)-6'-fluoro-N,N-dimethyl-4-phenyl-4',9'-dihydro-3'H-spiro[cyclohexane-1,1'-pyrano[3,4, b]indol]-4-amine employed in step (a-2) is in the form of a hydrate or solvate.

A further aspect of the present invention relates to a crystalline form E that is obtainable by the process as described above.

A further aspect of the present invention relates to a crystalline form F. Preferably, the crystalline form F according to the invention has one or more X-ray diffraction peaks selected from the group consisting of about 9.0±0.2 (2Θ), about 15.4±0.2 (2Θ), about 16.1±0.2 (2Θ), about 17.9±0.2 (2Θ), about 18.2±0.2 (2Θ), about 18.7±0.2 (2Θ), about 19.4±0.2 (2Θ), about 20.1±0.2 (2Θ), about 20.6±0.2 (2Θ), about 21.8±0.2 (2Θ), about 24.6±0.2 (2Θ), about 25.6±0.2 (2Θ), about 27.1±0.2 (2Θ), about 27.4±0.2 (2Θ) and about 29.3±0.2 (2Θ). In some preferred embodiments, the crystalline form comprises an X-ray diffraction peak at about 20.1±0.2 (2Θ).

In some preferred embodiments, crystalline form F comprises X-ray diffraction peaks at about 9.0±0.2 (2Θ), about 17.9±0.2 (2Θ), about 18.7±0.2 (2Θ), about 20.1±0.2 (2Θ) and optionally 16.1±0.2 (2Θ).

The crystalline form F according to the invention may additionally have at least one X-ray diffraction peak selected from the group consisting of about 21.9±0.2 (2Θ), about 25.0±0.2 (2Θ), about 27.9±0.2 (2Θ) and about 30.3±0.2 (2Θ).

Furthermore, the crystalline form F according to the invention may be characterized in that as well as one or more X-ray diffraction peaks selected from the group consisting of about 9.0±0.2 (2Θ), about 15.4±0.2 (2Θ), about 16.1±0.2 (2Θ), about 17.9±0.2 (2Θ), about 18.2±0.2 (2Θ), about 18.7±0.2 (2Θ), about 19.4±0.2 (2Θ), about 20.1±0.2 (2Θ), about 20.6±0.2 (2Θ), about 21.8±0.2 (2Θ), about 24.6±0.2 (2Θ), about 25.6±0.2 (2Θ), about 27.1±0.2 (2Θ), about 27.4±0.2 (2Θ) and about 29.3±0.2 (2Θ), and optionally one or more X-ray diffraction peaks selected from the group consisting of about 21.9±0.2 (2Θ), about 25.0±0.2 (2Θ), about 27.9±0.2 (2Θ) and about 30.3±0.2 (2Θ), it additionally has at least one X-ray diffraction peak selected from the group consisting of about 14.5±0.2 (2Θ), about 22.9±0.2 (2Θ), about 23.5±0.2 (2Θ), about 30.0±0.2 (2Θ), about 30.8±0.2 (2Θ), about 31.4±0.2 (2Θ), about 31.6±0.2 (2Θ) and about 32.2±0.2 (2Θ).

The crystalline form F according to the invention may further be characterized in that as well as one or more X-ray diffraction peaks selected from the group consisting of about 9.0±0.2 (2Θ), about 15.4±0.2 (2Θ), about 16.1±0.2 (2Θ), about 17.9±0.2 (2Θ), about 18.2±0.2 (2Θ), about 18.7±0.2 (2Θ), about 19.4±0.2 (2Θ), about 20.1±0.2 (2Θ), about 20.6±0.2 (2Θ), about 21.8±0.2 (2Θ), about 24.6±0.2 (2Θ), about 25.6±0.2 (2Θ), about 27.1±0.2 (2Θ), about 27.4±0.2 (2Θ) and about 29.3±0.2 (2Θ), and optionally one or more X-ray diffraction peaks selected from the group consisting of about 21.9±0.2 (2Θ), about 25.0±0.2 (2Θ), about 27.9±0.2 (2Θ) and about 30.3±0.2 (2Θ), and optionally one or more X-ray diffraction peaks selected from the group consisting of about 14.5±0.2 (2Θ), about 22.9±0.2 (2Θ), about 23.5±0.2 (2Θ), about 30.0±0.2 (2Θ), about 30.8±0.2 (2Θ), about 31.4±0.2 (2Θ), about 31.6±0.2 (2Θ) and about 32.2±0.2 (2Θ), it additionally has at least one X-ray diffraction peak selected from the group consisting of about 8.0±0.2 (2Θ), about 10.6±0.2 (2Θ), about 24.0±0.2 (2Θ), about 32.2±0.2 (2Θ), about 32.8±0.2 (2Θ), about 33.3±0.2 (2Θ), about 34.4±0.2 (2Θ) and about 34.4±0.2 (2Θ).

All 2Θ values indicated above refer to a X-ray diffractogram measured using CuKα radiation having a wavelength of 1.54060 Å.

The crystalline form F according to the present invention may further be characterized in that it has one or more Raman peaks selected from the group consisting of about 171±2 $cm^{-1}$, about 921±2 $cm^{-1}$, about 1002±2 $cm^{-1}$, about 1299±2 $cm^{-1}$, about 1570±2 $cm^{-1}$, about 1581±2 $cm^{-1}$, about 2952±2 $cm^{-1}$ and about 3070±2 $cm^{-1}$.

The crystalline form F according to the present invention may further be characterized in that it has one or more Raman peaks selected from the group consisting of about 171±2 $cm^{-1}$, about 921±2 $cm^{-1}$, about 1002±2 $cm^{-1}$, about 1299±2 $cm^{-1}$, about 1570±2 $cm^{-1}$, about 1581±2 $cm^{-1}$, 2952±2 $cm^{-1}$ and about 3070±2 $cm^{-1}$; and/or one or more Raman peaks selected from the group consisting of about 157±2 $cm^{-1}$, about 183±2 $cm^{-1}$, about 682±2 $cm^{-1}$, about 1463±2 $cm^{-1}$, about 1477±2 $cm^{-1}$, 2889±2 $cm^{-1}$, about 2932±2 $cm^{-1}$, about 2977±2 $cm^{-1}$ and about 3058±2 $cm^{-1}$; and/or one or more Raman peaks selected from the group consisting of about 212±2 $cm^{-1}$, about 253±2 $cm^{-1}$, about 370±2 $cm^{-1}$, about 491±2 $cm^{-1}$, about 620±2 $cm^{-1}$, about 632±2 $cm^{-1}$, about 828±2 $cm^{-1}$, about 912±2 $cm^{-1}$, about 982±2 $cm^{-1}$, about 1027±2 $cm^{-1}$, about 1036±2 $cm^{-1}$, about 1050±2 $cm^{-1}$, about 1056±2 $cm^{-1}$, about 1110±2 $cm^{-1}$, about 1159±2 $cm^{-1}$, about 1189±2 $cm^{-1}$, about 1202±2 $cm^{-1}$, about 1373±2 $cm^{-1}$, about 1438±2 $cm^{-1}$, about 1453±2 $cm^{-1}$, about 2843±2 $cm^{-1}$, about 2860±2 $cm^{-1}$ and about 2992±2 $cm^{-1}$.

The crystalline form F according to the present invention may further be characterized in that it has one or more Raman peaks selected from the group consisting of about 291±2 $cm^{-1}$, about 394±2 $cm^{-1}$, about 424±2 $cm^{-1}$, about 471±2 $cm^{-1}$, about 519±2 $cm^{-1}$, about 542±2 $cm^{-1}$, about 560±2 $cm^{-1}$, about 602±2 $cm^{-1}$, about 607±2 $cm^{-1}$, about 712±2 $cm^{-1}$, about 762±2 $cm^{-1}$, about 786±2 $cm^{-1}$, about 848±2 $cm^{-1}$, about 870±2 $cm^{-1}$, about 894±2 $cm^{-1}$, about 946±2 $cm^{-1}$, about 970±2 $cm^{-1}$, about 1076±2 $cm^{-1}$, about 1119±2 $cm^{-1}$, about 1146±2 $cm^{-1}$, about 1172±2 $cm^{-1}$, about 1229±2 $cm^{-1}$, about 1263±2 $cm^{-1}$, about 1338±2 $cm^{-1}$, about 1353±2 $cm^{-1}$, about 1498±2 $cm^{-1}$, about 1630±2 $cm^{-1}$, about 2566±2 $cm^{-1}$, about 2748±2 $cm^{-1}$ and about 2795±2 $cm^{-1}$.

Another aspect of the present invention relates to a process for the production of the crystalline form F described above comprising the step of (a-1) suspending (1r,4r)-6'-fluoro-N,N-dimethyl-4-phenyl-4',9'-dihydro-3'H-spiro[cyclo-hexane-1,1'-pyrano[3,4, b]indol]-4-amine in a solvent comprising n-propanol.

Preferably, the solvent is n-propanol.

Preferably, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-1) separating, preferably filtering off the solid obtained in step (a-1).

Preferably, the process according to the invention further comprises the step (c-1) drying of the solid obtained in step (b-1).

Preferably, in the process according to the invention, step (c-1) takes place under air or inert gas flow, such as argon or nitrogen flow. Preferably, step (c-1) is performed at ambient temperature.

A further aspect of the present invention relates to a crystalline form F that is obtainable by the process as described above.

A further aspect of the present invention relates to a crystalline form G. Preferably, the crystalline form G according to the invention has one or more X-ray diffraction peaks selected from the group consisting of about 16.3±0.2 (2Θ), about 18.8±0.2 (2Θ), about 19.1±0.2 (2Θ), about 19.4±0.2 (2Θ), about 20.3±0.2 (2Θ), about 22.2±0.2 (2Θ) and about 29.1±0.2 (2Θ). In some preferred embodiments, the crystalline form comprises an X-ray diffraction peak at about 19.1±0.2 (2Θ).

In some preferred embodiments, crystalline form G comprises X-ray diffraction peaks at about 18.8±0.2 (2Θ), about 19.1±0.2 (2Θ), about 22.2±0.2 (2Θ), about 29.1±0.2 (2Θ) and optionally 20.3±0.2 (2Θ).

The crystalline form G according to the invention may additionally have at least one X-ray diffraction peak selected from the group consisting of about 15.4±0.2 (2Θ), about 15.9±0.2 (2Θ), about 17.2±0.2 (2Θ), about 17.4±0.2 (2Θ), about 17.8±0.2 (2Θ), about 20.7±0.2 (2Θ), about 21.0±0.2 (2Θ), about 22.6±0.2 (2Θ), about 24.2±0.2 (2Θ), about 24.7±0.2 (2Θ), about 25.4±0.2 (2Θ), about 25.9±0.2 (2Θ), about 26.6±0.2 (2Θ), about 28.0±0.2 (2Θ), about 28.3±0.2 (2Θ), about 28.8±0.2 (2Θ), about 29.4±0.2 (2Θ) and about 33.0±0.2 (2Θ).

Furthermore, the crystalline form G according to the invention may be characterized in that as well as one or more X-ray diffraction peaks selected from the group consisting of about 16.3±0.2 (2Θ), about 18.8±0.2 (2Θ), about 19.1±0.2 (2Θ), about 19.4±0.2 (2Θ), about 20.3±0.2 (2Θ), about 22.2±0.2 (2Θ) and about 29.1±0.2 (2Θ), and optionally one or more X-ray diffraction peaks selected from the group consisting of about 15.4±0.2 (2Θ), about 15.9±0.2 (2Θ), about 17.2±0.2 (2Θ), about 17.4±0.2 (2Θ); about 17.8±0.2 (2Θ), about 20.7±0.2 (2Θ), about 21.0±0.2 (2Θ), about 22.6±0.2 (2Θ), about 24.2±0.2 (2Θ), about 24.7±0.2 (2Θ), about 25.4±0.2 (2Θ), about 25.9±0.2 (2Θ), about 26.6±0.2 (2Θ), about 28.0±0.2 (2Θ), about 28.3±0.2 (2Θ), about 28.8±0.2 (2Θ), about 29.4±0.2 (2Θ) and about 33.0±0.2 (2Θ), it additionally has at least one X-ray diffraction peak selected from the group consisting of about 11.5±0.2 (2Θ), about 15.1±0.2 (2Θ), about 30.2±0.2 (2Θ), about 31.6±0.2 (2Θ), about 32.3±0.2 (2Θ), about 33.9±0.2 (2Θ) and about 34.7±0.2 (2Θ).

The crystalline form G according to the invention may further be characterized in that as well as one or more X-ray diffraction peaks selected from the group consisting of about 16.3±0.2 (2Θ), about 18.8±0.2 (2Θ), about 19.1±0.2 (2Θ), about 19.4±0.2 (2Θ), about 20.3±0.2 (2Θ), about 22.2±0.2 (2Θ) and about 29.1±0.2 (2Θ), and optionally one or more X-ray diffraction peaks selected from the group consisting of about 15.4±0.2 (2Θ), about 15.9±0.2 (2Θ), about 17.2±0.2 (2Θ), about 17.4±0.2 (2Θ), about 17.8±0.2 (2Θ), about 20.7±0.2 (2Θ), about 21.0±0.2 (2Θ), about 22.6±0.2 (2Θ), about 24.2±0.2 (2Θ), about 24.7±0.2 (2Θ), about 25.4±0.2 (2Θ), about 25.9±0.2 (2Θ), about 26.6±0.2 (2Θ), about 28.0±0.2 (2Θ), about 28.3±0.2 (2Θ), about 28.8±0.2 (2Θ), about 29.4±0.2 (2Θ) and about 33.0±0.2 (2Θ), and optionally one or more X-ray diffraction peaks selected from the group consisting of about 11.5±0.2 (2Θ), about 15.1±0.2 (2Θ), about 30.2±0.2 (2Θ), about 31.6±0.2 (2Θ), about 32.3±0.2 (2Θ), about 33.9±0.2 (2Θ) and about 34.7±0.2 (2Θ), it additionally has at least one X-ray diffraction peak selected from the group consisting of about 8.1±0.2 (2Θ), about 8.9±0.2 (2Θ), about 11.1±0.2 (2Θ), about 13.5±0.2 (2Θ) and about 33.5±0.2 (2Θ).

All 2Θ values indicated above refer to a X-ray diffractogram measured using CuKα radiation having a wavelength of 1.54060 Å.

The crystalline form G according to the present invention may further be characterized in that it has one or more Raman peaks selected from the group consisting of about 675±2 $cm^{-1}$, about 1569±2 $cm^{-1}$ and about 2917±2 $cm^{-1}$.

The crystalline form G according to the present invention may further be characterized in that it has one or more Raman peaks selected from the group consisting of about 675±2 $cm^{-1}$, about 1569±2 $cm^{-1}$ and about 2917±2 $cm^{-1}$; and/or one or more Raman peaks selected from the group consisting of about 169±2 $cm^{-1}$, about 921±2 $cm^{-1}$, about 1002±2 $cm^{-1}$, about 3069±2 $cm^{-1}$; and/or one or more Raman peaks selected from the group consisting of about 180±2 $cm^{-1}$, about 202±2 $cm^{-1}$, about 254±2 $cm^{-1}$, about 306±2 $cm^{-1}$, about 706±2 $cm^{-1}$, about 1029±2 $cm^{-1}$, about 1047±2 $cm^{-1}$, about 1292±2 $cm^{-1}$, about 1309±2 $cm^{-1}$, about 1418±2 $cm^{-1}$, about 1437±2 $cm^{-1}$, about 1475±2 $cm^{-1}$, about 1597±2 $cm^{-1}$, about 2945±2 $cm^{-1}$, about 2960±2 $cm^{-1}$, about 2999±2 $cm^{-1}$, about 3058±2 $cm^{-1}$.

The crystalline form G according to the present invention may further be characterized in that it has one or more Raman peaks selected from the group consisting of about 334±2 $cm^{-1}$, about 365±2 $cm^{-1}$, about 387±2 $cm^{-1}$, about 424±2 $cm^{-1}$, about 438±2 $cm^{-1}$, about 491±2 $cm^{-1}$, about 522±2 $cm^{-1}$, about 546±2 $cm^{-1}$, about 608±2 $cm^{-1}$, about 621±2 $cm^{-1}$, about 638±2 $cm^{-1}$, about 769±2 $cm^{-1}$, about 786±2 $cm^{-1}$, about 830±2 $cm^{-1}$, about 868±2 $cm^{-1}$, about 948±2 $cm^{-1}$, about 982±2 $cm^{-1}$, about 1038±2 $cm^{-1}$, about 1073±2 $cm^{-1}$, about 1108±2 $cm^{-1}$, about 1122±2 $cm^{-1}$, about 1136±2 $cm^{-1}$, about 1161±2 $cm^{-1}$, about 1171±2 $cm^{-1}$, about 1190±2 $cm^{-1}$, about 1201±2 $cm^{-1}$, about 1234±2 $cm^{-1}$, about 1260±2 $cm^{-1}$, about 1338±2 $cm^{-1}$, about 1373±2 $cm^{-1}$, about 1629±2 $cm^{-1}$, about 2777±2 $cm^{-1}$, about 2815±2 $cm^{-1}$, about 2841±2 $cm^{-1}$, about 2862±2 $cm^{-1}$, about 3156±2 $cm^{-1}$.

Another aspect of the present invention relates to a process for the production of the crystalline form G described above comprising the step of (a-1) suspending (1r,4r)-6'-fluoro-N,N-dimethyl-4-phenyl-4',9'-dihydro-3'H-spiro[cyclo-hexane-1,1'-pyrano[3,4,b]indol]-4-amine in a solvent comprising dimethyl sulfoxide.

Preferably, the solvent is dimethyl sulfoxide.

Preferably, step (a-1) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, the suspension obtained in step (a-1) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-1) separating, preferably filtering off the solid obtained in step (a-1).

Preferably, the process according to the invention further comprises the step (c-1) drying of the solid obtained in step (b-1).

Preferably, in the process according to the invention, step (c-1) takes place under air or inert gas flow, such as argon or nitrogen flow. Preferably, step (c-1) is performed at ambient temperature.

A further aspect of the present invention relates to a crystalline form G that is obtainable by the process as described above.

A further aspect of the present invention relates to a crystalline form H. Preferably, the crystalline form H according to the invention has one or more X-ray diffraction peaks selected from the group consisting of about 11.4±0.2 (2Θ), about 18.3±0.2 (2Θ) and about 19.2±0.2 (2Θ). In some preferred embodiments, the crystalline form comprises an X-ray diffraction peak at about 19.2±0.2 (2Θ).

In some preferred embodiments, crystalline form H comprises X-ray diffraction peaks at about 11.4±0.2 (2Θ), about 18.3±0.2 (2Θ), about 19.2±0.2 (2Θ), about 23.0±0.2 (2Θ) and optionally 18.0±0.2 (2Θ).

The crystalline form H according to the invention may additionally have at least one X-ray diffraction peak selected from the group consisting of about 17.1±0.2 (2Θ), about 18.0±0.2 (2Θ), about 20.6±0.2 (2Θ), about 21.4±0.2 (2Θ), about 23.0±0.2 (2Θ), about 25.5±0.2 (2Θ), about 26.3±0.2 (2Θ) and about 27.9±0.2 (2Θ).

Furthermore, the crystalline form H according to the invention may be characterized in that as well as one or more X-ray diffraction peaks selected from the group consisting of about 11.4±0.2 (2Θ), about 18.3±0.2 (2Θ) and about 19.2±0.2 (2Θ), and optionally one or more X-ray diffraction peaks selected from the group consisting of about 17.1±0.2 (2Θ), about 18.0±0.2 (2Θ), about 20.6±0.2 (2Θ), about 21.4±0.2 (2Θ), about 23.0±0.2 (2Θ), about 25.5±0.2 (2Θ), about 26.3±0.2 (2Θ) and about 27.9±0.2 (2Θ), it additionally has at least one X-ray diffraction peak selected from the group consisting of about 7.4±0.2 (2Θ), about 10.8±0.2 (2Θ), about 15.7±0.2 (2Θ), about 16.2±0.2 (2Θ), about 19.8±0.2 (2Θ), about 20.3±0.2 (2Θ), about 22.2±0.2 (2Θ), about 23.8±0.2 (2Θ), about 24.5±0.2 (2Θ), about 25.8±0.2 (2Θ), about 27.0±0.2 (2Θ), about 28.3±0.2 (2Θ), about 28.8±0.2 (2Θ), about 29.4±0.2 (2Θ), about 30.0±0.2 (2Θ), about 31.0±0.2 (2Θ) and about 33.3±0.2 (2Θ).

The crystalline form H according to the invention may further be characterized in that as well as one or more X-ray diffraction peaks selected from the group consisting of about 11.4±0.2 (2Θ), about 18.3±0.2 (2Θ) and about 19.2±0.2 (2Θ), and optionally one or more X-ray diffraction peaks selected from the group consisting of about 17.1±0.2 (2Θ), about 18.0±0.2 (2Θ), about 20.6±0.2 (2Θ), about 21.4±0.2 (2Θ), about 23.0±0.2 (2Θ), about 25.5±0.2 (2Θ), about 26.3±0.2 (2Θ) and about 27.9±0.2 (2Θ), and optionally one or more X-ray diffraction peaks selected from the group consisting of about 7.4±0.2 (2Θ), about 10.8±0.2 (2Θ), about 15.7±0.2 (2Θ), about 16.2±0.2 (2Θ), about 19.8±0.2 (2Θ), about 20.3±0.2 (2Θ), about 22.2±0.2 (2Θ), about 23.8±0.2 (2Θ), about 24.5±0.2 (2Θ), about 25.8±0.2 (2Θ), about 27.0±0.2 (2Θ), about 28.3±0.2 (2Θ), about 28.8±0.2 (2Θ), about 29.4±0.2 (2Θ), about 30.0±0.2 (2Θ), about 31.0±0.2 (2Θ) and about 33.3±0.2 (2Θ), it additionally has at least one X-ray diffraction peak selected from the group consisting of about 8.5±0.2 (2Θ), about 9.0±0.2 (2Θ), about 9.8±0.2 (2Θ), about 12.2±0.2 (2Θ), about 12.8±0.2 (2Θ), about 13.1±0.2 (2Θ), about 14.8±0.2 (2Θ), about 16.6±0.2 (2Θ), about 27.6±0.2 (2Θ) and about 32.7±0.2 (2Θ).

All 2Θ values indicated above refer to a X-ray diffractogram measured using CuKα radiation having a wavelength of 1.54060 Å.

The crystalline form H according to the present invention may further be characterized in that it has one or more Raman peaks selected from the group consisting of about 171±2 $cm^{-1}$, about 203±2 $cm^{-1}$, about 258±2 $cm^{-1}$, about 918±2 $cm^{-1}$, about 1002±2 $cm^{-1}$, about 1305±2 $cm^{-1}$ and about 1568±2 $cm^{-1}$.

The crystalline form H according to the present invention may further be characterized in that as well as one or more Raman peaks selected from the group consisting of about 171±2 $cm^{-1}$, about 203±2 $cm^{-1}$, about 258±2 $cm^{-1}$, about 918±2 $cm^{-1}$, about 1002±2 $cm^{-1}$, about 1305±2 $cm^{-1}$ and about 1568±2 $cm^{-1}$; it additionally has one or more Raman peaks selected from the group consisting of about 369±2 $cm^{-1}$, about 391±2 $cm^{-1}$, about 490±2 $cm^{-1}$, about 599±2 $cm^{-1}$, about 685±2 $cm^{-1}$, about 828±2 $cm^{-1}$, about 1030±2 $cm^{-1}$, about 1375±2 $cm^{-1}$, about 1464±2 $cm^{-1}$, about 2989±2 $cm^{-1}$.

The crystalline form H according to the present invention may further be characterized in that it has one or more Raman peaks selected from the group consisting of about 517±2 $cm^{-1}$, about 557±2 $cm^{-1}$, about 620±2 $cm^{-1}$, about 713±2 $cm^{-1}$, about 734±2 $cm^{-1}$, about 787±2 $cm^{-1}$, about 889±2 $cm^{-1}$, about 982±2 $cm^{-1}$, about 1048±2 $cm^{-1}$, about 1073±2 $cm^{-1}$, about 1117±2 $cm^{-1}$, about 1199±2 $cm^{-1}$, about 1219±2 $cm^{-1}$, about 1263±2 $cm^{-1}$, about 1629±2 $cm^{-1}$, about 2788±2 $cm^{-1}$, about 2921±2 $cm^{-1}$, about 2945±2 $cm^{-1}$ and about 3069±2 $cm^{-1}$.

Another aspect of the present invention relates to a process for the production of the crystalline form H described above comprising the step of (a-1) dissolving (1r,4r)-6'-fluoro-N,N-dimethyl-4-phenyl-4', 9'-dihydro-3'H-spiro[cyclohexane-1,1'-pyrano[3,4, b]indol]-4-amine in an organic solvent.

In a preferred embodiment, the organic solvent is 1,4-dioxane. In another preferred embodiment, the organic solvent contains at least 5 wt.-%, more preferably at least 10 wt.-%, still more preferably at least 20 wt.-%, yet more preferably at least 30 wt.-%, most preferably at least 40 wt.-%, and in particular at least 50 wt.-% 1,4-dioxane.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In a preferred embodiment, the process according to the invention further comprises the step (b-1) evaporating off the solvent of the solution obtained in step (a-1).

Suitable methods for evaporating the solvent are known to a person skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible.

Preferably, in the process according to the invention, the solvent is evaporated at room temperature. However, evaporating off the solvent at an elevated temperature, e.g. within the range of 20° C. to 60° C., is also possible.

A further aspect of the present invention relates to a crystalline form H that is obtainable by the process as described above.

A further aspect of the present invention relates to a crystalline form I. Preferably, the crystalline form I according to the invention has one or more X-ray diffraction peaks selected from the group consisting of about 10.9±0.2 (2Θ), about 14.6±0.2 (2Θ), about 15.5±0.2 (2Θ), about 17.1±0.2 (2Θ), about 18.5±0.2 (2Θ), about 18.8±0.2 (2Θ), about 21.1±0.2 (2Θ), about 21.9±0.2 (2Θ), about 23.6±0.2 (2Θ), about 25.9±0.2 (2Θ) and about 28.0±0.2 (2Θ). In some preferred embodiments, the crystalline form comprises an X-ray diffraction peak at about 17.1±0.2.

In some preferred embodiments, crystalline form I comprises X-ray diffraction peaks at about 10.9±0.2 (2Θ), about 15.5±0.2 (2Θ), about 17.1±0.2 (2Θ), about 18.5±0.2 (2Θ) and optionally 18.8±0.2 (2Θ) and/or 23.6±0.2 (2Θ).

The crystalline form I according to the invention may additionally have at least one X-ray diffraction peak selected from the group consisting of about 16.5±0.2 (2Θ), about 18.1±0.2 (2Θ), about 24.0±0.2 (2Θ), about 28.0±0.2 (2Θ), about 28.8±0.2 (2Θ), about 30.6±0.2 (2Θ) and about 31.9±0.2 (2Θ).

Furthermore, the crystalline form I according to the invention may be characterized in that as well as one or more X-ray diffraction peaks selected from the group consisting of about 10.9±0.2 (2Θ), about 14.6±0.2 (2Θ), about 15.5±0.2 (2Θ), about 17.1±0.2 (2Θ), about 18.5±0.2 (2Θ), about 18.8±0.2 (2Θ), about 21.1±0.2 (2Θ), about 21.9±0.2 (2Θ), about 23.6±0.2 (2Θ), about 25.9±0.2 (2Θ), and about 28.0±0.2 (2Θ), and optionally one or more X-ray diffraction peaks selected from the group consisting of about 16.5±0.2 (2Θ), about 18.1±0.2 (2Θ), about 24.0±0.2 (2Θ), about 28.0±0.2 (2Θ), about 28.8±0.2 (2Θ), about 30.6±0.2 (2Θ) and about 31.9±0.2 (2Θ), it additionally has at least one X-ray diffraction peak selected from the group consisting of about 19.4±0.2 (2Θ), about 19.9±0.2 (2Θ), about 20.2±0.2 (2Θ), about 22.3±0.2 (2Θ), about 22.8±0.2 (2Θ), about 23.0±0.2 (2Θ), about 25.2±0.2 (2Θ), about 26.6±0.2 (2Θ), about 30.0±0.2 (2Θ) and about 34.8±0.2 (2Θ).

The crystalline form I according to the invention may further be characterized in that as well as one or more X-ray diffraction peaks selected from the group consisting of about 10.9±0.2 (2Θ), about 14.6±0.2 (2Θ), about 15.5±0.2 (2Θ), about 17.1±0.2 (2Θ), about 18.5±0.2 (2Θ), about 18.8±0.2 (2Θ), about 21.1±0.2 (2Θ), about 21.9±0.2 (2Θ), about 23.6±0.2 (2Θ), about 25.9±0.2 (2Θ), and about 28.0±0.2 (2Θ), and optionally one or more X-ray diffraction peaks selected from the group consisting of about 16.5±0.2 (2Θ), about 18.1±0.2 (2Θ), about 24.0±0.2 (2Θ), about 28.0±0.2 (2Θ), about 28.8±0.2 (2Θ), about 30.6±0.2 (2Θ) and about 31.9±0.2 (2Θ), and optionally one or more X-ray diffraction peaks selected from the group consisting of about 19.4±0.2 (2Θ), about 19.9±0.2 (2Θ), about 20.2±0.2 (2Θ), about 22.3±0.2 (2Θ), about 22.8±0.2 (2Θ), about 23.0±0.2 (2Θ), about 25.2±0.2 (2Θ), about 26.6±0.2 (2Θ), about 30.0±0.2 (2Θ) and about 34.8±0.2 (2Θ), it additionally has at least one X-ray diffraction peak selected from the group consisting of about 9.5±0.2 (2Θ), about 10.1±0.2 (2Θ), about 13.9±0.2 (2Θ), about 27.6±0.2 (2Θ), about 29.1±0.2 (2Θ), about 33.1±0.2 (2Θ) and about 34.2±0.2 (2Θ).

All 2Θ values indicated above refer to a X-ray diffractogram measured using CuKα radiation having a wavelength of 1.54060 Å.

The crystalline form I according to the present invention may further be characterized in that it has one or more Raman peaks selected from the group consisting of about 924±2 $cm^{-1}$, about 1001±2 $cm^{-1}$, about 1305±2 $cm^{-1}$, about 1572±2 $cm^{-1}$, about 2925±2 $cm^{-1}$, about 3066±2 $cm^{-1}$.

The crystalline form I according to the present invention may further be characterized in that as well as one or more Raman peaks selected from the group consisting of about 924±2 $cm^{-1}$, about 1001±2 $cm^{-1}$, about 1305±2 $cm^{-1}$, about 1572±2 $cm^{-1}$, about 2925±2 $cm^{-1}$, about 3066±2 $cm^{-1}$; it additionally has one or more Raman peaks selected from the group consisting of about 155±2 $cm^{-1}$, about 172±2 $cm^{-1}$, about 256±2 $cm^{-1}$, about 680±2 $cm^{-1}$, about 1031±2 $cm^{-1}$, about 1434±2 $cm^{-1}$, about 1459±2 $cm^{-1}$, about 1474±2 $cm^{-1}$, about 1589±2 $cm^{-1}$, about 1596±2 $cm^{-1}$, about 2911±2 $cm^{-1}$, about 2964±2 $cm^{-1}$ and about 2984±2 $cm^{-1}$.

The crystalline form I according to the present invention may further be characterized in that it has one or more Raman peaks selected from the group consisting of about 202±2 $cm^{-1}$, about 280±2 $cm^{-1}$, about 315±2 $cm^{-1}$, about 367±2 $cm^{-1}$, about 392±2 $cm^{-1}$, about 421±2 $cm^{-1}$, about 438±2 $cm^{-1}$, about 466±2 $cm^{-1}$, about 489±2 $cm^{-1}$, about 519±2 $cm^{-1}$, about 544±2 $cm^{-1}$, about 558±2 $cm^{-1}$, about 605±2 $cm^{-1}$, about 621±2 $cm^{-1}$, about 636±2 $cm^{-1}$, about 697±2 $cm^{-1}$, about 715±2 $cm^{-1}$, about 767±2 $cm^{-1}$, about 784±2 $cm^{-1}$, about 810±2 $cm^{-1}$, about 825±2 $cm^{-1}$, about 895±2 $cm^{-1}$, about 912±2 $cm^{-1}$, about 948±2 $cm^{-1}$, about 983±2 $cm^{-1}$, about 1047±2 $cm^{-1}$, about 1066±2 $cm^{-1}$, about 1091±2 $cm^{-1}$, 1113±2 $cm^{-1}$, about 1123±2 $cm^{-1}$, about 1141±2 $cm^{-1}$, about 1159±2 $cm^{-1}$, about 1188±2 $cm^{-1}$, about 1199±2 $cm^{-1}$, 1232±2 $cm^{-1}$, about 1265±2 $cm^{-1}$, about 1291±2 $cm^{-1}$, about 1339±2 $cm^{-1}$, about 1354±2 $cm^{-1}$, about 1375±2 $cm^{-1}$, 1404±2 $cm^{-1}$, about 1417±2 $cm^{-1}$, about 1630±2 $cm^{-1}$, about 2699±2 $cm^{-1}$, about 2775±2 $cm^{-1}$, about 2787±2 $cm^{-1}$, 2820±2 $cm^{-1}$, about 2845±2 $cm^{-1}$, about 2875±2 $cm^{-1}$, about 2953±2 $cm^{-1}$, about 2998±2 $cm^{-1}$, about 3011±2 $cm^{-1}$, 3051±2 $cm^{-1}$ and about 3085±2 $cm^{-1}$.

Another aspect of the present invention relates to a process for the production of the crystalline form I described above comprising the step of (a-1) dissolving (1r,4r)-6'-fluoro-N,N-dimethyl-4-phenyl-4', 9'-dihydro-3'H-spiro[cyclohexane-1,1-pyrano[3,4, b]indol]-4-amine in an organic solvent.

Preferably, the solvent is selected from the group consisting of the C4 to C6 alcohols such as n-butanol, esters such as ethyl acetate, n-propyl acetate, iso-propyl acetate, n-butyl acetate, iso-butyl acetate, ketones such as acetone, 2-butanone, pentan-2-one, pentan-3-one, hexan-2-one, hexan-3-one, ethers such as tert-butyl methyl ether, diethylether, tetrahydrofuran, diisopropylether and 1,4-dioxane, nitriles such as acetonitril, saturated hydrocarbons such as n-pentane, n-hexane and n-heptane, aromatic hydrocarbons such as toluene, chlorinated hydrocarbons such as dichloromethane and chloroform, and mixtures thereof. Mixtures of saturated hydrocarbons, such as n-pentane, n-hexane and n-heptane, further containing at least one solvent selected from the group consisting of ketones, ethers and chlorinated hydrocarbons are particularly preferred.

In some preferred embodiments, the organic solvent is a mixture of dichloromethane and n-heptane. Preferably, the ratio between dichloromethane and n-heptane is within the range of from 10:1 to 1:10, more preferably within the range of from 7:1 to 1:7, still more preferably within the range of from 5:1 to 1:6, yet more preferably within the range of from 3:1 to 1:5, most preferably within the range of from 1:1 to 1:3, and in particular within the range of from 1:1.5 to 1:2.5 (volume/volume).

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In a preferred embodiment, the process according to the invention further comprises the step (b-1) evaporating off the solvent of the solution obtained in step (a-1).

Suitable methods for evaporating the solvent are known to a person skilled in the art. Preferably, in the process according to the invention, the solvent is evaporated in air, air flow, or inert gas flow, in particular argon or nitrogen flow. However, evaporating off the solvent under vacuum, for example by means of a rotary evaporator, is also possible.

Preferably, in the process according to the invention, the solvent is evaporated at room temperature. However, evaporating off the solvent at an elevated temperature, e.g. within the range of 20° C. to 60° C., is also possible.

A further aspect of the present invention relates to a crystalline form I that is obtainable by the process as described above.

A further aspect of the present invention relates to a crystalline form L. Preferably, the crystalline form L according to the invention has one or more X-ray diffraction peaks selected from the group consisting of about 8.6±0.2 (2Θ), about 10.3±0.2 (2Θ), about 16.7±0.2 (2Θ), about 17.2±0.2 (2Θ), about 18.2±0.2 (2Θ), about 18.8±0.2 (2Θ), about 21.2±0.2 (2Θ), about 26.0±0.2 (2Θ), and about 27.4±0.2 (2Θ). In some preferred embodiments, the crystalline form comprises an X-ray diffraction peak at about 18.8±0.2 (2Θ).

In some preferred embodiments, crystalline form L comprises X-ray diffraction peaks at about 16.7±0.2 (2Θ), about 17.2±0.2 (2Θ), about 18.2±0.2 (2Θ), about 18.8±0.2 (2Θ) and optionally 10.3±0.2 (2Θ).

The crystalline form L according to the invention may additionally have at least one X-ray diffraction peak selected from the group consisting of about 14.0±0.2 (2Θ), about 20.7±0.2 (2Θ), about 23.0±0.2 (2Θ), about 28.9±0.2 (2Θ) and about 30.2±0.2 (2Θ).

Furthermore, the crystalline form L according to the invention may be characterized in that as well as one or more X-ray diffraction peaks selected from the group consisting of about 8.6±0.2 (2Θ), about 10.3±0.2 (2Θ), about 16.7±0.2 (2Θ), about 17.2±0.2 (2Θ), about 18.2±0.2 (2Θ), about 18.8±0.2 (2Θ), about 21.2±0.2 (2Θ), about 26.0±0.2 (2Θ), and about 27.4±0.2 (2Θ), and optionally one or more X-ray diffraction peaks selected from the group consisting of about 14.0±0.2 (2Θ), about 20.7±0.2 (2Θ), about 23.0±0.2 (2Θ), about 28.9±0.2 (2Θ) and about 30.2±0.2 (2Θ), it additionally has at least one X-ray diffraction peak selected from the group consisting of about 9.1±0.2 (2Θ), about 9.5±0.2 (2Θ), about 12.2±0.2 (2Θ), about 22.3±0.2 (2Θ) and about 24.5±0.2 (2Θ).

All 2Θ values indicated above refer to a X-ray diffractogram measured using CuKα radiation having a wavelength of 1.54060 Å.

The crystalline form L according to the present invention may further be characterized in that it has one or more Raman peaks selected from the group consisting of about 1001±2 $cm^{-1}$, about 1577±2 $cm^{-1}$, about 1590±2 $cm^{-1}$ and about 3069±2 $cm^{-1}$.

The crystalline form L according to the present invention may further be characterized in that it has one or more Raman peaks selected from the group consisting of about 1001±2 $cm^{-1}$, about 1577±2 $cm^{-1}$, about 1590±2 $cm^{-1}$ and about 3069±2 $cm^{-1}$; and/or one or more Raman peaks selected from the group consisting of about 172±2 $cm^{-1}$, about 679±2 $cm^{-1}$, about 924±2 $cm^{-1}$, about 1307±2 $cm^{-1}$, about 1475±2 $cm^{-1}$, about 2922±2 $cm^{-1}$, about 2987±2 $cm^{-1}$; and/or one or more Raman peaks selected from the group consisting of about 150±2 $cm^{-1}$, about 199±2 $cm^{-1}$, about 249±2 $cm^{-1}$, about 488±2 $cm^{-1}$, about 620±2 $cm^{-1}$, about 693±2 $cm^{-1}$, about 828±2 $cm^{-1}$, about 913±2 $cm^{-1}$, about 985±2 $cm^{-1}$, about 1029±2 $cm^{-1}$, about 1201±2 $cm^{-1}$, about 1293±2 $cm^{-1}$, about 1376±2 $cm^{-1}$, about 1438±2 $cm^{-1}$, about 1631±2 $cm^{-1}$, about 2843±2 $cm^{-1}$, about 2859±2 $cm^{-1}$, about 2879±2 $cm^{-1}$ and about 3042±2 $cm^{-1}$.

The crystalline form L according to the present invention may further be characterized in that it has one or more Raman peaks selected from the group consisting of about 362±2 $cm^{-1}$, about 390±2 $cm^{-1}$, about 423±2 $cm^{-1}$, about 522±2 $cm^{-1}$, about 544±2 $cm^{-1}$, about 610±2 $cm^{-1}$, about 637±2 $cm^{-1}$, about 714±2 $cm^{-1}$, about 763±2 $cm^{-1}$, about 784±2 $cm^{-1}$, about 872±2 $cm^{-1}$, about 950±2 $cm^{-1}$, about 1049±2 $cm^{-1}$, about 1077±2 $cm^{-1}$, about 1129±2 $cm^{-1}$, about 1157±2 $cm^{-1}$, about 1186±2 $cm^{-1}$, about 1235±2 $cm^{-1}$, about 1267±2 $cm^{-1}$, about 1338±2 $cm^{-1}$, about 1353±2 $cm^{-1}$, about 1418±2 $cm^{-1}$, about 2364±2 $cm^{-1}$, about 2787±2 $cm^{-1}$ and about 2828±2 $cm^{-1}$.

Another aspect of the present invention relates to a process for the production of the crystalline form L described above comprising the step of (a) drying of the crystal crystalline form B according to the invention under vacuum, preferably at a vacuum of at most 900 mbar, more preferably at a vacuum of at most 500 mbar, still more preferably at a vacuum of at most 300 mbar, yet more preferably at a vacuum of at most 200 mbar, and most preferably at a vacuum of at most 100 mbar.

Accordingly, the crystalline form L may be obtained according to the process for the production of the crystalline form B as described above, wherein the drying step (c-3) or respectively (d-4) takes place under vacuum, i.e. the respective drying step may be replaced by the step (a).

A further aspect of the present invention relates to a crystalline form L that is obtainable by the process as described above.

In some embodiments, the crystalline forms make it possible to obtain (1r,4r)-6'-fluoro-N,N-dimethyl-4-phenyl-4', 9'-dihydro-3'H-spiro[cyclohexane-1,1'-pyrano[3,4b]indol]-4-amine in the form of the free base with high yields and high purity. These forms are further distinguished in that they have fundamentally different properties, which may provide advantages.

In some embodiments, the crystalline forms of the present invention are characterized by their simplicity for handling and metering of the active ingredient, i.e. of (1r,4r)-6'-fluoro-N,N-dimethyl-4-phenyl-4',9'-dihydro-3'H-spiro[cyclohexane-1,1'-pyrano[3,4b]indol]-4-amine.

For the purpose of the specification, the term "active ingredient" preferably refers to the pharmacologically active ingredient (1r,4r)-6'-fluoro-N,N-dimethyl-4-phenyl-4',9'-dihydro-3'H-spiro[cyclohexane-1,1'-pyrano[3,4b]indol]-4-amine and its physiologically acceptable salts. Unless expressly stated otherwise, it preferably refers to the free base.

In some embodiments, it has been surprisingly found that (1r,4r)-6'-fluoro-N,N-dimethyl-4-phenyl-4',9'-dihydro-3'H-spiro[cyclohexane-1,1'-pyrano[3,4b]indol]-4-amine is capable of forming two ansolvate forms (crystalline forms A and I), two different hydrates (crystalline forms B and H), a partly dehydrated form (crystalline form L) and five different solvates with organic solvents (crystalline forms C, D, E, F, G).

In some embodiments, it has been surprisingly found that crystalline form A is thermodynamically stable at a relative humidity equal or below 60%. In some embodiments, it has been found that crystalline form B is the most thermodynamically stable form at higher relative humidity (r.h.≥40%).

In some embodiments, it has been surprisingly found that the crystalline forms according to the invention are useful for the separation of (1r,4r)-6'-fluoro-N,N-dimethyl-4-phenyl-4', 9'-dihydro-3'H-spiro[cyclohexane-1,1'-pyrano[3,4, b]indol]-4-amine from its diastereomer, i.e. (1s,4s)-6'-fluoro-N,N-dimethyl-4-phenyl-4',9'-dihydro-3'H-spiro[cyclo-hexane-1, 1'-pyrano[3,4, b]indol]-4-amine. Chemical synthesis of (1r,4r)-6'-fluoro-N,N-dimethyl-4-phenyl-4',9'-dihydro-3'H-spiro[cyclohexane-1,1'-pyrano[3,4, b]indol]-4-amine typically yields mixtures of both diastereomers in various ratios and there is a demand for methods that allow easy and efficient purification of (1r,4r)-6'-fluoro-N,N-dimethyl-4-phenyl-4',9'-dihydro-3'H-spiro[cyclohexane-1,1'-pyrano[3,4, b]indol]-4-amine.

Another aspect of the invention relates to a method for the separation of (1r,4r)-6'-fluoro-N,N-dimethyl-4-phenyl-4',9'-dihydro-3'H-spiro[cyclohexane-1,1'-pyrano[3,4, b]indol]-4-amine from (1s,4s)-6'-fluoro-N,N-dimethyl-4-phenyl-4',9'-dihydro-3'H-spiro[cyclohexane-1,1'-pyrano[3,4, b]indol]-4-amine comprising the process for obtaining a crystalline form of (1r,4r)-6'-fluoro-N,N-dimethyl-4-phenyl-4',9'-dihydro-3'H-spiro[cyclohexane-1,1'-pyrano[3,4, b]indol]-4-amine according to the invention as described above, preferably for obtaining any of crystalline forms C, D, E or F.

Another aspect of the invention relates to a method for the preparation or for the purification of (1r,4r)-6'-fluoro-N,N-dimethyl-4-phenyl-4',9'-dihydro-3'H-spiro[cyclohexane-1,1'-pyrano[3,4, b]indol]-4-amine, the free base or a physiologically acceptable salt thereof, the method comprising the steps of (i) providing a mixture of diastereomers comprising (1r,4r)-6'-fluoro-N,N-dimethyl-4-phenyl-4',9'-dihydro-3'H-spiro[cyclohexane-1,1'-pyrano[3,4, b]indol]-4-amine and (1s,4s)-6'-fluoro-N,N-dimethyl-4-phenyl-4',9'-dihydro-3'H-spiro[cyclohexane-1,1'-pyrano[3,4, b]indol]-4-amine; preferably with an excess of (1r,4r)-6'-fluoro-N,N-dimethyl-4-phenyl-4',9'-dihydro-3'H-spiro[cyclohexane-1,1'-pyrano[3,4, b]indol]-4-amine; and (ii) employing said mixture of diastereomers obtained in step (i) as starting material and preparing therefrom a crystalline form of (1r,4r)-6'-fluoro-N,N-dimethyl-4-phenyl-4',9'-dihydro-3'H-spiro[cyclohexane-1,1'-pyrano[3,4, b]indol]-4-amine selected from the group consisting of crystalline forms A, B, C, D, E, F, G, H, I and L according to any of the processes according to the invention as described above; and (iii) separating the crystalline form of (1r,4r)-6'-fluoro-N,N-dimethyl-4-phenyl-4',9'-dihydro-3'H-spiro[cyclohexane-1,1'-pyrano[3,4, b]indol]-4-amine obtained in step (ii) from the remainder of the mixture of diastereomers; preferably by precipitation and filtering; and (iv) optionally, converting the crystalline form of (1r,4r)-6'-fluoro-N,N-dimethyl-4-phenyl-4',9'-dihydro-3'H-spiro[cyclohexane-1,1'-pyrano[3,4, b]indol]-4-amine into another crystalline form of crystalline form of (1r,4r)-6'-fluoro-N,N-dimethyl-4-phenyl-4',9'-dihydro-3'H-spiro[cyclohexane-1,1'-pyrano[3,4, b]indol]-4-amine obtained in step, preferably by drying, preferably into crystalline form A.

Preferably, step (ii) involves the sub-steps of (ii-a) dissolving said mixture of diastereomers in a solvent or solvent mixture comprising dimethyl sulfoxide or another dipolar aprotic solvent;

(ii-b) adding an alcohol, preferably selected from the group consisting of methanol, ethanol, 1-propanol and 2-propanol, more preferably 2-propanol;

(ii-c) precipitating the alcoholate of (1r,4r)-6'-fluoro-N,N-dimethyl-4-phenyl-4',9'-dihydro-3'H-spiro[cyclohexane-1,1'-pyrano[3,4, b]indol]-4-amine, preferably crystalline form C, D, E or F according to the invention; and (ii-d) separating the precipitate obtained in step (ii-c) from the remainder of the solution containing (1s,4s)-6'-fluoro-N,N-dimethyl-4-phenyl-4',9'-dihydro-3'H-spiro[cyclohexane-1,1'-pyrano[3,4, b]indol]-4-amine.

It has been surprisingly found that (1r,4r)-6'-fluoro-N,N-dimethyl-4-phenyl-4',9'-dihydro-3'H-spiro[cyclohexane-1,1'-pyrano[3,4, b]indol]-4-amine forms crystalline alcoholates under conditions where its diastereomer, (1s,4s)-6'-fluoro-N,N-dimethyl-4-phenyl-4',9'-dihydro-3'H-spiro[cyclohexane-1,1'-pyrano[3,4, b]indol]-4-amine, does not form alcoholates or forms alcoholates having a substantially different solubility, thereby allowing for easy and efficient separation of diastereomers. Further, it has been found that the precipitation can be effected by providing solutions of both diastereomers in dimethyl sulfoxide (DMSO) and adding the alcohol as antisolvens. There is indication that surprisingly, the crystalline alcohol solvate of (1r,4r)-6'-fluoro-N,N-dimethyl-4-phenyl-4',9'-dihydro-3'H-spiro[cyclohexane-1,1'-pyrano[3,4, b]indol]-4-amine is formed without simultaneously forming significant amounts of crystalline dimethyl sulfoxide solvate. This is advantageous for several reasons, particularly in view of the high boiling point of DMSO—there is no need to evaporate DMSO from the precipitate.

Another aspect of the invention relates to the crystalline form of (1r,4r)-6'-fluoro-N,N-dimethyl-4-phenyl-4',9'-dihydro-3'H-spiro[cyclohexane-1,1'-pyrano[3,4,b]indol]-4-amine that is obtainable by the method described above.

Mixtures of the crystalline forms A, B, C, D, E, F, G, H, I and L, preferably mixtures of two of these crystalline forms, are also included within the scope of the present invention. For example, such mixtures of two crystalline forms may be obtained from crystalline form A, B, C, D, E, F, G, H, I or L during a crystallization process (e.g. cooling or evaporation) or respectively during a separation process (e.g. filtration), or respectively during a process where heat is applied (e.g. drying), or respectively during a process where mechanical energy is inserted (e.g. milling or grinding). Furthermore, such mixtures of two crystalline forms may be obtained from crystalline form A, B, C, D, E, F, G, H, I or L by a partial uptake of hydrate water or respectively by a partial loss of hydrate water, or respectively by a solvent/water exchange.

The modifications A, B, C, D, E, F, G, H, I and L according to the invention may optionally also form co-crystals and/or clathrates. These are all included within the scope of the present invention.

In a preferred embodiment, the crystalline form according to the invention is subsequently converted into an amorphous form.

Suitable methods for the preparation of amorphous forms are known to a person skilled in the art. For example, amorphous forms or amorphous mixtures may be obtained by means of the following methods or combinations thereof:
i) precipitation from solution,
ii) lyophilization,
iii) spray drying,
iv) melts extrusion,
v) flash evaporation,
vi) quench cooling of the melt,
vii) grinding at ambient or liquid nitrogen temperatures,
viii) working under protection of an inert atmosphere (e.g. gaseous nitrogen or argon), and/or
ix) using capillary crystallization technology.

Another aspect of the invention relates to an amorphous form, preferably to an amorphous form that is obtainable by any of the above methods or combinations thereof.

Another aspect of the invention relates to a pharmaceutical composition comprising a mixture of at least two crystalline forms as described herein; or a mixture of at least one crystalline form as described herein with an amorphous form; or a mixture of at least one crystalline form as described herein with a salt of (1r,4r)-6'-fluoro-N,N-dimethyl-4-phenyl-4',9'-dihydro-3'H-spiro[cyclohexane-1,1'-pyrano[3,4, b]indol]-4-amine with sulfuric acid, preferably the hydrogen sulfate salt; in any mixing ratio.

The pharmaceutical composition according to the invention preferably comprises
(i) at least about one pharmaceutically acceptable additive and/or adjuvant; and
(ii) an active ingredient that comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine.

The active ingredient in the pharmaceutical composition according to the invention comprises
a crystalline form of (1r,4r)-6'-fluoro-N,N-dimethyl-4-phenyl-4',9'-dihydro-3'H-spiro[cyclohexane-1,1'-pyrano[3,4b]indol]-4-amine,
and may additionally comprise other constituents, e.g.
a non-crystalline form of (1r,4r)-6'-fluoro-N,N-dimethyl-4-phenyl-4',9'-dihydro-3'H-spiro[cyclohexane-1,1'-pyrano[3,4b]indol]-4-amine; and/or
physiologically acceptable salts and/or solvates of (1r,4r)-6'-fluoro-N,N-dimethyl-4-phenyl-4',9'-dihydro-3'H-spiro[cyclohexane-1,1'-pyrano[3,4b]indol]-4-amine; and/or
crystalline or non-crystalline forms of (1s,4s)-6'-fluoro-N,N-dimethyl-4-phenyl-4',9'-dihydro-3'H-spiro[cyclohexane-1,1'-pyrano[3,4b]indol]-4-amine; and/or
physiologically acceptable salts and/or solvates of (1s,4s)-6'-fluoro-N,N-dimethyl-4-phenyl-4',9'-dihydro-3'H-spiro[cyclohexane-1,1'-pyrano[3,4b]indol]-4-amine; and/or
other pharmacologically active substances.

Preferably, in DSC analyses, the active ingredient contained in the pharmaceutical composition according to the present invention preferably exhibits an endothermal event with a peak temperature above 295° C., or above 296° C., or above 297° C., or above 298° C., or above 299° C. or above 300° C.; preferably at about 295-310° C. (i.e., the active ingredient has a melting endotherm at about 295-310° C.) or at about 300-310° C., such as for example at about 298-308° C., or even at about 300-306° C., or at about 301-307° C., or at about 302-308° C., or at about 303-309° C., or at about 302-305° C. In some preferred embodiments, the active ingredient exhibits an endothermal event with a peak temperature at about 303-304° C., or at about 304-305° C., or at about 305-306° C.

In a preferred embodiment, the active ingredient contained in the pharmaceutical dosage form according to the invention comprises (1r,4r)-6'-fluoro-N,N-dimethyl-4-phenyl-4',9'-dihydro-3'H-spiro[cyclohexane-1,1'-pyrano[3,4b]indol]-4-amine, optionally its (1s,4s)-diastereomer, namely (1s,4s)-6'-fluoro-N,N-dimethyl-4-phenyl-4',9'-dihydro-3'H-spiro[cyclo-hexane-1,1'-pyrano[3,4b]indol]-4-amine, in combination with one or more other pharmacologically active substances.

In another preferred embodiment, the pharmaceutical dosage form according to the invention does not comprise other pharmacologically active substances. According to this embodiment, the active ingredient contained in the pharmaceutical dosage form according to the invention does not comprise other pharmacologically active substances, but consists of 6'-fluoro-N,N-dimethyl-4-phenyl-4',9'-dihydro-3'H-spiro[cyclohexane-1,1'-pyrano[3,4b]indol]-4-amine, i.e. the (1r,4r)-diastereomer, namely (1r,4r)-6'-fluoro-N,N-dimethyl-4-phenyl-4',9'-dihydro-3'H-spiro[cyclohexane-1,1'-pyrano[3,4b]indol]-4-amine, and its optionally present (1s,4s)-diastereomer, namely (1s,4s)-6'-fluoro-N,N-dimethyl-4-phenyl-4',9'-dihydro-3'H-spiro[cyclohexane-1,1'-pyrano[3,4b]indol]-4-amine, whereas both diastereomers can be present in crystalline or non-crystalline form, as free bases or physiologically acceptable salts thereof, as ansolvates or solvates.

In the following, unless expressly stated otherwise, all percentages defined relative to the "total content of 6'-fluoro-N,N-dimethyl-4-phenyl-4',9'-dihydro-3'H-spiro[cyclohexane-1,1'-pyrano[3,4b]indol]-4-amine" refer to the overall sum of
the content of (1r,4r)-6'-fluoro-N,N-dimethyl-4-phenyl-4',9'-dihydro-3'H-spiro[cyclo-hexane-1,1'-pyrano[3,4b]indol]-4-amine, in any crystalline and non-crystalline form, in form of the free base or any physiologically acceptable salt, in form of any solvate or ansolvate; and
the content of (1s,4s)-6'-fluoro-N,N-dimethyl-4-phenyl-4',9'-dihydro-3'H-spiro[cyclo-hexane-1,1'-pyrano[3,4b]indol]-4-amine, in any crystalline and non-crystalline form, in form of the free base or any physiologically acceptable salt, in form of any solvate or ansolvate.

In particularly preferred embodiments of the invention, the pharmaceutical composition according to the invention comprises
(i) at least about one pharmaceutically acceptable additive and/or adjuvant; and
(ii) an active ingredient that comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern:
comprising characteristic peaks at about 18.3±0.2 degrees 2θ, about 18.6±0.2 degrees 2θ and about 26.3±0.2 degrees 2θ,
preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
wherein preferably the diastereomeric excess (de) of (1r,4r)-6'-fluoro-N,N-dimethyl-4-phenyl-4',9'-dihydro-3'H-spiro[cyclohexane-1,1'-pyrano[3,4b]indol]-4-amine in the pharmaceutical composition is at least about 97.6% de.

Preferably, the diastereomeric excess of (1r,4r)-6'-fluoro-N,N-dimethyl-4-phenyl-4',9'-dihydro-3'H-spiro[cyclohexane-1,1'-pyrano[3,4b]indol]-4-amine with respect to its (1s,4s)-diastereomer, i.e. (1s,4s)-6'-fluoro-N,N-dimethyl-4-phenyl-4',9'-dihydro-3'H-spiro[cyclo-hexane-1,1'-pyrano[3,4b]indol]-4-amine, in the pharmaceutical composition according to the invention is at least about 90% de, or at least about 91% de, or at least about 92% de, or at least about 93% de, or at least about 94% de, or at least about 95.0% de, or at least about 95.5% de, or at least about 96.0% de, or at least about 96.5% de, or at least about 97.0% de, or at least about 97.2% de, or at least about 97.4% de, or at least about 97.6% de, or at least about 97.8% de, or at least about 98.0% de, or at least about 98.2% de, or at least about 98.4% de, or at least about 98.6% de, or at least about 98.8% de, or at least about 99.0% de, or at least about 99.2% de, or at least about 99.4% de, or at least about 99.6% de, or at least about 99.8% de. Preferably, the diastereomeric excess is based on mole fractions, not on weight fractions, such that the weight of solvent molecules in solvates, if any, and the weight of conjugate salt moieties in physiologically acceptable salts, if any, respectively, does not influence the value of the diastereomeric excess. The diastereomeric excess of the (1r,4r)-diastereomer can be calculated by the following formula:

$$de[\%] = \frac{[(1r, 4r)\text{diastereomer}] - [(1s, 4s)\text{diastereomer}]}{[(1r, 4r)\text{diastereomer}] + [(1s, 4s)\text{diastereomer}]} * 100$$

In a preferred embodiment, the content of (1r,4r)-6'-fluoro-N,N-dimethyl-4-phenyl-4',9'-dihydro-3'H-spiro[cyclohexane-1,1'-pyrano[3,4b]indol]-4-amine in the pharmaceutical composition according to the invention is at least about 95 wt.-%, or at least about 96 wt.-%, or at least about 97 wt.-%, or at least about 97.5 wt.-%, or at least about 98.0 wt.-%, or at least about 98.2 wt.-%, or at least about 98.4 wt.-%, or at least about 98.6 wt.-%, or at least about 98.8 wt.-%, or at least about 99.0 wt.-%, or at least about 99.2 wt.-%, or at least about 99.4 wt.-%, or at least about 99.6 wt.-%, or at least about 99.8 wt.-%, relative to the total content of 6'-fluoro-N,N-dimethyl-4-phenyl-4',9'-dihydro-3'H-spiro[cyclohexane-1,1'-pyrano-[3,4b]indol]-4-amine.

In a preferred embodiment, the content of (1r,4r)-6'-fluoro-N,N-dimethyl-4-phenyl-4',9'-dihydro-3'H-spiro[cyclohexane-1,1'-pyrano[3,4b]indol]-4-amine in the pharmaceutical composition according to the invention is at least about 95 mole.-%, or at least about 96 mole.-%, or at least about 97 mole.-%, or at least about 97.5 mole.-%, or at least about 98.0 mole.-%, or at least about 98.2 mole.-%, or at least about 98.4 mole.-%, or at least about 98.6 mole.-%, at least about 98.8 mole.-%, or at least about 99.0 mole.-%, or at least about 99.2 mole.-%, or at least about 99.4 mole.-%, or at least about 99.6 mole.-%, or at least about 99.8 mole.-%, relative to the total content of 6'-fluoro-N,N-dimethyl-4-phenyl-4',9'-dihydro-3'H-spiro[cyclohexane-1,1'-pyrano[3,4b]indol]-4-amine.

In a preferred embodiment, the content of (1s,4s)-6'-fluoro-N,N-dimethyl-4-phenyl-4',9'-dihydro-3'H-spiro[cyclohexane-1,1'-pyrano[3,4b]indol]-4-amine in the pharmaceutical composition according to the invention is at most about 5 wt.-%, or at most about 4 wt.-%, or at most about 3 wt.-%, or at most about 2.5 wt.-%, or at most about 2.0 wt.-%, or at most about 1.5 wt.-%, or at most about 1.2 wt.-%, or at most about 1.0 wt.-%, or at most about 0.8 wt.-%, or at most about 0.6 wt.-%, or at most about 0.4 wt.-%, or at most about 0.2 wt.-%, relative to the total content of 6'-fluoro-N,N-dimethyl-4-phenyl-4',9'-dihydro-3'H-spiro[cyclo-hexane-1,1'-pyrano[3,4b]indol]-4-amine.

In a preferred embodiment, the content of (1s,4s)-6'-fluoro-N,N-dimethyl-4-phenyl-4',9'-dihydro-3'H-spiro[cyclohexane-1,1'-pyrano[3,4b]indol]-4-amine in the pharmaceutical composition according to the invention is at most about 5 mole.-%, or at most about 4 mole.-%, or at most about 3 mole.-%, or at most about 2.5 mole.-%, or at most about 2.0 mole.-%, or at most about 1.5 mole.-%, or at most about 1.2 mole.-%, or at most about 1.0 mole.-%, or at most about 0.8 mole.-%, or at most about 0.6 mole.-%, or at most about 0.4 mole.-%, or at most about 0.2 mole.-%, relative to the total content of 6'-fluoro-N,N-dimethyl-4-phenyl-4',9'-dihydro-3'H-spiro[cyclohexane-1,1'-pyrano[3,4b]indol]-4-amine.

The content of the diastereomers and the diastereomeric excess can be determined by routine experimentation, e.g. by HPLC.

In particularly preferred embodiments of the invention, the active ingredient of the pharmaceutical composition according to the invention comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
and may additionally comprise other crystalline or non-crystalline forms of (1r,4r)-6'-fluoro-N,N-dimethyl-4-phenyl-4',9'-dihydro-3'H-spiro[cyclohexane-1,1'-pyrano[3,4b]indol]-4-amine or of its physiologically acceptable salts.

Preferably, the content of the crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
is at least about 60 wt.-%, or at least about 65 wt.-%, or at least about 70 wt.-%, or at least about 75 wt.-%, or at least about 80 wt.-%, or at least about 85 wt.-%, or at least about 90 wt.-%, or at least about 92 wt.-%, or at least about 94 wt.-%, or at least about 96 wt.-%, or at least about 98.0 wt.-%, or at least about 98.1 wt.-%, or at least about 98.2 wt.-%, or at least about 98.3 wt.-%, or at least about 98.4 wt.-%, or at least about 98.5 wt.-%, or at least about 98.6 wt.-%, or at least about 98.7 wt.-%, or at least about 98.8 wt.-%, or at least about 98.9 wt.-%, or at least about 99.0 wt.-%, or at least about 99.1 wt.-%, or at least about 99.2 wt.-%, or at least about 99.3 wt.-%, or at least about 99.4 wt.-%, or at least about 99.5 wt.-%, or at least about 99.6 wt.-%, or at least about 99.7 wt.-%, or at least about 99.8 wt.-%, or at least about 99.9 wt.-%, relative to the total content of (1r,4r)-6'-fluoro-N,N-dimethyl-4-phenyl-4',9'-dihydro-3'H-spiro[cyclohexane-1,1'-pyrano[3,4b]indol]-4-amine in the pharmaceutical composition, i.e. relative to the total content of all crystalline and non-crystalline forms of (1r,4r)-6'-fluoro-N,N-dimethyl-4-phenyl-4',9'-dihydro-3'H-spiro[cyclohexane-1,1'-pyrano-[3,4b]indol]-4-amine including its physiologically acceptable salts and/or any solvates and ansolvates.

Preferably, the content of the crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
is at least about 60 mole.-%, or at least about 65 mole.-%, or at least about 70 mole.-%, or at least about 75 mole.-%, or at least about 80 mole.-%, or at least about 85 mole.-%, or at least about 90 mole.-%, or at least about 92 mole.-%, or at least about 94 mole.-%, or at least about 96 mole.-%, or at least about 98.0 mole.-%, or at least about 98.1 mole.-%, or at least about 98.2 mole.-%, or at least about 98.3 mole.-%, or at least about 98.4 mole.-%, or at least about 98.5 mole.-%, or at least about 98.6 mole.-%, or at least about 98.7 mole.-%, or at least about 98.8 mole.-%, or at least about 98.9 mole.-%, or at least about 99.0 mole.-%, or at least about 99.1 mole.-%, or at least about 99.2 mole.-%, or at least about 99.3 mole.-%, or at least about 99.4 mole.-%, or at least about 99.5 mole.-%, or at least about 99.6 mole.-%, or at least about 99.7 mole.-%, or at least about 99.8 mole.-%, or at least about 99.9 mole.-%, relative to the total content of (1r,4r)-6'-fluoro-N,N-dimethyl-4-phenyl-4',9'-dihydro-3'H-spiro[cyclohexane-1,1'-pyrano [3,4b]indol]-4-amine in the pharmaceutical composition, i.e. relative to the total content of all crystalline and non-crystalline forms of (1r,4r)-6'-fluoro-N,N-dimethyl-4-phenyl-4',9'-dihydro-3'H-spiro[cyclohexane-1,1'-pyrano-[3,4b]indol]-4-amine including its physiologically acceptable salts and/or any solvates and ansolvates.

Preferably, the content of the crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
in the pharmaceutical composition according to the invention is at least about 60 wt.-%, or at least about 65 wt.-%, or at least about 70 wt.-%, or at least about 75 wt.-%, or at least about 80 wt.-%, or at least about 85 wt.-%, or at least about 90 wt.-%, or at least about 92 wt.-%, or at least about 94 wt.-%, or at least about 96 wt.-%, or at least about 98.0 wt.-%, or at least about 98.1 wt.-%, or at least about 98.2 wt.-%, or at least about 98.3 wt.-%, or at least about 98.4 wt.-%, or at least about 98.5 wt.-%, or at least about 98.6 wt.-%, or at least about 98.7 wt.-%, or at least about 98.8 wt.-%, or at least about 98.9 wt.-%, or at least about 99.0 wt.-%, or at least about 99.1 wt.-%, or at least about 99.2 wt.-%, or at least about 99.3 wt.-%, or at least about 99.4 wt.-%, or at least about 99.5 wt.-%, or at least about 99.6 wt.-%, or at least about 99.7 wt.-%, or at least about 99.8 wt.-%, or at least about 99.9 wt.-%, relative to the total content of 6'-fluoro-N,N-dimethyl-4-phenyl-4',9'-dihydro-3'H-spiro[cyclohexane-1,1'-pyrano[3,4b]indol]-4-amine in the pharmaceutical composition, i.e. relative to the total content of 6'-fluoro-N,N-dimethyl-4-phenyl-4',9'-dihydro-3'H-spiro[cyclohexane-1,1'-pyrano[3,4b]-indol]-4-amine.

Preferably, the content of the crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
in the pharmaceutical composition according to the invention is at least about 60 mole.-%, or at least about 65 mole.-%, or at least about 70 mole.-%, or at least about 75 mole.-%, or at least about 80 mole.-%, or at least about 85 mole.-%, or at least about 90 mole.-%, or at least about 92 mole.-%, or at least about 94 mole.-%, or at least about 96 mole.-%, or at least about 98.0 mole.-%, or at least about 98.1 mole.-%, or at least about 98.2 mole.-%, or at least about 98.3 mole.-%, or at least about 98.4 mole.-%, or at least about 98.5 mole.-%, or at least about 98.6 mole.-%, or at least about 98.7 mole.-%, or at least about 98.8 mole.-%, or at least about 98.9 mole.-%, or at least about 99.0 mole.-%, or at least about 99.1 mole.-%, or at least about 99.2 mole.-%, or at least about 99.3 mole.-%, or at least about 99.4 mole.-%, or at least about 99.5 mole.-%, or at least about 99.6 mole.-%, or at least about 99.7 mole.-%, or at least about 99.8 mole.-%, or at least about 99.9 mole.-%, relative to the total content of 6'-fluoro-N,N-dimethyl-4-phenyl-4',9'-dihydro-3'H-spiro[cyclohexane-1,1'-pyrano[3,4b]indol]-4-amine in the pharmaceutical composition, i.e. relative to the total content of 6'-fluoro-N,N-dimethyl-4-phenyl-4',9'-dihydro-3'H-spiro[cyclohexane-1,1'-pyrano-[3,4b]indol]-4-amine.

In a preferred embodiment of the invention, the pharmaceutical composition according to the invention comprises
(i) at least about one pharmaceutically acceptable additive and/or adjuvant; and
(ii) an active ingredient that comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
wherein the pharmaceutical composition of the invention does not contain detectable amounts of 4-dimethylamino-4-phenylcyclohexanone. In case that the pharmaceutical composition does contain detectable amounts of 4-dimethylamino-4-phenylcyclohexanone, the content of 4-dimethylamino-4-phenylcyclohexanone is preferably at most about 5.0 wt.-%, or at most about 4.0 wt.-%, or at most about 3.0 wt.-%, or at most about 2.5 wt.-%, or at most about 2.0 wt.-%, or at most about 1.5 wt.-%, or at most about 1.0 wt.-%, or at most about 0.8 wt.-%, or at most about 0.6 wt.-%, or at most about 0.4 wt.-%, or at most about 0.2 wt.-%, or at most about 0.1 wt.-%, relative to the total content of 6'-fluoro-N,N-dimethyl-4-phenyl-4',9'-dihydro-3'H-spiro[cyclohexane-1,1'-pyrano[3,4b]indol]-4-amine.

In a preferred embodiment of the invention, the pharmaceutical composition according to the invention comprises
(i) at least about one pharmaceutically acceptable additive and/or adjuvant; and
(ii) an active ingredient that comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
    comprising characteristic peaks at about 18.3±0.2 degrees 2θ, about 18.6±0.2 degrees 2θ and about 26.3±0.2 degrees 2θ,
    preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
wherein the pharmaceutical composition of the invention does not contain detectable amounts of 2-(2-(4-(dimethylamino)-4-phenylcyclohex-1-enyl)-5-fluoro-1H-indol-3-yl)ethanol. In case that the pharmaceutical composition does contain detectable amounts of 2-(2-(4-(dimethylamino)-4-phenylcyclohex-1-enyl)-5-fluoro-1H-indol-3-yl)ethanol, the content of 2-(2-(4-(dimethylamino)-4-phenylcyclohex-1-enyl)-5-fluoro-1H-indol-3-yl)ethanol is preferably at most about 3.0 wt.-%, or at most about 2.5 wt.-%, or at most about 2.0 wt.-%, or at most about 1.5 wt.-%, or at most about 1.0 wt.-%, or at most about 0.8 wt.-%, or at most about 0.6 wt.-%, or at most about 0.4 wt.-%, or at most about 0.2 wt.-%, or at most about 0.1 wt.-%, relative to the total content of 6'-fluoro-N,N-dimethyl-4-phenyl-4',9'-dihydro-3'H-spiro[cyclo-hexane-1,1'-pyrano[3,4b]indol]-4-amine.

In a preferred embodiment of the invention, the pharmaceutical composition according to the invention comprises
(i) at least about one pharmaceutically acceptable additive and/or adjuvant; and
(ii) an active ingredient that comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
comprising characteristic peaks at about 18.3±0.2 degrees 2θ, about 18.6±0.2 degrees 2θ and about 26.3±0.2 degrees 2θ,
preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
wherein the pharmaceutical composition of the invention does not contain detectable amounts of methanol, or if the pharmaceutical composition does contain detectable amounts of methanol, the content of methanol is preferably at most about 0.6 wt.-%, or at most about 0.4 wt.-%, or at most about 0.2 wt.-%, or at most about 0.1 wt.-%, relative to the total content of 6'-fluoro-N,N-dimethyl-4-phenyl-4',9'-dihydro-3'H-spiro[cyclohexane-1,1'-pyrano-[3,4b]indol]-4-amine.

In a preferred embodiment of the invention, the pharmaceutical composition according to the invention comprises
(i) at least about one pharmaceutically acceptable additive and/or adjuvant; and
(ii) an active ingredient that comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine having an X-ray powder diffraction pattern
comprising characteristic peaks at about 18.3±0.2 degrees 2θ, about 18.6±0.2 degrees 2θ and about 26.3±0.2 degrees 2θ,
preferably further comprising one or more characteristics peaks at about 31.6±0.2 degrees 2θ, and/or about 11.7±0.2 degrees 2θ, and/or about 7.8±0.2 degrees 2θ, and/or about 33.6±0.2 degrees 2θ, and/or about 17.6±0.2 degrees 2θ, and/or about 19.4±0.2 degrees 2θ;
wherein the pharmaceutical composition of the invention does not contain detectable amounts of crystalline form E as described herein, or if the pharmaceutical composition does contain detectable amounts of crystalline form E as described herein, the content of crystalline form E as described herein is preferably at most about 3.0 wt.-%, or at most about 2.5 wt.-%, or at most about 2.0 wt.-%, or at most about 1.5 wt.-%, or at most about 1.0 wt.-%, or at most about 0.8 wt.-%, or at most about 0.6 wt.-%, or at most about 0.4 wt.-%, or at most about 0.2 wt.-%, or at most about 0.1 wt.-%, relative to the total content of 6'-fluoro-N,N-di-methyl-4-phenyl-4',9'-dihydro-3'H-spiro[cyclohexane-1,1'-pyrano[3,4b]indol]-4-amine.

In one preferred embodiment, the pharmaceutical composition according to the invention comprises a crystalline ansolvate of (1r,4r)-6'-fluoro-N,N-dimethyl-4-phenyl-4',9'-dihydro-3'H-spiro[cyclohexane-1,1'-pyrano[3,4, b]indol]-4-amine as well as crystalline solvate of (1r,4r)-6'-fluoro-N,N-dimethyl-4-phenyl-4',9'-dihydro-3'H-spiro[cyclohexane-1,1'-pyrano-[3,4, b]indol]-4-amine, preferably an alcohol solvate, such as an alcohol solvate for example wherein the alcohol is selected from ethanol and isopropanol (in some especially preferred embodiments isopropanol).

Preferably, the content of the crystalline ansolvate of (1r,4r)-6'-fluoro-N,N-dimethyl-4-phenyl-4',9'-dihydro-3'H-spiro[cyclohexane-1,1'-pyrano[3,4, b]indol]-4-amine relative to the total content of (1r,4r)-6'-fluoro-N,N-dimethyl-4-phenyl-4',9'-dihydro-3'H-spiro[cyclohexane-1,1'-pyrano[3,4, b]indol]-4-amine (ansolvate(s)+solvate(s)) is at least about 40 wt.-%, more preferably at least about 60 wt.-%, still more preferably at least about 80 wt.-%, yet more preferably at least about 90 wt.-%, even more preferably at least about 95 wt.-%, most preferably at least about 99 wt.-%, and in particular at least about 99.5 wt.-%.

Preferably, the content of the crystalline ansolvate of (1r,4r)-6'-fluoro-N,N-dimethyl-4-phenyl-4',9'-dihydro-3'H-spiro[cyclohexane-1,1'-pyrano[3,4, b]indol]-4-amine relative to the total content of (1r,4r)-6'-fluoro-N,N-dimethyl-4-phenyl-4',9'-dihydro-3'H-spiro[cyclohexane-1,1'-pyrano[3,4, b]indol]-4-amine (ansolvate(s)+solvate(s)) is at most about 99.5 wt.-%, more preferably at most about 99 wt.-%, still more preferably at most about 95 wt.-%, yet more preferably at most about 90 wt.-%, even more preferably at most about 80 wt.-%, most preferably at most about 60 wt.-%, and in particular at most about 40 wt.-%.

In another preferred embodiment, the pharmaceutical composition according to the invention comprises crystalline form A of (1r,4r)-6'-fluoro-N,N-dimethyl-4-phenyl-4',9'-dihydro-3'H-spiro[cyclohexane-1,1'-pyrano3,4, b]indol]-4-amine as well as crystalline form I of (1r,4r)-6'-fluoro-N,N-dimethyl-4-phenyl-4',9'-dihydro-3'H-spiro[cyclohexane-1,1'-pyrano[3,4, b]indol]-4-amine.

In a preferred embodiment, the relative weight content of crystalline form A is greater than the relative weight content of crystalline form I. In another preferred embodiment, the relative weight content of crystalline form I is greater than the relative weight content of crystalline form A.

Preferably, the content of the crystalline form A of (1r,4r)-6'-fluoro-N,N-dimethyl-4-phenyl-4',9'-dihydro-3'H-spiro[cyclohexane-1,1'-pyrano[3,4, b]indol]-4-amine relative to the total content of (1r,4r)-6'-fluoro-N,N-dimethyl-4-phenyl-4',9'-dihydro-3'H-spiro[cyclohexane-1,1'-pyrano[3,4, b]indol]-4-amine (crystalline form A+crystalline form I) is at least 40 wt.-%, more preferably at least about 60 wt.-%, still more preferably at least about 80 wt.-%, yet more preferably at least about 90 wt.-%, even more preferably at least about 95 wt.-%, most preferably at least about 99 wt.-%, and in particular at least about 99.5 wt.-%.

Preferably, the content of the crystalline form A of (1r,4r)-6'-fluoro-N,N-dimethyl-4-phenyl-4',9'-dihydro-3'H-spiro[cyclohexane-1,1'-pyrano[3,4, b]indol]-4-amine relative to the total content of (1r,4r)-6'-fluoro-N,N-dimethyl-4-phenyl-4',9'-dihydro-3'H-spiro[cyclohexane-1,1'-pyrano[3,4, b]indol]-4-amine (crystalline form A+crystalline form I) is at most 99.5 wt.-%, more preferably at most about 99 wt.-%, still more preferably at most about 95 wt.-%, yet more preferably at most about 90 wt.-%, even more preferably at most about 80 wt.-%, most preferably at most about 60 wt.-%, and in particular at most about 40 wt.-%.

In still another preferred embodiment, the pharmaceutical composition according to the invention additionally comprises a salt of (1r,4r)-6'-fluoro-N,N-dimethyl-4-phenyl-4',9'-dihydro-3'H-spiro[cyclohexane-1,1'-pyrano[3,4, b]indol]-4-amine with sulfuric acid, preferably the hydrogen sulfate salt or the sulfate salt, more preferably the hydrogen sulfate salt. Thus, according to this embodiment, the pharmaceutical composition comprises a mixture of both, the crystalline form of (1r,4r)-6'-fluoro-N,N-dimethyl-4-phenyl-4',9'-dihydro- 3'H-spiro-[cyclohexane-1,1'-pyrano[3,4, b]indol]-4-amine (free base), preferably selected from the group consisting of crystalline forms A, B, C, D, E, F, G, H, I and L, as well as a sulfuric acid salt thereof, preferably the hydrogen sulfate salt.

Preferably, the total content of the sulfuric acid salt of (1r,4r)-6'-fluoro-N,N-dimethyl-4-phenyl-4',9'-dihydro-3'H-spiro[cyclohexane-1,1'-pyrano[3,4, b]indol]-4-amine in the pharmaceutical composition, dosage form or active ingredient, such as the hydrogen sulfate salt, is at most about 2000 ppm, more preferably at most about 1000 ppm, still more preferably at most about 750 ppm, yet more preferably at most about 500 ppm, even more preferably at most about 250 ppm, most preferably at most about 100 ppm, and in particular at most about 50 ppm, relative to the total amount (1r,4r)-6'-fluoro-N,N-dimethyl-4-phenyl-4',9'-dihydro-3'H-spiro [cyclohexane-1,1'-pyrano[3,4, b]indol]-4-amine (free base+salts).

Preferably, the total content of the sulfuric acid salt of (1r,4r)-6'-fluoro-N,N-dimethyl-4-phenyl-4',9'-dihydro-3'H-spiro[cyclohexane-1,1'-pyrano[3,4, b]indol]-4-amine in the pharmaceutical composition, dosage form or active ingredient, preferably the hydrogen sulfate salt, is within the range of from about 1 ppm to about 500 ppm, more preferably about 4 ppm to about 440 ppm, still more preferably about 7 ppm to about 380 ppm, yet more preferably about 10 ppm to about 300 ppm, even more preferably about 13 ppm to about 220 ppm, most preferably about 17 ppm to about 140 ppm, and in particular about 20 ppm to about 60 ppm, relative to the total amount (1r,4r)-6'-fluoro-N,N-dimethyl-4-phenyl-4',9'-dihydro-3'H-spiro[cyclohexane-1,1'-pyrano[3,4, b]indol]-4-amine (free base+salts).

Suitable methods for determining the content of the sulfuric acid salt of (1r,4r)-6'-fluoro-N,N-dimethyl-4-phenyl-4',9'-dihydro-3'H-spiro[cyclohexane-1,1'-pyrano[3,4, b]indol]-4-amine are known to those skilled in the art and include e.g. XRPD, elemental analysis, Raman spectroscopy, infrared spectroscopy, chromatographic methods, NMR spectroscopy, thermal analysis, electrophoresis, atom absorption spectroscopy, energy dispersive X-ray spectroscopy thermal methods comprise, among others, e.g. DSC, TGA, modulated temperature DSC, high-speed DSC, melting point, hot-stage XRPD, hot-stage microscopy, heat of solution, microthermal analysis, calorimetry, micro-calorimetry.

In yet another preferred embodiment, the pharmaceutical composition according to the invention comprises a crystalline form of (1r,4r)-6'-fluoro-N,N-dimethyl-4-phenyl-4',9'-dihydro-3'H-spiro[cyclohexane-1,1'-pyrano[3,4, b]indol]-4-amine, preferably selected from the group consisting of crystalline forms A, B, C, D, E, F, G, H, I and L, as well as an amorphous form of (1r,4r)-6'-fluoro-N,N-dimethyl-4-phenyl-4',9'-dihydro-3'H-spiro[cyclohexane-1,1'-pyrano[3,4, b]indol]-4-amine.

Preferably, the degree of crystallinity, i.e. the content of crystalline form(s) of (1r,4r)-6'-fluoro-N,N-dimethyl-4-phenyl-4',9'-dihydro-3'H-spiro[cyclohexane-1,1'-pyrano[3,4, b]indol]-4-amine relative to the total content of (1r,4r)-6'-fluoro-N,N-dimethyl-4-phenyl-4',9'-dihydro-3'H-spiro[cyclohexane-1,1'-pyrano[3,4, b]indol]-4-amine (crystalline form(s)+amorphous form(s)) is at least about 40 wt.-%, more preferably at least about 60 wt.-%, still more preferably at least about 80 wt.-%, yet more preferably at least about 90 wt.-%, even more preferably at least about 95 wt.-%, most preferably at least about 99 wt.-%, and in particular at least about 99.5 wt.-%.

Preferably, the degree of crystallinity, i.e. the content of crystalline form(s) of (1r,4r)-6'-fluoro-N,N-dimethyl-4-phenyl-4',9'-dihydro-3' H-spiro[cyclohexane-1,1'-pyrano[3,4, b]indol]-4-amine relative to the total content of (1r,4r)-6'-fluoro-N,N-dimethyl-4-phenyl-4',9'-dihydro-3'H-spiro[cyclohexane-1,1'-pyrano[3,4, b]indol]-4-amine (crystalline form(s)+amorphous form(s)) is at most about 99.5 wt.-%, more preferably at most about 99 wt.-%, still more preferably at most about 95 wt.-%, yet more preferably at most about 90 wt.-%, even more preferably at most about 80 wt.-%, most preferably at most about 60 wt.-%, and in particular at most about 40 wt.-%.

In another aspect the present invention relates to methods of treating pain, comprising administering a crystalline form as described herein to a patient in need thereof (for example, a patient who has been diagnosed with a pain disorder).

In some preferred embodiments, the present invention relates to a method of treating pain in a patient diagnosed with a pain disorder comprising orally administering to the patient an effective amount of a pharmaceutical composition comprising one or more additives or adjuvants and an active ingredient comprising the crystalline form disclosed herein. In some embodiments, the pharmaceutical composition comprises about 40±20 µg of the active ingredient. In some embodiments, the pharmaceutical composition comprises about 400±50 µg of the active ingredient. In some embodiments, the pharmaceutical composition comprises about 200±50 µg of the active ingredient. In some embodiments, the pharmaceutical composition comprises about 600±50 µg of the active ingredient. In some preferred embodiments, the crystalline form is present in the active ingredient in substantially pure form (for example, the active ingredient comprises at least about 50%, about least about 60%, about least about 70%, about least about 80%, about least about 90%, about least about 95%, or even about least about 99% of the crystalline form).

In another aspect the present invention relates to methods of treating pain, comprising administering a pharmaceutical composition that comprises a crystalline form as described herein to a patient in need thereof (for example, a patient who has been diagnosed with a pain disorder).

The term pain as used herein preferably includes but is not limited to pain selected from the group consisting of inflammatory pain, postoperative pain, neuropathic pain, diabetic neuropathic pain, acute pain, chronic pain, visceral pain, migraine pain and cancer pain.

In some preferred embodiments, the crystalline form according to the invention is for use in the treatment of acute, visceral, neuropathic or chronic pain (cf. WO 2008/040481).

In another aspect the present invention relates to a pharmaceutical composition comprising a crystalline form as described herein and optionally one or more suitable additives and/or adjuvants such as described below.

In some preferred embodiments, the pharmaceutical composition comprises between about 0.001% by weight and about 40% by weight of one or more of the crystalline forms described herein. In some preferred embodiments, the pharmaceutical composition comprises between about 0.001% by weight and about 20% by weight of one or more of the crystalline forms described herein. In some preferred embodiments, the pharmaceutical composition comprises between about 0.001% by weight and about 10% by weight of one or more of the crystalline forms described herein. In some preferred embodiments, the pharmaceutical composition comprises between about 0.001% by weight and about 5% by weight of one or more of the crystalline forms described herein. In some preferred embodiments, the pharmaceutical composition comprises between about 0.001% by weight and about 1% by weight of one or more of the crystalline forms described herein. In some preferred embodiments, the pharmaceutical composition comprises between about 0.01% by weight and about 1% by weight of one or more of the crystalline forms described herein. In some preferred embodiments, the pharmaceutical composition comprises between about 0.01% by weight and about 1% by weight of one or more of the crystalline forms described herein.

In another aspect, the present invention relates to a pharmaceutical composition comprising an active ingredient that comprises a crystalline form as described herein and optionally one or more suitable additives and/or adjuvants such as described below, wherein the content of the active ingredient is within the range of from about 0.001 to about 99.999 wt.-%, or from about 0.001 to about 99.9 wt.-%, or from about 0.001 to about 99 wt.-%, or from about 0.001 to about 98 wt.-%, or from about 0.001 to about 97 wt.-%, relative to the total weight of the pharmaceutical composition.

In some preferred embodiments, the pharmaceutical composition comprises between about 0.001% by weight and about 40% by weight of active ingredient. In some preferred embodiments, the pharmaceutical composition comprises between about 0.001% by weight and about 20% by weight of active ingredient. In some preferred embodiments, the pharmaceutical composition comprises between about 0.001% by weight and about 10% by weight of active ingredient. In some preferred embodiments, the pharmaceutical composition comprises between about 0.001% by weight and about 5% by weight of active ingredient. In some preferred embodiments, the pharmaceutical composition comprises between about 0.001% by weight and about 1% by weight of active ingredient. In some preferred embodiments, the pharmaceutical composition comprises between about 0.01% by weight and about 1% by weight of active ingredient. In some preferred embodiments, the pharmaceutical composition comprises between about 0.01% by weight and about 1% by weight of active ingredient.

Preferably said pharmaceutical composition may be used for the treatment of pain.

In still another aspect the present invention relates to a medicament comprising a crystalline form as described herein, preferably a pharmaceutical composition as described herein. In a preferred embodiment, the medicament is a solid drug form. The medicament is preferably manufactured for oral administration. However, other forms of administration are also possible, e.g. for buccal, sublingual, transmucosal, rectal, intralumbal, intraperitoneal, transdermal, intravenous, intramuscular, intragluteal, intracutaneous and subcutaneous application.

Depending on the configuration, the medicament (dosage form) preferably contains suitable additives and/or adjuvants. Suitable additives and/or adjuvants in the sense of the invention are all substances known to a person skilled in the art for the formation of galenic formulations. The choice of these adjuvants and also the quantities to be used are dependent on how the medication is to be administered, i.e. orally, intravenously, intraperitoneally, intradermally, intramuscularly, intranasally, buccally or locally.

Preferably, the dosage form comprises about 5 µg to about 1250 µg of one or more of the crystalline forms described herein.

In some preferred embodiments, the dosage form comprises about 40±35 µg, more preferably about 40±30 µg, still more preferably about 40±25 µg, yet more preferably about 40±20 µg, even more preferably about 40±15 µg, most preferably about 40±10 µg, and in particular about 40±5 µg of one or more of the crystalline forms described herein. In some other preferred embodiments, the dosage form comprises about 400±375 µg or about 400±350 µg, more preferably about 400±300 µg, still more preferably about 400±250 µg, yet more preferably about 400±200 µg, even more preferably about 400±150 µg, most preferably about 40±100 µg, and in particular about 400±50 µg of one or more of the crystalline forms described herein. In some other preferred embodiments, the dosage form comprises about 40±5 µg of the crystalline or (or of an active ingredient comprising the crystalline form). In some other preferred embodiments, the dosage form comprises about 100±10 µg of the crystalline or (or of an active ingredient comprising the crystalline form). In some other preferred embodiments, the dosage form comprises about 200±50 µg of the crystalline or (or of an active ingredient comprising the crystalline form). In some other preferred embodiments, the dosage form comprises about 400±50 µg of the crystalline or (or of an active ingredient comprising the crystalline form). In some other preferred embodiments, the dosage form comprises about 600±50 µg of the crystalline or (or of an active ingredient comprising the crystalline form).

Preferably, the dosage form comprises about 5 µg to about 1250 µg of active ingredient.

In some preferred embodiments, the dosage form comprises about 40±35 µg, more preferably about 40±30 µg, still more preferably about 40±25 µg, yet more preferably about 40±20 µg, even more preferably about 40±15 µg, most preferably about 40±10 µg, and in particular about 40±5 µg of active ingredient. In some other preferred embodiments, the dosage form comprises about 400±375 µg or about 400±350 µg, more preferably about 400±300 µg, still more preferably about 400±250 µg, yet more preferably about 400±200 µg, even more preferably about 400±150 µg, most preferably about 40±100 µg, and in particular about 400±50 µg of active ingredient. In some other preferred embodiments, the dosage form comprises about 40±5 µg of active ingredient. In some other preferred embodiments, the dosage form comprises about 100±10 µg of active ingredient. In some other preferred embodiments, the dosage form comprises about 200±50 µg of active ingredient. In some other preferred embodiments, the dosage form comprises about 400±50 µg of active ingredient. In some other preferred embodiments, the dosage form comprises about 600±50 µg of active ingredient.

Preparations suitable for oral administration are those in the form of tablets, chewable tablets, lozenges, capsules, granules, drops, liquids or syrups, and those suitable for parenteral, topical and inhalatory administration are solutions, suspensions, easily reconstituted dry preparations and sprays. A further possibility is suppositories for rectal administration. The application in a depot in dissolved form, a patch or a plaster, possibly with the addition of agents promoting skin penetration, are examples of suitable percutaneous forms of application.

Examples of adjuvants and additives for oral forms of application are disintegrants, lubricants, binders, fillers, mould release agents, possibly solvents, flavourings, sugar, in particular carriers, diluents, coloring agents, antioxidants etc.

Waxes or fatty acid esters, amongst others, can be used for suppositories and carrier substances, preservatives, suspension aids etc. can be used for parenteral forms of application.

Adjuvants can be, for example: water, ethanol, 2-propanol, glycerine, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl-cellulose, cellulose acetate, shellac, cetyl alcohol, polyvinylpyrrolidone, paraffins, waxes, natural and synthetic rubbers, acacia gum, alginates, dextran, saturated and unsaturated fatty acids, stearic acid, magnesium stearate, zinc stearate, glyceryl stearate, sodium lauryl sulphate, edible oils, sesame oil, coconut oil, peanut oil, soybean oil, lecithin, sodium lactate, polyoxyethylene and propylene fatty acid esters, sorbitane fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talc, kaolin, pectin, crosspovidon, agar and bentonite.

The production of these medicaments and pharmaceutical compositions is conducted using means, devices, methods and processes that are well known in the art of pharmaceutical technology, as described, for example, in *"Remington's Pharmaceutical Sciences"*, A. R. Gennaro, 17th ed., Mack Publishing Company, Easton, Pa. (1985), in particular in part 8, chapters 76 to 93.

Thus, for example, for a solid formulation such as a tablet, the active substance of the drug can be granulated with a pharmaceutical carrier substance, e.g. conventional tablet constituents such as cornstarch, lactose, saccharose, sorbitol, talc, magnesium stearate, dicalcium phosphate or pharmaceutically acceptable rubbers, and pharmaceutical diluents such as water, for example, in order to form a solid composition that contains the active substance in a homogenous dispersion. Homogenous dispersion is understood here to mean that the active substances are uniformly dispersed throughout the composition, so that this can be readily divided into identically effective standard dosage forms such as tablets, capsules, lozenges. The solid composition is then divided into standard dosage forms. The tablets or pills can also be coated or otherwise compounded to prepare a slow release dosage form. Suitable coating agents include polymeric acids and mixtures of polymeric acids with materials such as shellac, cetyl alcohol and/or cellulose acetate, for example.

In one embodiment of the present invention the crystalline form as described herein is present in immediate release form.

In another embodiment of the present invention the crystalline form as described herein is at least partially present in controlled-release form. In particular, the active ingredient can be released slowly from preparations that can be applied orally, rectally or percutaneously.

The medicament can preferably be manufactured for administration once daily, twice daily (bid), or three times daily, the once daily or twice daily administration (bid) being preferred.

The term controlled release as used herein refers to any type of release other than immediate release such as delayed release, sustained release, slow release, extended release and the like. These terms are well known to any person skilled in the art as are the means, devices, methods and processes for obtaining such type of release.

In another embodiment of the present invention
the medicament is manufactured for oral administration; and/or
the medicament is a solid and/or compressed and/or film-coated drug form; and/or
the medicament releases the crystalline form as described herein slowly from a matrix; and/or
the medicament contains the crystalline form in a quantity of 0.001 to 99.999% by wt., more preferred 0.1 to 99.9% by wt., still more preferred 1.0 to 99.0% by wt., even more preferred 2.5 to 80% by wt., most preferred 5.0 to 50% by wt. and in particular 7.5 to 40% by wt., based on the total weight of the medicament; and/or
the medicament contains a pharmaceutically compatible carrier and/or pharmaceutically compatible adjuvants; and/or
the medicament has a total mass in the range of 25 to 2000 mg, more preferred 50 to 1800 mg, still more preferred 60 to 1600 mg, more preferred 70 to 1400 mg, most preferred 80 to 1200 mg and in particular 100 to 1000 mg; and/or
the medicament is selected from the group comprising tablets, capsules, pellets and granules.

The medicament can be provided as a simple tablet and as a coated tablet (e.g. as film-coated tablet or lozenge). The tablets are usually round and biconvex, but oblong forms are also possible. Granules, spheres, pellets or microcapsules, which are contained in sachets or capsules or are compressed to form disintegrating tablets, are also possible.

In yet another one of its aspects, the present invention relates to the use of the crystalline form as described herein for the production of a medicament. Preferably said medicament is suitable for the treatment of pain.

In still another one of its aspects, the present invention relates to the use of the crystalline form as described herein for the treatment of pain.

The phrase "consisting essentially of," when used in reference to the pharmaceutical composition means that the composition contains no active pharmaceutical ingredients other than those specified, but that it may contain additional inactive components or excipients. For example, if a pharmaceutical composition is described as consisting essentially of (1r,4r)-6'-fluoro-N,N-dimethyl-4-phenyl-4',9'-dihydro-3'H-spiro[cyclohexane-1,1'-pyrano-[3,4,b]indol]-4-amine, it should be understood that the pharmaceutical composition contains (1r,4r)-6'-fluoro-N,N-dimethyl-4-phenyl-4',9'-dihydro-3'H-spiro[cyclohexane-1,1'-pyrano-[3,4,b]indol]-4-amine (i.e., crystalline and/or amorphous form(s) thereof) and no other active pharmaceutical ingredients but that the dosage form may contain any number of additional inactive components or excipients. The phrase "consisting of", when used in reference to the pharmaceutical composition, means that the composition contains no other active pharmaceutical ingredient other than that specified but may contain additional components that are unrelated to the invention and/or impurities ordinarily associated with the recited components. Similarly, when the phrase "consisting of" is used to define the active ingredient, it means that the active ingredient contains substantially no other crystalline form other than that specified but may contain additional components that are unrelated to the invention and/or impurities ordinarily associated with the recited components.

Furthermore, the present invention relates to a method for treating pain in a patient, preferably in a mammal, which comprises administering an effective amount of a crystalline form as described herein to a patient.

Additional preferred embodiments of the invention (Emb-1 to Emb-17) are as follows:

Emb-1. A crystalline form of (1r,4r)-6'-fluoro-N,N-dimethyl-4-phenyl-4',9'-dihydro-3'H-spiro-[cyclohexane-1,1'-pyrano[3,4, b]indol]-4-amine.

Emb-2. The crystalline form according to Emb-1, which has an X-ray diffraction peak (CuKα radiation) at 18.9±0.5 (2Θ).

Emb-3. The crystalline form according to Emb-1 or 2, which has a Raman peak at 921±5 cm$^{-1}$, at 1002±5 cm$^{-1}$ and at 1572±5 cm$^{-1}$.

Emb-4. The crystalline form according to any of the preceding Embs-, which is an ansolvate or a solvate.

Emb-5. The crystalline form according to Emb-4, which is an alcohol solvate.

Emb-6. The crystalline form according to any of the preceding Embs-, which has
- A: one or more X-ray diffraction peaks (CuKα radiation) selected from the group consisting of 17.6±0.2 (2Θ), 18.3±0.2 (2Θ), 18.6±0.2 (2Θ), 25.8±0.2 (2Θ), and 26.3±0.2 (2Θ); and/or one or more Raman peaks selected from the group consisting of 921±2 cm$^{-1}$, 1002±2 cm$^{-1}$, 1308±2 cm$^{-1}$, 1569±2 cm$^{-1}$, 1583±2 cm$^{-1}$, 3057±2 cm$^{-1}$; or
- B: one or more X-ray diffraction peaks (CuKα radiation) selected from the group consisting of 8.9±0.2 (2Θ), 9.8±0.2 (2Θ), 15.7±0.2 (2Θ), 16.7±0.2 (2Θ), 17.8±0.2 (2Θ), 18.4±0.2 (2Θ), 19.2±0.2 (2Θ), 19.7±0.2 (2Θ), 20.4±0.2 (2Θ), 21.8±0.2 (2Θ), 24.1±0.2 (2Θ), 25.1±0.2 (2Θ), 26.0±0.2 (2Θ), and 31.1±0.2 (2Θ); and/or one or more Raman peaks selected from the group consisting of 154±2 cm$^{-1}$, 173±2 cm$^{-1}$, 923±2 cm$^{-1}$, 1003±2 cm$^{-1}$, 1299±2 cm$^{-1}$, 1476±2 cm$^{-1}$, 1571±2 cm$^{-1}$, 1581±2 cm$^{-1}$, 3064±2 cm$^{-1}$, 3072±2 cm$^{-1}$; or
- C: one or more X-ray diffraction peaks (CuKα radiation) selected from the group consisting of 9.1±0.2 (2Θ), 9.5±0.2 (2Θ), 16.8±0.2 (2Θ), 18.2±0.2 (2Θ), 18.6±0.2 (2Θ), 19.0±0.2 (2Θ), 19.3±0.2 (2Θ), 19.5±0.2 (2Θ), 22.2±0.2 (2Θ), 25.4±0.2 (2Θ), and 27.5±0.2 (2Θ); and/or one or more Raman peaks selected from the group consisting of 156±2 cm$^{-1}$, 171±2 cm$^{-1}$, 183±2 cm$^{-1}$, 922±2 cm$^{-1}$, 1003±2 cm$^{-1}$, 1299±2 cm$^{-1}$, 1478±2 cm$^{-1}$, 1570±2 cm$^{-1}$, 1587±2 cm$^{-1}$, 2932±2 cm$^{-1}$, 2951±2 cm$^{-1}$, 3070±2 cm$^{-1}$; or
- D: one or more X-ray diffraction peaks (CuKα radiation) selected from the group consisting of 8.4±0.2 (2Θ), 8.8±0.2 (2Θ), 15.0±0.2 (2Θ), 15.2±0.2 (2Θ), 17.0±0.2 (2Θ), 17.6±0.2 (2Θ), 18.9±0.2 (2Θ), 21.2±0.2 (2Θ), 22.4±0.2 (2Θ), 23.2±0.2 (2Θ), 26.0±0.2 (2Θ), 29.5±0.2 (2Θ), and 30.7±0.2 (2Θ); and/or one or more Raman peaks selected from the group consisting of 169±2 cm$^{-1}$, 254±2 cm$^{-1}$, 367±2 cm$^{-1}$, 491±2 cm$^{-1}$, 683±2 cm$^{-1}$, 922±2 cm$^{-1}$, 1002±2 cm$^{-1}$, 1302±2 cm$^{-1}$, 1437±2 cm$^{-1}$, 1479±2 cm$^{-1}$, 1570±2 cm$^{-1}$, 2935±2 cm$^{-1}$, 2957±2 cm$^{-1}$, 3067±2 cm$^{-1}$; or
- E: one or more X-ray diffraction peaks (CuKα radiation) selected from the group consisting of 8.8±0.2 (2Θ), 11.9±0.2 (2Θ), 17.0±0.2 (2Θ), 17.7±0.2 (2Θ), and 18.7±0.2 (2Θ); and/or one or more Raman peaks selected from the group consisting of 159±2 cm$^{-1}$, 188±2 cm$^{-1}$, 680±2 cm$^{-1}$, 923±2 cm$^{-1}$, 1003±2 cm$^{-1}$, 1297±2 cm$^{-1}$, 1434±2 cm$^{-1}$, 1461±2 cm$^{-1}$, 1570±2 cm$^{-1}$, 1585±2 cm$^{-1}$, 2943±2 cm$^{-1}$, 2961±2 cm$^{-1}$, 3070±2 cm$^{-1}$; or
- F: one or more X-ray diffraction peaks (CuKα radiation) selected from the group consisting of 9.0±0.2 (2Θ), 15.4±0.2 (2Θ), 16.1±0.2 (2Θ), 17.9±0.2 (2Θ), 18.2±0.2 (2Θ), 18.7±0.2 (2Θ), 19.4±0.2 (2Θ), 20.1±0.2 (2Θ), 20.6±0.2 (2Θ), 21.8±0.2 (2Θ), 24.6±0.2 (2Θ), 25.6±0.2 (2Θ), 27.1±0.2 (2Θ), 27.4±0.2 (2Θ), and 29.3±0.2 (2Θ); and/or one or more Raman peaks selected from the group consisting of 157±2 cm$^{-1}$, 171±2 cm$^{-1}$, 183±2 cm$^{-1}$, 682±2 cm$^{-1}$, 921±2 cm$^{-1}$, 1002±2 cm$^{-1}$, 1299±2 cm$^{-1}$, 1463±2 cm$^{-1}$, 1477±2 cm$^{-1}$, 1570±2 cm$^{-1}$, 1581±2 cm$^{-1}$, 2889±2 cm$^{-1}$, 2932±2 cm$^{-1}$, 2952±2 cm$^{-1}$, 2977±2 cm$^{-1}$, 3058±2 cm$^{-1}$, 3070±2 cm$^{-1}$; or
- G: one or more X-ray diffraction peaks (CuKα radiation) selected from the group consisting of 15.4±0.2 (2Θ), 15.9±0.2 (2Θ), 16.3±0.2 (2Θ), 17.2±0.2 (2Θ), 17.4±0.2 (2Θ), 17.8±0.2 (2Θ), 18.8±0.2 (2Θ), 19.1±0.2 (2Θ), 19.4±0.2 (2Θ), 20.3±0.2 (2Θ), 20.7±0.2 (2Θ), 21.0±0.2 (2Θ), 22.2±0.2 (2Θ), 22.6±0.2 (2Θ), 24.2±0.2 (2Θ), 24.7±0.2 (2Θ), 25.4±0.2 (2Θ), 25.9±0.2 (2Θ), 26.6±0.2 (2Θ), 28.0±0.2 (2Θ), 28.3±0.2 (2Θ), 28.8±0.2 (2Θ), 29.1±0.2 (2Θ), 29.4±0.2 (2Θ), and 33.0±0.2 (2Θ); and/or one or more Raman peaks selected from the group consisting of 169±2 cm$^{-1}$, 675±2 cm$^{-1}$, 921±2 cm$^{-1}$, 1002±2 cm$^{-1}$, 1569±2 cm$^{-1}$, 2917±2 cm$^{-1}$, 3069±2 cm$^{-1}$; or
- H: one or more X-ray diffraction peaks (CuKα radiation) selected from the group consisting of 11.4±0.2 (2Θ), 18.3±0.2 (2Θ), and 19.2±0.2 (2Θ); and/or one or more Raman peaks selected from the group consisting of 171±2 cm$^{-1}$, 203±2 cm$^{-1}$, 258±2 cm$^{-1}$, 369±2 cm$^{-1}$, 391±2 cm$^{-1}$, 490±2 cm$^{-1}$, 599±2 cm$^{-1}$, 685±2 cm$^{-1}$, 828±2 cm$^{-1}$, 918±2 cm$^{-1}$, 1002±2 cm$^{-1}$, 1030±2 cm$^{-1}$, 1305±2 cm$^{-1}$, 1375±2 cm$^{-1}$, 1464±2 cm$^{-1}$, 1568±2 cm$^{-1}$, 2989±2 cm$^{-1}$; or
- I: one or more X-ray diffraction peaks (CuKα radiation) selected from the group consisting of 10.9±0.2 (2Θ), 14.6±0.2 (2Θ), 15.5±0.2 (2Θ), 17.1±0.2 (2Θ), 18.5±0.2 (2Θ), 18.8±0.2 (2Θ), 21.1±0.2 (2Θ), 21.9±0.2 (2Θ), 23.6±0.2 (2Θ), 25.9±0.2 (2Θ), and 28.0±0.2 (29); and/or one or more Raman peaks selected from the group consisting of 924±2 cm$^{-1}$, 1001±2 cm$^{-1}$, 1305±2 cm$^{-1}$, 1572±2 cm$^{-1}$, 2925±2 cm$^{-1}$, 3066±2 cm$^{-1}$; or
- L: one or more X-ray diffraction peaks (CuKα radiation) selected from the group consisting of 8.6±0.2 (2Θ), 10.3±0.2 (2Θ), 16.7±0.2 (2Θ), 17.2±0.2 (2Θ), 18.2±0.2 (2Θ), 18.8±0.2 (2Θ), 21.2±0.2 (2Θ), 26.0±0.2 (2Θ), and 27.4±0.2 (2Θ); and/or one or more Raman peaks selected from the group consisting of 172±2 cm$^{-1}$, 679±2 cm$^{-1}$, 924±2 cm$^{-1}$, 1001±2 cm$^{-1}$, 1307±2 cm$^{-1}$, 1475±2 cm$^{-1}$, 1577±2 cm$^{-1}$, 1590±2 cm$^{-1}$, 2922±2 cm$^{-1}$, 2987±2 cm$^{-1}$, 3069±2 cm$^{-1}$.

Emb-7. The crystalline form A according to Emb-6, which in DSC analysis exhibits an endothermal event with an onset temperature or a peak temperature in the range of 298-308° C.

Emb-8. The crystalline form B according to Emb-6, which in DSC analysis exhibits an endothermal event with an onset temperature or a peak temperature in the range of 108-118° C. and/or an endothermal event with an onset temperature or a peak temperature in the range of 184-194° C.

Emb-9. A pharmaceutical composition comprising at least one crystalline form according to any of Embs-1 to 8.

Emb-10. A process for obtaining a crystalline form of (1r,4r)-6'-fluoro-N,N-dimethyl-4-phenyl-4',9'-dihydro-3'H-spiro[cyclohexane-1,1'-pyrano[3,4, b]indol]-4-amine according to any of Embs-1 to 8, comprising the steps of
- a-1) suspending (1r,4r)-6'-fluoro-N,N-dimethyl-4-phenyl-4',9'-dihydro-3'H-spiro-[cyclohexane-1,1'-pyrano[3,4, b]indol]-4-amine in a solvent, and stirring the resulting suspension; and
- b-1) separating, preferably filtering off the solid; or
- b-2) dissolving (1r,4r)-6'-fluoro-N,N-dimethyl-4-phenyl-4',9'-dihydro-3'H-spiro-[cyclohexane-1,1'-pyrano[3,4, b]indol]-4-amine in a solvent; and
- b-2) evaporating off the solvent from the solution; or
- b-2') precipitating (1r,4r)-6'-fluoro-N,N-dimethyl-4-phenyl-4',9'-dihydro-3'H-spiro-[cyclohexane-1,1'-pyrano [3,4, b]indol]-4-amine from the solution, preferably by the addition of a precipitant.

Emb-11. A method for the separation of (1r,4r)-6'-fluoro-N,N-dimethyl-4-phenyl-4',9'-dihydro-3'H-spiro[cyclohexane-1,1'-pyrano[3,4, b]indol]-4-amine from (1s,4s)-6'-fluoro-N,N-dimethyl-4-phenyl-4',9'-dihydro-3'H-spiro

[cyclohexane-1,1'-pyrano-[3,4, b]indol]-4-amine comprising the process of Emb-10.

Emb-12. A crystalline form of (1r,4r)-6'-fluoro-N,N-dimethyl-4-phenyl-4',9'-dihydro-3'H-spiro[cyclohexane-1,1'-pyrano[3,4, b]indol]-4-amine according to Emb-1 having a X-ray powder diffraction pattern comprising characteristic peaks at about 17.6±0.2 (2Θ), about 18.3±0.2 (2Θ), about 18.6±0.2 (2Θ), about 26.3±0.2 (2Θ), and optionally 25.8±0.2 (2Θ).

Emb-13. The crystalline form of Emb-12, wherein the crystalline form has an endothermal event with a peak temperature at about 298-308° C., as determined by DSC.

Emb-14. A pharmaceutical composition comprising the crystalline form of Emb-12 or 13.

Emb-15. The pharmaceutical composition of Emb-14, which comprises between about 0.001% by weight and about 20% by weight of the crystalline form.

Emb-16. The pharmaceutical composition of any of Embs-9, 14 or 15, which additionally comprises a salt of (1r,4r)-6'-fluoro-N,N-dimethyl-4-phenyl-4',9'-dihydro-3'H-spiro-[cyclohexane-1,1'-pyrano[3,4, b]indol]-4-amine with sulfuric acid, preferably the hydrogen sulfate salt.

Emb-17. The pharmaceutical composition of Emb-16, wherein the total content of the salt of (1r,4r)-6'-fluoro-N,N-dimethyl-4-phenyl-4',9'-dihydro-3'H-spiro[cyclohexane-1,1'-pyrano[3,4, b]indol]-4-amine with sulfuric acid is within the range of from 1 ppm to 500 ppm, relative to the total amount (1r,4r)-6'-fluoro-N,N-dimethyl-4-phenyl-4', 9'-dihydro-3'H-spiro[cyclohexane-1,1'-pyrano[3,4, b]indol]-4-amine.

EXAMPLES

The following examples serve to explain the invention in more detail, but should not be interpreted as restrictive.

The following abbreviations are used in the examples:
iBuOAc iso-butyl acetate
1BuOH n-butanol (1-butanol)
DMSO dimethyl sulfoxide
EtOAc ethyl acetate
EtOH ethanol
Ex example
FT-Raman Fourier transformation Raman spectroscopy
IPE diisopropyl ether
Δm change in mass
MeCN acetonitril
MEK 2-butanone
MeOH methanol
min minute
NMP N-methyl-2-pyrrolidone
1 PrOH n-propanol (1-propanol)
2PrOH iso-propanol (2-propanol)
PXRD powder x-ray diffraction
r.h. relative humidity
RT room temperature, preferably 20-25° C.
SCXRD single crystal X-ray diffraction
sec seconds
t time (duration)
TBME tert-butyl methyl ether
TG-FTIR thermogravimetry coupled with Fourier transform infrared spectroscopy
THF tetrahydrofuran
XRPD X-ray powder diffraction
Unless otherwise specified, solvent mixtures are always volume/volume.

A) Synthesis of Crystalline Form a
Alternative I:
100 mg (1r,4r)-6'-fluoro-N,N-dimethyl-4-phenyl-4',9'-dihydro-3'H-spiro[cyclohexane-1,1'-pyrano[3,4, b]indol]-4-amine [crystalline form D according to D)] was suspended in 0.5 mL TBME. The suspension was stirred at RT for six days. The resulting solid was filtered out and dried in air. A crystalline solid of crystalline form A was obtained and characterized by FT Raman, TG-FTIR and PXRD.

Alternative II:
It has been found that when stirring the reaction mixture of the starting materials in the presence of acid under thermodynamic control (i.e., for several hours at elevated temperature), the yield of the desired (1r,4r)-diastereomer can be substantially increased. Diastereomeric purity can then subsequently further increased by recrystallization from isopropanol and ethyl acetate.

23.65 g (0.132 mol) of 2-(5-fluoro-1H-indol-3-yl)ethanol and 28.68 g (0.132 mol) of 4-(dimethylamino)-4-phenylcyclohexanone are dissolved in 717 ml of acetic acid. The mixture is warmed up to 45° C. under stirring. At 45° C. 8.44 ml (0.158 mol) of sulfuric acid are added. The resulting solid is stirred for 18 h at 50° C. The mixture is cooled to 20° C., filtered off and washed subsequently with each 72 ml of acetic acid and isopropanol. The solid, i.e. an acid addition salt of (1r,4r)-1 and sulfuric acid, is suspended in 618 ml of isopropanol and 42 ml of diethyl amine are added. The resulting suspension is stirred at room temperature for 18 h. The solid is filtered off and washed with 143 ml of isopropanol. 450 ml of DMSO are added to dissolve the solid at 88° C. Then 1204 ml of isopropanol are added and the mixture is cooled to room temperature over 120 min. The resulting solid is filtered off and washed with 201 ml of isopropanol. The solid is suspended in 250 ml of ethyl acetate and stirred at 60° C. for 18 h. The solid is filtered off and dried in vacuum. Yield of (1r,4r)-1: 28.4 g (57%). Purity HPLC: 100%.

B) Synthesis of Crystalline Form B
100 mg crystalline form D [according to D)] was suspended in 0.5 mL THF/$H_2O$. The suspension was stirred at RT for six days. The resulting solid was filtered out and dried in air. A crystalline solid of crystalline form B was obtained and characterized by FT Raman, TG-FTIR and PXRD.

C) Synthesis of Crystalline Form C
107.5 g 5-Fluorotryptophol were charged into a vessel. Subsequently, 138.7 g DMAPh-cyclohexanon (4-(dimethylamino)-4-phenylcyclohexanone) and 8.40 kg dichloromethane were added. A dropping funnel was mounted on the vessel and the vessel was flushed with gaseous nitrogen. The mixture was stirred and heated to 39.4° C. 160.0 g TMS-triflate (trifluoromethane sulfonic acid trimethylsilylester) were filled under nitrogen atmosphere into the funnel and subsequently 0.2 kg dichloromethane were added to the dropping funnel and mixed with the TMS-triflate. This mixture was dosed into the vessel over 2 hrs. The reaction mixture was than stirred for 23 hrs at 40±5° C. and 40 hrs at 22±2° C. A 1 N sodium hydroxide solution was prepared by diluting 224 g of a sodium hydroxide solution (30%) with 1.45 kg deionised water. This 1 N sodium hydroxide solution was added at 21-22° C. to the reaction mixture until the product (1r,4r)-6'-fluoro-N,N-dimethyl-4-phenyl-4',9'-dihydro-3'H-spiro[cyclohexane-1,1'-pyrano[3,4, b]indol]-4-amine crystallized as a yellowish solid. The solution was cooled from 21.5° C. to 4.3° C. in 1 hr and stirred for 3.5 hrs at 1 to 5° C. The resulting suspension was transferred to a nutsche, filtered out by applying pressure and washed 2 times with 0.65 L Ethanol for 15-20 min. Pressure was applied after filtration for further 5 min. The purity of the product (HPLC) was 99.5%. The product was than dried in vacuum (50° C., 17.5 hrs, 2 bar) until the mass remained constant. Yield: 206.9 g, 91%.

D) Synthesis of Crystalline Form D (4-(dimethylamino)-4-phenylcyclohexanone (3 g, 13.82 mmol), 2-(5-fluoro-1H-indol-3-yl)ethanol (2.47 g, 13.82 mmol) and 150 mL dichloromethane were charged to a flask at 0° C. A solution of trifluoromethane sulfonic acid trimethylsilylester (3 mL, 15.5 mmol) in 3 mL dichloromethane were added quickly. The reaction mixture changed color to violet and the temperature rose to 10° C. The reaction mixture was cooled in an ice bath and stirred for 20 min. Meanwhile a solid precipitated. The ice bath was removed and the reaction mixture was stirred for 3 to 3.5 hours at room temperature. Subsequently 50 mL of NaOH (1N) were added and the reaction mixture was stirred further 10 min. The color changed to yellow and a solid precipitated. In order to complete the precipitation the reaction mixture (two liquid phases) was stirred for further 20 min while cooled in an ice bath. Eventually the solid was filtered out. The resulting solid (4.2 g) was subsequently recrystallized in 800 mL 2-Propanol. Yield: 3.5 g.

To enhance the yield, the liquid (Water and Dichloromethane) filtrate was separated. The aqueous solution with extracted 3 times with 20 mL Dichloromethane. The organic phases were united and dried with $MgSO_4$ and subsequently the solvent was stripped off until dryness. The resulting solid (1.7 g) was subsequently recrystallized under reflux in 800 mL 2-Propanol.

Crystallization Tests

Example 1

Crystalline form C [according to C)] was suspended in different solvents and the suspension was stirred at RT for eight days. The resulting solids were filtered out, dried in air and characterized by FT Raman. One sample of each obtained form was further characterized by TG-FTIR and PXRD.

The detailed experimental conditions and results are summarized in the table here below. For characterization details of the obtained forms see Section "Analysis".

1-17) The new "crystalline form K" (sample of Ex. 1-16) was further analyzed by the following experiments:

100 mg of "crystalline form K" were stored at RT in vacuum (100 mbar) before being characterized by FT Raman, TG-FTIR and PXRD. The analyses revealed the presence of a new crystalline form (crystalline form L), a desolvated form. After the data of crystalline form L were available, the starting material ("crystalline form K") was identified as a mixture of crystalline forms B and L by FT Raman.

TG-FTIR after four weeks of storage (RT, 100 mbar) revealed that the sample still contained $H_2O$. Additionally, the sample contained EtOH, indicating that the used hydrate (sample 1-16) was contaminated with traces of EtOH from the starting material. Whereas most of the water was removed in vacuum (reduction from 9% to 1.5% $H_2O$), the remaining EtOH content changed less (reduction from 1.8% to 0.8% EtOH). Neither FT Raman nor PXRD showed any indication for the presence of form C (EtOH solvate).

Crystalline form L is probably metastable. At ambient conditions (RT, 40-60% r.h.) crystalline form L slowly reconverts into crystalline form B.

Example 2

Solutions of crystalline form C [according to C), 50 mg] were prepared in THF, 1,4-dioxane and DMSO. 6 mL precipitant ($H_2O$, EtOH, TBME, IPE) was added quickly.

A second set of experiments was performed using acetone, MEK, $CH_2Cl_2$ and THF as solvents and heptane, hexane and EtOH as precipitants (antisolvents). Solvents and precipitants were selected based on the approximate solubility determination in phase A. The resulting solids were filtered out, dried in air and characterized by FT Raman. The detailed experimental conditions and results are summarized in the table here below. For characterization details of the obtained forms see Section "Analysis".

TABLE 1

| Ex. | solvent | amount crystalline form C/ amount solvent | t [days] | Result | TG-FTIR | crystalline modification |
|---|---|---|---|---|---|---|
| 1-1 | acetone | 120 mg/5 mL | 8 | white crystalline solid | solvent free | A |
| 1-2 | $CH_2Cl_2$ | 120 mg/5 mL | 8 | white crystalline solid | — | A |
| 1-3 | EtOAc | 120 mg/5 mL | 8 | white crystalline solid | — | A |
| 1-4 | toluene | 120 mg/5 mL | 8 | yellowish crystalline solid | — | A |
| 1-5 | MeCN | 120 mg/5 mL | 8 | yellowish crystalline solid | — | A |
| 1-6 | EtOH | 120 mg/5 mL | 8 | yellowish crystalline solid | contains EtOH | C |
| 1-7 | MeOH | 120 mg/5 mL | 8 | yellowish crystalline solid | contains MeOH | E |
| 1-8 | 2PrOH | 120 mg/5 mL | 8 | white crystalline solid | contains 2PrOH | D |
| 1-9 | $H_2O$ | 120 mg/5 mL | 8 | yellowish crystalline solid | contains $H_2O$ | B |
| 1-10 | TBME | 120 mg/5 mL | 8 | white crystalline solid | — | A |
| 1-11 | 1BuOH | 150 mg/4 mL | 4 | white crystalline solid | — | A |
| 1-12 | 1PrOH | 150 mg/4 mL | 4 | yellowish crystalline solid | contains 1PrOH | F |
| 1-13 | iBuOAc | 150 mg/4 mL | 4 | white crystalline solid | — | A |
| 1-14 | NMP | 150 mg/4 mL | 4 | no precipitate was obtained | | — |
| 1-15 | DMSO | 150 mg/4 mL | 4 | yellowish crystalline solid | contains DMSO | G |
| 1-16 | $H_2O$ | 400 mg/5 mL | 2 | yellowish crystalline solid | contains $H_2O$, EtOH (traces) | "K" |

"K": a new FT Raman spectrum was obtained, which slightly differed to that of crystalline form B

TABLE 2

| Ex. | solvent/precipitant | amounts solvent/precipitant | result/characterization | crystalline form |
|---|---|---|---|---|
| 2-1 | THF/H$_2$O (MeOH) | 3 mL/6 mL | crystalline solid | E |
| 2-2 | THF/EtOH | 3 mL/6 mL | crystalline solid | C |
| 2-3 | THF/TBME | 3 mL/6 mL | clear solution | — |
| 2-4 | THF/IPE | 3 mL/6 mL | clear solution | — |
| 2-5 | 1,4-dioxane/H$_2$O (MeOH) | 3 mL/6 mL | crystalline solid | E |
| 2-6 | 1,4-dioxane/EtOH | 3 mL/6 mL | crystalline solid | C |
| 2-7 | 1,4-dioxane/TBME | 3 mL/6 mL | crystalline solid | — |
| 2-8 | 1,4-dioxane/IPE | 3 mL/6 mL | crystalline solid | — |
| 2-9 | DMSO/H$_2$O | 3 mL/6 mL | crystalline solid | B |
| 2-10 | DMSO/EtOH (MeOH) | 3 mL/6 mL | crystalline solid | E |
| 2-11 | DMSO/TBME | 3 mL/6 mL | clear solution | — |
| 2-12 | DMSO/IPE | 3 mL/6 mL | clear solution | — |
| 2-13 | acetone/n-heptane | 12 mL/20 mL | clear solution | — |
| 2-14 | MEK/n-heptane | 10 mL/20 mL | clear solution | — |
| 2-15 | CH$_2$Cl$_2$/n-heptane | 10 mL/20 mL | clear solution | — |
| 2-16 | THF/n-heptane + EtOH | 3 mL/15 mL/5 mL | crystalline solid | C |
| 2-17 | acetone/n-hexane | 12 mL/20 mL | clear solution | — |
| 2-18 | MEK/n-hexane | 10 mL/20 mL | clear solution | — |
| 2-19 | CH$_2$Cl$_2$/n-hexane | 10 mL/20 mL | clear solution | — |
| 2-20 | THF/n-hexane | 3 mL/15 mL | crystalline solid | B |

(MeOH): the samples were washed with 0.5 mL of MeOH

Enough precipitate for characterization was obtained from experiments with H$_2$O or EtOH as precipitant and from THF/hexane. Whereas the addition of water resulted immediate precipitation, in case of EtOH or n-alkanes clear solutions were obtained. The precipitation started with a delay of 10 sec (THF/EtOH) to several minutes (DMSO/EtOH; THF/n-hexane; THF/n-heptane+EtOH).

Some obtained solids were very wet and hard to filter. The samples were washed with 0.5 mL of MeOH in order to improve filterability. The filtration was accelerated, but the solids were converted into the MeOH solvate (crystalline form E) indicating a very short conversion time.

From THF/n-hexane a hydrate was obtained (identified by FT Raman). The hydrate formation must be caused by residual water in the used solvents or by the high humidity on the preparation day during filtration.

When TBME or IPE was used as precipitant no or very small amounts of solid were obtained (occurring after days), not enough for characterization.

Example 3

Crystalline form C [according to C)] was dissolved in different solvents. The solvent was evaporated at RT under nitrogen flow (8-10 mL/min). Clear solutions or suspensions obtained from precipitation experiments with not sufficient material for characterization were used for further evaporation experiment at about 50° C.

The evaporation time was adjusted as short as possible in order to advantage metastable forms. Because of the rather low solubility in most solvent or because of low vapor pressure the evaporation time was at least one day.

Crystalline solids were obtained in all cases and characterized by FT Raman. In most cases material of crystalline form A was obtained.

Forms with new Raman spectra were obtained from dioxane (or mixtures containing dioxane, crystalline form H, hemi-hydrate) and from CH$_2$Cl$_2$/heptane (crystalline form I, ansolvate 2, containing traces of water). These two samples were further characterized by TG-FTIR and PXRD.

The detailed experimental conditions and results are summarized in the table here below. For characterization details of the obtained forms see Section "Analysis".

TABLE 3

| Ex. | solvent | T (evap.) | amount crystalline form C/amount solvent | TG-FTIR | crystalline modification |
|---|---|---|---|---|---|
| 3-1 | THF | RT | 40 mg/10 mL | — | A |
| 3-2 | 1,4-dioxane | RT | 40 mg/10 mL | contains H$_2$O | H |
| 3-3 | MEK | RT | 40 mg/10 mL | — | A |
| 3-4 | acetone | RT | 40 mg/10 mL | — | A |
| 3-5 | CH$_2$Cl$_2$ | RT | 40 mg/10 mL | — | A |
| 3-6 | THF/TBME | 50° C. | 50 mg/3 mL/6 mL | — | A |
| 3-7 | THF/IPE | 50° C. | 50 mg/3 mL/6 mL | — | A |
| 3-8 | 1,4-dioxane/TBME | 50° C. | 50 mg/3 mL/6 mL | — | H |
| 3-9 | 1,4-dioxane/IPE | 50° C. | 50 mg/3 mL/6 mL | — | H |
| 3-10 | CH$_2$Cl$_2$/n-heptane | 50° C. | 50 mg/10 mL/20 mL | contains H$_2$O | I |
| 3-11 | CH$_2$Cl$_2$/n-hexane | 50° C. | 50 mg/10 mL/20 mL | — | A |
| 3-12 | acetone/n-heptane | 50° C. | 50 mg/12 mL/20 mL | — | A |
| 3-13 | acetone/n-hexane | 50° C. | 50 mg/12 mL/20 mL | — | A |
| 3-14 | MEK/n-hexane | 50° C. | 50 mg/10 mL/20 mL | — | A |

Example 4

The effect of mechanical stress from grinding with an agate mortar was analyzed.

4-1) 30 mg of crystalline form A was ground in an agate mortar for 10 min. The resulting solid was characterized by FT Raman spectroscopy. No effect was observed.

4-2) 30 mg of crystalline form C was grinded in an agate mortar for 10 min. The resulting solid was characterized by FT Raman. No effect was observed.

Example 5

Seven experiments with the aim to obtain single crystals of crystalline form A (ansolvate), crystalline form (di-hydrate) and crystalline form (EtOH solvate) were performed. Vapor diffusion and slow cooling of saturated solutions were used as reliable techniques for single crystal growth.

5-1) 17 mL acetone was added to 179 mg crystalline form C [according to C)] and the mixture was stirred at 45° C. for 30 min. The resulting suspension was filtered (hot) and the resulting solution was cooled from 40° C. to 5° C. with 0.5° C./h and then stored at 5° C. for two weeks. Small crystals were obtained.

5-2) 2 ml THF was added to 179 mg crystalline form C [according to C)] and the mixture was stirred at 45° C. for 30 min. The resulting suspension was filtered (hot) and the obtained solution was cooled from 40° C. to 5° C. with 0.5° C./h and then stored at 5° C. for two weeks. Small crystals were obtained.

5-3) 9 mL DMSO was added to 179 mg crystalline form C [according to C)] and the mixture was stirred at 45° C. for 30 min. The resulting suspension was filtered (hot) and the obtained solution was cooled from 40° C. to 5° C. with 0.5° C./h and then stored at 5° C. for two weeks. Small crystals according to crystalline form G were obtained and characterized by FT Raman.

5-4) 12 mL DMSO was added to 179 mg crystalline for'm C [according to C)] and the mixture was stirred at RT for 30 min. The resulting suspension was filtered. 4 mL of the obtained solution was stored at RT in a saturated $H_2O$ atmosphere for two weeks. Needle-like crystals according to crystalline form G were obtained and characterized by FT Raman and SCXRD.

5-5) 12 mL DMSO was added to 179 mg crystalline form C [according to C)] and the mixture was stirred at RT for 30 min. The resulting suspension was filtered. 4 mL of the obtained solution was stored at RT in a saturated EtOH atmosphere for two weeks. Long, needle-like crystals according to crystalline form C were obtained and characterized by FT Raman and SCXRD.

5-6) 12 mL DMSO was added to 179 mg crystalline form C [according to C)] and the mixture was stirred at RT for 30 min. The resulting suspension was filtered. 4 mL of the obtained solution was stored at RT in a saturated TBME atmosphere for two weeks. No precipitation was observed.

5-7) 2 mL THF was added to 77 mg crystalline form A [according to A)] and the mixture was stirred at RT for 30 min. The resulting suspension was filtered. The obtained solution was stored at RT in a saturated n-hexane atmosphere for two weeks. Small crystals according to crystalline form A were obtained and characterized by FT Raman and SCXRD.

Analysis—XRPD (X-Ray Powder Diffraction) or PXRD (Powder X-Ray Diffraction)

XRPD analyses were carried out in transmission geometry with a Philips X'pert PW 3040 X-ray powder diffractometer, monochromatised CuKα radiation being used by means of a germanium monochrystal. d-distances were calculated from the 2θ values, the wavelength of 1.54060 Å being taken as basis. The d-value analysis was performed with the software EVA version 10, 0, 0, 0. The CuKα$_2$ was removed by the software and only lines up to 35° 2θ were listed. In general, the 2θ values have an error rate of ±0.2° in 2θ. The experimental error in the d-distance values is therefore dependent on the location of the peak. 2θ values may be converted into d-distance values using Bragg's law.

The samples were measured without any special treatment other than the application of slight pressure to get a flat surface. An ambient air atmosphere was used.

Figure 1B:
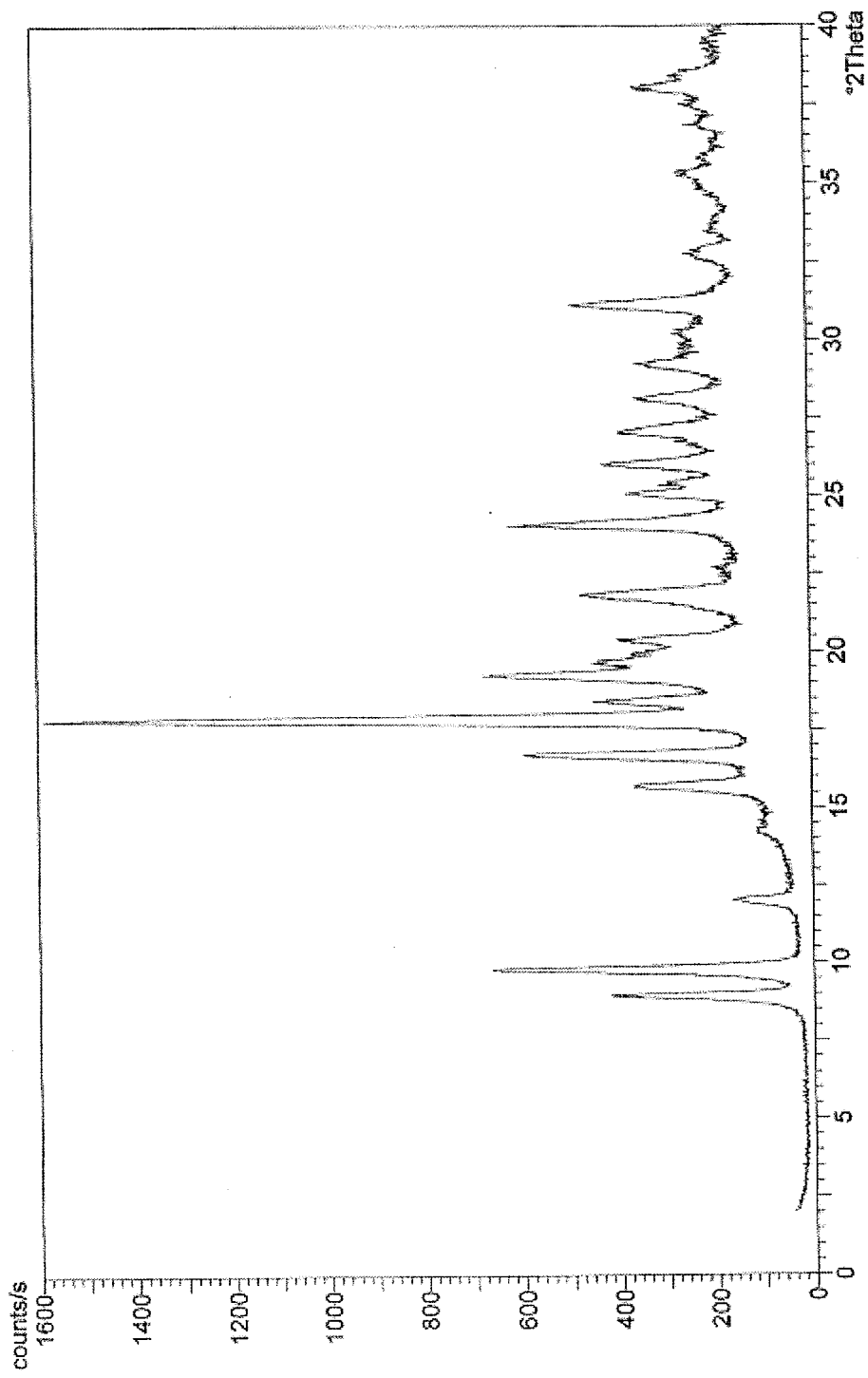
Figure 1C:
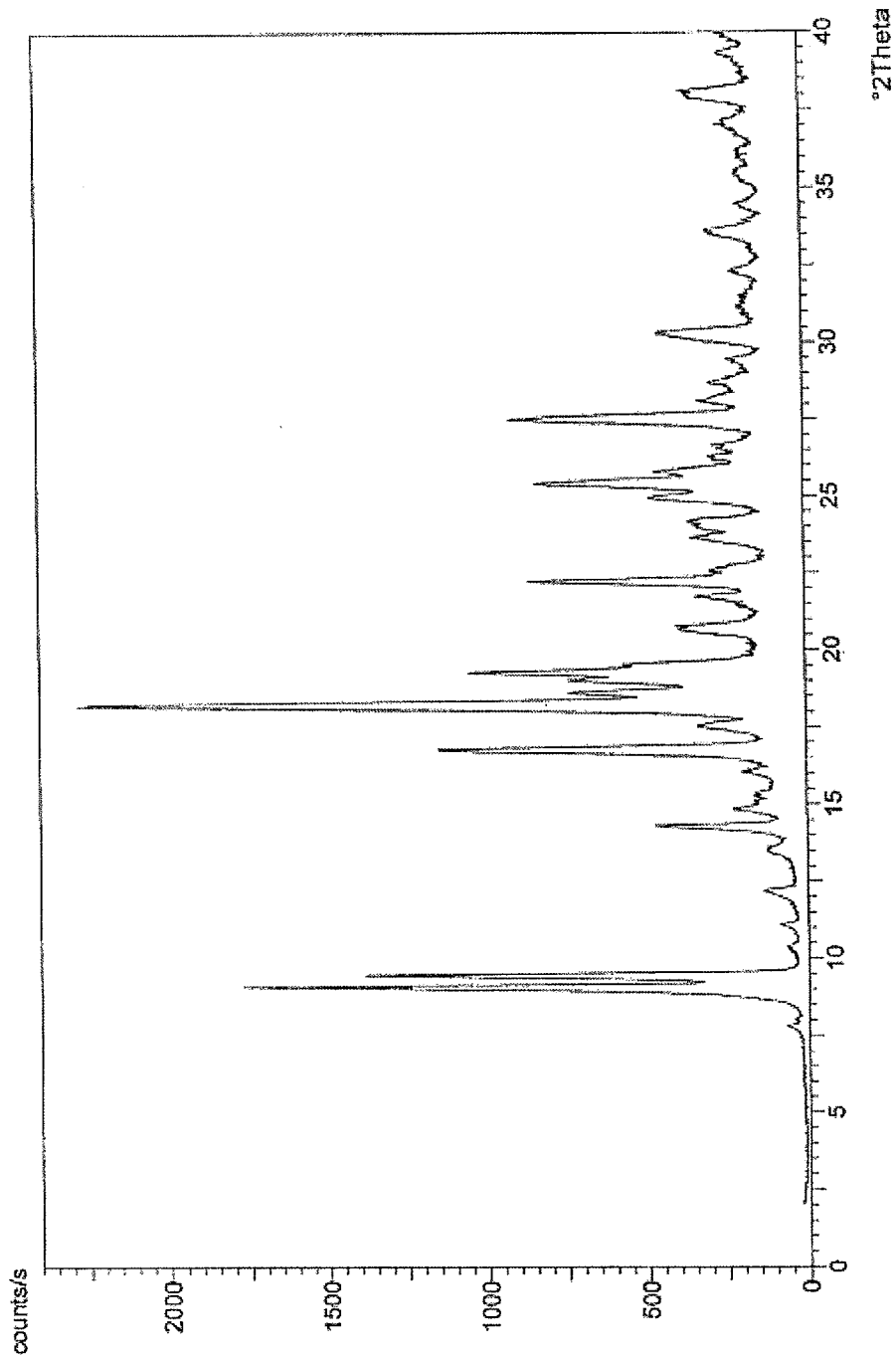
Figure 1D:
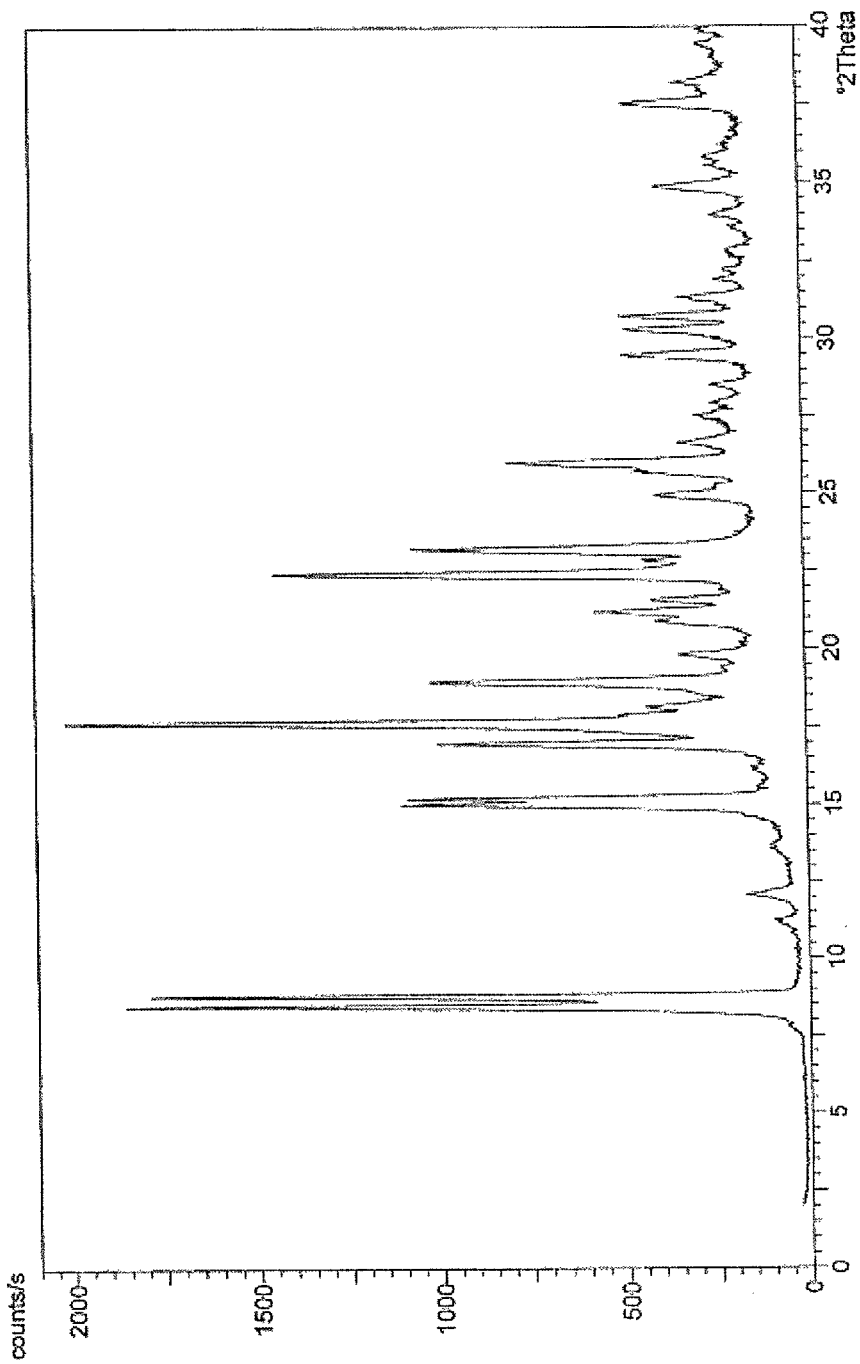
Figure 1E:
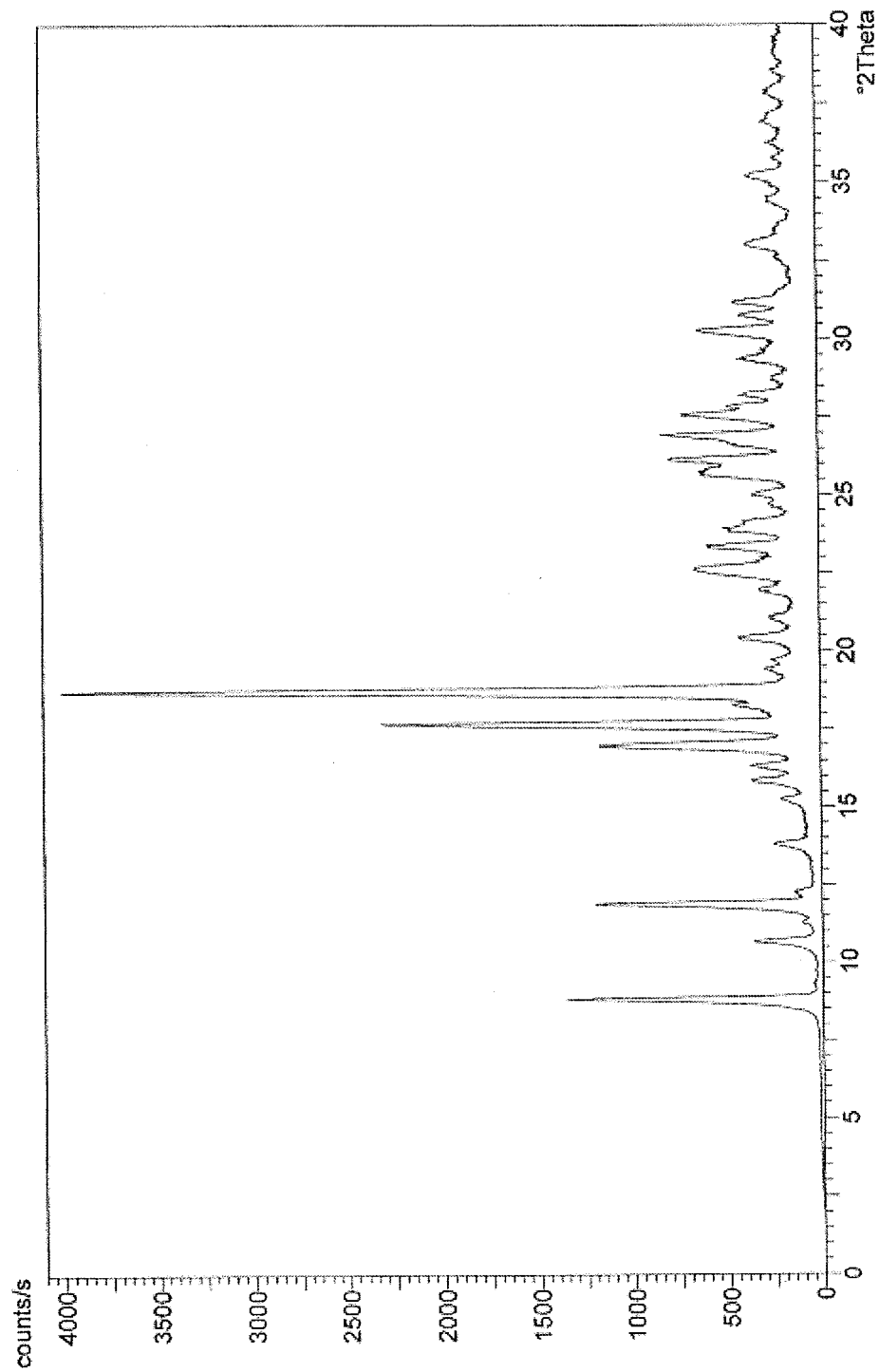
Figure 1F:
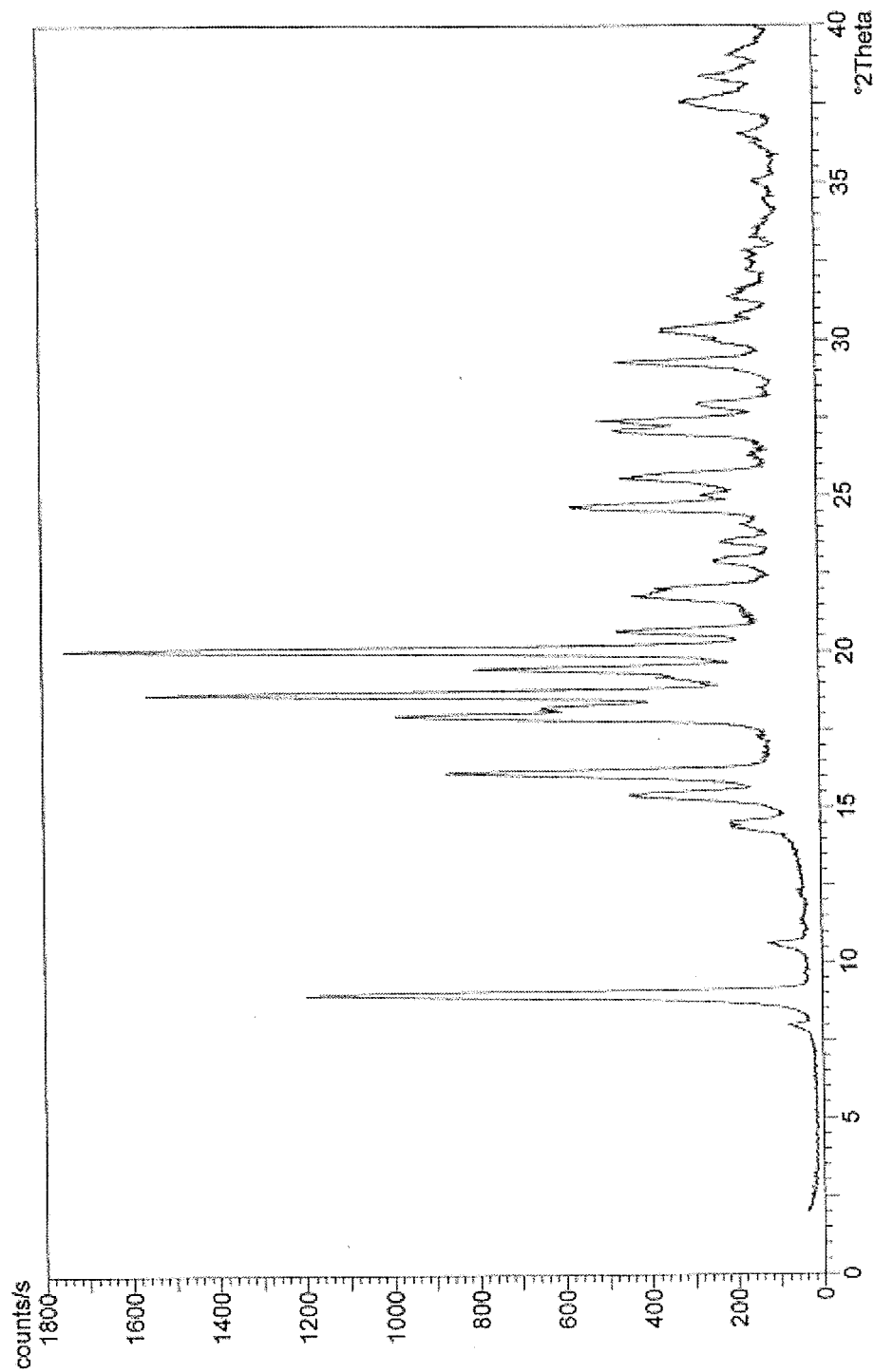
Figure 1G:
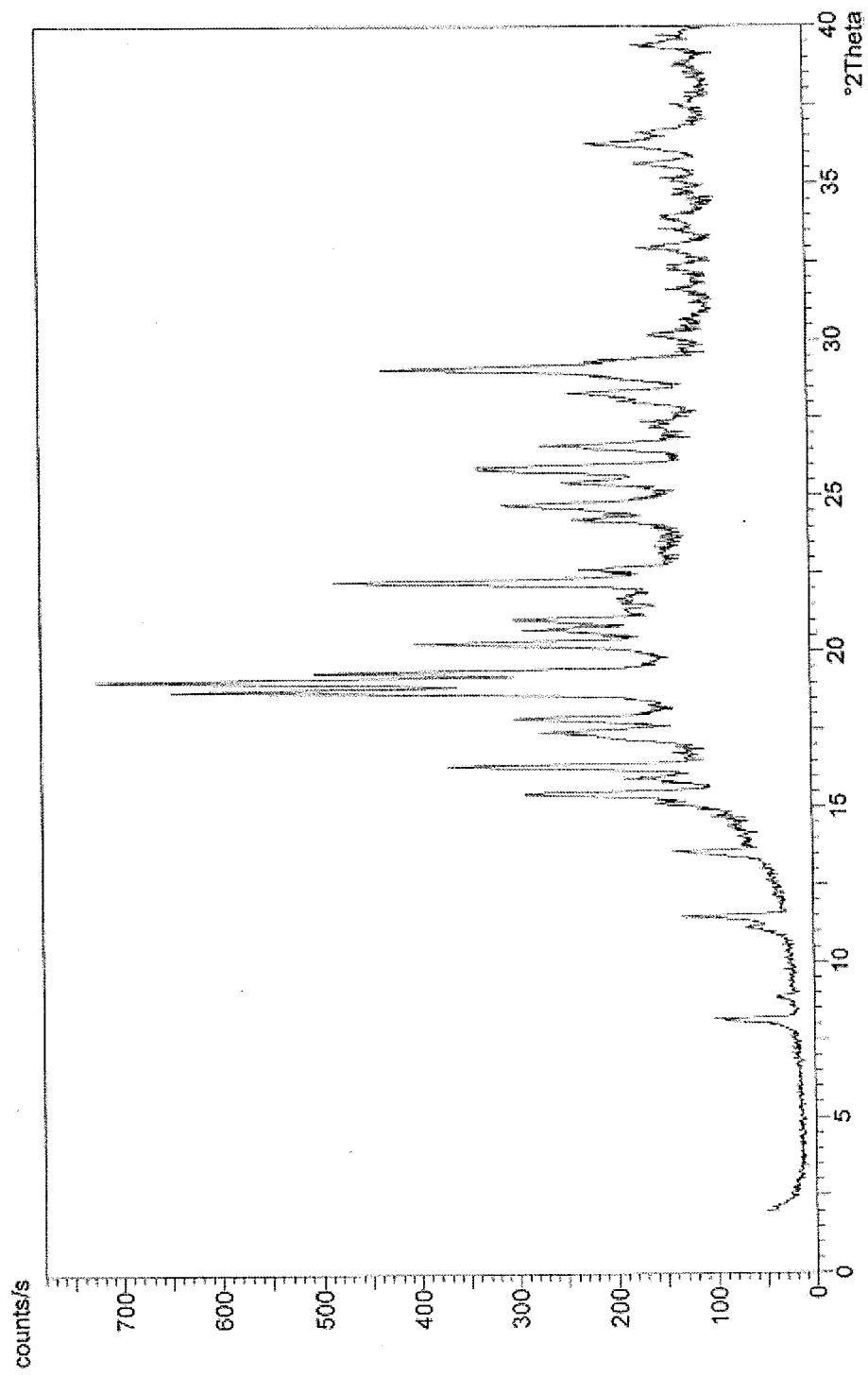
Figure 1H:
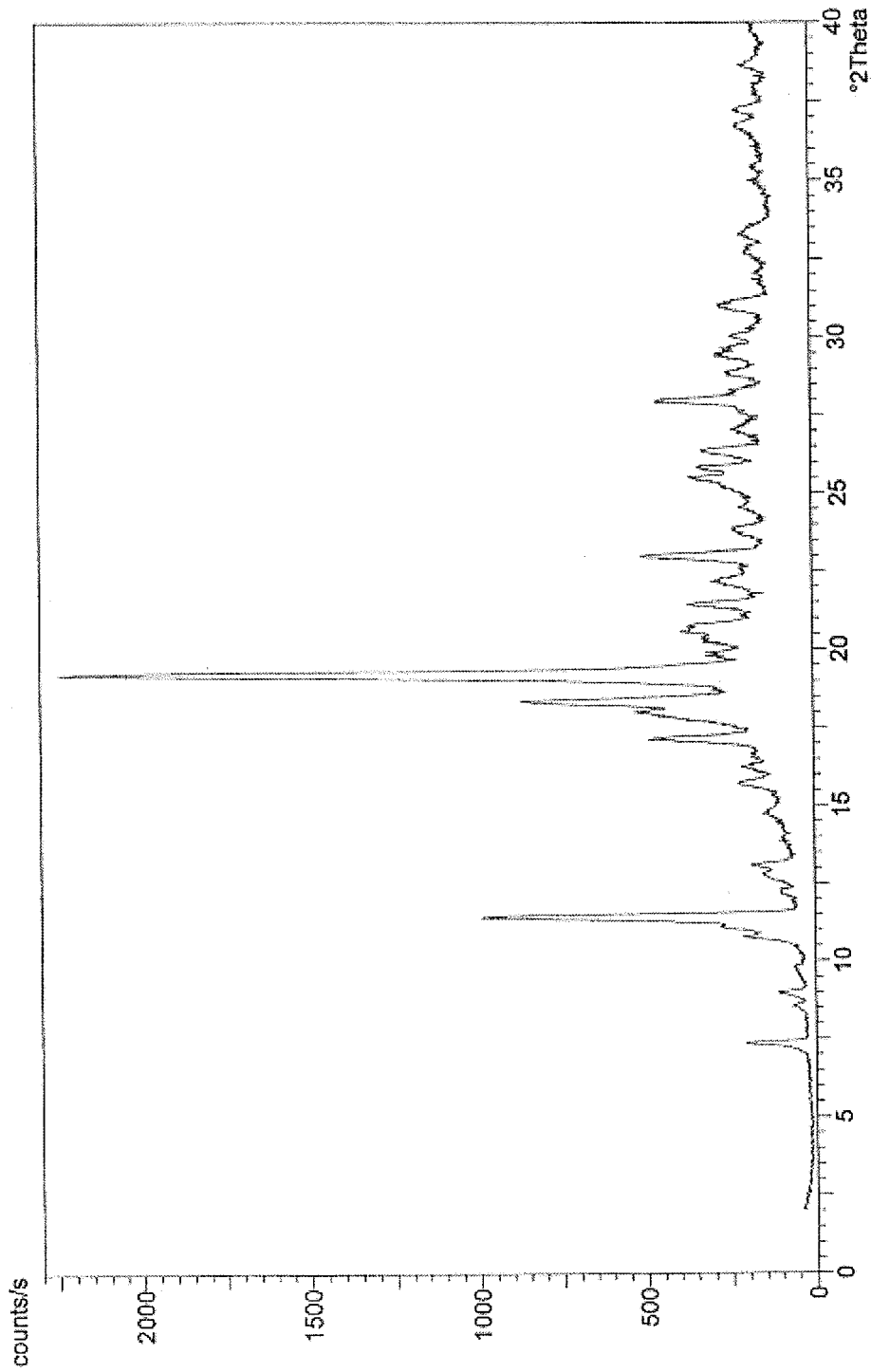
Figure 1I:
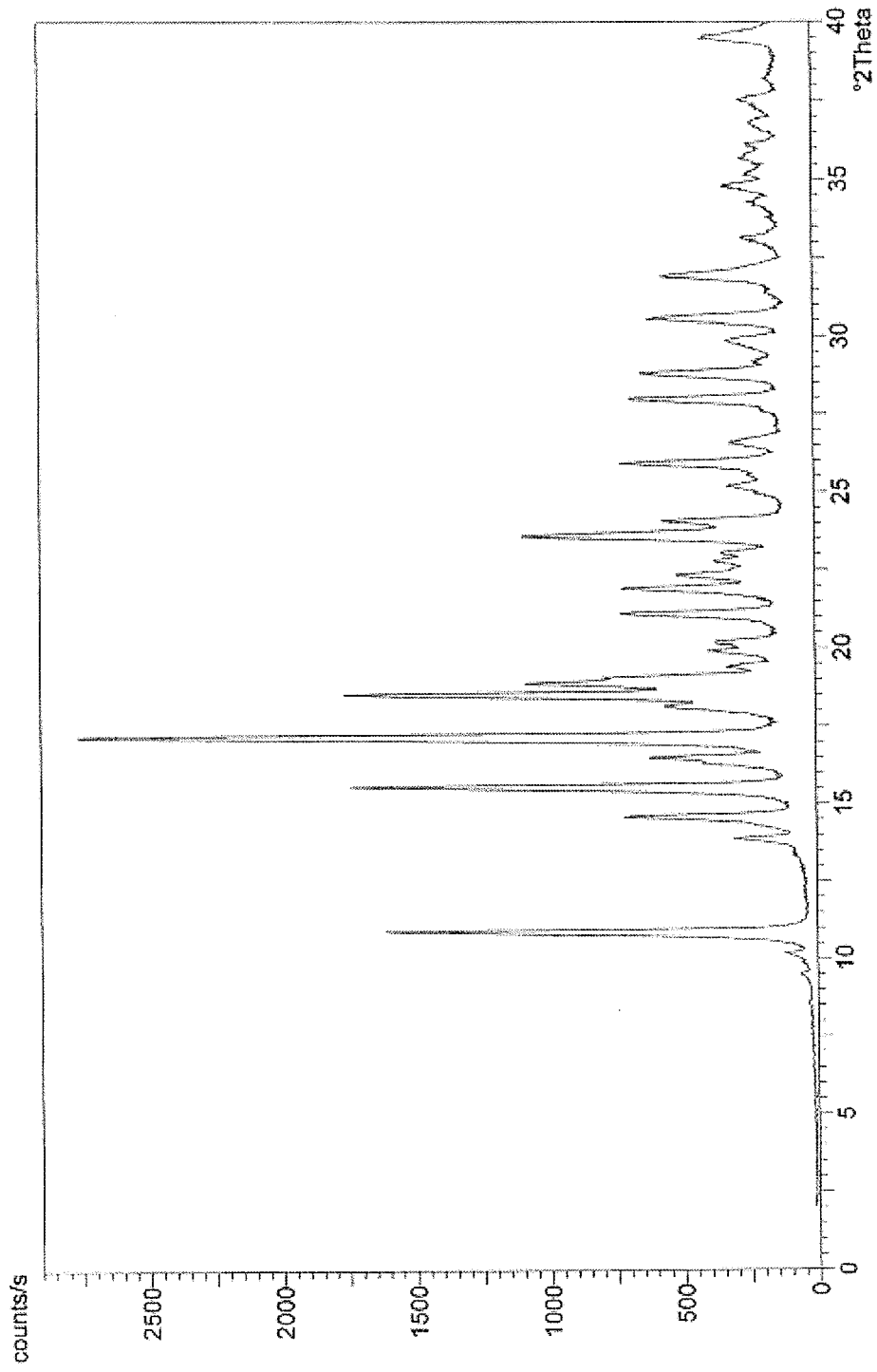
Figure 1I:
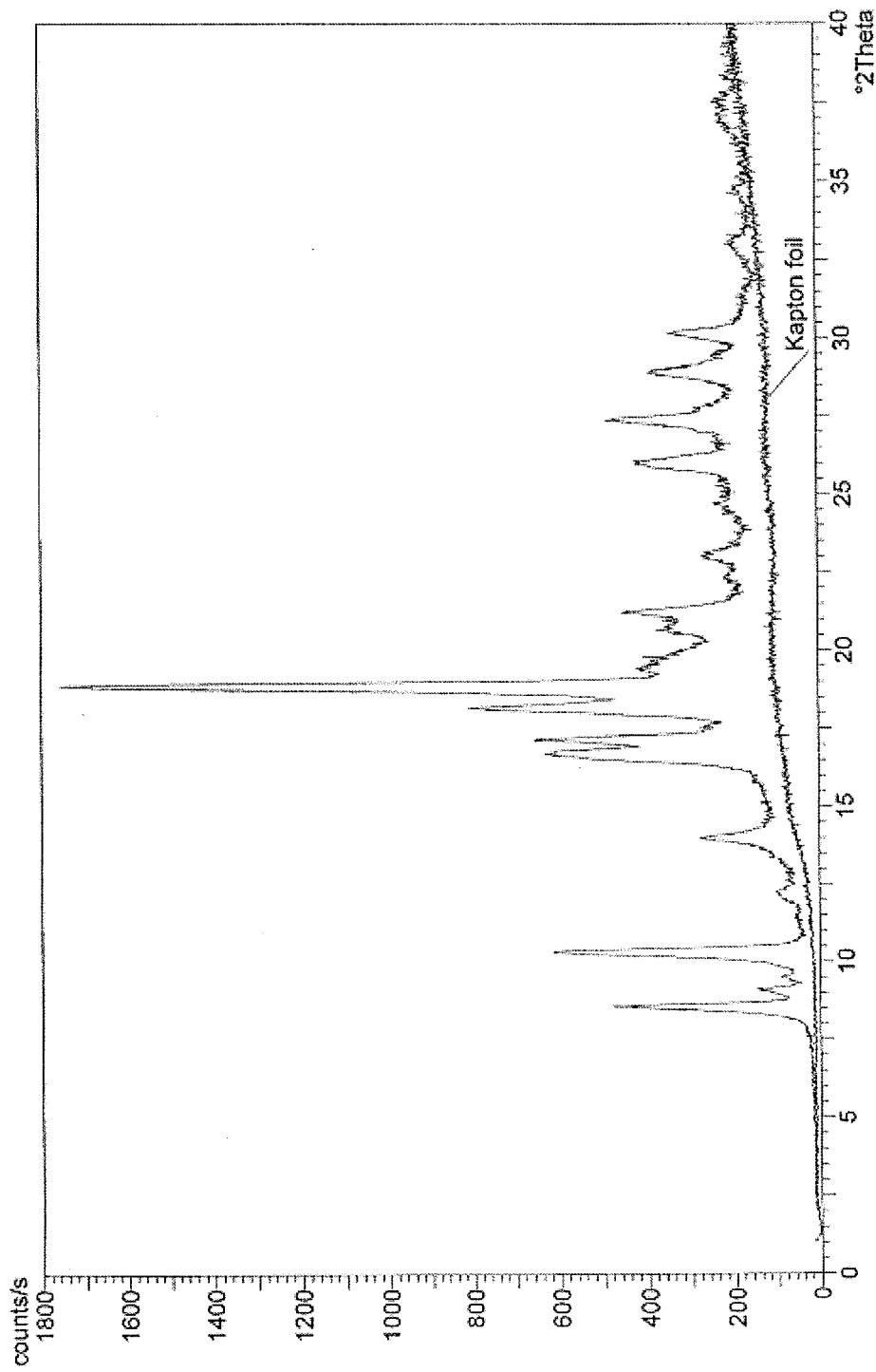

FIG. 1 shows the superposed PXRD patterns of crystalline forms A, B, C, D, E, F, G, H, I and L.

Crystalline Form A

Table 4 shows the peak list for crystalline form A. The uncertainty in the 2θ values is ±0.2° in 2θ; rel. I is the relative intensity of the respective peaks. Maximum intensity is 100.

TABLE 4

| 2θ | d value Å | Intensity Cps | rel. I % |
|---|---|---|---|
| 7.8 | 11.3 | 324 | 16 |
| 8.8 | 10.1 | 156 | 8 |
| 9.1 | 9.7 | 120 | 6 |
| 10.5 | 8.4 | 40 | 2 |
| 11.1 | 8.0 | 300 | 15 |
| 11.7 | 7.6 | 64 | 3 |
| 12.2 | 7.3 | 280 | 14 |
| 13.5 | 6.5 | 343 | 17 |
| 15.2 | 5.8 | 140 | 7 |
| 16.0 | 5.5 | 134 | 7 |
| 16.8 | 5.3 | 347 | 17 |
| 17.6 | 5.1 | 735 | 36 |
| 18.3 | 4.9 | 2044 | 100 |
| 18.6 | 4.8 | 1295 | 63 |
| 19.4 | 4.6 | 474 | 23 |
| 19.7 | 4.5 | 346 | 17 |
| 20.6 | 4.3 | 214 | 11 |
| 20.8 | 4.3 | 308 | 15 |
| 21.5 | 4.1 | 178 | 9 |
| 22.0 | 4.0 | 135 | 7 |
| 22.3 | 4.0 | 199 | 10 |
| 22.6 | 3.9 | 227 | 11 |
| 23.5 | 3.8 | 263 | 13 |
| 23.9 | 3.7 | 208 | 10 |
| 24.2 | 3.7 | 176 | 9 |
| 25.0 | 3.6 | 292 | 14 |
| 25.8 | 3.5 | 505 | 25 |
| 26.3 | 3.4 | 564 | 28 |
| 27.2 | 3.3 | 180 | 9 |
| 27.6 | 3.2 | 442 | 22 |
| 28.3 | 3.2 | 360 | 18 |
| 29.1 | 3.1 | 249 | 12 |
| 29.5 | 3.0 | 115 | 6 |
| 30.0 | 3.0 | 256 | 13 |
| 31.6 | 2.8 | 147 | 7 |
| 32.3 | 2.8 | 174 | 9 |
| 32.6 | 2.8 | 147 | 7 |
| 33.8 | 2.7 | 96 | 5 |

Crystalline Form B

Table 5 shows the peak list for crystalline form B. The uncertainty in the 2θ values is ±0.2° in 2θ; rel. I is the relative intensity of the respective peaks. Maximum intensity is 100.

TABLE 5

| 2θ | d value Å | Intensity Cps | rel. I % |
|---|---|---|---|
| 8.9 | 9.9 | 524 | 36 |
| 9.8 | 9.0 | 1241 | 86 |
| 10.5 | 8.4 | 59 | 4 |
| 12.0 | 7.4 | 189 | 13 |
| 14.2 | 6.2 | 91 | 6 |
| 14.6 | 6.1 | 85 | 6 |
| 15.7 | 5.6 | 485 | 34 |
| 16.2 | 5.5 | 142 | 10 |
| 16.7 | 5.3 | 798 | 55 |
| 17.8 | 5.0 | 1440 | 100 |
| 18.4 | 4.8 | 466 | 32 |
| 19.2 | 4.6 | 672 | 47 |
| 19.7 | 4.5 | 503 | 35 |
| 20.0 | 4.5 | 330 | 23 |
| 20.4 | 4.4 | 413 | 29 |
| 21.4 | 4.2 | 159 | 11 |
| 21.8 | 4.1 | 566 | 39 |
| 22.6 | 3.9 | 168 | 12 |
| 23.5 | 3.8 | 124 | 9 |

TABLE 5-continued

| 2θ | d value Å | Intensity Cps | rel. I % |
|---|---|---|---|
| 24.1 | 3.7 | 715 | 50 |
| 25.1 | 3.6 | 352 | 25 |
| 25.4 | 3.5 | 267 | 19 |
| 26.0 | 3.4 | 451 | 31 |
| 26.7 | 3.3 | 190 | 13 |
| 27.1 | 3.3 | 322 | 22 |
| 27.9 | 3.2 | 144 | 10 |
| 28.1 | 3.2 | 297 | 21 |
| 29.2 | 3.1 | 271 | 19 |
| 29.7 | 3.0 | 182 | 13 |
| 30.3 | 2.9 | 204 | 14 |
| 31.1 | 2.9 | 627 | 44 |
| 31.8 | 2.8 | 111 | 8 |
| 32.7 | 2.7 | 176 | 12 |
| 32.9 | 2.7 | 164 | 11 |
| 33.5 | 2.7 | 163 | 11 |
| 33.9 | 2.6 | 130 | 9 |
| 34.9 | 2.6 | 161 | 11 |

Crystalline Form C

Table 6 shows the peak list for crystalline form C. The uncertainty in the 2θ values is ±0.2° in 2θ; rel. I is the relative intensity of the respective peaks. Maximum intensity is 100.

TABLE 6

| 2θ | d value Å | Intensity Cps | rel. I % |
|---|---|---|---|
| 7.8 | 11.4 | 46 | 3 |
| 9.1 | 9.7 | 1188 | 76 |
| 9.5 | 9.3 | 939 | 60 |
| 10.4 | 8.5 | 52 | 3 |
| 11.1 | 8.0 | 55 | 4 |
| 12.2 | 7.3 | 97 | 6 |
| 13.5 | 6.6 | 86 | 6 |
| 14.3 | 6.2 | 292 | 19 |
| 14.8 | 6.0 | 156 | 10 |
| 15.3 | 5.8 | 118 | 8 |
| 16.1 | 5.5 | 143 | 9 |
| 16.8 | 5.3 | 772 | 49 |
| 17.5 | 5.1 | 238 | 15 |
| 18.2 | 4.9 | 1572 | 100 |
| 18.6 | 4.8 | 508 | 32 |
| 19.0 | 4.7 | 518 | 33 |
| 19.3 | 4.6 | 731 | 47 |
| 19.5 | 4.5 | 387 | 25 |
| 20.7 | 4.3 | 259 | 17 |
| 21.7 | 4.1 | 240 | 15 |
| 22.2 | 4.0 | 605 | 39 |
| 22.5 | 3.9 | 210 | 13 |
| 23.6 | 3.8 | 256 | 16 |
| 24.2 | 3.7 | 254 | 16 |
| 24.9 | 3.6 | 328 | 21 |
| 25.4 | 3.5 | 586 | 37 |
| 25.8 | 3.5 | 329 | 21 |
| 26.2 | 3.4 | 198 | 13 |
| 26.5 | 3.4 | 186 | 12 |
| 27.5 | 3.2 | 634 | 40 |
| 28.1 | 3.2 | 222 | 14 |
| 28.7 | 3.1 | 206 | 13 |
| 29.4 | 3.0 | 158 | 10 |
| 30.3 | 3.0 | 322 | 21 |
| 32.3 | 2.8 | 151 | 10 |
| 33.6 | 2.7 | 209 | 13 |
| 34.5 | 2.6 | 143 | 9 |

Crystalline Form D

Table 7 shows the peak list for crystalline form D. The uncertainty in the 2θ values is ±0.2° in 2θ; rel. I is the relative intensity of the respective peaks. Maximum intensity is 100.

TABLE 7

| 2θ | d value Å | Intensity Cps | rel. I % |
|---|---|---|---|
| 8.4 | 10.5 | 1238 | 88 |
| 8.8 | 10.1 | 1207 | 86 |
| 11.2 | 7.9 | 67 | 5 |
| 12.1 | 7.3 | 122 | 9 |
| 13.7 | 6.5 | 76 | 5 |
| 15.0 | 5.9 | 760 | 54 |
| 15.2 | 5.8 | 760 | 54 |
| 16.1 | 5.5 | 114 | 8 |
| 17.0 | 5.2 | 699 | 50 |
| 17.6 | 5.0 | 1408 | 100 |
| 18.1 | 4.9 | 297 | 21 |
| 18.9 | 4.7 | 690 | 49 |
| 19.4 | 4.6 | 157 | 11 |
| 19.8 | 4.5 | 239 | 17 |
| 20.9 | 4.3 | 281 | 20 |
| 21.2 | 4.2 | 399 | 28 |
| 21.6 | 4.1 | 286 | 20 |
| 22.4 | 4.0 | 1009 | 72 |
| 22.8 | 3.9 | 317 | 23 |
| 23.2 | 3.8 | 711 | 51 |
| 24.9 | 3.6 | 280 | 20 |
| 25.2 | 3.5 | 162 | 12 |
| 25.7 | 3.5 | 336 | 24 |
| 26.0 | 3.4 | 564 | 40 |
| 26.6 | 3.4 | 237 | 17 |
| 27.5 | 3.2 | 188 | 13 |
| 28.0 | 3.2 | 177 | 13 |
| 28.5 | 3.1 | 176 | 13 |
| 29.5 | 3.0 | 346 | 25 |
| 30.3 | 3.0 | 331 | 24 |
| 30.7 | 2.9 | 359 | 26 |
| 31.3 | 2.9 | 201 | 14 |
| 31.9 | 2.8 | 171 | 12 |
| 32.2 | 2.8 | 154 | 11 |
| 32.8 | 2.7 | 148 | 11 |
| 33.6 | 2.7 | 129 | 9 |
| 34.0 | 2.6 | 178 | 13 |
| 34.9 | 2.6 | 266 | 19 |

Crystalline Form E

Table 8 shows the peak list for crystalline form E. The uncertainty in the 2θ values is ±0.2° in 2θ; rel. I is the relative intensity of the respective peaks. Maximum intensity is 100.

TABLE 8

| 2θ | d value Å | Intensity Cps | rel. I % |
|---|---|---|---|
| 8.8 | 10.1 | 899 | 33 |
| 10.7 | 8.3 | 249 | 9 |
| 11.3 | 7.8 | 74 | 3 |
| 11.9 | 7.5 | 794 | 29 |
| 12.2 | 7.2 | 103 | 4 |
| 13.8 | 6.4 | 174 | 6 |
| 15.2 | 5.8 | 146 | 5 |
| 15.8 | 5.6 | 245 | 9 |
| 16.3 | 5.4 | 261 | 10 |
| 17.0 | 5.2 | 796 | 29 |
| 17.7 | 5.0 | 1594 | 59 |
| 18.2 | 4.9 | 316 | 12 |
| 18.7 | 4.7 | 2708 | 100 |
| 19.4 | 4.6 | 209 | 8 |
| 19.7 | 4.5 | 178 | 7 |
| 20.4 | 4.4 | 298 | 11 |
| 21.1 | 4.2 | 170 | 6 |
| 21.9 | 4.1 | 230 | 9 |
| 22.6 | 3.9 | 450 | 17 |
| 23.3 | 3.8 | 410 | 15 |
| 23.9 | 3.7 | 304 | 11 |
| 24.1 | 3.7 | 262 | 10 |
| 24.7 | 3.6 | 186 | 7 |
| 25.0 | 3.6 | 253 | 9 |
| 25.7 | 3.5 | 415 | 15 |

TABLE 8-continued

| 2θ | d value Å | Intensity Cps | rel. I % |
|---|---|---|---|
| 26.1 | 3.4 | 555 | 21 |
| 26.6 | 3.4 | 330 | 12 |
| 26.9 | 3.3 | 577 | 21 |
| 27.6 | 3.2 | 507 | 19 |
| 27.8 | 3.2 | 340 | 13 |
| 28.2 | 3.2 | 295 | 11 |
| 28.7 | 3.1 | 167 | 6 |
| 29.4 | 3.0 | 309 | 11 |
| 30.3 | 3.0 | 434 | 16 |
| 30.8 | 2.9 | 291 | 11 |
| 31.2 | 2.9 | 325 | 12 |
| 31.5 | 2.8 | 146 | 5 |
| 33.0 | 2.7 | 264 | 10 |
| 34.4 | 2.6 | 168 | 6 |

Crystalline Form F

Table 9 shows the peak list for crystalline form F. The uncertainty in the 2θ values is ±0.2° in 2θ; rel. I is the relative intensity of the respective peaks. Maximum intensity is 100.

TABLE 9

| 2θ | d value Å | Intensity Cps | rel. I % |
|---|---|---|---|
| 8.0 | 11.1 | 53 | 4 |
| 9.0 | 9.8 | 828 | 69 |
| 10.6 | 8.4 | 84 | 7 |
| 14.5 | 6.1 | 144 | 12 |
| 15.4 | 5.7 | 304 | 25 |
| 16.1 | 5.5 | 591 | 49 |
| 17.9 | 4.9 | 658 | 55 |
| 18.2 | 4.9 | 443 | 37 |
| 18.7 | 4.8 | 1068 | 89 |
| 19.4 | 4.6 | 544 | 46 |
| 20.1 | 4.4 | 1196 | 100 |
| 20.6 | 4.3 | 333 | 28 |
| 21.8 | 4.1 | 294 | 25 |
| 21.9 | 4.1 | 244 | 20 |
| 22.9 | 3.9 | 166 | 14 |
| 23.5 | 3.8 | 157 | 13 |
| 24.0 | 3.7 | 111 | 9 |
| 24.6 | 3.6 | 411 | 34 |
| 25.0 | 3.6 | 188 | 16 |
| 25.6 | 3.5 | 328 | 27 |
| 27.1 | 3.3 | 315 | 26 |
| 27.4 | 3.3 | 357 | 30 |
| 27.9 | 3.2 | 190 | 16 |
| 29.3 | 3.1 | 328 | 27 |
| 30.0 | 3.0 | 163 | 14 |
| 30.3 | 3.0 | 249 | 21 |
| 30.8 | 2.9 | 128 | 11 |
| 31.4 | 2.9 | 140 | 12 |
| 31.6 | 2.8 | 122 | 10 |
| 32.2 | 2.8 | 122 | 10 |
| 32.8 | 2.7 | 106 | 9 |
| 33.3 | 2.7 | 100 | 8 |
| 34.4 | 2.6 | 82 | 7 |
| 35.0 | 2.6 | 99 | 8 |

Crystalline Form G

Table 10 shows the peak list for crystalline form G. The uncertainty in the 2θ values is ±0.2° in 2θ; rel. I is the relative intensity of the respective peaks. Maximum intensity is 100.

TABLE 10

| 2θ | d value Å | Intensity Cps | rel. I % |
|---|---|---|---|
| 8.1 | 10.9 | 66 | 14 |
| 8.9 | 10.0 | 31 | 6 |
| 11.1 | 8.0 | 48 | 10 |
| 11.5 | 7.7 | 96 | 20 |
| 13.5 | 6.5 | 88 | 18 |
| 15.1 | 5.9 | 108 | 22 |
| 15.4 | 5.7 | 195 | 40 |
| 15.9 | 5.6 | 132 | 27 |
| 16.3 | 5.4 | 256 | 53 |
| 17.2 | 5.1 | 147 | 30 |
| 17.4 | 5.1 | 199 | 41 |
| 17.8 | 5.0 | 204 | 42 |
| 18.8 | 4.7 | 458 | 94 |
| 19.1 | 4.7 | 488 | 100 |
| 19.4 | 4.6 | 353 | 72 |
| 20.3 | 4.4 | 279 | 57 |
| 20.7 | 4.3 | 213 | 44 |
| 21.0 | 4.2 | 205 | 42 |
| 22.2 | 4.0 | 326 | 67 |
| 22.6 | 3.9 | 172 | 35 |
| 24.2 | 3.7 | 157 | 32 |
| 24.7 | 3.6 | 227 | 47 |
| 25.4 | 3.5 | 171 | 35 |
| 25.9 | 3.4 | 231 | 47 |
| 26.6 | 3.4 | 161 | 33 |
| 28.0 | 3.2 | 135 | 28 |
| 28.3 | 3.2 | 157 | 32 |
| 28.8 | 3.1 | 134 | 28 |
| 29.1 | 3.1 | 299 | 61 |
| 29.4 | 3.0 | 152 | 31 |
| 30.2 | 3.0 | 113 | 23 |
| 31.6 | 2.8 | 104 | 21 |
| 32.3 | 2.8 | 98 | 20 |
| 33.0 | 2.7 | 130 | 27 |
| 33.5 | 2.7 | 93 | 19 |
| 33.9 | 2.6 | 101 | 21 |
| 34.7 | 2.6 | 106 | 22 |

Crystalline Form H

Table 11 shows the peak list for crystalline form H. The uncertainty in the 2θ values is ±0.2° in 2θ; rel. I is the relative intensity of the respective peaks. Maximum intensity is 100.

TABLE 11

| 2θ | d value Å | Intensity Cps | rel. I % |
|---|---|---|---|
| 7.4 | 12.0 | 145 | 10 |
| 8.5 | 10.4 | 52 | 3 |
| 9.0 | 9.9 | 76 | 5 |
| 9.8 | 9.1 | 50 | 3 |
| 10.8 | 8.2 | 154 | 10 |
| 11.4 | 7.7 | 687 | 45 |
| 12.2 | 7.2 | 74 | 5 |
| 12.8 | 6.9 | 104 | 7 |
| 13.1 | 6.8 | 130 | 9 |
| 14.8 | 6.0 | 102 | 7 |
| 15.7 | 5.6 | 153 | 10 |
| 16.2 | 5.5 | 147 | 10 |
| 16.6 | 5.3 | 134 | 9 |
| 17.1 | 5.2 | 340 | 22 |
| 18.0 | 4.9 | 352 | 23 |
| 18.3 | 4.8 | 569 | 38 |
| 19.2 | 4.6 | 1515 | 100 |
| 19.8 | 4.5 | 211 | 14 |
| 20.3 | 4.4 | 219 | 14 |
| 20.6 | 4.3 | 261 | 17 |
| 21.4 | 4.1 | 252 | 17 |
| 22.2 | 4.0 | 205 | 14 |
| 23.0 | 3.9 | 354 | 23 |
| 23.8 | 3.7 | 152 | 10 |
| 24.5 | 3.6 | 154 | 10 |
| 25.5 | 3.5 | 235 | 16 |
| 25.8 | 3.5 | 218 | 14 |
| 26.3 | 3.4 | 220 | 15 |

TABLE 11-continued

| 2θ | d value Å | Intensity Cps | rel. I % |
|---|---|---|---|
| 27.0 | 3.3 | 149 | 10 |
| 27.6 | 3.2 | 138 | 9 |
| 27.9 | 3.2 | 335 | 22 |
| 28.3 | 3.2 | 159 | 11 |
| 28.8 | 3.1 | 161 | 11 |
| 29.4 | 3.0 | 203 | 13 |
| 30.0 | 3.0 | 159 | 11 |
| 31.0 | 2.9 | 184 | 12 |
| 32.7 | 2.7 | 141 | 9 |
| 33.3 | 2.7 | 150 | 10 |

Crystalline Form I

Table 12 shows the peak list for crystalline form I. The uncertainty in the 2θ values is ±0.2° in 2θ; rel. I is the relative intensity of the respective peaks. Maximum intensity is 100.

TABLE 12

| 2θ | d value Å | Intensity Cps | rel. I % |
|---|---|---|---|
| 9.5 | 9.3 | 48 | 3 |
| 10.1 | 8.7 | 73 | 4 |
| 10.9 | 8.1 | 1092 | 58 |
| 13.9 | 6.4 | 197 | 10 |
| 14.6 | 6.1 | 498 | 26 |
| 15.5 | 5.7 | 1188 | 63 |
| 16.5 | 5.4 | 436 | 23 |
| 17.1 | 5.2 | 1898 | 100 |
| 18.1 | 4.9 | 379 | 20 |
| 18.5 | 4.8 | 1207 | 64 |
| 18.8 | 4.7 | 744 | 39 |
| 19.4 | 4.6 | 229 | 12 |
| 19.9 | 4.5 | 273 | 14 |
| 20.2 | 4.4 | 268 | 14 |
| 21.1 | 4.2 | 503 | 27 |
| 21.9 | 4.1 | 501 | 26 |
| 22.3 | 4.0 | 349 | 18 |
| 22.8 | 3.9 | 267 | 14 |
| 23.0 | 3.9 | 240 | 13 |
| 23.6 | 3.8 | 735 | 39 |
| 24.0 | 3.7 | 391 | 21 |
| 25.2 | 3.5 | 227 | 12 |
| 25.9 | 3.4 | 486 | 26 |
| 26.6 | 3.4 | 229 | 12 |
| 27.6 | 3.2 | 144 | 8 |
| 28.0 | 3.2 | 474 | 25 |
| 28.8 | 3.1 | 442 | 23 |
| 29.1 | 3.1 | 154 | 8 |
| 30.0 | 3.0 | 223 | 12 |
| 30.6 | 2.9 | 443 | 23 |
| 31.9 | 2.8 | 408 | 22 |
| 33.1 | 2.7 | 192 | 10 |
| 34.2 | 2.6 | 150 | 8 |
| 34.8 | 2.6 | 247 | 13 |

Crystalline Form L

Table 13 shows the peak list for crystalline form L. The uncertainty in the 2θ values is ±0.2° in 2θ: rel. I is the relative intensity of the respective peaks. Maximum intensity is 100.

TABLE 13

| 2θ | d value Å | Intensity Cps | rel. I % |
|---|---|---|---|
| 8.6 | 10.3 | 319 | 27 |
| 9.1 | 9.7 | 109 | 9 |
| 9.5 | 9.3 | 64 | 6 |
| 10.3 | 8.6 | 422 | 36 |
| 12.2 | 7.3 | 66 | 6 |
| 14.0 | 6.3 | 192 | 17 |

TABLE 13-continued

| 2θ | d value Å | Intensity Cps | rel. I % |
|---|---|---|---|
| 16.7 | 5.3 | 428 | 37 |
| 17.2 | 5.2 | 474 | 41 |
| 18.2 | 4.9 | 548 | 47 |
| 18.8 | 4.7 | 1165 | 100 |
| 20.7 | 4.3 | 256 | 22 |
| 21.2 | 4.2 | 316 | 27 |
| 22.3 | 4.0 | 154 | 13 |
| 23.0 | 3.9 | 187 | 16 |
| 24.5 | 3.6 | 140 | 12 |
| 26.0 | 3.4 | 286 | 25 |
| 27.4 | 3.3 | 334 | 29 |
| 28.9 | 3.1 | 269 | 23 |
| 30.2 | 3.0 | 235 | 20 |

Analysis—FT Raman Spectroscopy

FT Raman spectra were recorded on a Bruker RFS100 Raman spectrometer (Nd-YAG 100 mW laser, excitation 1064 nm, Ge detector, 64 scans, 25-3500 cm$^{-1}$, resolution 2 cm$^{-1}$).

Figure 2A:
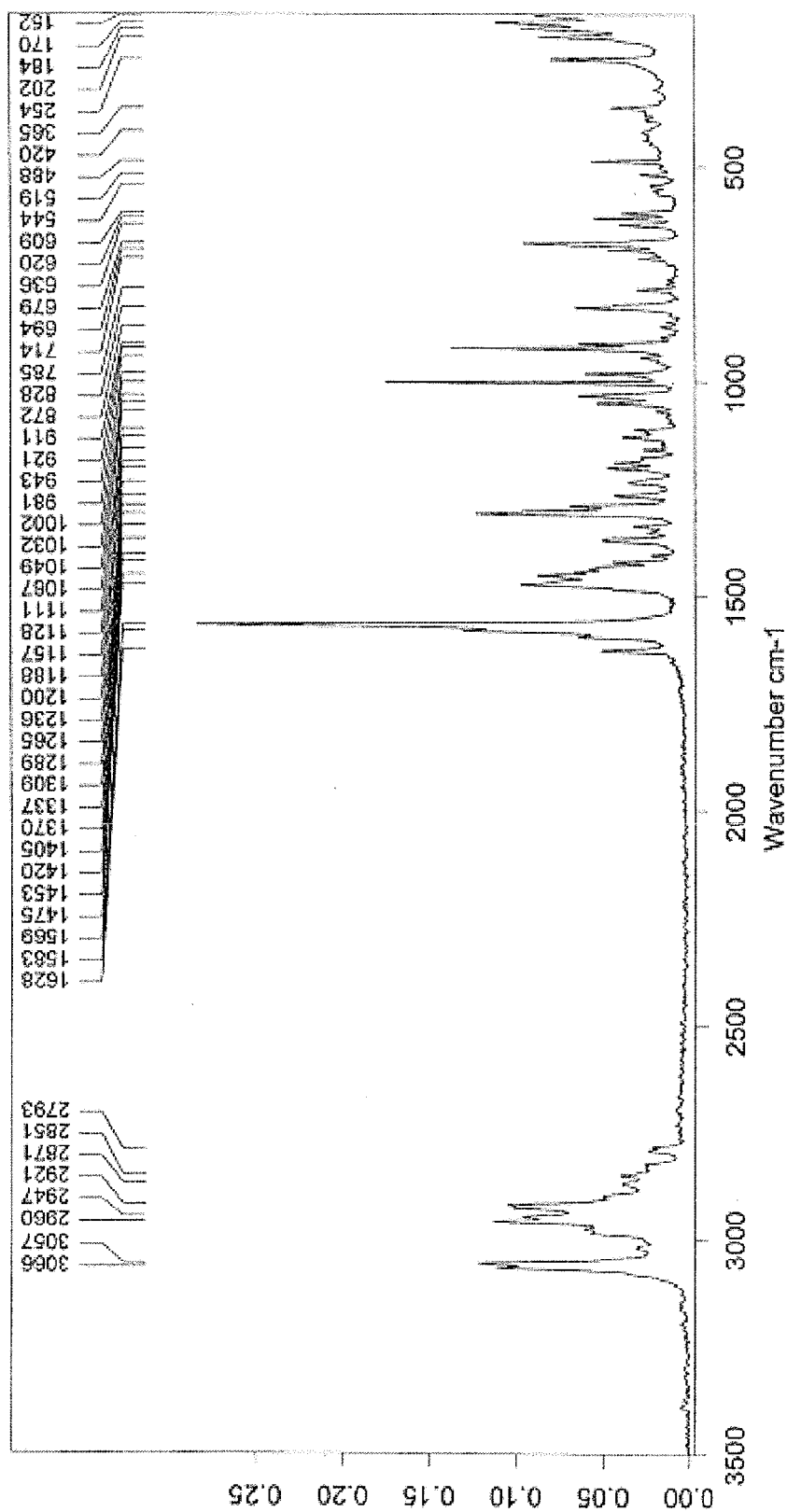
Figure 2B:
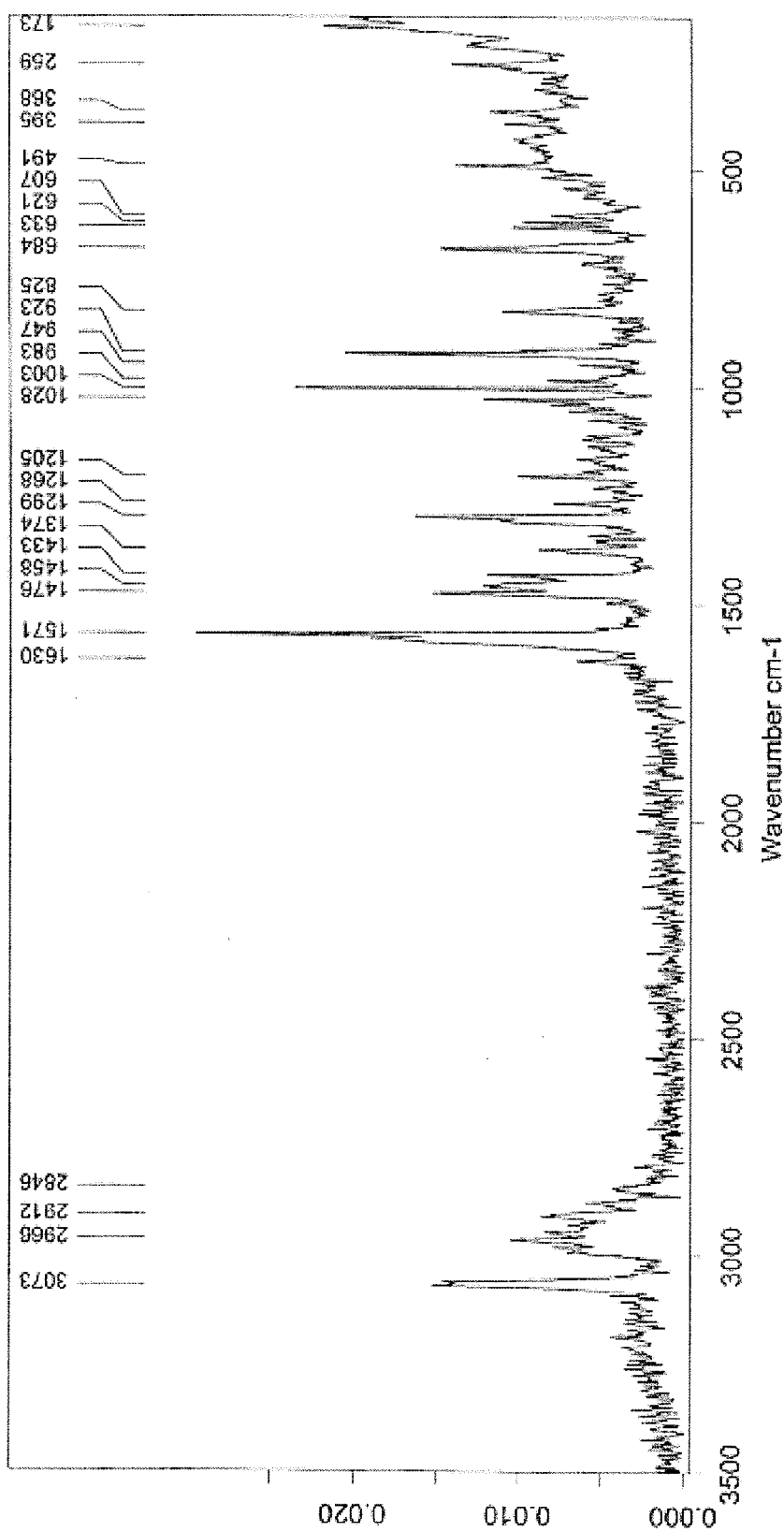
Figure 2C:
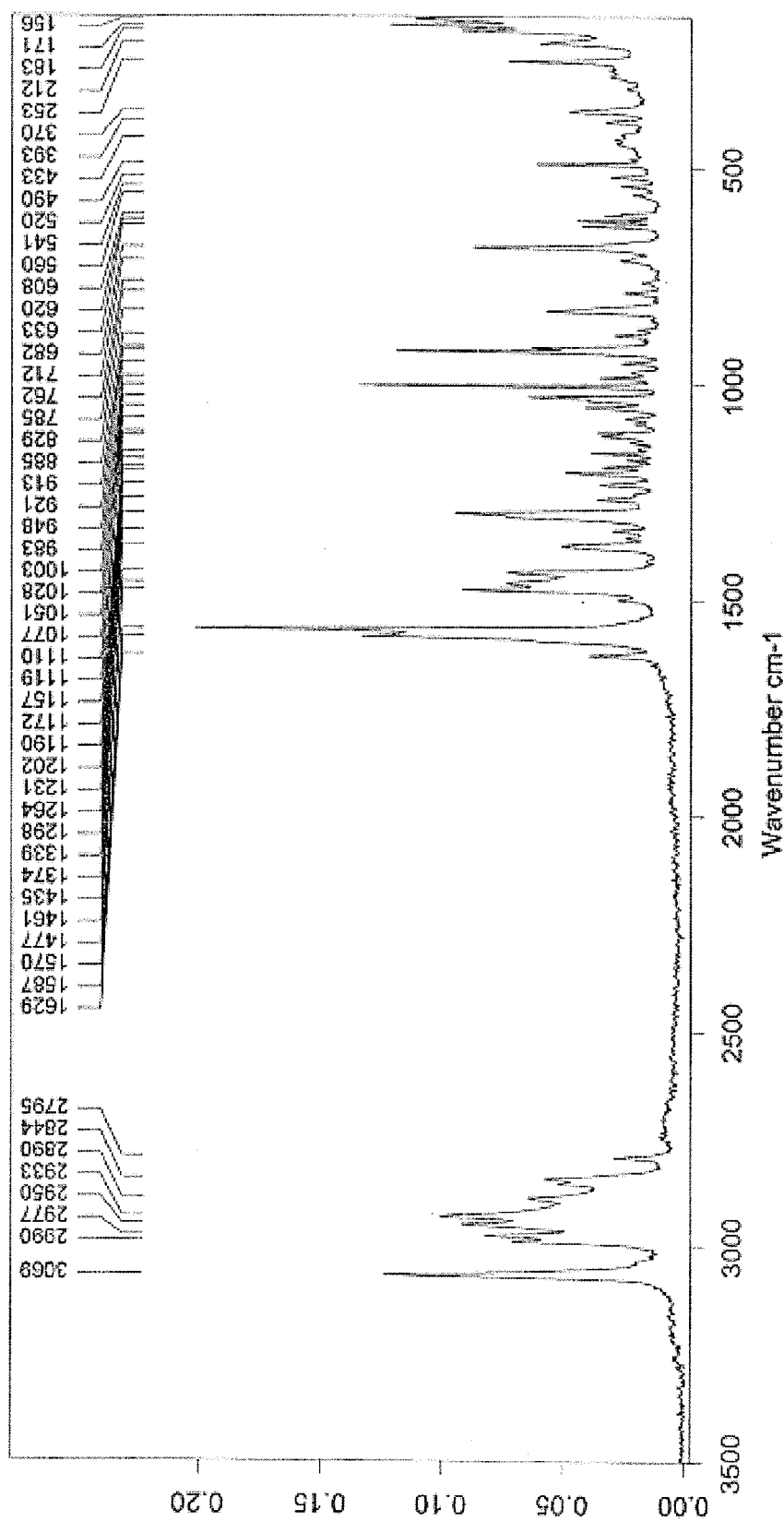
Figure 2D:
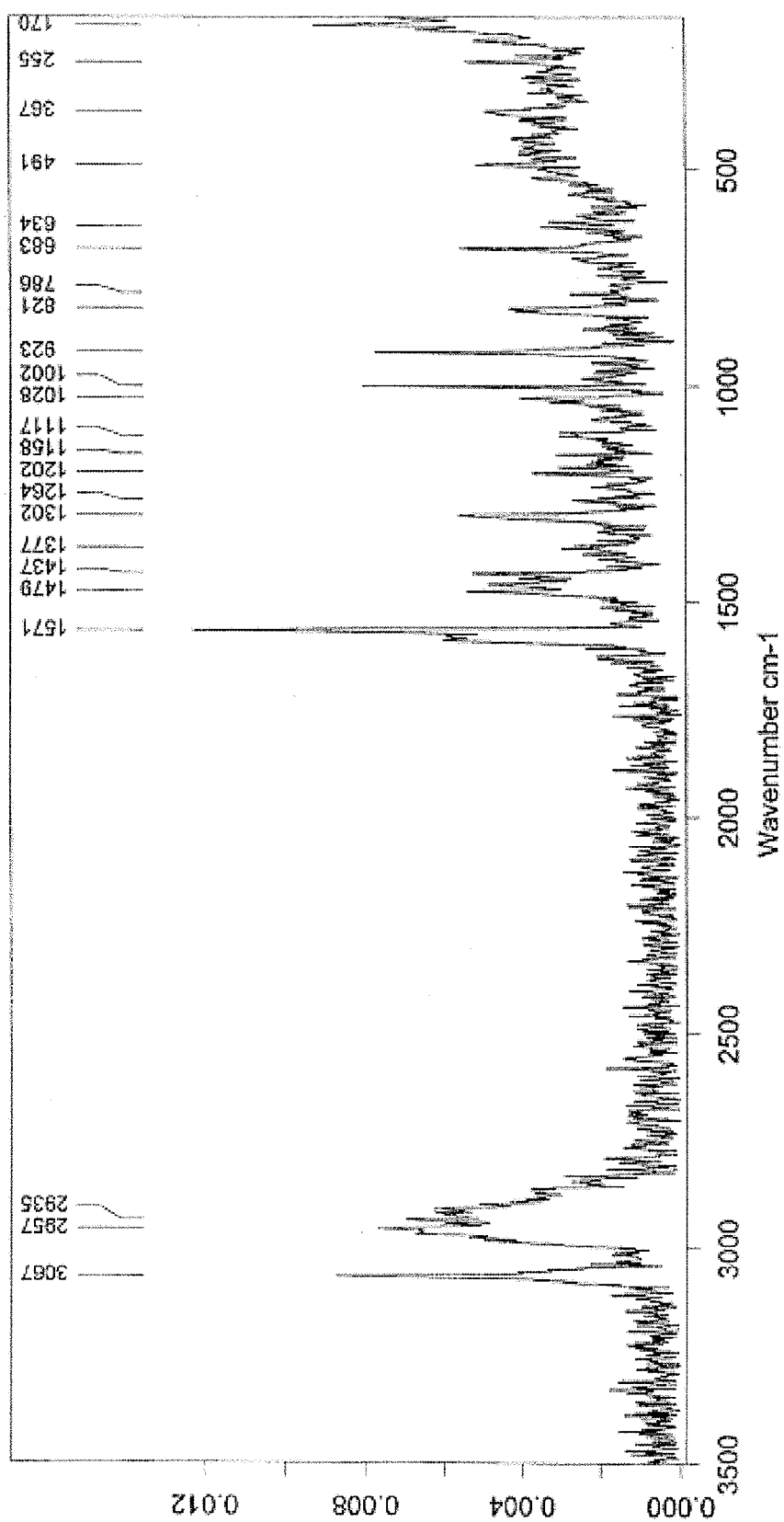
Figure 2E:
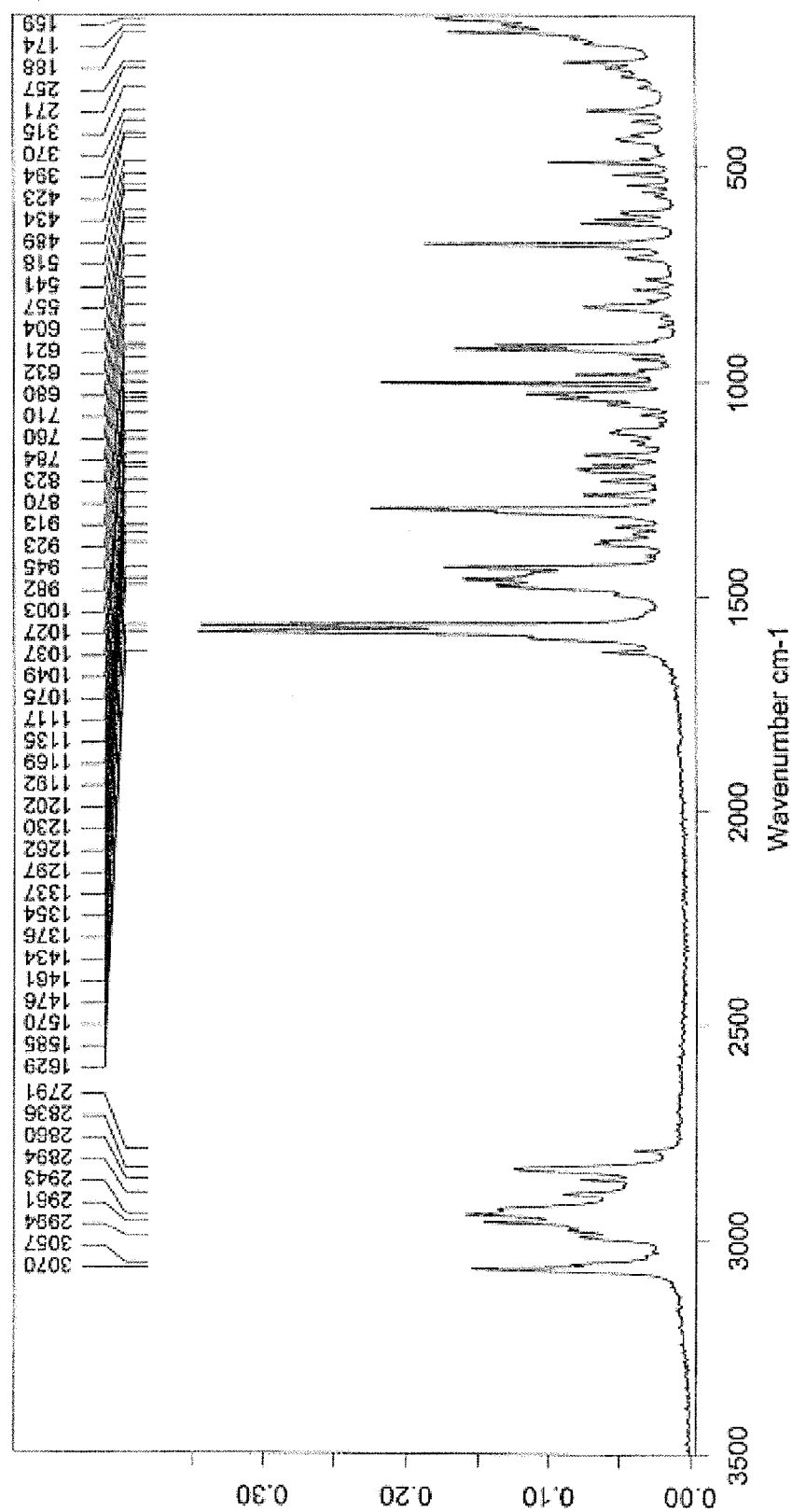
Figure 2F:
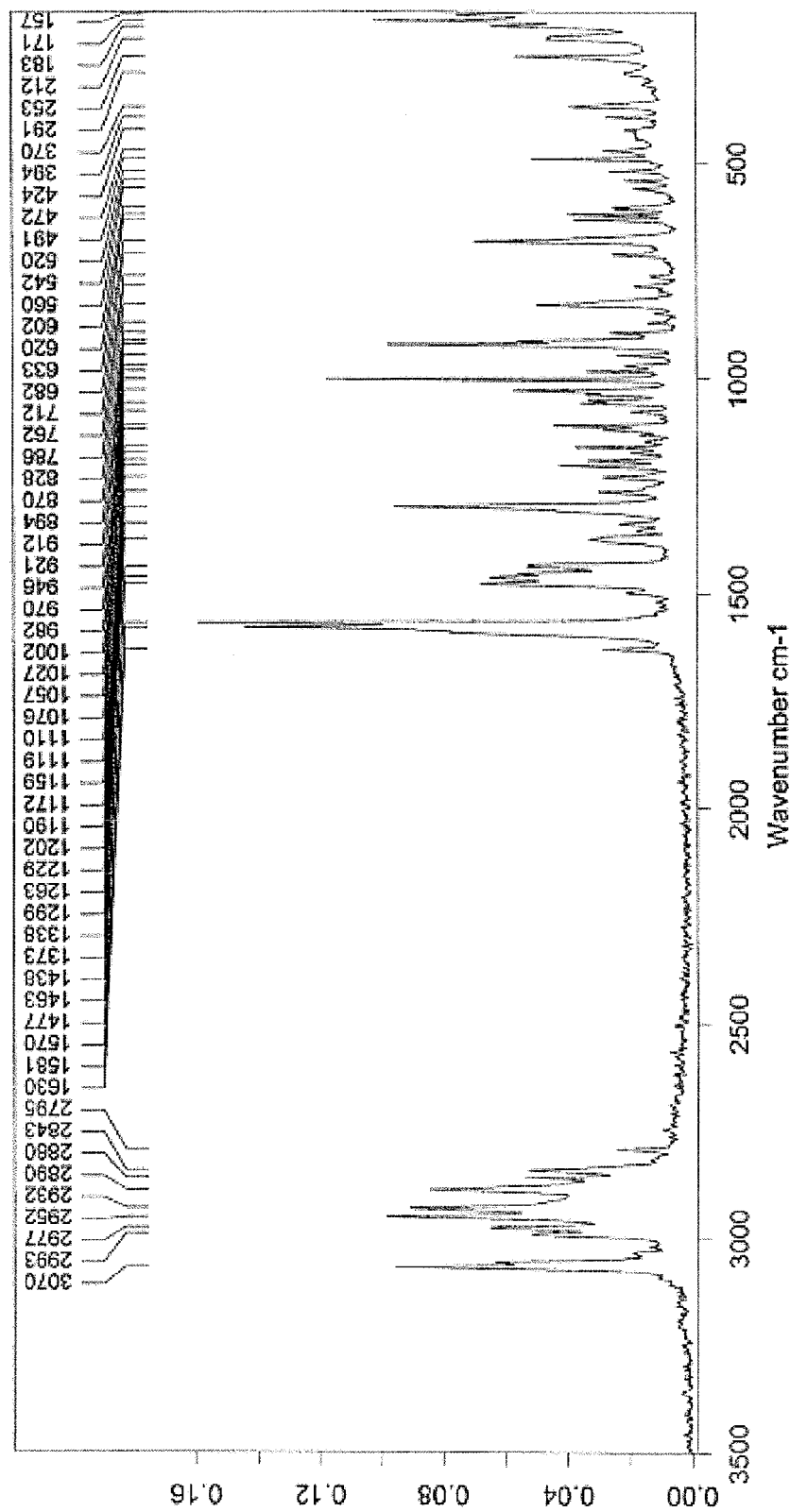
Figure 2G:
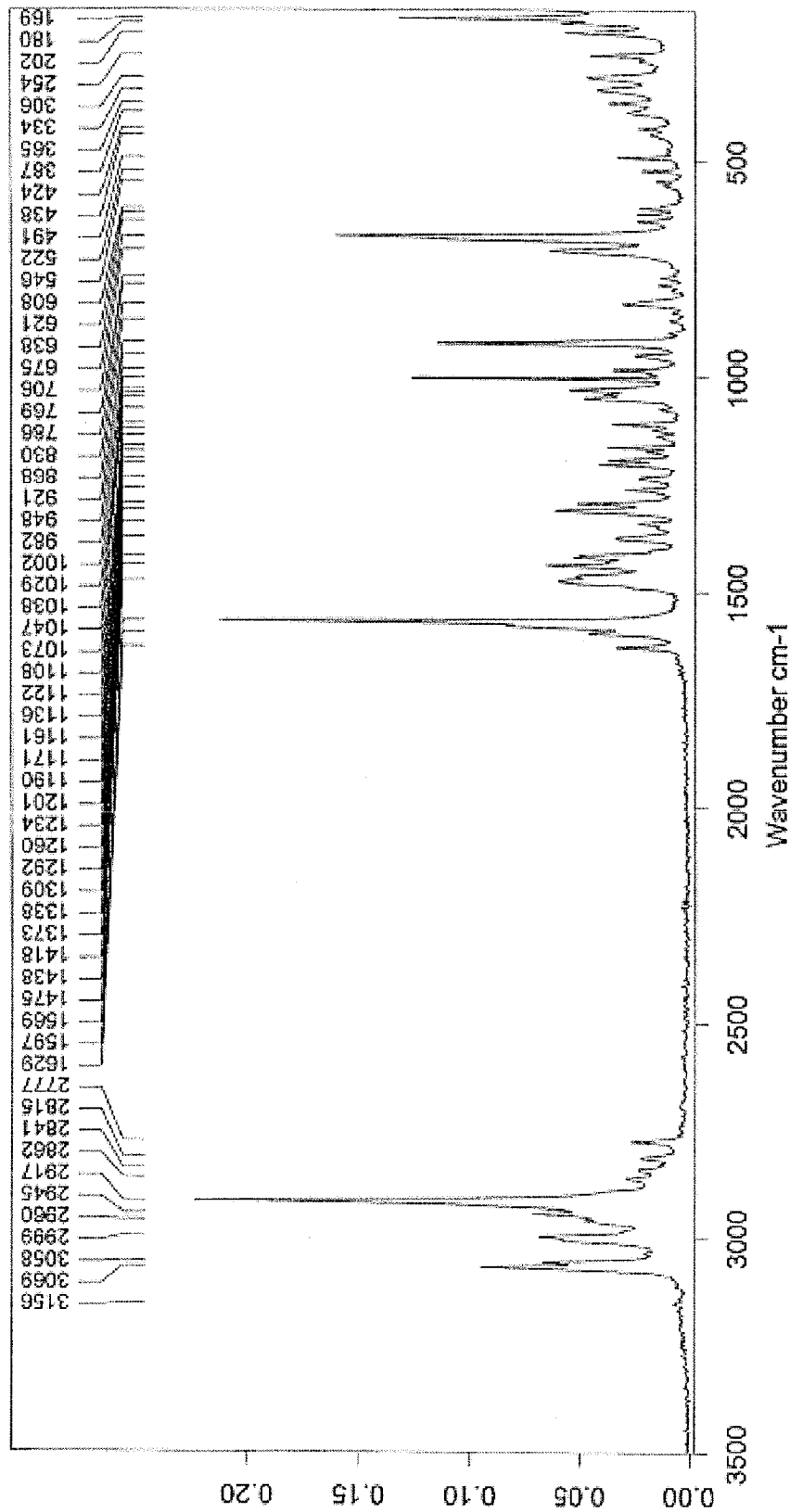
Figure 2H:
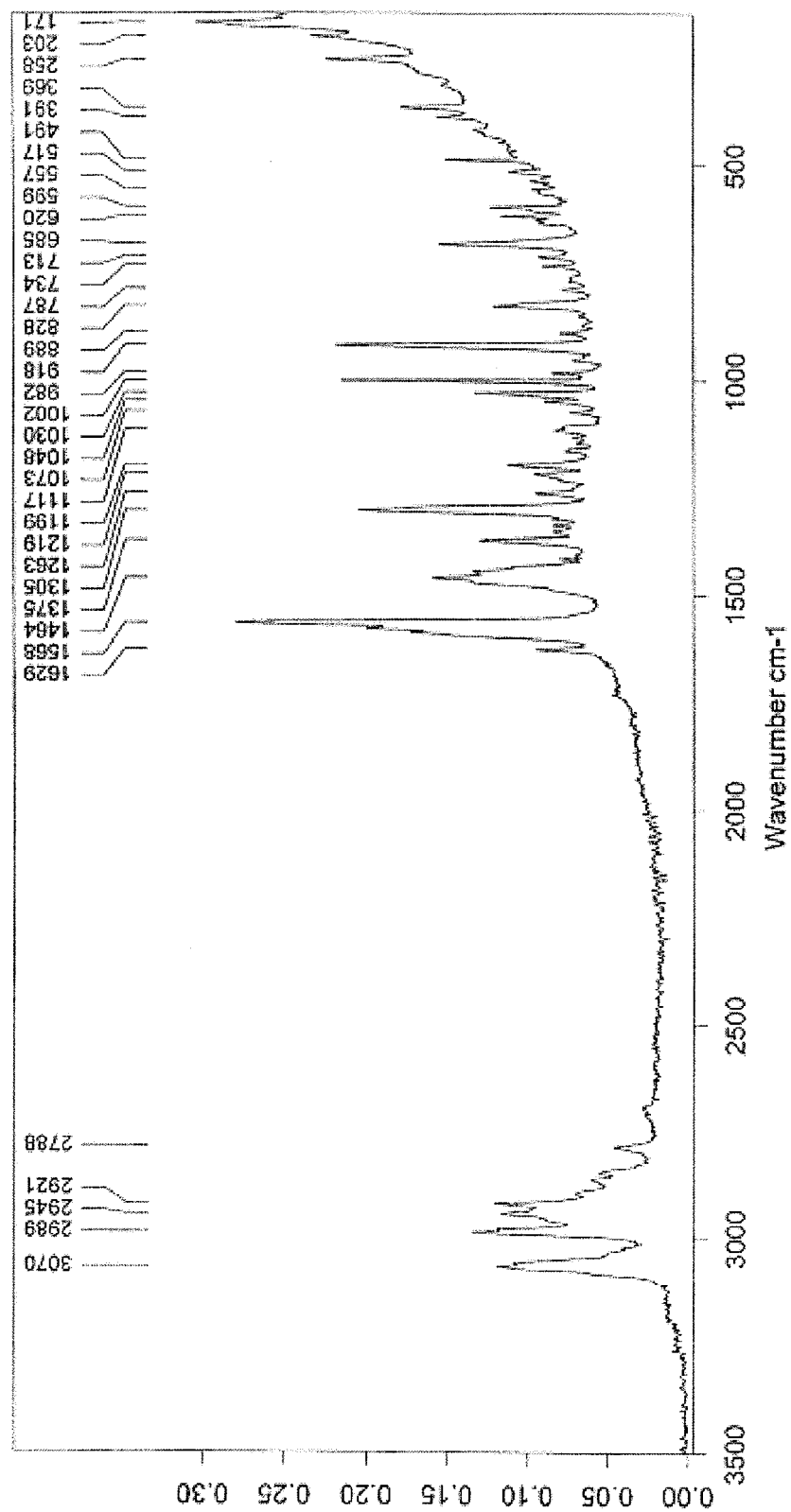
Figure 2I:
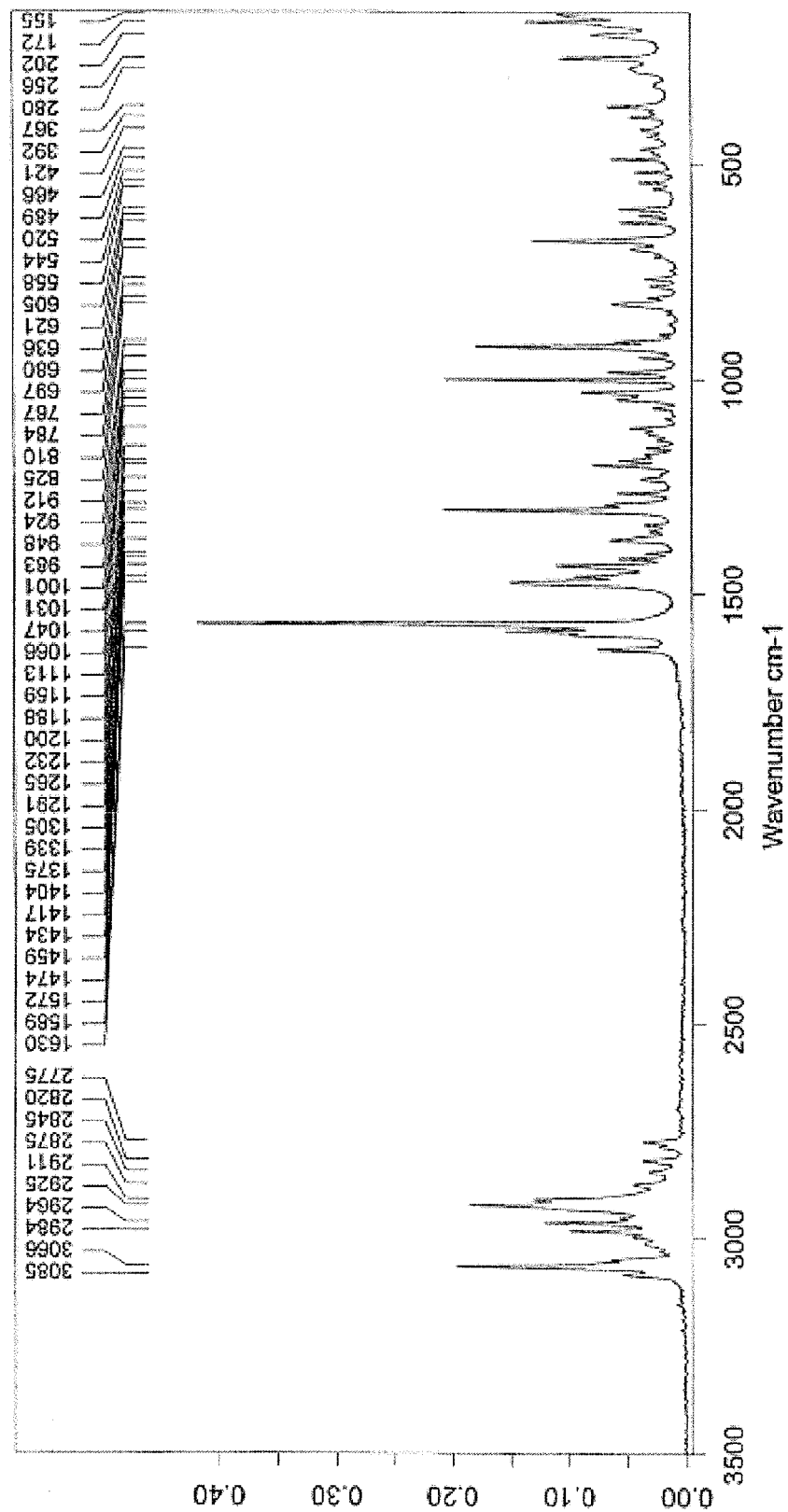
Figure 2I:
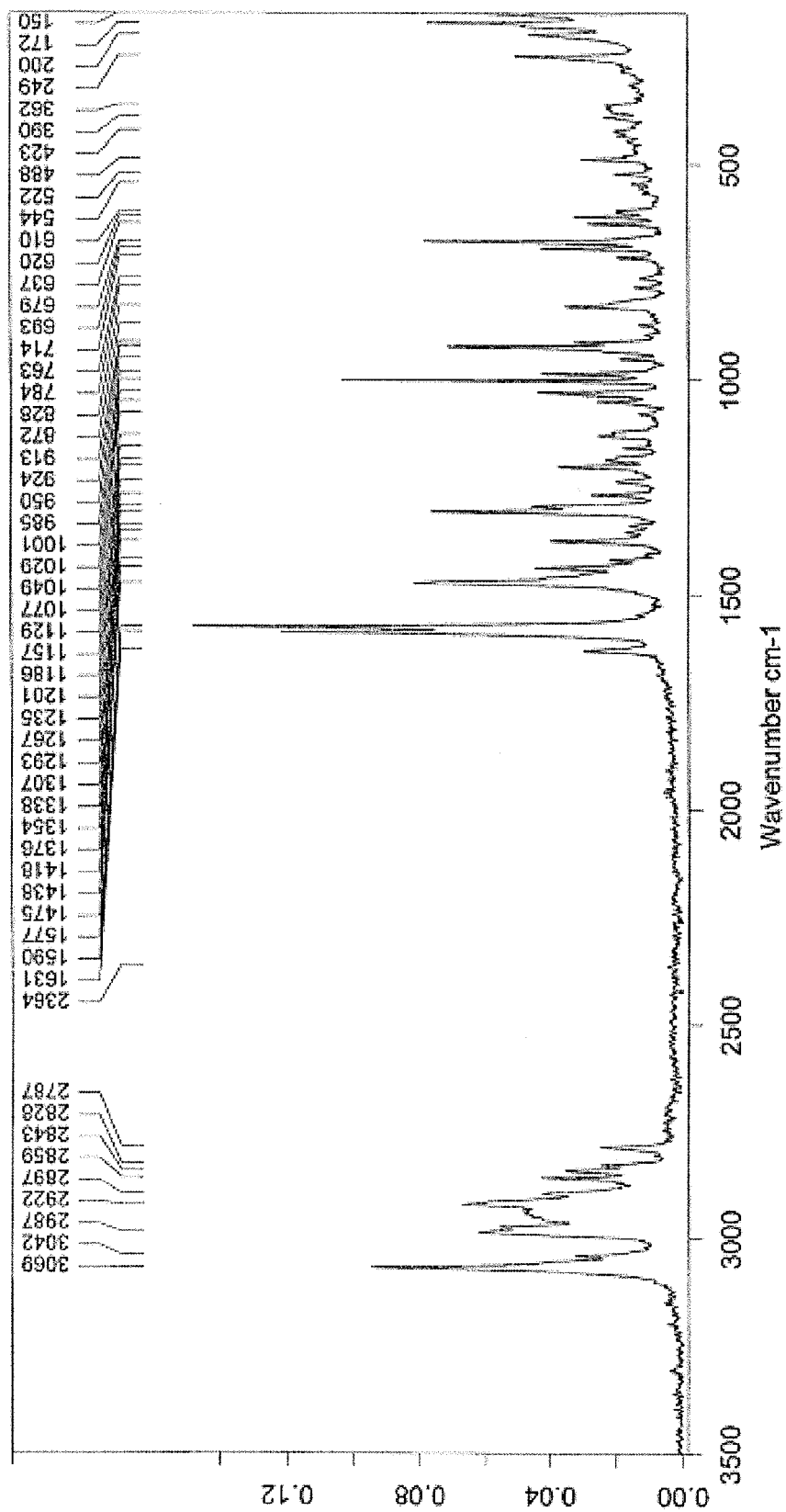

FIG. 2 shows the superposed Raman spectra of crystalline forms A, B, C, D, E, F, G, H, I and L.

Raman peak tables were generated using the software OPUS, version 3.1, build: 3, 0, 17 (20010216). The sensitivity of the peak picking function was chosen in a way that most of the peaks were found (typically between 0.5% to 3%). Features which were accidentally attributed to peaks and which were obviously noise, were removed by hand. Peaks are listed in a spectral region between 3200 cm$^{-1}$ and 150 cm$^{-1}$. For the intensity classification, the absolute intensity was used and the most intense peak was scaled to 100%. The classification is as follow: very strong (vs): I>80%; strong (s): 80%≥I>60%; medium (m): 60%≥I>40%; weak (w): 40%≥I>20%; and very weak (vw): 20%≥I.

Crystalline Form A 3066 (w); 3057 (m); 2960 (w); 2947 (w); 2921 (w); 2871 (vw); 2851 (vw); 2793 (vw); 1628 (vw); 1583 (m); 1569 (vs); 1475 (w); 1453 (w); 1420 (vw); 1405 (vw); 1370 (vw); 1337 (vw); 1308 (m); 1289 (w); 1265 (vw); 1235 (vw); 1200 (vw); 1188 (vw); 1156 (vw); 1128 (vw); 1111 (vw); 1067 (vw); 1049 (vw); 1031 (w); 1002 (s); 981 (w); 943 (vw); 921 (m); 911 (w); 872 (vw); 828 (w); 785 (vw); 714 (vw); 694 (vw); 679 (w); 636 (vw); 620 (vw); 609 (vw); 544 (vw); 519 (vw); 488 (w); 420 (vw); 365 (vw); 254 (w); 202 (w); 184 (w); 170 (w); 152 (w).

Crystalline Form B 3072 (m); 3064 (m); 2984 (w); 2965 (w); 2950 (w); 2911 (w); 2879 (vw); 2846 (vw); 2794 (vw); 1630 (vw); 1581 (s); 1571 (vs); 1476 (m); 1460 (w); 1433 (w); 1374 (w); 1356 (vw); 1341 (vw); 1299 (m); 1268 (w); 1233 (vw); 1204 (w); 1191 (vw); 1174 (vw); 1163 (vw); 1141 (vw); 1119 (vw); 1110 (vw); 1074 (vw); 1053 (vw); 1039 (vw); 1028 (w); 1003 (s); 983 (vw); 947 (vw); 923 (m); 865 (vw); 825 (w); 785 (vw); 764 (vw); 716 (vw); 683 (w); 633 (vw); 621 (vw); 607 (vw); 560 (vw); 545 (vw); 518 (vw); 492 (w); 437 (vw); 395 (vw); 370 (w); 318 (vw); 301 (vw); 259 (w); 217 (w); 173 (m); 154 (m).

Crystalline Form C 3070 (m); 2990 (w); 2977 (w); 2951 (m); 2932 (m); 2890 (w); 2856 (w); 2845 (w); 2794 (vw); 1630 (vw); 1587 (s); 1570 (vs); 1478 (m); 1462 (w); 1435 (w); 1373 (w); 1339 (vw); 1299 (m); 1265 (vw); 1231 (vw); 1203 (w); 1189 (vw); 1157 (vw); 1119 (vw); 1111 (vw); 1077 (vw); 1051 (vw); 1028 (w); 1003 (s); 983 (vw); 948 (vw); 922 (m); 913 (w); 885 (vw); 829 (w); 786 (vw); 712 (vw); 682 (w); 633 (vw);

621 (vw); 608 (vw); 560 (vw); 542 (vw); 520 (vw); 491 (w); 432 (vw); 394 (vw); 371 (vw); 253 (w); 210 (w); 183 (m); 171 (m); 156 (m).

Crystalline Form D 3067 (s); 2957 (s); 2935 (m); 1570 (vs); 1479 (m); 1437 (m); 1377 (w); 1302 (m); 1264 (w); 1202 (w); 1158 (w); 1117 (w); 1028 (w); 1002 (s); 922 (s); 821 (w); 786 (w); 683 (m); 633 (w); 491 (m); 367 (m); 254 (m); 169 (s).

Crystalline Form E 3070 (m); 3057 (w); 2994 (w); 2961 (m); 2943 (m); 2894 (w); 2860 (w); 2836 (w); 2791 (vw); 1629 (vw); 1585 (vs); 1570 (vs); 1476 (w); 1461 (m); 1434 (m); 1376 (vw); 1354 (vw); 1337 (vw); 1297 (s); 1262 (w); 1230 (vw); 1202 (w); 1192 (w); 1169 (w); 1135 (vw); 1117 (vw); 1075 (vw); 1049 (vw); 1037 (w); 1027 (w); 1003 (s); 982 (w); 945 (vw); 923 (m); 913 (w); 870 (vw); 823 (w); 784 (vw); 760 (vw); 710 (vw); 680 (m); 632 (w); 621 (vw); 604 (vw); 557 (vw); 541 (vw); 518 (vw); 489 (w); 434 (vw); 423 (vw); 394 (vw); 370 (w); 315 (vw); 271 (vw); 257 (w); 188 (m); 174 (w); 159 (m).

Crystalline Form F 3070 (s); 3058 (m); 2992 (w); 2977 (m); 2952 (s); 2932 (m); 2889 (m); 2860 (w); 2843 (w); 2795 (vw); 2748 (vw); 2566 (vw); 1630 (vw); 1581 (vs); 1570 (vs); 1498 (vw); 1477 (m); 1463 (m); 1453 (w); 1438 (w); 1373 (w); 1353 (vw); 1338 (vw); 1299 (s); 1263 (vw); 1229 (vw); 1202 (w); 1189 (w); 1172 (vw); 1159 (w); 1146 (vw); 1119 (vw); 1110 (w); 1076 (vw); 1056 (w); 1050 (w); 1036 (w); 1027 (w); 1002 (s); 982 (w); 970 (vw); 946 (vw); 921 (s); 912 (w); 894 (vw); 870 (vw); 848 (vw); 828 (w); 786 (vw); 762 (vw); 712 (vw); 682 (m); 632 (w); 620 (w); 607 (vw); 602 (vw); 560 (vw); 542 (vw); 519 (vw); 491 (w); 471 (vw); 424 (vw); 394 (vw); 370 (w); 291 (vw); 253 (w); 212 (w); 183 (m); 171 (s); 157 (m).

Crystalline Form G 3156 (vw); 3069 (m); 3058 (w); 2999 (w); 2960 (w); 2945 (w); 2917 (vs); 2862 (vw); 2841 (vw); 2815 (vw); 2777 (vw); 1629 (vw); 1597 (w); 1569 (vs); 1475 (w); 1437 (w); 1418 (w); 1373 (vw); 1338 (vw); 1309 (w); 1292 (w); 1260 (vw); 1234 (vw); 1201 (vw); 1190 (vw); 1171 (vw); 1161 (vw); 1136 (vw); 1122 (vw); 1108 (vw); 1073 (vw); 1047 (w); 1038 (vw); 1029 (w); 1002 (m); 982 (vw); 948 (vw); 921 (m); 868 (vw); 830 (vw); 786 (vw); 769 (vw); 706 (w); 675 (s); 638 (vw); 621 (vw); 608 (vw); 546 (vw); 522 (vw); 491 (vw); 438 (vw); 424 (vw); 387 (vw); 365 (vw); 334 (vw); 306 (w); 254 (w); 202 (w); 180 (w); 169 (m).

Crystalline Form H 3069 (w); 2989 (m); 2945 (w); 2921 (w); 2788 (vw); 1629 (w); 1568 (vs); 1464 (m); 1375 (m); 1305 (s); 1263 (w); 1219 (w); 1199 (w); 1117 (w); 1073 (w); 1048 (w); 1030 (m); 1002 (s); 982 (w); 918 (s); 889 (w); 828 (m); 787 (w); 734 (w); 713 (w); 685 (m); 620 (w); 599 (m); 557 (w); 517 (w); 490 (m); 391 (m); 369 (m); 258 (s); 203 (s); 171 (vs).

Crystalline Form I 3085 (vw); 3066 (m); 3051 (vw); 3011 (vw); 2998 (vw); 2984 (w); 2964 (w); 2953 (vw); 2925 (m); 2911 (w); 2875 (vw); 2845 (vw); 2820 (vw); 2787 (vw); 2775 (vw); 2699 (vw); 1630 (vw); 1596 (w); 1589 (vw); 1572 (vs); 1474 (w); 1459 (w); 1434 (w); 1417 (vw); 1404 (vw); 1375 (w); 1354 (vw); 1339 (vw); 1305 (m); 1291 (vw); 1265 (vw); 1232 (vw); 1199 (vw); 1188 (vw); 1159 (vw); 1141 (vw); 1123 (vw); 1113 (vw); 1091 (vw); 1066 (vw); 1047 (vw); 1031 (w); 1001 (m); 983 (vw); 948 (vw); 924 (m); 912 (vw); 895 (vw); 825 (vw); 810 (vw); 784 (vw); 767 (vw); 715 (vw); 697 (vw); 680 (w); 636 (vw); 621 (vw); 605 (vw); 558 (vw); 544 (vw); 519 (vw); 489 (vw); 466 (vw); 438 (vw); 421 (vw); 392 (vw); 367 (vw); 315 (vw); 280 (vw); 256 (w); 202 (vw); 172 (w); 155 (w).

Crystalline Form L 3069 (s); 3042 (w); 2987 (m); 2922 (m); 2897 (w); 2859 (w); 2843 (w); 2828 (vw); 2787 (vw); 2364 (vw); 1631 (w); 1590 (vs); 1577 (vs); 1475 (m); 1438 (w); 1418 (vw); 1376 (w); 1353 (vw); 1338 (vw); 1307 (m); 1293 (w); 1267 (vw); 1235 (vw); 1201 (w); 1186 (vw); 1157 (vw); 1129 (vw); 1077 (vw); 1049 (vw); 1029 (w); 1001 (s); 985 (w); 950 (vw); 924 (m); 913 (w); 872 (vw); 828 (w); 784 (vw); 763 (vw); 714 (vw); 693 (w); 679 (m); 637 (vw); 620 (w); 610 (vw); 544 (vw); 522 (vw); 488 (w); 423 (vw); 390 (vw); 362 (vw); 249 (w); 199 (w); 172 (m); 150 (w).

Analysis—DSC

Differential Scanning calorimetry (DSC): device reference Perkin Elmer DSC 7 or Perkin Elmer Pyris 1. Unless otherwise specified, the samples were weighed in a sealed gold crucible. The measurement took place in a nitrogen flow in a temperature range from −50° C. up to 350° C. with a heating rate of 10° C./min. The temperatures specified in relation to DSC analyses are, unless otherwise specified, the temperatures of the peak maxima. In the following tables, "ΔH" means "specific heat", and "peak" means that a thermal event was observed at the temperature with the given peak temperature.

TABLE 14

| | DSC |
|---|---|
| Crystalline Form A | peak, 305° C., ΔH = 137 J/g |
| Crystalline Form B | peak, 113° C., ΔH = 49 J/g |
| | peak, 189° C., ΔH = 102 J/g |
| | peak, 208° C., ΔH = −13 J/g |
| Crystalline Form C | event, 115° C, 51 mW |
| | peak, 135° C., ΔH = 80 J/g |
| Crystalline Form D | peak, 112° C., ΔH = 27 J/g |
| | peak, 123° C., ΔH = 46 J/g |
| | peak, 214° C., ΔH = 23 J/g |

Analysis—TG-FTIR

Thermogravimetry analytical experiments coupled with Fourier transform infrared (TG-FTIR) spectra were recorded with a Netzsch Thermo-Microwaage TG 209 and a Bruker FT-IR spectrometer Vector 22 (aluminium crucible (open or with micro-aperture), nitrogen atmosphere, heating rate 10° C./min, 25 up to 350° C.).

TG-FTIR analysis showed that crystalline form A does not contain any enclosed solvent and is thus an ansolvate form.

TG-FTIR analyses performed with samples of crystalline form B revealed that these samples contained 8-9% of water agreeing with a dihydrate.

TG-FTIR analyses performed with samples of crystalline form C revealed that these samples contained 6-22% of EtOH. Either the different drying times after filtration caused variation in the EtOH content or different but isomorphous solvates were obtained (EtOH content: ~6%—hemi-solvate, ~12%—mono-solvate).

TG-FTIR analyses performed with samples of crystalline form D revealed that these samples contained 12-13% of 2PrOH agreeing with a mono-solvate.

TG-FTIR analysis performed with a sample of crystalline form E revealed that this sample contained 7.2% of MeOH agreeing with a hemi-solvate.

TG-FTIR analysis performed with a sample of crystalline form F revealed that this sample contained 13% of 1PrOH agreeing with a hemi-solvate.

TG-FTIR analysis performed with a sample of crystalline form G revealed that this sample contained 40% of DMSO.

This DMSO content is very high, probably indicating enclosed and adsorbed solvent.

TG-FTIR analysis performed with a sample of crystalline form H revealed that this sample contained 2.8% of water agreeing with the hemi-hydrate.

TG-FTIR analysis performed with a sample of crystalline form I revealed that this sample contained 0.5% of water. This could be a second ansolvate form.

Analysis—DVS

Crystalline forms A, B, C and D were each characterized by dynamic vapor sorption (DVS) using a Projekt Messtechnik SPS 11-100n multi sample water vapor sorption analyzer. For the DVS analysis, each sample was allowed to equilibrate at 50% r.h. (relative humidity) before starting a pre-defined humidity program during which the change in weight of the sample is determined. All measurements were performed according to the following program: 2 h at 50% r.h.; 50% r.h.→0% r.h. (10%/h); 5 h at 0% r.h.; 0→95% r.h. (5%/h); 3 h at 95% r.h.; 95→50% (10%/h), and 2 h at 50% r.h.

Although hygroscopicity was measured in a slightly different manner, it was classified according to the European Pharmacopoeia as follows: very hygroscopic (vh): increase of the mass≥15%; hygroscopic (h): increase of the mass is less than 15% and equal or greater than 2%; slightly hygroscopic (sh): increase of the mass is less than 2% and equal or greater than 0.2%; not hygroscopic (nh): increase of the mass is less than 0.2%; deliquescent (d): sufficient water is absorbed to form a liquid.

Crystalline Form A

DVS with two cycles was performed on a sample of crystalline form A. The first cycle was not symmetric, the sample contained still water when the DVS cycle returned to 50% r.h. (relative humidity in %). The second cycle was reversible. Below 40% r.h. the relative mass returned to ~100% (water content=0%). The hysteresis between 40% and 70% r.h. indicates a metastable zone. The second cycle indicated the following transformations: hemi-hydrate→ansolvate (<38% r.h.)→hemi-hydrate (>70% r.h.). The sample was classified to be hygroscopic (Δm=3-4% at 85% r.h.; Δm: change in mass).

Crystalline Form B

DVS with two cycles was performed on a sample of crystalline form B. The DVS showed two reversible cycles with mass changes of 8-9% at 20% r.h. and 80% r.h; i.e. indicating the following transformations: dihydrate→desolvated form (<20% r.h.; −8% mass change)→dihydrate (>80% r.h.; +8% mass change). The sample was classified to be slightly hygroscopic (Δm=0.5% at 85% r.h.).

Crystalline Form C

DVS with two cycles was performed on a sample of crystalline form C. The first cycle was not symmetric and indicated a transformation of the EtOH solvate (crystalline form C) into the hemihydrate. The second cycle was reversible and indicated the following transformations: hemi-hydrate→ansolvate (<20% r.h.)→hemi-hydrate (>65% r.h.). The sample was classified to be hygroscopic (Δm=2% at 85% r.h.).

Crystalline Form D

The DVS cycle of a sample of crystalline form D was found to be not reversible and at 80-85% r.h. a mass change of 3-4% was observed. The sample was classified to be hygroscopic (Δm=3-4% at 85% r.h.). The water uptake—probably combined with 2PrOH/H$_2$O exchange starts at approximately 65% r.h.

Analysis—"Crystalline Form K" (Mixture of Crystalline Form B and L)

60 mg of "crystalline form K" (sample 1-16; mixture of modifications B and L) was stored for two weeks at RT over saturated Mg(NO$_3$)$_2$ (55% r.h.) for two weeks. According to FT Raman, a mixture of crystalline form B and "crystalline form K" was obtained.

60 mg of "crystalline form K" (sample 1-16; mixture of modifications B and L) was stored for two weeks at RT over saturated NH$_4$Cl (79% r.h.) for two weeks. According to FT Raman, a mixture of crystalline form B and "crystalline form K" was obtained.

60 mg of "crystalline form K" (sample 1-16; mixture of modifications B and L) was stored for two weeks at RT over saturated K$_2$SO$_4$ (97% r.h.) for two weeks. According to FT Raman, crystalline form B was obtained.

A comparison of the three FT Raman spectra revealed that "crystalline form K" is converted into crystalline form B with increasing r.h.

TG-FTIR analyses of the three samples revealed only small shifts in the water content (7.8% at 55% r.h. to 9.0% at 97% r.h.).

Analysis—Hygroscopicity of Crystalline Form A

The hygroscopicity of crystalline form A was further studied by storing samples of crystalline form A at different relative humidity values before analyzing them by TG-FTIR.

7-1) 54 mg of crystalline form A was stored for two weeks at RT over saturated Mg(NO$_3$)$_2$ (55% r.h.) for two weeks.

7-2) 52 mg of crystalline form A was stored for two weeks at RT over saturated NH$_4$Cl (79% r.h.) for two weeks.

7-3) 51 mg of crystalline form A was stored for two weeks at RT over saturated K$_2$SO$_4$ (97% r.h.) for two weeks.

TG-FTIR confirmed that the water content of the samples at 55% (0.7%) and 79% r.h. (1.1%) agrees with the DVS result. At 97% r.h. a higher water content (16.5%) was observed, probably caused by condensation of water at the powder surface. FT Raman analysis revealed that the water content did not change the crystal form or that the conversion is not detectable by Raman.

Analysis—Single Crystal Diffraction

Measurements were realized using MoKα-radiation (λ=0.71073 Å) and a Bruker D8-Goniometer equipped with a APEX-CCD detector. Crystal data of crystalline forms A, C, D, G and I are summarized in the following tables 15-39.

Crystalline Form A

TABLE 15

Crystal data and structure refinement for crystalline form A.

| | |
|---|---|
| Empirical formula | C$_{24}$H$_{27}$FN$_2$O |
| Formula weight | 378.48 |
| Temperature | 130(2) K |
| Wavelength | .71073 Å |
| Crystal system | Monoclinic |
| Space group | P 21/c |
| Unit cell dimensions | a = 14.7104(14) A alpha = 90 deg. |
| | b = 13.8726(14) A beta = 101.846(2) deg. |
| | c = 19.4704(19) A gamma = 90 deg. |
| Volume | 3888.7(7) Å$^3$ |
| Z | 8 |
| Density (calculated) | 1.293 Mg/m$^3$ |
| Absorption coefficient | 0.086 mm$^{-1}$ |
| F(000) | 1616 |
| Crystal size | 0.44 × 0.12 × 0.07 mm |
| Theta range for data collection | 2.43 to 30.52 deg. |
| Index ranges | −20 ≤ h ≤ 20, −19 ≤ k ≤ 19, −27 ≤ l ≤ 27 |
| Reflections collected | 58460 |
| Independent reflections | 11821 [R(int) = 0.0953] |
| Absorption correction | None |
| Refinement method | Full-matrix least-squares on F$^2$ |
| Data/restraints/parameters | 11821/0/517 |

TABLE 15-continued

Crystal data and structure refinement for crystalline form A.

| | |
|---|---|
| Goodness-of-fit on F^2 | 1.069 |
| Final R indices [I > 2sigma(I)] | R1 = 0.0607, wR2 = 0.0880 |
| R indices (all data) | R1 = 0.1235, wR2 = 0.0969 |
| Largest diff. peak and hole | .584 and −.384 e. Å$^{-3}$ |

TABLE 16

Atomic coordinates (×10$^4$) (i.e. (×10^4)) and equivalent isotropic displacement parameters ($^2$× 10$^3$) (i.e. (^2 × 10^3)) for crystalline form A. U(eq) is defined as one third of the trace of the orthogonalized Uij tensor.

| | x | y | Z | U(eq) |
|---|---|---|---|---|
| F(1) | 2425(1) | −1986(1) | 2620(1) | 35(1) |
| O(1) | −47(1) | 2184(1) | 4040(1) | 37(1) |
| N(1) | 1870(1) | 474(1) | 4675(1) | 25(1) |
| N(2) | 904(1) | 2525(1) | 6396(1) | 27(1) |
| C(1) | 2315(1) | −1375(1) | 3152(1) | 27(1) |
| C(2) | 1596(1) | −735(1) | 3022(1) | 26(1) |
| C(3) | 1494(1) | −125(1) | 3579(1) | 23(1) |
| C(4) | 2125(1) | −199(1) | 4228(1) | 23(1) |
| C(5) | 1096(1) | 961(1) | 4316(1) | 23(1) |
| C(6) | 584(1) | 1735(1) | 4618(1) | 26(1) |
| C(7) | −566(1) | 1554(1) | 3554(1) | 42(1) |
| C(8) | 6(1) | 964(1) | 3152(1) | 31(1) |
| C(9) | 845(1) | 608(1) | 3654(1) | 24(1) |
| C(10) | 70(1) | 1336(1) | 5160(1) | 27(1) |
| C(11) | −456(1) | 2118(1) | 5467(1) | 27(1) |
| C(12) | 180(1) | 2934(1) | 5822(1) | 22(1) |
| C(13) | 550(1) | 1917(1) | 6899(1) | 39(1) |
| C(14) | 1554(1) | 3232(1) | 6772(1) | 36(1) |
| C(15) | 664(1) | 3332(1) | 5253(1) | 27(1) |
| C(16) | 1207(1) | 2561(1) | 4949(1) | 27(1) |
| C(17) | −394(1) | 3723(1) | 6088(1) | 24(1) |
| C(18) | −125(1) | 4686(1) | 6125(1) | 30(1) |
| C(19) | −633(1) | 5387(1) | 6387(1) | 35(1) |
| C(20) | −1423(1) | 5140(1) | 6622(1) | 36(1) |
| C(21) | −1701(1) | 4191(1) | 6594(1) | 35(1) |
| C(22) | −1198(1) | 3497(1) | 6331(1) | 30(1) |
| C(23) | 2852(1) | −863(1) | 4338(1) | 25(1) |
| C(24) | 2941(1) | −1461(1) | 3785(1) | 27(1) |
| F(2) | 5985(1) | 9246(1) | 1447(1) | 50(1) |
| O(2) | 3180(1) | 4515(1) | 1030(1) | 28(1) |
| N(3) | 5608(1) | 5355(1) | 1314(1) | 23(1) |
| N(4) | 5231(1) | 1974(1) | 1207(1) | 23(1) |
| C(25) | 5909(1) | 8256(1) | 1415(1) | 34(1) |
| C(26) | 5054(1) | 7855(1) | 1352(1) | 32(1) |
| C(27) | 5004(1) | 6843(1) | 1322(1) | 25(1) |
| C(28) | 5836(1) | 6323(1) | 1358(1) | 24(1) |
| C(29) | 4661(1) | 5262(1) | 1243(1) | 22(1) |
| C(30) | 4174(1) | 4311(1) | 1167(1) | 22(1) |
| C(31) | 2921(1) | 5264(1) | 1462(1) | 33(1) |
| C(32) | 3258(1) | 6247(1) | 1272(1) | 32(1) |
| C(33) | 4270(1) | 6152(1) | 1259(1) | 24(1) |
| C(34) | 4452(1) | 3685(1) | 1819(1) | 24(1) |
| C(35) | 3981(1) | 2702(1) | 1725(1) | 24(1) |
| C(36) | 4208(1) | 2122(1) | 1108(1) | 22(1) |
| C(37) | 5672(1) | 1545(1) | 1878(1) | 30(1) |
| C(38) | 5509(1) | 1428(1) | 637(1) | 33(1) |
| C(39) | 3890(1) | 2755(1) | 452(1) | 23(1) |
| C(40) | 4337(1) | 3754(1) | 524(1) | 22(1) |
| C(41) | 3678(1) | 1156(1) | 1042(1) | 25(1) |
| C(42) | 3643(1) | 603(1) | 1637(1) | 31(1) |
| C(43) | 3172(1) | −265(1) | 1586(1) | 38(1) |
| C(44) | 2721(1) | −611(1) | 944(1) | 41(1) |
| C(45) | 2750(1) | −87(1) | 351(1) | 40(1) |
| C(46) | 3229(1) | 780(1) | 399(1) | 32(1) |
| C(47) | 6694(1) | 6755(1) | 1427(1) | 29(1) |
| C(48) | 6727(1) | 7747(1) | 1455(1) | 32(1) |

TABLE 17A

Bond lengths [Å] and angles [deg] for crystalline form A.

| | bond lengths [Å] and angles [deg] |
|---|---|
| F(1)—C(1) | 1.3733(18) |
| O(1)—C(7) | 1.3954(19) |
| O(1)—C(6) | 1.4443(18) |
| N(1)—C(4) | 1.381(2) |
| N(1)—C(5) | 1.383(2) |
| N(1)—H(1) | .866(15) |
| N(2)—C(14) | 1.458(2) |
| N(2)—C(13) | 1.466(2) |
| N(2)—C(12) | 1.4886(19) |
| C(1)—C(2) | 1.364(2) |
| C(1)—C(24) | 1.384(2) |
| C(2)—C(3) | 1.408(2) |
| C(2)—H(2) | .9500 |
| C(3)—C(4) | 1.409(2) |
| C(3)—C(9) | 1.423(2) |
| C(4)—C(23) | 1.394(2) |
| C(5)—C(9) | 1.357(2) |
| C(5)—C(6) | 1.500(2) |
| C(6)—C(16) | 1.524(2) |
| C(6)—C(10) | 1.525(2) |
| C(7)—C(8) | 1.504(2) |
| C(7)—H(7A) | .9900 |
| C(7)—H(7B) | .9900 |
| C(8)—C(9) | 1.492(2) |
| C(8)—H(8A) | .9900 |
| C(8)—H(8B) | .9900 |
| C(10)—C(11) | 1.522(2) |
| C(10)—H(10A) | .9900 |
| C(10)—H(10B) | .9900 |
| C(11)—C(12) | 1.539(2) |
| C(11)—H(11A) | .9900 |
| C(11)—H(11B) | .9900 |
| C(12)—C(17) | 1.536(2) |
| C(12)—C(15) | 1.537(2) |
| C(13)—H(13A) | .9800 |
| C(13)—H(13B) | .9800 |
| C(13)—H(13C) | .9800 |
| C(14)—H(14A) | .9800 |
| C(14)—H(14B) | .9800 |
| C(14)—H(14C) | .9800 |
| C(15)—C(16) | 1.525(2) |
| C(15)—H(15A) | .9900 |
| C(15)—H(15B) | .9900 |
| C(16)—H(16A) | .9900 |
| C(16)—H(16B) | .9900 |
| C(17)—C(18) | 1.392(2) |
| C(17)—C(22) | 1.395(2) |
| C(18)—C(19) | 1.386(2) |
| C(18)—H(18) | .9500 |
| C(19)—C(20) | 1.378(2) |
| C(19)—H(19) | .9500 |
| C(20)—C(21) | 1.377(2) |
| C(20)—H(20) | .9500 |
| C(21)—C(22) | 1.376(2) |
| C(21)—H(21) | .9500 |
| C(22)—H(22) | .9500 |
| C(23)—C(24) | 1.387(2) |
| C(23)—H(23) | .9500 |
| C(24)—H(24) | .9500 |
| F(2)—C(25) | 1.3780(18) |
| O(2)—C(31) | 1.4359(18) |
| O(2)—C(30) | 1.4587(17) |
| N(3)—C(29) | 1.3769(19) |
| N(3)—C(28) | 1.3823(19) |
| N(3)—H(3) | .850(15) |
| N(4)—C(37) | 1.4622(19) |
| N(4)—C(38) | 1.4689(19) |
| N(4)—C(36) | 1.4911(19) |
| C(25)—C(26) | 1.358(2) |
| C(25)—C(48) | 1.383(2) |
| C(26)—C(27) | 1.406(2) |
| C(26)—H(26) | .9500 |
| C(27)—C(28) | 1.410(2) |
| C(27)—C(33) | 1.430(2) |
| C(28)—C(47) | 1.379(2) |

TABLE 17A-continued

Bond lengths [Å] and angles [deg] for crystalline form A.

| | bond lengths [Å] and angles [deg] |
|---|---|
| C(29)—C(33) | 1.365(2) |
| C(29)—C(30) | 1.494(2) |
| C(30)—C(34) | 1.525(2) |
| C(30)—C(40) | 1.532(2) |
| C(31)—C(32) | 1.522(2) |
| C(31)—H(31A) | .9900 |
| C(31)—H(31B) | .9900 |
| C(32)—C(33) | 1.500(2) |
| C(32)—H(32A) | .9900 |
| C(32)—H(32B) | .9900 |
| C(34)—C(35) | 1.523(2) |
| C(34)—H(34A) | .9900 |
| C(34)—H(34B) | .9900 |
| C(35)—C(36) | 1.539(2) |
| C(35)—H(35A) | .9900 |
| C(35)—H(35B) | .9900 |
| C(36)—C(39) | 1.541(2) |
| C(36)—C(41) | 1.543(2) |
| C(37)—H(37A) | .9800 |
| C(37)—H(37B) | .9800 |
| C(37)—H(37C) | .9800 |
| C(38)—H(38A) | .9800 |
| C(38)—H(38B) | .9800 |
| C(38)—H(38C) | .9800 |
| C(39)—C(40) | 1.528(2) |
| C(39)—H(39A) | .9900 |
| C(39)—H(39B) | .9900 |
| C(40)—H(40A) | .9900 |
| C(40)—H(40B) | .9900 |
| C(41)—C(46) | 1.391(2) |
| C(41)—C(42) | 1.399(2) |
| C(42)—C(43) | 1.384(2) |
| C(42)—H(42) | .9500 |
| C(43)—C(44) | 1.376(2) |
| C(43)—H(43) | .9500 |
| C(44)—C(45) | 1.373(2) |
| C(44)—H(44) | .9500 |
| C(45)—C(46) | 1.386(2) |
| C(45)—H(45) | .9500 |
| C(46)—H(46) | .9500 |
| C(47)—C(48) | 1.379(2) |
| C(47)—H(47) | .9500 |
| C(48)—H(48) | .9500 |

TABLE 17B (Table 17A continued) Bond lengths [Å] and angles [deg] for crystalline form A.

| | bond lengths [Å] and angles [deg] |
|---|---|
| C(7)—O(1)—C(6) | 115.69(13) |
| C(4)—N(1)—C(5) | 108.25(14) |
| C(4)—N(1)—H(1) | 123.5(11) |
| C(5)—N(1)—H(1) | 128.0(11) |
| C(14)—N(2)—C(13) | 109.77(14) |
| C(14)—N(2)—C(12) | 114.51(13) |
| C(13)—N(2)—C(12) | 115.04(13) |
| C(2)—C(1)—F(1) | 117.98(15) |
| C(2)—C(1)—C(24) | 124.74(16) |
| F(1)—C(1)—C(24) | 117.28(15) |
| C(1)—C(2)—C(3) | 116.76(15) |
| C(1)—C(2)—H(2) | 121.6 |
| C(3)—C(2)—H(2) | 121.6 |
| C(2)—C(3)—C(4) | 119.42(15) |
| C(2)—C(3)—C(9) | 133.52(16) |
| C(4)—C(3)—C(9) | 107.06(14) |
| N(1)—C(4)—C(23) | 130.50(15) |
| N(1)—C(4)—C(3) | 107.53(14) |
| C(23)—C(4)—C(3) | 121.98(15) |
| C(9)—C(5)—N(1) | 109.91(15) |
| C(9)—C(5)—C(6) | 124.72(15) |
| N(1)—C(5)—C(6) | 125.33(14) |
| O(1)—C(6)—C(5) | 107.32(13) |
| O(1)—C(6)—C(16) | 103.90(13) |
| C(5)—C(6)—C(16) | 113.47(14) |
| O(1)—C(6)—C(10) | 111.41(13) |
| C(5)—C(6)—C(10) | 111.84(13) |
| C(16)—C(6)—C(10) | 108.64(13) |
| O(1)—C(7)—C(8) | 114.03(15) |
| O(1)—C(7)—H(7A) | 108.7 |
| C(8)—C(7)—H(7A) | 108.7 |
| O(1)—C(7)—H(7B) | 108.7 |
| C(8)—C(7)—H(7B) | 108.7 |
| H(7A)—C(7)—H(7B) | 107.6 |
| C(9)—C(8)—C(7) | 108.37(14) |
| C(9)—C(8)—H(8A) | 110.0 |
| C(7)—C(8)—H(8A) | 110.0 |
| C(9)—C(8)—H(8B) | 110.0 |
| C(7)—C(8)—H(8B) | 110.0 |
| H(8A)—C(8)—H(8B) | 108.4 |
| C(5)—C(9)—C(3) | 107.25(14) |
| C(5)—C(9)—C(8) | 122.05(15) |
| C(3)—C(9)—C(8) | 130.67(15) |
| C(11)—C(10)—C(6) | 112.14(13) |
| C(11)—C(10)—H(10A) | 109.2 |
| C(6)—C(10)—H(10A) | 109.2 |
| C(11)—C(10)—H(10B) | 109.2 |
| C(6)—C(10)—H(10B) | 109.2 |
| H(10A)—C(10)—H(10B) | 107.9 |
| C(10)—C(11)—C(12) | 112.93(13) |
| C(10)—C(11)—H(11A) | 109.0 |
| C(12)—C(11)—H(11A) | 109.0 |
| C(24)—C(23)—H(23) | 121.1 |
| C(4)—C(23)—H(23) | 121.1 |
| C(1)—C(24)—C(23) | 119.22(16) |
| C(1)—C(24)—H(24) | 120.4 |
| C(23)—C(24)—H(24) | 120.4 |
| C(31)—O(2)—C(30) | 114.21(12) |
| C(29)—N(3)—C(28) | 108.97(14) |
| C(29)—N(3)—H(3) | 125.5(11) |
| C(28)—N(3)—H(3) | 125.4(11) |
| C(37)—N(4)—C(38) | 108.87(13) |
| C(37)—N(4)—C(36) | 114.99(12) |
| C(38)—N(4)—C(36) | 113.84(12) |
| C(26)—C(25)—F(2) | 118.52(17) |
| C(26)—C(25)—C(48) | 125.10(16) |
| F(2)—C(25)—C(48) | 116.38(17) |
| C(25)—C(26)—C(27) | 116.90(17) |
| C(25)—C(26)—H(26) | 121.6 |
| C(27)—C(26)—H(26) | 121.6 |
| C(26)—C(27)—C(28) | 118.12(16) |
| C(26)—C(27)—C(33) | 134.82(16) |
| C(28)—C(27)—C(33) | 107.05(14) |
| C(47)—C(28)—N(3) | 129.33(16) |
| C(47)—C(28)—C(27) | 123.41(16) |
| N(3)—C(28)—C(27) | 107.26(15) |
| C(33)—C(29)—N(3) | 109.57(14) |
| C(33)—C(29)—C(30) | 127.23(15) |
| N(3)—C(29)—C(30) | 123.19(14) |
| O(2)—C(30)—C(29) | 106.83(12) |
| O(2)—C(30)—C(34) | 110.44(13) |
| C(29)—C(30)—C(34) | 112.28(13) |
| O(2)—C(30)—C(40) | 105.56(12) |
| C(29)—C(30)—C(40) | 112.04(13) |
| C(34)—C(30)—C(40) | 109.45(13) |
| O(2)—C(31)—C(32) | 111.56(14) |
| O(2)—C(31)—H(31A) | 109.3 |
| C(32)—C(31)—H(31A) | 109.3 |
| O(2)—C(31)—H(31B) | 109.3 |
| C(32)—C(31)—H(31B) | 109.3 |
| H(31A)—C(31)—H(31B) | 108.0 |
| C(33)—C(32)—C(31) | 107.39(13) |
| C(33)—C(32)—H(32A) | 110.2 |
| C(31)—C(32)—H(32A) | 110.2 |

TABLE 17B-continued (Table 17A continued) Bond lengths [Å] and angles [deg] for crystalline form A.

| | bond lengths [Å] and angles [deg] |
|---|---|
| C(33)—C(32)—H(32B) | 110.2 |
| C(31)—C(32)—H(32B) | 110.2 |
| H(32A)—C(32)—H(32B) | 108.5 |
| C(29)—C(33)—C(27) | 107.11(14) |
| C(29)—C(33)—C(32) | 120.28(15) |
| C(27)—C(33)—C(32) | 132.37(15) |
| C(35)—C(34)—C(30) | 111.89(13) |
| C(35)—C(34)—H(34A) | 109.2 |
| C(30)—C(34)—H(34A) | 109.2 |
| C(35)—C(34)—H(34B) | 109.2 |
| C(30)—C(34)—H(34B) | 109.2 |
| H(34A)—C(34)—H(34B) | 107.9 |
| C(48)—C(47)—C(28) | 117.49(17) |
| C(48)—C(47)—H(47) | 121.3 |
| C(28)—C(47)—H(47) | 121.3 |
| C(47)—C(48)—C(25) | 118.99(17) |
| C(47)—C(48)—H(48) | 120.5 |
| C(25)—C(48)—H(48) | 120.5 |
| C(10)—C(11)—H(11B) | 109.0 |
| C(12)—C(11)—H(11B) | 109.0 |
| H(11A)—C(11)—H(11B) | 107.8 |
| N(2)—C(12)—C(17) | 112.08(13) |
| N(2)—C(12)—C(15) | 108.20(13) |
| C(17)—C(12)—C(15) | 110.81(13) |
| N(2)—C(12)—C(11) | 109.41(13) |
| C(17)—C(12)—C(11) | 110.51(13) |
| C(15)—C(12)—C(11) | 105.61(13) |
| N(2)—C(13)—H(13A) | 109.5 |
| N(2)—C(13)—H(13B) | 109.5 |
| H(13A)—C(13)—H(13B) | 109.5 |
| N(2)—C(13)—H(13C) | 109.5 |
| H(13A)—C(13)—H(13C) | 109.5 |
| H(13B)—C(13)—H(13C) | 109.5 |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |
| H(14A)—C(14)—H(14C) | 109.5 |
| H(14B)—C(14)—H(14C) | 109.5 |
| C(16)—C(15)—C(12) | 112.57(13) |
| C(16)—C(15)—H(15A) | 109.1 |
| C(12)—C(15)—H(15A) | 109.1 |
| C(16)—C(15)—H(15B) | 109.1 |
| C(12)—C(15)—H(15B) | 109.1 |
| H(15A)—C(15)—H(15B) | 107.8 |
| C(6)—C(16)—C(15) | 112.03(13) |
| C(6)—C(16)—H(16A) | 109.2 |
| C(15)—C(16)—H(16A) | 109.2 |
| C(6)—C(16)—H(16B) | 109.2 |
| C(15)—C(16)—H(16B) | 109.2 |
| H(16A)—C(16)—H(16B) | 107.9 |
| C(18)—C(17)—C(22) | 116.77(15) |
| C(18)—C(17)—C(12) | 122.07(15) |
| C(22)—C(17)—C(12) | 121.12(14) |
| C(19)—C(18)—C(17) | 121.57(17) |
| C(19)—C(18)—H(18) | 119.2 |
| C(17)—C(18)—H(18) | 119.2 |
| C(20)—C(19)—C(18) | 120.22(17) |
| C(20)—C(19)—H(19) | 119.9 |
| C(18)—C(19)—H(19) | 119.9 |
| C(21)—C(20)—C(19) | 119.23(17) |
| C(21)—C(20)—H(20) | 120.4 |
| C(19)—C(20)—H(20) | 120.4 |
| C(22)—C(21)—C(20) | 120.41(18) |
| C(22)—C(21)—H(21) | 119.8 |
| C(20)—C(21)—H(21) | 119.8 |
| C(21)—C(22)—C(17) | 121.79(16) |
| C(21)—C(22)—H(22) | 119.1 |
| C(17)—C(22)—H(22) | 119.1 |
| C(24)—C(23)—C(4) | 117.88(15) |
| C(34)—C(35)—C(36) | 113.26(13) |
| C(34)—C(35)—H(35A) | 108.9 |
| C(36)—C(35)—H(35A) | 108.9 |
| C(34)—C(35)—H(35B) | 108.9 |
| C(36)—C(35)—H(35B) | 108.9 |
| H(35A)—C(35)—H(35B) | 107.7 |
| N(4)—C(36)—C(35) | 110.26(12) |
| N(4)—C(36)—C(39) | 108.21(12) |
| C(35)—C(36)—C(39) | 105.72(13) |
| N(4)—C(36)—C(41) | 111.75(12) |
| C(35)—C(36)—C(41) | 109.41(13) |
| C(39)—C(36)—C(41) | 111.32(13) |
| N(4)—C(37)—H(37A) | 109.5 |
| N(4)—C(37)—H(37B) | 109.5 |
| H(37A)—C(37)—H(37B) | 109.5 |
| N(4)—C(37)—H(37C) | 109.5 |
| H(37A)—C(37)—H(37C) | 109.5 |
| H(37B)—C(37)—H(37C) | 109.5 |
| N(4)—C(38)—H(38A) | 109.5 |
| N(4)—C(38)—H(38B) | 109.5 |
| H(38A)—C(38)—H(38B) | 109.5 |
| N(4)—C(38)—H(38C) | 109.5 |
| H(38A)—C(38)—H(38C) | 109.5 |
| H(38B)—C(38)—H(38C) | 109.5 |
| C(40)—C(39)—C(36) | 112.93(13) |
| C(40)—C(39)—H(39A) | 109.0 |
| C(36)—C(39)—H(39A) | 109.0 |
| C(40)—C(39)—H(39B) | 109.0 |
| C(36)—C(39)—H(39B) | 109.0 |
| H(39A)—C(39)—H(39B) | 107.8 |
| C(39)—C(40)—C(30) | 113.29(13) |
| C(39)—C(40)—H(40A) | 108.9 |
| C(30)—C(40)—H(40A) | 108.9 |
| C(39)—C(40)—H(40B) | 108.9 |
| C(30)—C(40)—H(40B) | 108.9 |
| H(40A)—C(40)—H(40B) | 107.7 |
| C(46)—C(41)—C(42) | 116.62(16) |
| C(46)—C(41)—C(36) | 122.66(15) |
| C(42)—C(41)—C(36) | 120.71(15) |
| C(43)—C(42)—C(41) | 121.42(17) |
| C(43)—C(42)—H(42) | 119.3 |
| C(41)—C(42)—H(42) | 119.3 |
| C(44)—C(43)—C(42) | 120.61(18) |
| C(44)—C(43)—H(43) | 119.7 |
| C(42)—C(43)—H(43) | 119.7 |
| C(45)—C(44)—C(43) | 119.16(18) |
| C(45)—C(44)—H(44) | 120.4 |
| C(43)—C(44)—H(44) | 120.4 |
| C(44)—C(45)—C(46) | 120.31(18) |
| C(44)—C(45)—H(45) | 119.8 |
| C(46)—C(45)—H(45) | 119.8 |
| C(45)—C(46)—C(41) | 121.86(17) |
| C(45)—C(46)—H(46) | 119.1 |
| C(41)—C(46)—H(46) | 119.1 |

TABLE 18

Hydrogen coordinates ($\times 10^4$) (i.e. ($\times 10^{\hat{}}4$)) and isotropic displacement parameters ($^2\times 10^3$) (i.e. ($^{\hat{}}2 \times 10^{\hat{}}3$)) for crystalline form A.

| | x | y | Z | U(eq) |
|---|---|---|---|---|
| H(1) | 2191(11) | 592(11) | 5092(8) | 31(5) |
| H(2) | 1185 | −702 | 2578 | 32 |
| H(7A) | −1024 | 1933 | 3216 | 50 |
| H(7B) | −916 | 1113 | 3803 | 50 |
| H(8A) | −363 | 412 | 2922 | 37 |
| H(8B) | 195 | 1364 | 2783 | 37 |
| H(10A) | −374 | 836 | 4938 | 33 |
| H(10B) | 522 | 1028 | 5544 | 33 |
| H(11A) | −775 | 1824 | 5815 | 32 |
| H(11B) | −936 | 2395 | 5087 | 32 |
| H(13A) | 1067 | 1714 | 7273 | 59 |
| H(13B) | 245 | 1347 | 6657 | 59 |
| H(13C) | 100 | 2284 | 7103 | 59 |

TABLE 18-continued

Hydrogen coordinates (×10⁴) (i.e. (×10^4)) and isotropic displacement parameters ($Å^2 \times 10^3$) (i.e. ($^2 \times 10^3$)) for crystalline form A.

| | x | y | z | U(eq) |
|---|---|---|---|---|
| H(14A) | 1224 | 3673 | 7029 | 54 |
| H(14B) | 1829 | 3600 | 6436 | 54 |
| H(14C) | 2046 | 2900 | 7103 | 54 |
| H(15A) | 191 | 3614 | 4870 | 32 |
| H(15B) | 1094 | 3855 | 5457 | 32 |
| H(16A) | 1508 | 2856 | 4590 | 32 |
| H(16B) | 1701 | 2302 | 5327 | 32 |
| H(18) | 419 | 4868 | 5966 | 36 |
| H(19) | −435 | 6040 | 6404 | 42 |
| H(20) | −1773 | 5620 | 6802 | 43 |
| H(21) | −2244 | 4014 | 6757 | 42 |
| H(22) | −1402 | 2846 | 6314 | 36 |
| H(23) | 3273 | −905 | 4778 | 30 |
| H(24) | 3426 | −1925 | 3840 | 32 |
| H(3) | 5986(11) | 4895(11) | 1304(8) | 24(5) |
| H(26) | 4515 | 8240 | 1328 | 38 |
| H(31A) | 3190 | 5123 | 1961 | 39 |
| H(31B) | 2237 | 5276 | 1403 | 39 |
| H(32A) | 2905 | 6453 | 806 | 38 |
| H(32B) | 3168 | 6733 | 1624 | 38 |
| H(34A) | 5135 | 3595 | 1923 | 29 |
| H(34B) | 4282 | 4018 | 2224 | 29 |
| H(35A) | 3300 | 2794 | 1649 | 29 |
| H(35B) | 4177 | 2325 | 2163 | 29 |
| H(37A) | 5460 | 877 | 1898 | 46 |
| H(37B) | 5504 | 1915 | 2262 | 46 |
| H(37C) | 6348 | 1553 | 1924 | 46 |
| H(38A) | 6188 | 1379 | 727 | 49 |
| H(38B) | 5287 | 1761 | 190 | 49 |
| H(38C) | 5239 | 780 | 614 | 49 |
| H(39A) | 4045 | 2425 | 41 | 28 |
| H(39B) | 3206 | 2829 | 366 | 28 |
| H(40A) | 4084 | 4132 | 96 | 26 |
| H(40B) | 5014 | 3682 | 555 | 26 |
| H(42) | 3950 | 829 | 2085 | 37 |
| H(43) | 3159 | −626 | 1999 | 46 |
| H(44) | 2393 | −1205 | 911 | 49 |
| H(45) | 2440 | −318 | −95 | 48 |
| H(46) | 3251 | 1126 | −18 | 38 |
| H(47) | 7243 | 6382 | 1455 | 34 |
| H(48) | 7302 | 8077 | 1501 | 39 |

TABLE 19

Anisotropic displacement parameters ($Å^2 \times 10^3$) (i.e. ($^2 \times 10^3$)) for crystalline form A. The anisotropic displacement factor exponent takes the form: $-2\pi^2[h^2 a^{*2} U11 + \ldots + 2 h k a^* b^* U12]$.

| | U11 | U22 | U33 | U23 | U13 | U12 |
|---|---|---|---|---|---|---|
| F(1) | 42(1) | 31(1) | 35(1) | −9(1) | 13(1) | 1(1) |
| O(1) | 38(1) | 32(1) | 34(1) | −4(1) | −5(1) | 11(1) |
| N(1) | 24(1) | 27(1) | 21(1) | −1(1) | 1(1) | −1(1) |
| N(2) | 25(1) | 29(1) | 27(1) | 4(1) | 6(1) | 0(1) |
| C(1) | 30(1) | 23(1) | 30(1) | −6(1) | 11(1) | −6(1) |
| C(2) | 30(1) | 26(1) | 23(1) | 0(1) | 4(1) | −6(1) |
| C(3) | 25(1) | 22(1) | 24(1) | 0(1) | 6(1) | −6(1) |
| C(4) | 23(1) | 21(1) | 25(1) | −2(1) | 6(1) | −6(1) |
| C(5) | 22(1) | 21(1) | 26(1) | 1(1) | 4(1) | −1(1) |
| C(6) | 26(1) | 26(1) | 24(1) | 1(1) | 2(1) | 3(1) |
| C(7) | 32(1) | 44(1) | 42(1) | −6(1) | −9(1) | 7(1) |
| C(8) | 32(1) | 30(1) | 27(1) | −1(1) | −2(1) | 3(1) |
| C(9) | 26(1) | 22(1) | 24(1) | 2(1) | 5(1) | 0(1) |
| C(10) | 27(1) | 21(1) | 35(1) | −3(1) | 7(1) | −2(1) |
| C(11) | 24(1) | 22(1) | 36(1) | −1(1) | 9(1) | −1(1) |
| C(12) | 23(1) | 18(1) | 26(1) | 2(1) | 6(1) | −1(1) |
| C(13) | 48(1) | 35(1) | 36(1) | 12(1) | 12(1) | 6(1) |
| C(14) | 24(1) | 48(1) | 36(1) | −5(1) | 3(1) | 0(1) |
| C(15) | 34(1) | 21(1) | 28(1) | −1(1) | 11(1) | −4(1) |
| C(16) | 31(1) | 24(1) | 29(1) | 1(1) | 12(1) | −3(1) |
| C(17) | 26(1) | 23(1) | 21(1) | 2(1) | 4(1) | 2(1) |
| C(18) | 39(1) | 24(1) | 29(1) | 3(1) | 11(1) | 0(1) |

TABLE 19-continued

Anisotropic displacement parameters ($Å^2 \times 10^3$) (i.e. ($^2 \times 10^3$)) for crystalline form A. The anisotropic displacement factor exponent takes the form: $-2\pi^2[h^2 a^{*2} U11 + \ldots + 2 h k a^* b^* U12]$.

| | U11 | U22 | U33 | U23 | U13 | U12 |
|---|---|---|---|---|---|---|
| C(19) | 50(1) | 23(1) | 29(1) | 3(1) | 4(1) | 7(1) |
| C(20) | 36(1) | 40(1) | 28(1) | −5(1) | −1(1) | 17(1) |
| C(21) | 24(1) | 45(1) | 36(1) | −9(1) | 5(1) | 0(1) |
| C(22) | 27(1) | 26(1) | 37(1) | −5(1) | 6(1) | −1(1) |
| C(23) | 21(1) | 24(1) | 28(1) | 2(1) | 3(1) | −4(1) |
| C(24) | 23(1) | 22(1) | 36(1) | 0(1) | 8(1) | −3(1) |
| F(2) | 81(1) | 19(1) | 51(1) | −2(1) | 19(1) | −2(1) |
| O(2) | 20(1) | 32(1) | 29(1) | −8(1) | 2(1) | 4(1) |
| N(3) | 23(1) | 17(1) | 29(1) | −1(1) | 5(1) | 5(1) |
| N(4) | 20(1) | 27(1) | 22(1) | 1(1) | 4(1) | 2(1) |
| C(25) | 61(1) | 14(1) | 26(1) | −2(1) | 7(1) | −1(1) |
| C(26) | 46(1) | 24(1) | 24(1) | −1(1) | 5(1) | 10(1) |
| C(27) | 38(1) | 22(1) | 16(1) | −1(1) | 4(1) | 5(1) |
| C(28) | 32(1) | 18(1) | 19(1) | −2(1) | 4(1) | 1(1) |
| C(29) | 22(1) | 24(1) | 18(1) | −2(1) | 1(1) | 4(1) |
| C(30) | 17(1) | 26(1) | 22(1) | −2(1) | 1(1) | 3(1) |
| C(31) | 24(1) | 40(1) | 36(1) | −10(1) | 10(1) | 8(1) |
| C(32) | 32(1) | 32(1) | 30(1) | −7(1) | 4(1) | 10(1) |
| C(33) | 27(1) | 24(1) | 19(1) | −4(1) | 1(1) | 7(1) |
| C(34) | 25(1) | 26(1) | 20(1) | −1(1) | 3(1) | 2(1) |
| C(35) | 25(1) | 25(1) | 24(1) | −1(1) | 6(1) | 0(1) |
| C(36) | 21(1) | 22(1) | 22(1) | −1(1) | 3(1) | 1(1) |
| C(37) | 27(1) | 34(1) | 29(1) | 4(1) | 4(1) | 1(1) |
| C(38) | 29(1) | 39(1) | 31(1) | 0(1) | 9(1) | 6(1) |
| C(39) | 23(1) | 22(1) | 22(1) | −2(1) | 2(1) | 0(1) |
| C(40) | 23(1) | 22(1) | 20(1) | 1(1) | 3(1) | 2(1) |
| C(41) | 20(1) | 24(1) | 31(1) | −2(1) | 8(1) | 2(1) |
| C(42) | 30(1) | 28(1) | 35(1) | 1(1) | 9(1) | 0(1) |
| C(43) | 40(1) | 28(1) | 50(1) | 3(1) | 18(1) | 1(1) |
| C(44) | 34(1) | 24(1) | 67(2) | −1(1) | 15(1) | −3(1) |
| C(45) | 36(1) | 31(1) | 50(1) | −8(1) | 2(1) | −1(1) |
| C(46) | 31(1) | 26(1) | 37(1) | −2(1) | 4(1) | 1(1) |
| C(47) | 35(1) | 26(1) | 25(1) | −2(1) | 6(1) | 0(1) |
| C(48) | 44(1) | 26(1) | 27(1) | −3(1) | 9(1) | −10(1) |

Crystalline Form C

TABLE 20

Crystal data and structure refinement for crystalline form C.

| | |
|---|---|
| Empirical formula | $C_{26}H_{33}FN_2O_2$ |
| Formula weight | 424.54 |
| Temperature | 130(2) K |
| Wavelength | .71073 Å |
| Crystal system | Triclinic |
| Space group | P-1 |
| Unit cell dimensions | a = 9.6987(14) Å alpha = 110.528(3) deg. |
| | b = 11.1173(16) Å beta = 98.919(3) deg. |
| | c = 12.5467(18) Å gamma = 113.367(3) deg. |
| Volume | 1092.8(3) Å³ |
| Z | 2 |
| Density (calculated) | 1.290 Mg/m³ |
| Absorption coefficient | 0.087 mm⁻¹ |
| F(000) | 456 |
| Crystal size | 0.36 × 0.13 × 0.08 mm |
| Theta range for data collection | 2.16 to 28.49 deg. |
| Index ranges | −13 ≤ h ≤ 12, −14 ≤ k ≤ 14, −16 ≤ l ≤ 16 |
| Reflections collected | 14533 |
| Independent reflections | 5293 [R(int) = 0.0634] |
| Absorption correction | None |
| Refinement method | Full-matrix least-squares on $F^2$ |
| Data/restraints/parameters | 5293/0/290 |
| Goodness-of-fit on $F^2$ | 1.005 |
| Final R indices [I > 2sigma(I)] | R1 = 0.0491, wR2 = 0.0932 |
| R indices (all data) | R1 = 0.0681, wR2 = 0.0981 |
| Largest diff. peak and hole | .269 and −.265 e. Å⁻³ |

TABLE 21

Atomic coordinates (×10⁴) (i.e. (x10^4)) and equivalent isotropic displacement parameters (²× 10³) (i.e. (^2 x 10^3)) for crystalline form C. U(eq) is defined as one third of the trace of the orthogonalized Uij tensor.

|  | x | y | z | U(eq) |
|---|---|---|---|---|
| F(1) | −511(1) | 2563(1) | −6080(1) | 28(1) |
| O(1) | 3958(1) | 7981(1) | 719(1) | 21(1) |
| N(1) | 1717(1) | 3970(1) | −1311(1) | 18(1) |
| N(2) | 3395(1) | 5029(1) | 2670(1) | 18(1) |
| C(1) | 50(2) | 2878(2) | −4885(1) | 20(1) |
| C(2) | 914(2) | 4324(2) | −4035(1) | 19(1) |
| C(3) | 1442(2) | 4604(2) | −2822(1) | 16(1) |
| C(4) | 1083(2) | 3407(2) | −2550(1) | 16(1) |
| C(5) | 2436(2) | 5478(2) | −810(1) | 17(1) |
| C(6) | 3232(2) | 6469(2) | 529(1) | 17(1) |
| C(7) | 3053(2) | 8287(2) | −59(1) | 23(1) |
| C(8) | 2910(2) | 7498(2) | −1375(1) | 22(1) |
| C(9) | 2302(2) | 5914(2) | −1689(1) | 17(1) |
| C(10) | 4624(2) | 6281(2) | 1050(1) | 18(1) |
| C(11) | 5346(2) | 7112(2) | 2426(1) | 18(1) |
| C(12) | 4122(2) | 6661(2) | 3051(1) | 16(1) |
| C(13) | 2133(2) | 4490(2) | 3165(1) | 26(1) |
| C(14) | 4568(2) | 4569(2) | 2982(1) | 25(1) |
| C(15) | 2817(2) | 6989(2) | 2581(1) | 18(1) |
| C(16) | 2036(2) | 6197(2) | 1204(1) | 18(1) |
| C(17) | 4931(2) | 7559(2) | 4435(1) | 18(1) |
| C(18) | 6456(2) | 7836(2) | 4998(1) | 21(1) |
| C(19) | 7171(2) | 8583(2) | 6246(1) | 24(1) |
| C(20) | 6396(2) | 9102(2) | 6965(1) | 26(1) |
| C(21) | 4893(2) | 8853(2) | 6431(1) | 27(1) |
| C(22) | 4165(2) | 8091(2) | 5184(1) | 23(1) |
| C(23) | 201(2) | 1954(2) | −3443(1) | 19(1) |
| C(24) | −328(2) | 1693(2) | −4629(1) | 20(1) |
| O(2) | 1709(1) | 2687(1) | 288(1) | 26(1) |
| C(25) | 2152(2) | 1585(2) | 142(1) | 30(1) |
| C(26) | 1434(2) | 485(2) | −1175(1) | 44(1) |

TABLE 22A

Bond lengths [Å] and angles [deg] for crystalline form C.

| | bond lengths [Å] and angles [deg] |
|---|---|
| F(1)—C(1) | 1.3758(15) |
| O(1)—C(7) | 1.4291(16) |
| O(1)—C(6) | 1.4512(16) |
| N(1)—C(5) | 1.3747(17) |
| N(1)—C(4) | 1.3787(17) |
| N(1)—H(1) | .885(15) |
| N(2)—C(13) | 1.4700(17) |
| N(2)—C(14) | 1.4737(18) |
| N(2)—C(12) | 1.5132(17) |
| C(1)—C(2) | 1.3694(19) |
| C(1)—C(24) | 1.387(2) |
| C(2)—C(3) | 1.4051(18) |
| C(2)—H(2) | .9500 |
| C(3)—C(4) | 1.4141(19) |
| C(3)—C(9) | 1.4332(19) |
| C(4)—C(23) | 1.3908(19) |
| C(5)—C(9) | 1.3609(19) |
| C(5)—C(6) | 1.5019(18) |
| C(6)—C(10) | 1.5299(19) |
| C(6)—C(16) | 1.5367(19) |
| C(7)—C(8) | 1.5276(19) |
| C(7)—H(7A) | .9900 |
| C(7)—H(7B) | .9900 |
| C(8)—C(9) | 1.4906(19) |
| C(8)—H(8A) | .9900 |
| C(8)—H(8B) | .9900 |
| C(10)—C(11) | 1.5229(18) |
| C(10)—H(10A) | .9900 |
| C(10)—H(10B) | .9900 |
| C(11)—C(12) | 1.5392(18) |
| C(11)—H(11A) | .9900 |
| C(11)—H(11B) | .9900 |

TABLE 22A-continued

Bond lengths [Å] and angles [deg] for crystalline form C.

| | bond lengths [Å] and angles [deg] |
|---|---|
| C(12)—C(17) | 1.5385(19) |
| C(12)—C(15) | 1.5387(19) |
| C(13)—H(13A) | .9800 |
| C(13)—H(13B) | .9800 |
| C(13)—H(13C) | .9800 |
| C(14)—H(14A) | .9800 |
| C(14)—H(14B) | .9800 |
| C(14)—H(14C) | .9800 |
| C(15)—C(16) | 1.5270(18) |
| C(15)—H(15A) | .9900 |
| C(15)—H(15B) | .9900 |
| C(16)—H(16A) | .9900 |
| C(16)—H(16B) | .9900 |
| C(17)—C(18) | 1.394(2) |
| C(17)—C(22) | 1.4012(19) |
| C(18)—C(19) | 1.3848(19) |
| C(18)—H(18) | .9500 |
| C(19)—C(20) | 1.378(2) |
| C(19)—H(19) | .9500 |
| C(20)—C(21) | 1.378(2) |
| C(20)—H(20) | .9500 |
| C(21)—C(22) | 1.384(2) |
| C(21)—H(21) | .9500 |
| C(22)—H(22) | .9500 |
| C(23)—C(24) | 1.3804(19) |
| C(23)—H(23) | .9500 |
| C(24)—H(24) | .9500 |
| O(2)—C(25) | 1.4157(17) |
| O(2)—H(2A) | .934(16) |
| C(25)—C(26) | 1.503(2) |
| C(25)—H(25A) | .9900 |
| C(25)—H(25B) | .9900 |
| C(26)—H(26A) | .9800 |
| C(26)—H(26B) | .9800 |
| C(26)—H(26C) | .9800 |

TABLE 22B (Table 22A continued) Bond lengths [Å] and angles [deg] for crystalline form C.

| | bond lengths [Å] and angles [deg] |
|---|---|
| C(7)—O(1)—C(6) | 115.64(10) |
| C(5)—N(1)—C(4) | 108.27(12) |
| C(5)—N(1)—H(1) | 127.5(10) |
| C(4)—N(1)—H(1) | 124.3(10) |
| C(13)—N(2)—C(14) | 107.81(12) |
| C(13)—N(2)—C(12) | 113.17(11) |
| C(14)—N(2)—C(12) | 113.94(11) |
| C(2)—C(1)—F(1) | 118.28(13) |
| C(2)—C(1)—C(24) | 124.68(13) |
| F(1)—C(1)—C(24) | 117.03(12) |
| C(1)—C(2)—C(3) | 116.77(13) |
| C(1)—C(2)—H(2) | 121.6 |
| C(3)—C(2)—H(2) | 121.6 |
| C(2)—C(3)—C(4) | 119.16(13) |
| C(2)—C(3)—C(9) | 134.20(13) |
| C(4)—C(3)—C(9) | 106.63(12) |
| N(1)—C(4)—C(23) | 130.01(13) |
| N(1)—C(4)—C(3) | 107.84(12) |
| C(23)—C(4)—C(3) | 122.14(13) |
| C(9)—C(5)—N(1) | 110.48(12) |
| C(9)—C(5)—C(6) | 126.12(13) |
| N(1)—C(5)—C(6) | 123.40(12) |
| O(1)—C(6)—C(5) | 108.18(11) |
| O(1)—C(6)—C(10) | 105.02(11) |
| C(5)—C(6)—C(10) | 111.02(11) |
| O(1)—C(6)—C(16) | 110.68(10) |
| C(5)—C(6)—C(16) | 111.50(11) |
| C(10)—C(6)—C(16) | 110.23(11) |

TABLE 22B-continued (Table 22A continued) Bond lengths [Å] and angles [deg] for crystalline form C.

| | bond lengths [Å] and angles [deg] |
|---|---|
| O(1)—C(7)—C(8) | 111.55(12) |
| O(1)—C(7)—H(7A) | 109.3 |
| C(8)—C(7)—H(7A) | 109.3 |
| O(1)—C(7)—H(7B) | 109.3 |
| C(8)—C(7)—H(7B) | 109.3 |
| H(7A)—C(7)—H(7B) | 108.0 |
| C(9)—C(8)—C(7) | 107.20(11) |
| C(9)—C(8)—H(8A) | 110.3 |
| C(7)—C(8)—H(8A) | 110.3 |
| C(9)—C(8)—H(8B) | 110.3 |
| C(7)—C(8)—H(8B) | 110.3 |
| H(8A)—C(8)—H(8B) | 108.5 |
| C(5)—C(9)—C(3) | 106.78(12) |
| C(5)—C(9)—C(8) | 120.97(12) |
| C(3)—C(9)—C(8) | 132.14(13) |
| C(11)—C(10)—C(6) | 113.43(11) |
| C(11)—C(10)—H(10A) | 108.9 |
| C(6)—C(10)—H(10A) | 108.9 |
| C(11)—C(10)—H(10B) | 108.9 |
| C(6)—C(10)—H(10B) | 108.9 |
| H(10A)—C(10)—H(10B) | 107.7 |
| C(10)—C(11)—C(12) | 113.01(11) |
| C(10)—C(11)—H(11A) | 109.0 |
| C(12)—C(11)—H(11A) | 109.0 |
| C(10)—C(11)—H(11B) | 109.0 |
| C(12)—C(11)—H(11B) | 109.0 |
| H(11A)—C(11)—H(11B) | 107.8 |
| N(2)—C(12)—C(17) | 110.91(11) |
| N(2)—C(12)—C(15) | 109.29(11) |
| C(17)—C(12)—C(15) | 111.53(11) |
| N(2)—C(12)—C(11) | 109.78(10) |
| C(17)—C(12)—C(11) | 109.99(11) |
| C(15)—C(12)—C(11) | 105.19(11) |
| N(2)—C(13)—H(13A) | 109.5 |
| N(2)—C(13)—H(13B) | 109.5 |
| H(13A)—C(13)—H(13B) | 109.5 |
| N(2)—C(13)—H(13C) | 109.5 |
| H(13A)—C(13)—H(13C) | 109.5 |
| H(13B)—C(13)—H(13C) | 109.5 |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |
| H(14A)—C(14)—H(14C) | 109.5 |
| H(14B)—C(14)—H(14C) | 109.5 |
| C(16)—C(15)—C(12) | 113.95(11) |
| C(16)—C(15)—H(15A) | 108.8 |
| C(12)—C(15)—H(15A) | 108.8 |
| C(16)—C(15)—H(15B) | 108.8 |
| C(12)—C(15)—H(15B) | 108.8 |
| H(15A)—C(15)—H(15B) | 107.7 |
| C(15)—C(16)—C(6) | 113.84(11) |
| C(15)—C(16)—H(16A) | 108.8 |
| C(6)—C(16)—H(16A) | 108.8 |
| C(15)—C(16)—H(16B) | 108.8 |
| C(6)—C(16)—H(16B) | 108.8 |
| H(16A)—C(16)—H(16B) | 107.7 |
| C(18)—C(17)—C(22) | 117.14(13) |
| C(18)—C(17)—C(12) | 120.72(12) |
| C(22)—C(17)—C(12) | 122.12(13) |
| C(19)—C(18)—C(17) | 121.38(14) |
| C(19)—C(18)—H(18) | 119.3 |
| C(17)—C(18)—H(18) | 119.3 |
| C(20)—C(19)—C(18) | 120.42(14) |
| C(20)—C(19)—H(19) | 119.8 |
| C(18)—C(19)—H(19) | 119.8 |
| C(21)—C(20)—C(19) | 119.39(14) |
| C(21)—C(20)—H(20) | 120.3 |
| C(19)—C(20)—H(20) | 120.3 |
| C(20)—C(21)—C(22) | 120.43(14) |
| C(20)—C(21)—H(21) | 119.8 |
| C(22)—C(21)—H(21) | 119.8 |
| C(21)—C(22)—C(17) | 121.23(14) |
| C(21)—C(22)—H(22) | 119.4 |

TABLE 22B-continued (Table 22A continued) Bond lengths [Å] and angles [deg] for crystalline form C.

| | bond lengths [Å] and angles [deg] |
|---|---|
| C(17)—C(22)—H(22) | 119.4 |
| C(24)—C(23)—C(4) | 118.11(13) |
| C(24)—C(23)—H(23) | 120.9 |
| C(4)—C(23)—H(23) | 120.9 |
| C(23)—C(24)—C(1) | 119.13(13) |
| C(23)—C(24)—H(24) | 120.4 |
| C(1)—C(24)—H(24) | 120.4 |
| C(25)—O(2)—H(2A) | 108.0(10) |
| O(2)—C(25)—C(26) | 108.43(12) |
| O(2)—C(25)—H(25A) | 110.0 |
| C(26)—C(25)—H(25A) | 110.0 |
| O(2)—C(25)—H(25B) | 110.0 |
| C(26)—C(25)—H(25B) | 110.0 |
| H(25A)—C(25)—H(25B) | 108.4 |
| C(25)—C(26)—H(26A) | 109.5 |
| C(25)—C(26)—H(26B) | 109.5 |
| H(26A)—C(26)—H(26B) | 109.5 |
| C(25)—C(26)—H(26C) | 109.5 |
| H(26A)—C(26)—H(26C) | 109.5 |
| H(26B)—C(26)—H(26C) | 109.5 |

Symmetry Transformations Used to Generate Equivalent Atoms:

TABLE 23

Hydrogen coordinates (×10$^4$) (i.e. (×10$^4$)) and isotropic displacement parameters ($Å^2$× 10$^3$) (i.e. ($Å^2$ × 10$^3$)) for crystalline form C.

| | x | y | z | U(eq) |
|---|---|---|---|---|
| H(1) | 1646(18) | 3427(16) | −927(13) | 26(4) |
| H(2) | 1145 | 5099 | −4255 | 23 |
| H(7A) | 3578 | 9361 | 211 | 28 |
| H(7B) | 1971 | 7969 | 0 | 28 |
| H(8A) | 2160 | 7612 | −1913 | 26 |
| H(8B) | 3966 | 7917 | −1472 | 26 |
| H(10A) | 4245 | 5221 | 793 | 21 |
| H(10B) | 5468 | 6629 | 706 | 21 |
| H(11A) | 5809 | 8180 | 2680 | 21 |
| H(11B) | 6226 | 6930 | 2698 | 21 |
| H(13A) | 1682 | 3425 | 2864 | 39 |
| H(13B) | 1289 | 4707 | 2911 | 39 |
| H(13C) | 2586 | 4979 | 4052 | 39 |
| H(14A) | 5068 | 5040 | 3864 | 37 |
| H(14B) | 5391 | 4864 | 2620 | 37 |
| H(14C) | 4026 | 3498 | 2670 | 37 |
| H(15A) | 1979 | 6700 | 2944 | 21 |
| H(15B) | 3293 | 8062 | 2858 | 21 |
| H(16A) | 1274 | 6523 | 976 | 22 |
| H(16B) | 1418 | 5127 | 939 | 22 |
| H(18) | 7018 | 7506 | 4516 | 25 |
| H(19) | 8201 | 8738 | 6610 | 29 |
| H(20) | 6894 | 9627 | 7821 | 32 |
| H(21) | 4352 | 9207 | 6922 | 32 |
| H(22) | 3127 | 7927 | 4831 | 28 |
| H(23) | −31 | 1163 | −3242 | 23 |
| H(24) | −942 | 714 | −5262 | 24 |
| H(2A) | 2332(19) | 3467(18) | 1062(15) | 40 |
| H(25A) | 1757 | 1092 | 638 | 35 |
| H(25B) | 3331 | 2032 | 412 | 35 |
| H(26A) | 271 | 74 | −1442 | 67 |
| H(26B) | 1693 | −308 | −1286 | 67 |
| H(26C) | 1870 | 972 | −1655 | 67 |

TABLE 24

Anisotropic displacement parameters ($Å^2 \times 10^3$) (i.e. ($^2 \times 10^{\wedge}3$)) for crystalline form C. The anisotropic displacement factor exponent takes the form: $-2\pi^2 [h^2 a^{*2} U11 + \ldots + 2 h k a^* b^* U12]$.

| | U11 | U22 | U33 | U23 | U13 | U12 |
|---|---|---|---|---|---|---|
| F(1) | 33(1) | 32(1) | 14(1) | 7(1) | 4(1) | 14(1) |
| O(1) | 23(1) | 18(1) | 17(1) | 6(1) | 3(1) | 10(1) |
| N(1) | 19(1) | 18(1) | 17(1) | 8(1) | 6(1) | 11(1) |
| N(2) | 17(1) | 20(1) | 18(1) | 8(1) | 7(1) | 10(1) |
| C(1) | 18(1) | 28(1) | 12(1) | 7(1) | 4(1) | 13(1) |
| C(2) | 19(1) | 22(1) | 19(1) | 10(1) | 8(1) | 11(1) |
| C(3) | 13(1) | 20(1) | 18(1) | 7(1) | 6(1) | 10(1) |
| C(4) | 12(1) | 21(1) | 15(1) | 7(1) | 6(1) | 10(1) |
| C(5) | 15(1) | 17(1) | 18(1) | 6(1) | 7(1) | 9(1) |
| C(6) | 17(1) | 18(1) | 15(1) | 6(1) | 4(1) | 9(1) |
| C(7) | 29(1) | 20(1) | 21(1) | 9(1) | 7(1) | 13(1) |
| C(8) | 25(1) | 20(1) | 18(1) | 8(1) | 5(1) | 11(1) |
| C(9) | 15(1) | 20(1) | 16(1) | 7(1) | 6(1) | 10(1) |
| C(10) | 17(1) | 20(1) | 16(1) | 7(1) | 7(1) | 10(1) |
| C(11) | 15(1) | 22(1) | 16(1) | 8(1) | 6(1) | 10(1) |
| C(12) | 15(1) | 19(1) | 14(1) | 5(1) | 5(1) | 10(1) |
| C(13) | 26(1) | 25(1) | 28(1) | 12(1) | 14(1) | 11(1) |
| C(14) | 27(1) | 24(1) | 25(1) | 9(1) | 7(1) | 16(1) |
| C(15) | 17(1) | 22(1) | 18(1) | 8(1) | 9(1) | 12(1) |
| C(16) | 16(1) | 21(1) | 18(1) | 7(1) | 6(1) | 11(1) |
| C(17) | 20(1) | 15(1) | 17(1) | 7(1) | 6(1) | 7(1) |
| C(18) | 19(1) | 22(1) | 19(1) | 9(1) | 6(1) | 9(1) |
| C(19) | 24(1) | 21(1) | 22(1) | 10(1) | 2(1) | 7(1) |
| C(20) | 38(1) | 20(1) | 14(1) | 6(1) | 3(1) | 12(1) |
| C(21) | 39(1) | 25(1) | 20(1) | 9(1) | 14(1) | 19(1) |
| C(22) | 24(1) | 25(1) | 21(1) | 10(1) | 8(1) | 14(1) |
| C(23) | 18(1) | 19(1) | 22(1) | 9(1) | 8(1) | 11(1) |
| C(24) | 16(1) | 20(1) | 19(1) | 3(1) | 5(1) | 9(1) |
| O(2) | 34(1) | 25(1) | 19(1) | 8(1) | 5(1) | 17(1) |
| C(25) | 37(1) | 22(1) | 26(1) | 9(1) | 4(1) | 16(1) |
| C(26) | 66(1) | 30(1) | 30(1) | 6(1) | −2(1) | 29(1) |

Crystalline Form D

TABLE 25

Crystal data and structure refinement for crystalline form D.

| | |
|---|---|
| Empirical formula | $C_{27}H_{35}FN_2O_2$ |
| Formula weight | 438.57 |
| Temperature | 100(2) K |
| Wavelength | 0.71073 Å |
| Crystal system | Triclinic |
| Space group | P-1 |
| Unit cell dimensions | a = 9.909(3) A alpha = 115.704(5) deg. |
| | b = 11.701(4) A beta = 106.324(5) deg. |
| | c = 11.830(4) A gamma = 94.399(6) deg. |
| Volume | 1154.4(7) Å$^3$ |
| Z | 2 |
| Density (calculated) | 1.262 Mg/m$^3$ |
| Absorption coefficient | 0.085 mm$^{-1}$ |
| F(000) | 472 |
| Crystal size | 0.29 × 0.12 × 0.08 mm |
| Theta range for data collection | 1.98 to 25.10 deg. |
| Index ranges | −11 ≤ h ≤ 11, −13 ≤ k ≤ 13, −13 ≤ l ≤ 14 |
| Reflections collected | 18119 |
| Independent reflections | 4085 [R(int) = 0.0836] |
| Absorption correction | None |
| Refinement method | Full-matrix least-squares on F$^2$ |
| Data/restraints/parameters | 4085/1/303 |
| Goodness-of-fit on F$^2$ | 1.082 |
| Final R indices [I > 2sigma(I)] | R1 = 0.0651, wR2 = 0.1559 |
| R indices (all data) | R1 = 0.0931, wR2 = 0.1710 |
| Largest diff. peak and hole | 0.510 and −0.325 eÅ$^{-3}$ |

TABLE 26

Atomic coordinates ($\times 10^4$) (i.e. ($\times 10^{\wedge}4$)) and equivalent isotropic displacement parameters ($Å^2 \times 10^3$) (i.e.($^2 \times 10^{\wedge}3$)) for crystalline form D. U(eq) is defined as one third of the trace of the orthogonalized Uij tensor.

| | x | y | z | U(eq) |
|---|---|---|---|---|
| F(1) | 866(2) | −3098(2) | −2007(2) | 48(1) |
| O(1) | 3245(2) | 2553(2) | 5183(2) | 28(1) |
| N(1) | 2086(3) | −1043(2) | 3364(3) | 25(1) |
| N(2) | 2884(3) | 630(2) | 7839(2) | 24(1) |
| C(1) | 1160(4) | −2626(3) | −659(3) | 35(1) |
| C(2) | 1496(3) | −1297(3) | 139(3) | 32(1) |
| C(3) | 1809(3) | −831(3) | 1513(3) | 26(1) |
| C(4) | 1739(3) | −1733(3) | 2007(3) | 24(1) |
| C(5) | 2381(3) | 267(3) | 3741(3) | 24(1) |
| C(6) | 2824(3) | 1330(3) | 5162(3) | 24(1) |
| C(7) | 2321(4) | 2703(3) | 4107(3) | 34(1) |
| C(8) | 2379(3) | 1766(3) | 2753(3) | 30(1) |
| C(9) | 2217(3) | 438(3) | 2646(3) | 26(1) |
| C(10) | 4171(3) | 1180(3) | 6060(3) | 26(1) |
| C(11) | 4558(3) | 2091(3) | 7557(3) | 26(1) |
| C(12) | 3307(3) | 2005(3) | 8070(3) | 24(1) |
| C(13) | 1527(3) | 350(3) | 8042(3) | 31(1) |
| C(14) | 4010(4) | 286(3) | 8665(3) | 34(1) |
| C(15) | 2055(3) | 2303(3) | 7200(3) | 26(1) |
| C(16) | 1596(3) | 1359(3) | 5713(3) | 25(1) |
| C(17) | 3729(3) | 2984(3) | 9560(3) | 28(1) |
| C(18) | 5164(4) | 3456(3) | 10423(3) | 33(1) |
| C(19) | 5532(4) | 4258(3) | 11782(3) | 36(1) |
| C(20) | 4475(4) | 4616(3) | 12336(3) | 36(1) |
| C(21) | 3047(4) | 4164(3) | 11498(3) | 35(1) |
| C(22) | 2673(4) | 3371(3) | 10135(3) | 31(1) |
| C(23) | 1402(3) | −3077(3) | 1163(3) | 29(1) |
| C(24) | 1115(3) | −3518(3) | −188(3) | 34(1) |
| O(2) | 1858(2) | −1693(2) | 5352(2) | 38(1) |
| C(25A) | 2047(4) | −2854(3) | 5459(3) | 31(1) |
| C(26) | 3583(4) | −2995(4) | 5551(5) | 46(1) |
| C(27) | 930(4) | −3962(4) | 4274(4) | 39(1) |
| C(25B) | 2047(4) | −2854(3) | 5459(3) | 31(1) |
| C(28) | 2190(30) | −3910(20) | 4320(20) | 30 |

TABLE 27A

Bond lengths [Å] and angles [deg] for crystalline form D.

| | bond lengths [Å] and angles [deg] |
|---|---|
| F(1)—C(1) | 1.372(4) |
| O(1)—C(7) | 1.433(4) |
| O(1)—C(6) | 1.447(3) |
| N(1)—C(4) | 1.368(4) |
| N(1)—C(5) | 1.378(4) |
| N(1)—H(1N) | 0.92(3) |
| N(2)—C(13) | 1.469(4) |
| N(2)—C(14) | 1.469(4) |
| N(2)—C(12) | 1.513(4) |
| C(1)—C(2) | 1.375(5) |
| C(1)—C(24) | 1.383(5) |
| C(2)—C(3) | 1.399(4) |
| C(2)—H(2) | 0.9500 |
| C(3)—C(4) | 1.417(4) |
| C(3)—C(9) | 1.429(4) |
| C(4)—C(23) | 1.397(4) |
| C(5)—C(9) | 1.363(4) |
| C(5)—C(6) | 1.501(4) |
| C(6)—C(16) | 1.529(4) |
| C(6)—C(10) | 1.530(4) |
| C(7)—C(8) | 1.520(4) |
| C(7)—H(7A) | 0.9900 |
| C(7)—H(7B) | 0.9900 |
| C(8)—C(9) | 1.495(4) |
| C(8)—H(8A) | 0.9900 |
| C(8)—H(8B) | 0.9900 |
| C(10)—C(11) | 1.530(4) |
| C(10)—H(10A) | 0.9900 |
| C(10)—H(10B) | 0.9900 |

TABLE 27A-continued

Bond lengths [Å] and angles [deg] for crystalline form D.

| | bond lengths [Å] and angles [deg] |
|---|---|
| C(11)—C(12) | 1.539(4) |
| C(11)—H(11A) | 0.9900 |
| C(11)—H(11B) | 0.9900 |
| C(12)—C(17) | 1.534(4) |
| C(12)—C(15) | 1.543(4) |
| C(13)—H(13A) | 0.9800 |
| C(13)—H(13B) | 0.9800 |
| C(13)—H(13C) | 0.9800 |
| C(14)—H(14A) | 0.9800 |
| C(14)—H(14B) | 0.9800 |
| C(14)—H(14C) | 0.9800 |
| C(15)—C(16) | 1.520(4) |
| C(15)—H(15A) | 0.9900 |
| C(15)—H(15B) | 0.9900 |
| C(16)—H(16A) | 0.9900 |
| C(16)—H(16B) | 0.9900 |
| C(17)—C(18) | 1.393(4) |
| C(17)—C(22) | 1.404(4) |
| C(18)—C(19) | 1.381(5) |
| C(18)—H(18) | 0.9500 |
| C(19)—C(20) | 1.384(5) |
| C(19)—H(19) | 0.9500 |
| C(20)—C(21) | 1.381(5) |
| C(20)—H(20) | 0.9500 |
| C(21)—C(22) | 1.383(4) |
| C(21)—H(21) | 0.9500 |
| C(22)—H(22) | 0.9500 |
| C(23)—C(24) | 1.381(4) |
| C(23)—H(23) | 0.9500 |
| C(24)—H(24) | 0.9500 |
| O(2)—C(25A) | 1.439(4) |
| O(2)—H(2A) | 0.8400 |
| C(25A)—C(27) | 1.484(5) |
| C(25A)—C(26) | 1.522(5) |
| C(25A)—H(25) | 1.0000 |
| C(26)—H(26A) | 0.9800 |
| C(26)—H(26B) | 0.9800 |
| C(26)—H(26C) | 0.9800 |
| C(27)—H(27A) | 0.9800 |
| C(27)—H(27B) | 0.9800 |
| C(27)—H(27C) | 0.9800 |
| C(28)—H(28A) | 0.9800 |
| C(28)—H(28B) | 0.9800 |
| C(28)—H(28C) | 0.9800 |

TABLE 27B (Table 27A continued) Bond lengths [Å] and angles [deg] for crystalline form D.

| | bond lengths [Å] and angles [deg] |
|---|---|
| C(7)—O(1)—C(6) | 115.0(2) |
| C(4)—N(1)—C(5) | 108.5(3) |
| C(4)—N(1)—H(1N) | 126(2) |
| C(5)—N(1)—H(1N) | 125(2) |
| C(13)—N(2)—C(14) | 108.2(2) |
| C(13)—N(2)—C(12) | 114.0(2) |
| C(14)—N(2)—C(12) | 113.1(2) |
| F(1)—C(1)—C(2) | 117.9(3) |
| F(1)—C(1)—C(24) | 117.9(3) |
| C(2)—C(1)—C(24) | 124.2(3) |
| C(1)—C(2)—C(3) | 117.3(3) |
| C(1)—C(2)—H(2) | 121.4 |
| C(3)—C(2)—H(2) | 121.4 |
| C(2)—C(3)—C(4) | 119.2(3) |
| C(2)—C(3)—C(9) | 134.3(3) |
| C(4)—C(3)—C(9) | 106.5(3) |
| N(1)—C(4)—C(23) | 130.3(3) |
| N(1)—C(4)—C(3) | 108.0(3) |
| C(23)—C(4)—C(3) | 121.7(3) |

TABLE 27B-continued (Table 27A continued) Bond lengths [Å] and angles [deg] for crystalline form D.

| | bond lengths [Å] and angles [deg] |
|---|---|
| C(9)—C(5)—N(1) | 110.1(3) |
| C(9)—C(5)—C(6) | 126.0(3) |
| N(1)—C(5)—C(6) | 123.9(3) |
| O(1)—C(6)—C(5) | 107.7(2) |
| O(1)—C(6)—C(16) | 110.7(2) |
| C(5)—C(6)—C(16) | 111.4(2) |
| O(1)—C(6)—C(10) | 105.7(2) |
| C(5)—C(6)—C(10) | 111.1(2) |
| C(16)—C(6)—C(10) | 110.1(2) |
| O(1)—C(7)—C(8) | 112.7(3) |
| O(1)—C(7)—H(7A) | 109.0 |
| C(8)—C(7)—H(7A) | 109.0 |
| O(1)—C(7)—H(7B) | 109.0 |
| C(8)—C(7)—H(7B) | 109.0 |
| H(7A)—C(7)—H(7B) | 107.8 |
| C(9)—C(8)—C(7) | 107.4(3) |
| C(9)—C(8)—H(8A) | 110.2 |
| C(7)—C(8)—H(8A) | 110.2 |
| C(9)—C(8)—H(8B) | 110.2 |
| C(7)—C(8)—H(8B) | 110.2 |
| H(8A)—C(8)—H(8B) | 108.5 |
| C(5)—C(9)—C(3) | 106.9(3) |
| C(5)—C(9)—C(8) | 121.5(3) |
| C(3)—C(9)—C(8) | 131.5(3) |
| C(11)—C(10)—C(6) | 114.4(2) |
| C(11)—C(10)—H(10A) | 108.7 |
| C(6)—C(10)—H(10A) | 108.7 |
| C(11)—C(10)—H(10B) | 108.7 |
| C(6)—C(10)—H(10B) | 108.7 |
| H(10A)—C(10)—H(10B) | 107.6 |
| C(10)—C(11)—C(12) | 113.7(2) |
| C(10)—C(11)—H(11A) | 108.8 |
| C(12)—C(11)—H(11A) | 108.8 |
| C(10)—C(11)—H(11B) | 108.8 |
| C(12)—C(11)—H(11B) | 108.8 |
| H(11A)—C(11)—H(11B) | 107.7 |
| N(2)—C(12)—C(17) | 110.4(2) |
| N(2)—C(12)—C(11) | 108.7(2) |
| C(17)—C(12)—C(11) | 111.5(2) |
| N(2)—C(12)—C(15) | 109.9(2) |
| C(17)—C(12)—C(15) | 111.2(2) |
| C(11)—C(12)—C(15) | 105.1(2) |
| N(2)—C(13)—H(13A) | 109.5 |
| N(2)—C(13)—H(13B) | 109.5 |
| H(13A)—C(13)—H(13B) | 109.5 |
| N(2)—C(13)—H(13C) | 109.5 |
| H(13A)—C(13)—H(13C) | 109.5 |
| H(13B)—C(13)—H(13C) | 109.5 |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |
| H(14A)—C(14)—H(14C) | 109.5 |
| H(14B)—C(14)—H(14C) | 109.5 |
| C(16)—C(15)—C(12) | 113.3(2) |
| C(16)—C(15)—H(15A) | 108.9 |
| C(12)—C(15)—H(15A) | 108.9 |
| C(16)—C(15)—H(15B) | 108.9 |
| C(12)—C(15)—H(15B) | 108.9 |
| H(15A)—C(15)—H(15B) | 107.7 |
| C(15)—C(16)—C(6) | 113.1(2) |
| C(15)—C(16)—H(16A) | 109.0 |
| C(6)—C(16)—H(16A) | 109.0 |
| C(15)—C(16)—H(16B) | 109.0 |
| C(6)—C(16)—H(16B) | 109.0 |
| H(16A)—C(16)—H(16B) | 107.8 |
| C(18)—C(17)—C(22) | 116.8(3) |
| C(18)—C(17)—C(12) | 121.9(3) |
| C(22)—C(17)—C(12) | 121.1(3) |
| C(19)—C(18)—C(17) | 121.8(3) |
| C(19)—C(18)—H(18) | 119.1 |
| C(17)—C(18)—H(18) | 119.1 |
| C(18)—C(19)—C(20) | 120.7(3) |
| C(18)—C(19)—H(19) | 119.7 |

TABLE 27B-continued (Table 27A continued) Bond lengths [Å] and angles [deg] for crystalline form D.

| | bond lengths [Å] and angles [deg] |
|---|---|
| C(20)—C(19)—H(19) | 119.7 |
| C(21)—C(20)—C(19) | 118.5(3) |
| C(21)—C(20)—H(20) | 120.7 |
| C(19)—C(20)—H(20) | 120.7 |
| C(20)—C(21)—C(22) | 121.0(3) |
| C(20)—C(21)—H(21) | 119.5 |
| C(22)—C(21)—H(21) | 119.5 |
| C(21)—C(22)—C(17) | 121.2(3) |
| C(21)—C(22)—H(22) | 119.4 |
| C(17)—C(22)—H(22) | 119.4 |
| C(24)—C(23)—C(4) | 118.2(3) |
| C(24)—C(23)—H(23) | 120.9 |
| C(4)—C(23)—H(23) | 120.9 |
| C(23)—C(24)—C(1) | 119.4(3) |
| C(23)—C(24)—H(24) | 120.3 |
| C(1)—C(24)—H(24) | 120.3 |
| C(25A)—O(2)—H(2A) | 109.5 |
| O(2)—C(25A)—C(27) | 107.4(3) |
| O(2)—C(25A)—C(26) | 108.6(3) |
| C(27)—C(25A)—C(26) | 113.3(3) |
| O(2)—C(25A)—H(25) | 109.2 |
| C(27)—C(25A)—H(25) | 109.2 |
| C(26)—C(25A)—H(25) | 109.2 |
| H(28A)—C(28)—H(28B) | 109.5 |
| H(28A)—C(28)—H(28C) | 109.5 |
| H(28B)—C(28)—H(28C) | 109.5 |

Symmetry Transformations Used to Generate Equivalent Atoms:

TABLE 28

Hydrogen coordinates (×10$^4$) (i.e. (×10^4)) and isotropic displacement parameters ($^2$× 10$^3$) (i.e. (^2 × 10^3)) for crystalline form D.

| | x | y | Z | U(eq) |
|---|---|---|---|---|
| H(1N) | 2050(30) | −1390(30) | 3930(30) | 31(9) |
| H(2) | 1515 | −719 | −227 | 39 |
| H(7A) | 2608 | 3608 | 4278 | 40 |
| H(7B) | 1314 | 2557 | 4085 | 40 |
| H(8A) | 1589 | 1770 | 2024 | 36 |
| H(8B) | 3312 | 2029 | 2681 | 36 |
| H(10A) | 4019 | 269 | 5899 | 31 |
| H(10B) | 5001 | 1344 | 5797 | 31 |
| H(11A) | 4864 | 2999 | 7743 | 31 |
| H(11B) | 5389 | 1878 | 8062 | 31 |
| H(13A) | 1274 | −575 | 7793 | 46 |
| H(13B) | 755 | 554 | 7483 | 46 |
| H(13C) | 1647 | 884 | 8986 | 46 |
| H(14A) | 4172 | 849 | 9614 | 52 |
| H(14B) | 4910 | 406 | 8495 | 52 |
| H(14C) | 3700 | −626 | 8437 | 52 |
| H(15A) | 1215 | 2271 | 7490 | 32 |
| H(15B) | 2355 | 3199 | 7350 | 32 |
| H(16A) | 797 | 1609 | 5217 | 30 |
| H(16B) | 1226 | 473 | 5554 | 30 |
| H(18) | 5908 | 3219 | 10067 | 39 |
| H(19) | 6521 | 4567 | 12343 | 43 |
| H(20) | 4727 | 5162 | 13272 | 44 |
| H(21) | 2309 | 4401 | 11864 | 42 |
| H(22) | 1684 | 3083 | 9578 | 37 |
| H(23) | 1371 | −3672 | 1508 | 35 |
| H(24) | 888 | −4425 | −788 | 40 |
| H(2A) | 2477 | −1047 | 6013 | 56 |
| H(25) | 1897 | −2770 | 6290 | 37 |
| H(26A) | 3734 | −3084 | 4735 | 70 |
| H(26B) | 3736 | −3770 | 5647 | 70 |
| H(26C) | 4269 | −2221 | 6329 | 70 |
| H(27A) | −32 | −3818 | 4272 | 58 |
| H(27B) | 1034 | −4772 | 4314 | 58 |

TABLE 28-continued

Hydrogen coordinates (×10$^4$) (i.e. (×10^4)) and isotropic displacement parameters ($^2$× 10$^3$) (i.e. (^2 × 10^3)) for crystalline form D.

| | x | y | Z | U(eq) |
|---|---|---|---|---|
| H(27C) | 1051 | −4029 | 3455 | 58 |
| H(25A) | 2918 | −2619 | 6248 | 37 |
| H(25B) | 1209 | −3169 | 5631 | 37 |
| H(28A) | 2030 | −3687 | 3588 | 45 |
| H(28B) | 1481 | −4699 | 4026 | 45 |
| H(28C) | 3168 | −4058 | 4560 | 45 |

TABLE 29

Anisotropic displacement parameters ($^2$× 10$^3$) (i.e. (^2 × 10^3)) for crystalline form D. The anisotropic displacement factor exponent takes the form: −2 pi^2 [h^2 a*^2 U11 + ... + 2 h k a* b* U12].

| | U11 | U22 | U33 | U23 | U13 | U12 |
|---|---|---|---|---|---|---|
| F(1) | 56(1) | 51(1) | 28(1) | 10(1) | 17(1) | 9(1) |
| O(1) | 24(1) | 26(1) | 35(1) | 15(1) | 9(1) | 6(1) |
| N(1) | 21(1) | 27(1) | 29(2) | 14(1) | 11(1) | 10(1) |
| N(2) | 17(1) | 28(1) | 29(1) | 13(1) | 9(1) | 9(1) |
| C(1) | 25(2) | 47(2) | 29(2) | 13(2) | 13(1) | 10(2) |
| C(2) | 28(2) | 38(2) | 34(2) | 19(2) | 13(2) | 9(2) |
| C(3) | 15(2) | 34(2) | 31(2) | 15(1) | 10(1) | 9(1) |
| C(4) | 13(2) | 29(2) | 30(2) | 11(1) | 8(1) | 7(1) |
| C(5) | 15(2) | 25(2) | 32(2) | 12(1) | 8(1) | 8(1) |
| C(6) | 18(2) | 23(2) | 33(2) | 14(1) | 11(1) | 7(1) |
| C(7) | 30(2) | 32(2) | 42(2) | 21(2) | 11(2) | 12(2) |
| C(8) | 26(2) | 30(2) | 37(2) | 19(2) | 10(1) | 7(1) |
| C(9) | 15(2) | 33(2) | 33(2) | 16(2) | 10(1) | 9(1) |
| C(10) | 18(2) | 28(2) | 32(2) | 14(1) | 11(1) | 10(1) |
| C(11) | 18(2) | 30(2) | 32(2) | 14(1) | 10(1) | 7(1) |
| C(12) | 16(2) | 24(2) | 31(2) | 11(1) | 9(1) | 7(1) |
| C(13) | 26(2) | 32(2) | 38(2) | 16(2) | 16(2) | 8(1) |
| C(14) | 30(2) | 31(2) | 39(2) | 16(2) | 6(2) | 13(2) |
| C(15) | 16(2) | 30(2) | 35(2) | 14(1) | 12(1) | 13(1) |
| C(16) | 18(2) | 26(2) | 32(2) | 13(1) | 10(1) | 10(1) |
| C(17) | 25(2) | 24(2) | 32(2) | 11(1) | 10(1) | 10(1) |
| C(18) | 25(2) | 34(2) | 35(2) | 14(2) | 10(2) | 6(1) |
| C(19) | 27(2) | 37(2) | 34(2) | 11(2) | 6(2) | 4(2) |
| C(20) | 43(2) | 27(2) | 33(2) | 8(2) | 15(2) | 11(2) |
| C(21) | 40(2) | 31(2) | 38(2) | 14(2) | 20(2) | 18(2) |
| C(22) | 28(2) | 28(2) | 35(2) | 11(2) | 13(1) | 14(1) |
| C(23) | 19(2) | 30(2) | 37(2) | 13(2) | 12(1) | 9(1) |
| C(24) | 22(2) | 34(2) | 37(2) | 10(2) | 12(1) | 7(1) |
| O(2) | 37(1) | 33(1) | 42(1) | 17(1) | 12(1) | 11(1) |
| C(25A) | 32(2) | 28(2) | 40(2) | 19(2) | 18(2) | 15(2) |
| C(26) | 29(2) | 40(2) | 70(3) | 24(2) | 18(2) | 22(2) |
| C(27) | 30(2) | 28(2) | 49(2) | 10(2) | 13(2) | 12(2) |
| C(25B) | 32(2) | 28(2) | 40(2) | 19(2) | 18(2) | 15(1) |

Crystalline Form G

TABLE 30

Crystal data and structure refinement for crystalline form G.

| | |
|---|---|
| Empirical formula | $C_{26}H_{33}FN_2O_2S$ |
| Formula weight | 456.60 |
| Temperature | 130(2) K |
| Wavelength | .71073 Å |
| Crystal system | Monoclinic |
| Space group | P 21/c |
| Unit cell dimensions | a = 10.8279(12) A alpha = 90 deg. |
| | b = 11.5334(12) A beta = 99.991(2) deg. |
| | c = 18.822(2) A gamma = 90 deg. |
| Volume | 2314.9(4) Å$^3$ |
| Z | 4 |
| Density (calculated) | 1.310 Mg/m$^3$ |
| Absorption coefficient | 0.174 mm$^{-1}$ |
| F(000) | 976 |
| Crystal size | 0.57 × 0.35 × 0.13 mm |

TABLE 30-continued

Crystal data and structure refinement for crystalline form G.

| | |
|---|---|
| Theta range for data collection | 2.20 to 33.19 deg. |
| Index ranges | −16 ≤ h ≤ 15, −17 ≤ k ≤ 16, −29 ≤ l ≤ 27 |
| Reflections collected | 37663 |
| Independent reflections | 8514 [R(int) = 0.0802] |
| Absorption correction | None |
| Refinement method | Full-matrix least-squares on $F^2$ |
| Data/restraints/parameters | 8514/0/297 |
| Goodness-of-fit on $F^2$ | 1.070 |
| Final R indices [I > 2sigma(I)] | R1 = 0.0516, wR2 = 0.1253 |
| R indices (all data) | R1 = 0.0639, wR2 = 0.1301 |
| Largest diff. peak and hole | 1.045 and −.349 e.Å$^{-3}$ |

TABLE 31

Atomic coordinates (×10$^4$) (i.e. (×10$^4$)) and equivalent isotropic displacement parameters ($^2$× 10$^3$) (i.e. ($^2$ × 10$^3$)) for crystalline form G. U(eq) is defined as one third of the trace of the orthogonalized Uij tensor.

| | x | y | Z | U(eq) |
|---|---|---|---|---|
| F(1) | 8199(1) | 5868(1) | 4452(1) | 31(1) |
| O(1) | 2509(1) | 1818(1) | 3420(1) | 19(1) |
| N(1) | 5966(1) | 1682(1) | 3844(1) | 13(1) |
| N(2) | 4244(1) | −1808(1) | 3634(1) | 14(1) |
| C(1) | 7669(1) | 4803(1) | 4280(1) | 20(1) |
| C(2) | 6385(1) | 4727(1) | 4144(1) | 19(1) |
| C(3) | 5870(1) | 3620(1) | 3988(1) | 14(1) |
| C(4) | 6686(1) | 2661(1) | 3990(1) | 13(1) |
| C(5) | 4726(1) | 1997(1) | 3749(1) | 13(1) |
| C(6) | 3658(1) | 1161(1) | 3598(1) | 13(1) |
| C(7) | 2417(1) | 2800(1) | 3872(1) | 22(1) |
| C(8) | 3370(1) | 3740(1) | 3784(1) | 19(1) |
| C(9) | 4621(1) | 3170(1) | 3833(1) | 14(1) |
| C(10) | 3743(1) | 428(1) | 2931(1) | 16(1) |
| C(11) | 2802(1) | −566(1) | 2813(1) | 16(1) |
| C(12) | 2924(1) | −1382(1) | 3469(1) | 12(1) |
| C(13) | 4584(1) | −2440(1) | 4309(1) | 17(1) |
| C(14) | 4629(1) | −2483(1) | 3055(1) | 23(1) |
| C(15) | 2667(1) | −604(1) | 4094(1) | 13(1) |
| C(16) | 3624(1) | 374(1) | 4252(1) | 13(1) |
| C(17) | 2000(1) | −2397(1) | 3342(1) | 14(1) |
| C(18) | 1739(1) | −3057(1) | 3920(1) | 15(1) |
| C(19) | 1010(1) | −4051(1) | 3811(1) | 18(1) |
| C(20) | 498(1) | −4404(1) | 3120(1) | 22(1) |
| C(21) | 718(2) | −3751(1) | 2541(1) | 28(1) |
| C(22) | 1463(1) | −2761(1) | 2651(1) | 22(1) |
| C(23) | 7986(1) | 2773(1) | 4124(1) | 15(1) |
| C(24) | 8478(1) | 3872(1) | 4270(1) | 18(1) |
| S(1) | 2104(1) | 3668(1) | 948(1) | 22(1) |
| O(2) | 2254(1) | 4947(1) | 1046(1) | 39(1) |
| C(25) | 684(1) | 3480(1) | 320(1) | 25(1) |
| C(26) | 1565(2) | 3135(2) | 1726(1) | 35(1) |

TABLE 32A

Bond lengths [Å] and angles [deg] for crystalline form G.

| | bond lengths [Å] and angles [deg] |
|---|---|
| F(1)—C(1) | 1.3707(14) |
| O(1)—C(7) | 1.4303(16) |
| O(1)—C(6) | 1.4452(14) |
| N(1)—C(5) | 1.3718(15) |
| N(1)—C(4) | 1.3729(15) |
| N(1)—H(1N) | .781(17) |
| N(2)—C(13) | 1.4553(15) |
| N(2)—C(14) | 1.4579(15) |
| N(2)—C(12) | 1.4923(15) |

TABLE 32A-continued

Bond lengths [Å] and angles [deg] for crystalline form G.

| | bond lengths [Å] and angles [deg] |
|---|---|
| C(1)—C(2) | 1.3716(18) |
| C(1)—C(24) | 1.3888(19) |
| C(2)—C(3) | 1.4045(16) |
| C(2)—H(2) | .9500 |
| C(3)—C(4) | 1.4154(16) |
| C(3)—C(9) | 1.4304(16) |
| C(4)—C(23) | 1.3923(16) |
| C(5)—C(9) | 1.3695(16) |
| C(5)—C(6) | 1.4951(16) |
| C(6)—C(10) | 1.5298(16) |
| C(6)—C(16) | 1.5350(16) |
| C(7)—C(8) | 1.5247(18) |
| C(7)—H(7A) | .9900 |
| C(7)—H(7B) | .9900 |
| C(8)—C(9) | 1.4941(16) |
| C(8)—H(8A) | .9900 |
| C(8)—H(8B) | .9900 |
| C(10)—C(11) | 1.5231(16) |
| C(10)—H(10A) | .9900 |
| C(10)—H(10B) | .9900 |
| C(11)—C(12) | 1.5401(16) |
| C(11)—H(11A) | .9900 |
| C(11)—H(11B) | .9900 |
| C(12)—C(17) | 1.5314(15) |
| C(12)—C(15) | 1.5427(15) |
| C(13)—H(13A) | .9800 |
| C(13)—H(13B) | .9800 |
| C(13)—H(13C) | .9800 |
| C(14)—H(14A) | .9800 |
| C(14)—H(14B) | .9800 |
| C(14)—H(14C) | .9800 |
| C(15)—C(16) | 1.5258(16) |
| C(15)—H(15A) | .9900 |
| C(15)—H(15B) | .9900 |
| C(16)—H(16A) | .9900 |
| C(16)—H(16B) | .9900 |
| C(17)—C(22) | 1.3940(16) |
| C(17)—C(18) | 1.3969(16) |
| C(18)—C(19) | 1.3870(16) |
| C(18)—H(18) | .9500 |
| C(19)—C(20) | 1.3842(18) |
| C(19)—H(19) | .9500 |
| C(20)—C(21) | 1.379(2) |
| C(20)—H(20) | .9500 |
| C(21)—C(22) | 1.3920(18) |
| C(21)—H(21) | .9500 |
| C(22)—H(22) | .9500 |
| C(23)—C(24) | 1.3837(17) |
| C(23)—H(23) | .9500 |
| C(24)—H(24) | .9500 |
| S(1)—O(2) | 1.4910(11) |
| S(1)—C(26) | 1.7784(16) |
| S(1)—C(25) | 1.7825(14) |
| C(25)—H(25A) | .9800 |
| C(25)—H(25B) | .9800 |
| C(25)—H(25C) | .9800 |
| C(26)—H(26A) | .9800 |
| C(26)—H(26B) | .9800 |
| C(26)—H(26C) | .9800 |

TABLE 32B (Table 32A continued) Bond lengths [Å] and angles [deg] for crystalline form G.

| | bond lengths [Å] and angles [deg] |
|---|---|
| C(7)—O(1)—C(6) | 115.09(9) |
| C(5)—N(1)—C(4) | 108.49(10) |
| C(5)—N(1)—H(1N) | 127.7(12) |
| C(4)—N(1)—H(1N) | 123.8(12) |

TABLE 32B-continued (Table 32A continued) Bond lengths [Å] and angles [deg] for crystalline form G.

| | bond lengths [Å] and angles [deg] |
|---|---|
| C(13)—N(2)—C(14) | 108.86(10) |
| C(13)—N(2)—C(12) | 115.75(9) |
| C(14)—N(2)—C(12) | 114.08(9) |
| F(1)—C(1)—C(2) | 118.04(12) |
| F(1)—C(1)—C(24) | 117.21(11) |
| C(2)—C(1)—C(24) | 124.74(11) |
| C(1)—C(2)—C(3) | 116.71(11) |
| C(1)—C(2)—H(2) | 121.6 |
| C(3)—C(2)—H(2) | 121.6 |
| C(2)—C(3)—C(4) | 119.04(11) |
| C(2)—C(3)—C(9) | 134.39(11) |
| C(4)—C(3)—C(9) | 106.55(10) |
| N(1)—C(4)—C(23) | 129.36(11) |
| N(1)—C(4)—C(3) | 108.03(10) |
| C(23)—C(4)—C(3) | 122.60(11) |
| C(9)—C(5)—N(1) | 110.24(10) |
| C(9)—C(5)—C(6) | 125.60(10) |
| N(1)—C(5)—C(6) | 124.14(10) |
| O(1)—C(6)—C(5) | 108.22(9) |
| O(1)—C(6)—C(10) | 105.83(9) |
| C(5)—C(6)—C(10) | 110.99(9) |
| O(1)—C(6)—C(16) | 110.82(9) |
| C(5)—C(6)—C(16) | 110.71(9) |
| C(10)—C(6)—C(16) | 110.16(9) |
| O(1)—C(7)—C(8) | 112.34(11) |
| O(1)—C(7)—H(7A) | 109.1 |
| C(8)—C(7)—H(7A) | 109.1 |
| O(1)—C(7)—H(7B) | 109.1 |
| C(8)—C(7)—H(7B) | 109.1 |
| H(7A)—C(7)—H(7B) | 107.9 |
| C(9)—C(8)—C(7) | 107.71(10) |
| C(9)—C(8)—H(8A) | 110.2 |
| C(7)—C(8)—H(8A) | 110.2 |
| C(9)—C(8)—H(8B) | 110.2 |
| C(7)—C(8)—H(8B) | 110.2 |
| H(8A)—C(8)—H(8B) | 108.5 |
| C(5)—C(9)—C(3) | 106.69(10) |
| C(5)—C(9)—C(8) | 121.33(11) |
| C(3)—C(9)—C(8) | 131.94(11) |
| C(11)—C(10)—C(6) | 113.66(10) |
| C(11)—C(10)—H(10A) | 108.8 |
| C(6)—C(10)—H(10A) | 108.8 |
| C(11)—C(10)—H(10B) | 108.8 |
| C(6)—C(10)—H(10B) | 108.8 |
| H(10A)—C(10)—H(10B) | 107.7 |
| C(10)—C(11)—C(12) | 112.41(9) |
| C(10)—C(11)—H(11A) | 109.1 |
| C(12)—C(11)—H(11A) | 109.1 |
| C(10)—C(11)—H(11B) | 109.1 |
| C(12)—C(11)—H(11B) | 109.1 |
| H(11A)—C(11)—H(11B) | 107.9 |
| N(2)—C(12)—C(17) | 110.91(9) |
| N(2)—C(12)—C(11) | 108.28(9) |
| C(17)—C(12)—C(11) | 112.27(9) |
| N(2)—C(12)—C(15) | 109.03(9) |
| C(17)—C(12)—C(15) | 111.38(9) |
| C(11)—C(12)—C(15) | 104.72(9) |
| N(2)—C(13)—H(13A) | 109.5 |
| N(2)—C(13)—H(13B) | 109.5 |
| H(13A)—C(13)—H(13B) | 109.5 |
| N(2)—C(13)—H(13C) | 109.5 |
| H(13A)—C(13)—H(13C) | 109.5 |
| H(13B)—C(13)—H(13C) | 109.5 |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |
| H(14A)—C(14)—H(14C) | 109.5 |
| H(14B)—C(14)—H(14C) | 109.5 |
| C(16)—C(15)—C(12) | 111.85(9) |
| C(16)—C(15)—H(15A) | 109.2 |
| C(12)—C(15)—H(15A) | 109.2 |
| C(16)—C(15)—H(15B) | 109.2 |
| C(12)—C(15)—H(15B) | 109.2 |
| H(15A)—C(15)—H(15B) | 107.9 |
| C(15)—C(16)—C(6) | 113.01(9) |
| C(15)—C(16)—H(16A) | 109.0 |
| C(6)—C(16)—H(16A) | 109.0 |
| C(15)—C(16)—H(16B) | 109.0 |
| C(6)—C(16)—H(16B) | 109.0 |
| H(16A)—C(16)—H(16B) | 107.8 |
| C(22)—C(17)—C(18) | 117.06(11) |
| C(22)—C(17)—C(12) | 122.12(10) |
| C(18)—C(17)—C(12) | 120.63(10) |
| C(19)—C(18)—C(17) | 121.45(11) |
| C(19)—C(18)—H(18) | 119.3 |
| C(17)—C(18)—H(18) | 119.3 |
| C(20)—C(19)—C(18) | 120.49(12) |
| C(20)—C(19)—H(19) | 119.8 |
| C(18)—C(19)—H(19) | 119.8 |
| C(21)—C(20)—C(19) | 119.06(12) |
| C(21)—C(20)—H(20) | 120.5 |
| C(19)—C(20)—H(20) | 120.5 |
| C(20)—C(21)—C(22) | 120.39(12) |
| C(20)—C(21)—H(21) | 119.8 |
| C(22)—C(21)—H(21) | 119.8 |
| C(21)—C(22)—C(17) | 121.52(12) |
| C(21)—C(22)—H(22) | 119.2 |
| C(17)—C(22)—H(22) | 119.2 |
| C(24)—C(23)—C(4) | 117.62(11) |
| C(24)—C(23)—H(23) | 121.2 |
| C(4)—C(23)—H(23) | 121.2 |
| C(23)—C(24)—C(1) | 119.27(11) |
| C(23)—C(24)—H(24) | 120.4 |
| C(1)—C(24)—H(24) | 120.4 |
| O(2)—S(1)—C(26) | 106.52(8) |
| O(2)—S(1)—C(25) | 105.40(7) |
| C(26)—S(1)—C(25) | 97.75(8) |
| S(1)—C(25)—H(25A) | 109.5 |
| S(1)—C(25)—H(25B) | 109.5 |
| H(25A)—C(25)—H(25B) | 109.5 |
| S(1)—C(25)—H(25C) | 109.5 |
| H(25A)—C(25)—H(25C) | 109.5 |
| H(25B)—C(25)—H(25C) | 109.5 |
| S(1)—C(26)—H(26A) | 109.5 |
| S(1)—C(26)—H(26B) | 109.5 |
| H(26A)—C(26)—H(26B) | 109.5 |
| S(1)—C(26)—H(26C) | 109.5 |
| H(26A)—C(26)—H(26C) | 109.5 |
| H(26B)—C(26)—H(26C) | 109.5 |

Symmetry Transformations Used to Generate Equivalent Atoms:

TABLE 33

Hydrogen coordinates (×10$^4$) (i.e. (×10^4)) and isotropic displacement parameters ($^2$× 10$^3$) (i.e. ($^2$ × 10^3)) for crystalline form G.

| | x | y | Z | U(eq) |
|---|---|---|---|---|
| H(2) | 5870 | 5392 | 4155 | 23 |
| H(7A) | 2552 | 2546 | 4382 | 26 |
| H(7B) | 1562 | 3129 | 3753 | 26 |
| H(8A) | 3134 | 4127 | 3311 | 23 |
| H(8B) | 3398 | 4330 | 4168 | 23 |
| H(10A) | 3603 | 935 | 2500 | 19 |
| H(10B) | 4600 | 104 | 2978 | 19 |
| H(11A) | 2933 | −1017 | 2385 | 19 |
| H(11B) | 1943 | −243 | 2714 | 19 |
| H(13A) | 4157 | −3193 | 4270 | 26 |
| H(13B) | 4329 | −1993 | 4702 | 26 |
| H(13C) | 5493 | −2561 | 4410 | 26 |
| H(14A) | 5521 | −2678 | 3185 | 35 |
| H(14B) | 4491 | −2027 | 2609 | 35 |
| H(14C) | 4134 | −3198 | 2982 | 35 |

TABLE 33-continued

Hydrogen coordinates (×10⁴) (i.e. (x10^4)) and isotropic displacement parameters (²× 10³) (i.e. (^2 × 10^3)) for crystalline form G.

| | x | y | z | U(eq) |
|---|---|---|---|---|
| H(15A) | 1816 | −268 | 3968 | 16 |
| H(15B) | 2693 | −1082 | 4533 | 16 |
| H(16A) | 4466 | 35 | 4409 | 16 |
| H(16B) | 3421 | 850 | 4654 | 16 |
| H(18) | 2068 | −2819 | 4399 | 19 |
| H(19) | 861 | −4493 | 4214 | 22 |
| H(20) | 2 | −5087 | 3045 | 27 |
| H(21) | 360 | −3977 | 2065 | 33 |
| H(22) | 1609 | −2324 | 2246 | 27 |
| H(23) | 8516 | 2118 | 4116 | 18 |
| H(24) | 9360 | 3987 | 4362 | 22 |
| H(25A) | 7 | 3909 | 486 | 37 |
| H(25B) | 470 | 2654 | 282 | 37 |
| H(25C) | 795 | 3773 | −154 | 37 |
| H(26A) | 2239 | 3196 | 2145 | 53 |
| H(26B) | 1315 | 2322 | 1650 | 53 |
| H(26C) | 843 | 3594 | 1811 | 53 |
| H(1N) | 6242(15) | 1058(15) | 3829(9) | 19(4) |

TABLE 34

Anisotropic displacement parameters (²× 10³) (i.e. (^2 × 10^3)) for crystalline form G. The anisotropic displacement factor exponent takes the form: $-2\pi^2 [h^2 a^{*2} U11 + \ldots + 2 h k a^* b^* U12]$.

| | U11 | U22 | U33 | U23 | U13 | U12 |
|---|---|---|---|---|---|---|
| F(1) | 32(1) | 16(1) | 46(1) | −5(1) | 7(1) | −12(1) |
| O(1) | 15(1) | 16(1) | 26(1) | 1(1) | −2(1) | 2(1) |
| N(1) | 14(1) | 9(1) | 16(1) | 0(1) | 2(1) | 1(1) |
| N(2) | 14(1) | 15(1) | 12(1) | −2(1) | 4(1) | 0(1) |
| C(1) | 26(1) | 13(1) | 21(1) | −1(1) | 5(1) | −7(1) |
| C(2) | 25(1) | 12(1) | 21(1) | 0(1) | 6(1) | −1(1) |
| C(3) | 18(1) | 12(1) | 13(1) | 1(1) | 3(1) | 0(1) |
| C(4) | 17(1) | 12(1) | 10(1) | 0(1) | 3(1) | −1(1) |
| C(5) | 14(1) | 12(1) | 12(1) | 1(1) | 2(1) | 1(1) |
| C(6) | 13(1) | 11(1) | 15(1) | 1(1) | 1(1) | 0(1) |
| C(7) | 16(1) | 17(1) | 32(1) | 0(1) | 6(1) | 4(1) |
| C(8) | 17(1) | 14(1) | 26(1) | 0(1) | 4(1) | 4(1) |
| C(9) | 16(1) | 12(1) | 15(1) | 1(1) | 3(1) | 1(1) |
| C(10) | 21(1) | 16(1) | 12(1) | 1(1) | 3(1) | −4(1) |
| C(11) | 19(1) | 17(1) | 10(1) | 1(1) | 0(1) | −4(1) |
| C(12) | 14(1) | 13(1) | 10(1) | −1(1) | 2(1) | −2(1) |
| C(13) | 17(1) | 16(1) | 17(1) | 2(1) | 2(1) | 2(1) |
| C(14) | 24(1) | 28(1) | 20(1) | −8(1) | 9(1) | 4(1) |
| C(15) | 15(1) | 13(1) | 12(1) | −1(1) | 4(1) | −1(1) |
| C(16) | 16(1) | 13(1) | 11(1) | −1(1) | 2(1) | −1(1) |
| C(17) | 14(1) | 14(1) | 14(1) | −2(1) | 3(1) | −2(1) |
| C(18) | 15(1) | 17(1) | 15(1) | −1(1) | 3(1) | −3(1) |
| C(19) | 17(1) | 17(1) | 21(1) | 1(1) | 4(1) | −4(1) |
| C(20) | 20(1) | 19(1) | 26(1) | −3(1) | 1(1) | −7(1) |
| C(21) | 35(1) | 28(1) | 18(1) | −6(1) | 0(1) | −14(1) |
| C(22) | 29(1) | 24(1) | 14(1) | −2(1) | 2(1) | −10(1) |
| C(23) | 16(1) | 16(1) | 13(1) | 1(1) | 3(1) | 0(1) |
| C(24) | 18(1) | 20(1) | 17(1) | 1(1) | 4(1) | −5(1) |
| S(1) | 18(1) | 18(1) | 31(1) | −1(1) | 7(1) | −3(1) |
| O(2) | 37(1) | 20(1) | 62(1) | −4(1) | 12(1) | −13(1) |
| C(25) | 22(1) | 22(1) | 30(1) | 2(1) | 3(1) | 1(1) |
| C(26) | 43(1) | 37(1) | 26(1) | 1(1) | 6(1) | −13(1) |

Crystalline Form I

TABLE 35

Crystal data and structure refinement for crystalline form I.

| | |
|---|---|
| Empirical formula | $C_{24}H_{27}FN_2O$ |
| Formula weight | 378.48 |
| Temperature | 100(2) K |
| Wavelength | 0.71073 Å |
| Crystal system | Monoclinic |
| Space group | P 21/c |
| Unit cell dimensions | a = 10.809(3) Å alpha = 90 deg. |
| | b = 15.946(5) Å beta = 107.632(7) deg. |
| | c = 11.846(4) Å gamma = 90 deg. |
| Volume | 1945.9(10) Å³ |
| Z | 4 |
| Density (calculated) | 1.292 Mg/m³ |
| Absorption coefficient | 0.086 mm⁻¹ |
| F(000) | 808 |
| Crystal size | 0.14 × 0.11 × 0.09 mm |
| Theta range for data collection | 2.21 to 25.65 deg. |
| Index ranges | −13 ≤ h ≤ 12, −19 ≤ k ≤ 16, −14 ≤ l ≤ 14 |
| Reflections collected | 16947 |
| Independent reflections | 3673 [R(int) = 0.1071] |
| Absorption correction | None |
| Refinement method | Full-matrix least-squares on F^2 |
| Data/restraints/parameters | 3673/0/259 |
| Goodness-of-fit on F^2 | 1.094 |
| Final R indices [I > 2sigma(I)] | R1 = 0.0645, wR2 = 0.1618 |
| R indices (all data) | R1 = 0.0931, wR2 = 0.1779 |
| Largest diff. peak and hole | 0.382 and −0.320 e.Å⁻³ |

TABLE 36

Atomic coordinates (×10⁴) (i.e. (x10^4)) and equivalent isotropic displacement parameters (²× 10³) (i.e. (^2 × 10^3)) for crystalline form I. U(eq) is defined as one third of the trace of the orthogonalized Uij tensor.

| | x | y | z | U(eq) |
|---|---|---|---|---|
| F(1) | 7997(1) | 4716(1) | 2730(1) | 32(1) |
| O(1) | 2425(2) | 2871(1) | 4710(2) | 22(1) |
| N(1) | 3434(2) | 3016(1) | 1980(2) | 20(1) |
| N(2) | −600(2) | 1697(1) | 1517(2) | 22(1) |
| C(1) | 6852(2) | 4284(2) | 2510(2) | 22(1) |
| C(2) | 6307(2) | 4202(2) | 3405(2) | 22(1) |
| C(3) | 5135(2) | 3753(2) | 3149(2) | 19(1) |
| C(4) | 4584(2) | 3413(2) | 2000(2) | 19(1) |
| C(5) | 3269(2) | 3107(2) | 3091(2) | 20(1) |
| C(6) | 2143(2) | 2746(2) | 3440(2) | 20(1) |
| C(7) | 2957(2) | 3679(2) | 5144(2) | 23(1) |
| C(8) | 4324(2) | 3767(2) | 5062(2) | 24(1) |
| C(9) | 4276(2) | 3545(2) | 3822(2) | 19(1) |
| C(10) | 838(2) | 3164(2) | 2778(2) | 21(1) |
| C(11) | −292(2) | 2751(2) | 3111(2) | 21(1) |
| C(12) | −431(2) | 1809(2) | 2809(2) | 21(1) |
| C(13) | −1705(2) | 2152(2) | 737(2) | 26(1) |
| C(14) | −662(3) | 828(2) | 1124(2) | 30(1) |
| C(15) | 875(2) | 1416(2) | 3535(2) | 21(1) |
| C(16) | 2035(2) | 1801(2) | 3242(2) | 22(1) |
| C(17) | −1580(2) | 1410(2) | 3141(2) | 21(1) |
| C(18) | −2738(2) | 1849(2) | 3002(2) | 22(1) |
| C(19) | −3821(2) | 1465(2) | 3180(2) | 23(1) |
| C(20) | −3778(2) | 625(2) | 3484(2) | 25(1) |
| C(21) | −2633(2) | 184(2) | 3653(3) | 31(1) |
| C(22) | −1553(2) | 569(2) | 3487(2) | 27(1) |
| C(23) | 5176(2) | 3502(2) | 1107(2) | 22(1) |
| C(24) | 6333(2) | 3948(2) | 1377(2) | 24(1) |

TABLE 37A

Bond lengths [Å] and angles [deg] for crystalline form I.

| | bond lengths [Å] and angles [deg] |
|---|---|
| F(1)—C(1) | 1.370(3) |
| O(1)—C(7) | 1.441(3) |
| O(1)—C(6) | 1.456(3) |

TABLE 37A-continued

Bond lengths [Å] and angles [deg] for crystalline form I.

| | bond lengths [Å] and angles [deg] |
|---|---|
| N(1)—C(5) | 1.388(3) |
| N(1)—C(4) | 1.389(3) |
| N(1)—H(1) | 0.97(4) |
| N(2)—C(14) | 1.458(3) |
| N(2)—C(13) | 1.462(3) |
| N(2)—C(12) | 1.496(3) |
| C(1)—C(2) | 1.366(4) |
| C(1)—C(24) | 1.396(4) |
| C(2)—C(3) | 1.405(3) |
| C(2)—H(2) | 0.9500 |
| C(3)—C(4) | 1.419(4) |
| C(3)—C(9) | 1.434(3) |
| C(4)—C(23) | 1.400(4) |
| C(5)—C(9) | 1.361(3) |
| C(5)—C(6) | 1.512(3) |
| C(6)—C(16) | 1.523(4) |
| C(6)—C(10) | 1.543(3) |
| C(7)—C(8) | 1.517(3) |
| C(7)—H(7A) | 0.9900 |
| C(7)—H(7B) | 0.9900 |
| C(8)—C(9) | 1.496(4) |
| C(8)—H(8A) | 0.9900 |
| C(8)—H(8B) | 0.9900 |
| C(10)—C(11) | 1.541(3) |
| C(10)—H(10A) | 0.9900 |
| C(10)—H(10B) | 0.9900 |
| C(11)—C(12) | 1.540(4) |
| C(11)—H(11A) | 0.9900 |
| C(11)—H(11B) | 0.9900 |
| C(12)—C(15) | 1.547(3) |
| C(12)—C(17) | 1.548(3) |
| C(13)—H(13A) | 0.9800 |
| C(13)—H(13B) | 0.9800 |
| C(13)—H(13C) | 0.9800 |
| C(14)—H(14A) | 0.9800 |
| C(14)—H(14B) | 0.9800 |
| C(14)—H(14C) | 0.9800 |
| C(15)—C(16) | 1.528(3) |
| C(15)—H(15A) | 0.9900 |
| C(15)—H(15B) | 0.9900 |
| C(16)—H(16A) | 0.9900 |
| C(16)—H(16B) | 0.9900 |
| C(17)—C(18) | 1.399(3) |
| C(17)—C(22) | 1.400(4) |
| C(18)—C(19) | 1.392(3) |
| C(18)—H(18) | 0.9500 |
| C(19)—C(20) | 1.385(4) |
| C(19)—H(19) | 0.9500 |
| C(20)—C(21) | 1.384(4) |
| C(20)—H(20) | 0.9500 |
| C(21)—C(22) | 1.385(4) |
| C(21)—H(21) | 0.9500 |
| C(22)—H(22) | 0.9500 |
| C(23)—C(24) | 1.388(4) |
| C(23)—H(23) | 0.9500 |
| C(24)—H(24) | 0.9500 |

TABLE 37B (Table 37A continued) Bond lengths [Å] and angles [deg] for crystalline form I.

| | bond lengths [Å] and angles [deg] |
|---|---|
| C(7)—O(1)—C(6) | 115.28(18) |
| C(5)—N(1)—C(4) | 107.9(2) |
| C(5)—N(1)—H(1) | 133(2) |
| C(4)—N(1)—H(1) | 119(2) |
| C(14)—N(2)—C(13) | 108.7(2) |
| C(14)—N(2)—C(12) | 114.8(2) |
| C(13)—N(2)—C(12) | 114.3(2) |

TABLE 37B-continued (Table 37A continued) Bond lengths [Å] and angles [deg] for crystalline form I.

| | bond lengths [Å] and angles [deg] |
|---|---|
| C(2)—C(1)—F(1) | 118.5(2) |
| C(2)—C(1C(24) | 124.5(2) |
| F(1)—C(1)—C(24) | 116.9(2) |
| C(1)—C(2)—C(3) | 117.0(2) |
| C(1)—C(2)—H(2) | 121.5 |
| C(3)—C(2)—H(2) | 121.5 |
| C(2)—C(3)—C(4) | 119.4(2) |
| C(2)—C(3)—C(9) | 133.7(2) |
| C(4)—C(3)—C(9) | 106.9(2) |
| N(1)—C(4)—C(23) | 130.2(2) |
| N(1)—C(4)—C(3) | 107.7(2) |
| C(23)—C(4)—C(3) | 122.1(2) |
| C(9)—C(5)—N(1) | 110.4(2) |
| C(9)—C(5)—C(6) | 125.2(2) |
| N(1)—C(5)—C(6) | 124.4(2) |
| O(1)—C(6)—C(5) | 107.26(18) |
| O(1)—C(6)—C(16) | 106.06(19) |
| C(5)—C(6)—C(16) | 111.4(2) |
| O(1)—C(6)—C(10) | 109.80(19) |
| C(5)—C(6)—C(10) | 112.6(2) |
| C(16)—C(6)—C(10) | 109.50(19) |
| O(1)—C(7)—C(8) | 110.5(2) |
| O(1)—C(7)—H(7A) | 109.5 |
| C(8)—C(7)—H(7A) | 109.5 |
| O(1)—C(7)—H(7B) | 109.5 |
| C(8)—C(7)—H(7B) | 109.5 |
| H(7A)—C(7)—H(7B) | 108.1 |
| C(9)—C(8)—C(7) | 107.2(2) |
| C(9)—C(8)—H(8A) | 110.3 |
| C(7)—C(8)—H(8A) | 110.3 |
| C(9)—C(8)—H(8B) | 110.3 |
| C(7)—C(8)—H(8B) | 110.3 |
| H(8A)—C(8)—H(8B) | 108.5 |
| C(5)—C(9)—C(3) | 107.0(2) |
| C(5)—C(9)—C(8) | 122.0(2) |
| C(3)—C(9)—C(8) | 130.9(2) |
| C(11)—C(10)—C(6) | 111.0(2) |
| C(11)—C(10)—H(10A) | 109.4 |
| C(6)—C(10)—H(10A) | 109.4 |
| C(11)—C(10)—H(10B) | 109.4 |
| C(6)—C(10)—H(10B) | 109.4 |
| H(10A)—C(10)—H(10B) | 108.0 |
| C(12)—C(11)—C(10) | 112.8(2) |
| C(12)—C(11)—H(11A) | 109.0 |
| C(10)—C(11)—H(11A) | 109.0 |
| C(12)—C(11)—H(11B) | 109.0 |
| C(10)—C(11)—H(11B) | 109.0 |
| H(11A)—C(11)—H(11B) | 107.8 |
| N(2)—C(12)—C(11) | 109.1(2) |
| N(2)—C(12)—C(15) | 109.2(2) |
| C(11)—C(12)—C(15) | 104.96(19) |
| N(2)—C(12)—C(17) | 110.60(19) |
| C(11)—C(12)—C(17) | 111.8(2) |
| C(15)—C(12)—C(17) | 111.0(2) |
| N(2)—C(13)—H(13A) | 109.5 |
| N(2)—C(13)—H(13B) | 109.5 |
| H(13A)—C(13)—H(13B) | 109.5 |
| N(2)—C(13)—H(13C) | 109.5 |
| H(13A)—C(13)—H(13C) | 109.5 |
| H(13B)—C(13)—H(13C) | 109.5 |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |
| H(14A)—C(14)—H(14C) | 109.5 |
| H(14B)—C(14)—H(14C) | 109.5 |
| C(16)—C(15)—C(12) | 112.6(2) |
| C(16)—C(15)—H(15A) | 109.1 |
| C(12)—C(15)—H(15A) | 109.1 |
| C(16)—C(15)—H(15B) | 109.1 |
| C(12)—C(15)—H(15B) | 109.1 |
| H(15A)—C(15)—H(15B) | 107.8 |
| C(6)—C(16)—C(15) | 113.2(2) |
| C(6)—C(16)—H(16A) | 108.9 |

TABLE 37B-continued (Table 37A continued) Bond lengths [Å] and angles [deg] for crystalline form I.

| | bond lengths [Å] and angles [deg] |
|---|---|
| C(15)—C(16)—H(16A) | 108.9 |
| C(6)—C(16)—H(16B) | 108.9 |
| C(15)—C(16)—H(16B) | 108.9 |
| H(16A)—C(16)—H(16B) | 107.8 |
| C(18)—C(17)—C(22) | 116.9(2) |
| C(18)—C(17)—C(12) | 121.4(2) |
| C(22)—C(17)—C(12) | 121.4(2) |
| C(19)—C(18)—C(17) | 121.7(2) |
| C(19)—C(18)—H(18) | 119.2 |
| C(17)—C(18)—H(18) | 119.2 |
| C(20)—C(19)—C(18) | 120.1(2) |
| C(20)—C(19)—H(19) | 119.9 |
| C(18)—C(19)—H(19) | 119.9 |
| C(21)—C(20)—C(19) | 119.1(2) |
| C(21)—C(20)—H(20) | 120.4 |
| C(19)—C(20)—H(20) | 120.4 |
| C(20)—C(21)—C(22) | 120.7(3) |
| C(20)—C(21)—H(21) | 119.7 |
| C(22)—C(21)—H(21) | 119.7 |
| C(21)—C(22)—C(17) | 121.5(2) |
| C(21)—C(22)—H(22) | 119.3 |
| C(17)—C(22)—H(22) | 119.3 |
| C(24)—C(23)—C(4) | 117.6(2) |
| C(24)—C(23)—H(23) | 121.2 |
| C(4)—C(23)—H(23) | 121.2 |
| C(23)—C(24)—C(1) | 119.4(2) |
| C(23)—C(24)—H(24) | 120.3 |
| C(1)—C(24)—H(24) | 120.3 |

Symmetry Transformations Used to Generate Equivalent Atoms:

TABLE 38

Hydrogen coordinates ($\times 10^4$) (i.e. ($\times 10^{\wedge}4$)) and isotropic displacement parameters ($^2\times 10^3$) (i.e. ($^{\wedge}2 \times 10^{\wedge}3$)) for crystalline form I.

| | x | y | z | U(eq) |
|---|---|---|---|---|
| H(1) | 2900(30) | 2770(20) | 1240(30) | 51(10) |
| H(2) | 6703 | 4437 | 4166 | 26 |
| H(7A) | 2970 | 3745 | 5978 | 28 |
| H(7B) | 2400 | 4127 | 4671 | 28 |
| H(8A) | 4637 | 4349 | 5247 | 28 |
| H(8B) | 4921 | 3385 | 5632 | 28 |
| H(10A) | 877 | 3768 | 2980 | 25 |
| H(10B) | 684 | 3115 | 1913 | 25 |
| H(11A) | −150 | 2823 | 3971 | 25 |
| H(11B) | −1111 | 3040 | 2685 | 25 |
| H(13A) | −1764 | 2037 | −91 | 39 |
| H(13B) | −1586 | 2755 | 890 | 39 |
| H(13C) | −2506 | 1968 | 888 | 39 |
| H(14A) | −1471 | 573 | 1168 | 44 |
| H(14B) | 79 | 517 | 1635 | 44 |
| H(14C) | −637 | 809 | 305 | 44 |
| H(15A) | 988 | 1493 | 4390 | 25 |
| H(15B) | 852 | 805 | 3375 | 25 |
| H(16A) | 2841 | 1532 | 3740 | 26 |
| H(16B) | 1958 | 1681 | 2404 | 26 |
| H(18) | −2786 | 2424 | 2780 | 26 |
| H(19) | −4590 | 1780 | 3092 | 28 |
| H(20) | −4525 | 354 | 3576 | 30 |
| H(21) | −2588 | −388 | 3885 | 37 |
| H(22) | −776 | 255 | 3610 | 32 |
| H(23) | 4801 | 3265 | 343 | 26 |
| H(24) | 6766 | 4023 | 796 | 29 |

TABLE 39

Anisotropic displacement parameters ($^2\times 10^3$) (i.e. ($^{\wedge}2 \times 10^{\wedge}3$)) for crystalline form I. The anisotropic displacement factor exponent takes the form: $-2\,pi^{\wedge}2\,[h^{\wedge}2\,a^{*\wedge}2\,U11 + \ldots + 2\,h\,k\,a^*\,b^*\,U12]$.

| | U11 | U22 | U33 | U23 | U13 | U12 |
|---|---|---|---|---|---|---|
| F(1) | 26(1) | 35(1) | 35(1) | 2(1) | 11(1) | −8(1) |
| O(1) | 30(1) | 21(1) | 15(1) | 0(1) | 8(1) | −4(1) |
| N(1) | 21(1) | 23(1) | 16(1) | 0(1) | 7(1) | 0(1) |
| N(2) | 22(1) | 26(1) | 18(1) | −1(1) | 6(1) | 2(1) |
| C(1) | 18(1) | 21(1) | 26(1) | 4(1) | 6(1) | 0(1) |
| C(2) | 23(1) | 20(1) | 23(1) | 2(1) | 6(1) | 0(1) |
| C(3) | 23(1) | 14(1) | 20(1) | 2(1) | 7(1) | 3(1) |
| C(4) | 20(1) | 19(1) | 19(1) | 2(1) | 6(1) | 3(1) |
| C(5) | 21(1) | 19(1) | 20(1) | 0(1) | 8(1) | 3(1) |
| C(6) | 24(1) | 21(1) | 15(1) | −1(1) | 7(1) | 0(1) |
| C(7) | 33(1) | 21(2) | 19(1) | −3(1) | 13(1) | −3(1) |
| C(8) | 30(1) | 24(2) | 17(1) | −1(1) | 7(1) | −4(1) |
| C(9) | 23(1) | 18(1) | 18(1) | 0(1) | 8(1) | 2(1) |
| C(10) | 24(1) | 18(1) | 21(1) | 3(1) | 7(1) | 0(1) |
| C(11) | 22(1) | 22(2) | 21(1) | 2(1) | 8(1) | 0(1) |
| C(12) | 25(1) | 21(2) | 16(1) | 0(1) | 7(1) | 0(1) |
| C(13) | 27(1) | 30(2) | 22(2) | 4(1) | 8(1) | 2(1) |
| C(14) | 31(1) | 30(2) | 24(2) | −6(1) | 3(1) | 9(1) |
| C(15) | 24(1) | 19(1) | 20(1) | −1(1) | 7(1) | 0(1) |
| C(16) | 22(1) | 22(2) | 22(1) | 1(1) | 8(1) | 1(1) |
| C(17) | 24(1) | 21(1) | 18(1) | −3(1) | 7(1) | −4(1) |
| C(18) | 29(1) | 22(2) | 14(1) | −2(1) | 8(1) | −2(1) |
| C(19) | 24(1) | 28(2) | 18(1) | −3(1) | 7(1) | −2(1) |
| C(20) | 28(1) | 29(2) | 19(1) | −3(1) | 9(1) | −9(1) |
| C(21) | 34(1) | 24(2) | 34(2) | 2(1) | 12(1) | −4(1) |
| C(22) | 27(1) | 22(2) | 33(2) | 0(1) | 10(1) | 0(1) |
| C(23) | 25(1) | 22(1) | 18(1) | −1(1) | 6(1) | 3(1) |
| C(24) | 27(1) | 26(2) | 23(1) | 5(1) | 12(1) | 3(1) |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A pharmaceutical composition comprising at least one pharmaceutically acceptable additive and/or adjuvant and about 25 μg to about 600 μg of an active ingredient that comprises a crystalline form of (1r,4r)-6'-fluoro-N,N-dimethyl-4-phenyl-4',9'-dihydro-3'H-spiro-[cyclohexane-1,1'-pyrano-[3,4,b]indol]-4-amine having an X-ray powder diffraction pattern comprising characteristic peaks at 7.8±0.2 degrees 2θ and at 31.6±0.2 degrees 2θ, and wherein the active ingredient comprises (1r,4r)-6'-fluoro-N,N-dimethyl-4-phenyl-4',9'-dihydro-3'H-spiro-[cyclohexane-1,1'-pyrano-[3,4,b]indol]-4-amine at a diasteromeric excess of about 90% de.

2. The pharmaceutical composition of claim 1, wherein the crystalline form further comprises a characteristic peak at 11.7±0.2 degrees 2θ.

3. The pharmaceutical composition of claim 1, wherein the crystalline form further comprises a characteristic peak at 18.3±0.2 degrees 2θ.

4. The pharmaceutical composition of claim 1, wherein the crystalline form further comprises characteristic peaks at 8.8±0.2 degrees 2θ and/or at 15.8±0.2 degrees 2θ.

5. The pharmaceutical composition of claim 1, wherein the crystalline form further comprises characteristic peaks at about 20.4±0.2 degrees 2θ and/or at 23.3±0.2 degrees 2θ.

6. The pharmaceutical composition of claim 1, wherein the crystalline form further comprises characteristic peaks at 11.7±0.2 degrees 2θ, at one or both of 8.8±0.2 degrees 2θ and/or 15.8±0.2 degrees 2θ, and at one or both of 20.4±0.2 degrees 2θ and/or 23.3±0.2 degrees 2θ.

7. The pharmaceutical composition of claim 1, wherein the crystalline form has an endothermal event with a peak temperature at about 298-308° C., as determined by DSC.

8. The pharmaceutical composition of claim 1, wherein the crystalline form has a Raman peak at about 1569±2 cm−1 and/or at about 1002±2 cm−1.

9. The pharmaceutical composition of claim 1, wherein the active ingredient comprises a (1r,4r)-6'-fluoro-N,N-dimethyl-4-phenyl-4',9'-dihydro-3'H-spiro-[cyclohexane-1,1'-pyrano-[3,4,b]indol]-4-amine at a diasteromeric excess of at least about 95%de.

10. The pharmaceutical composition of claim 1, wherein the active ingredient comprises a (1r,4r)-6'-fluoro-N,N-dimethyl-4-phenyl-4',9'-dihydro-3'H-spiro-[cyclohexane-1,1'-pyrano-[3,4,b]indol]-4-amine at a diasteromeric excess of at least about 97%de.

11. The pharmaceutical composition of claim 1, wherein the active ingredient comprises a (1r,4r)-6'-fluoro-N,N-dimethyl-4-phenyl-4',9'-dihydro-3'H-spiro-[cyclohexane-1,1'-pyrano-[3,4,b]indol]-4-amine at a diasteromeric excess of at least about 99%de.

12. The pharmaceutical composition of claim 1, wherein the crystalline form is present in the active ingredient in an amount of at least about 60 wt. % relative to the total weight of all crystalline and non-crystalline forms of (1r,4r-6'-fluoro-N,N-dimethyl-4-phenyl-4',9'-dihydro-3'H-spiro-[cyclohexane-1,1'-pyrano-[3,4,b]indol]-4-amine.

13. The pharmaceutical composition of claim 1, wherein the crystalline form is present in the active ingredient in an amount of at least about 80 wt. % relative to the total weight of all crystalline and non-crystalline forms of (1r,4r-6'-fluoro-N,N-dimethyl-4-phenyl-4',9'-dihydro-3'H-spiro-[cyclohexane-1,1'-pyrano-[3,4,b]indol]-4-amine.

14. The pharmaceutical composition of claim 1, wherein the crystalline form is present in the active ingredient in an amount of at least about 90 wt. % relative to the total weight of all crystalline and non-crystalline forms of (1r,4r-6'-fluoro-N,N-dimethyl-4-phenyl-4',9'-dihydro-3'H-spiro-[cyclohexane-1,1'-pyrano-[3,4,b]indol]-4-amine.

15. The pharmaceutical composition of claim 1, wherein the crystalline form is present in the active ingredient in an amount of at least about 95 wt. % relative to the total weight of all crystalline and non-crystalline forms of (1r,4r)-6'-fluoro-N,N-dimethyl-4-phenyl-4',9'-dihydro-3'H-spiro-[cyclohexane-1,1'-pyrano-[3,4,b]indol]-4-amine.

16. The pharmaceutical composition of claim 1, wherein the pharmaceutical composition comprises 40±20 μg, 100±10 μg or 400±200 μg of the active ingredient.

17. The pharmaceutical composition of claim 13, wherein the pharmaceutical composition comprises 40±20 μg, 100±10 μg or 400±200 μg of the active ingredient.

18. The pharmaceutical composition of claim 1, wherein the pharmaceutical composition contains at most about 1.0 wt.-% 4-dimethylamino-4-phenylcyclohexanone, relative to the total content of 6'-fluoro-N,N-dimethyl-4-phenyl-4',9'-dihydro-3'H-spiro[cyclohexane-1,1'-pyran [3,4b]indol]-4-amine.

19. The pharmaceutical composition of claim 13, wherein the pharmaceutical composition contains at most about 1.0 wt.-% 4-dimethylamino-4-phenylcyclohexanone, relative to the total content of 6'-fluoro-N,N-dimethyl-4-phenyl-4',9'-dihydro-3'H-spiro[cyclohexane-1,1'-pyran [3,4b]indol]-4-amine.

20. A pharmaceutical composition comprising at least one pharmaceutically acceptable additive and/or adjuvant and about 25 μg to about 600 μg of an active ingredient that comprises a crystalline form of (1r,4r)-6'-fluoro-N,N-dimethyl-4-phenyl-4',9'-dihydro-3'H-spiro-[cyclohexane-1,1'-pyrano-[3,4,b]indol]-4-amine having an X-ray powder diffraction pattern comprising characteristic peaks at 7.8±0.2 degrees 2θ and at 31.6±0.2 degrees 2θ, and wherein the crystalline form is present in the active ingredient in an amount of at least about 60 wt. % relative to the total weight of all crystalline and non-crystalline forms of (1r,4r)-6'-fluoro-N,N-dimethyl-4-phenyl-4',9'-dihydro-3'H-spiro-[cyclohexane-1,1'-pyrano-[3,4,b]indol]-4-amine.

21. The pharmaceutical composition of claim 20, wherein the crystalline form further comprises a characteristic peak at 11.7±0.2 degrees 2θ.

22. The pharmaceutical composition of claim 20, wherein the crystalline form further comprises a characteristic peak at 18.3±0.2 degrees 2θ.

23. The pharmaceutical composition of claim 20, wherein the crystalline form further comprises characteristic peaks at 8.8±0.2 degrees 2θ and/or at 15.8±0.2 degrees 2θ.

24. The pharmaceutical composition of claim 20, wherein the crystalline form further comprises characteristic peaks at about 20.4±0.2 degrees 2θ and/or at 23.3±0.2 degrees 2θ.

25. The pharmaceutical composition of claim 20, wherein the crystalline form further comprises characteristic peaks at 11.7±0.2 degrees 2θ, at one or both of 8.8±0.2 degrees 2θ and/or 15.8±0.2 degrees 2θ, and at one or both of 20.4±0.2 degrees 2θ and/or 23.3±0.2 degrees 2θ.

26. The pharmaceutical composition of claim 20, wherein the crystalline form has an endothermal event with a peak temperature at about 298-308° C., as determined by DSC.

27. The pharmaceutical composition of claim 20, wherein the crystalline form has a Raman peak at about 1569±2 cm−1 and/or at about 1002±2 cm−1.

28. The pharmaceutical composition of claim 20, wherein the crystalline form is present in the active ingredient in an amount of at least about 70 wt. % relative to the total weight of all crystalline and non-crystalline forms of (1r,4r)-6'-fluoro-N,N-dimethyl-4-phenyl-4',9'-dihydro-3'H-spiro-[cyclohexane-1,1'-pyrano-[3,4,b]indol]-4-amine.

29. The pharmaceutical composition of claim 20, wherein the crystalline form is present in the active ingredient in an amount of at least about 80 wt. % relative to the total weight of all crystalline and non-crystalline forms of (1r,4r)-6'-fluoro-N,N-dimethyl-4-phenyl-4',9'-dihydro-3'H-spiro-[cyclohexane-1,1'-pyrano-[3,4,b]indol]-4-amine.

30. The pharmaceutical composition of claim 20, wherein the crystalline form is present in the active ingredient in an amount of at least about 90 wt. % relative to the total weight of all crystalline and non-crystalline forms of (1r,4r)-6'-fluoro-N,N-dimethyl-4-phenyl-4',9'-dihydro-3'H-spiro-[cyclohexane-1,1'-pyrano-[3,4,b]indol]-4-amine.

31. The pharmaceutical composition of claim 20, wherein the crystalline form is present in the active ingredient in an amount of at least about 95 wt. % relative to the total weight of all crystalline and non-crystalline forms of (1r,4r)-6'-fluoro-N,N-dimethyl-4-phenyl-4',9'-dihydro-3'H-spiro-[cyclohexane-1,1'-pyrano-[3,4,b]indol]-4-amine.

32. The pharmaceutical composition of claim 20, wherein the pharmaceutical composition contains at most about 1.0 wt.-% 4-dimethylamino-4-phenylcyclohexanone, relative to the total content of 6'-fluoro-N,N-dimethyl-4-phenyl-4',9'-dihydro-3'H-spiro[cyclohexane-1,1'-pyrano[3,4b]indol]-4-amine.

33. A pharmaceutical composition comprising at least one pharmaceutically acceptable additive and/or adjuvant and about 25 μg to about 600 μg of an active ingredient that comprises a crystalline form of (1r,4r)-6'-fluoro-N,N-dimethyl-4-phenyl-4',9'-dihydro-3'H-spiro-[cyclohexane-1,1'- pyrano-[3,4,b]indol]-4-amine having an X-ray powder diffraction pattern comprising characteristic peaks at 7.8±0.2 degrees 2θ and at 31.6±0.2 degrees 2θ, wherein the pharmaceutical composition contains at most about 1.0 wt.-% 4-dimethylamino-4-phenylcyclohexanone, relative to the total content of 6'-fluoro-N,N-dimethyl-4-phenyl-4',9'-dihydro-3'H-spiro[cyclohexane-1,1'-pyrano[3,4b]indol]-4-amine.

34. The pharmaceutical composition of claim 33, wherein the crystalline form further comprises a characteristic peak at 11.7±0.2 degrees 2θ.

35. The pharmaceutical composition of claim 33, wherein the crystalline form further comprises a characteristic peak at 18.3±0.2 degrees 2θ.

36. The pharmaceutical composition of claim 33, wherein the crystalline form further comprises characteristic peaks at 8.8±0.2 degrees 2θ and/or at 15.8±0.2 degrees 2θ.

37. The pharmaceutical composition of claim 33, wherein the crystalline form further comprises characteristic peaks at about 20.4±0.2 degrees 2θ and/or at 23.3±0.2 degrees 2θ.

38. The pharmaceutical composition of claim 33, wherein the crystalline form further comprises characteristic peaks at 11.7±0.2 degrees 2θ, at one or both of 8.8±0.2 degrees 2θ and/or 15.8±0.2 degrees 2θ, and at one or both of 20.4±0.2 degrees 2θ and/or 23±0.2 degrees 2θ.

39. A method for treating chronic pain in a patient, comprising orally administering to a patient diagnosed with a chronic pain disorder the pharmaceutical composition of claim 1.

40. A method for treating chronic pain in a patient, comprising orally administering to a patient diagnosed with a chronic pain disorder the pharmaceutical composition of claim 20.

41. A method for treating chronic pain in a patient, comprising orally administering to a patient diagnosed with a chronic pain disorder the pharmaceutical composition of claim 33.

* * * * *